(12) United States Patent
Lissy et al.

(10) Patent No.: US 11,464,620 B2
(45) Date of Patent: Oct. 11, 2022

(54) PIVOT-BASED MEDICAL HOLDING SYSTEM AND METHOD

(71) Applicant: United Health Services Hospitals, Inc., Binghamton, NY (US)

(72) Inventors: Micah E. Lissy, Vestal, NY (US); Norman L. Barrigas, Danbury, CT (US)

(73) Assignee: United Health Services Hospitals, Inc., Binghamton, NY (US)

( * ) Notice: Subject to any disclaimer, the term of this patent is extended or adjusted under 35 U.S.C. 154(b) by 0 days.

(21) Appl. No.: 16/850,118

(22) Filed: Apr. 16, 2020

(65) Prior Publication Data
US 2020/0323621 A1 Oct. 15, 2020

Related U.S. Application Data

(63) Continuation-in-part of application No. 16/385,427, filed on Apr. 16, 2019.
(Continued)

(51) Int. Cl.
*A61F 2/08* (2006.01)
*A61B 90/50* (2016.01)
(Continued)

(52) U.S. Cl.
CPC ............ *A61F 2/0805* (2013.01); *A61B 17/28* (2013.01); *A61B 90/50* (2016.02); *A61B 2017/00526* (2013.01); *A61F 2002/0852* (2013.01)

(58) Field of Classification Search
CPC .. A61F 2/0805; A61F 2002/0852; A61F 2/08; A61F 2/0811; A61F 2220/0075; A61B 90/50; A61B 17/28; A61B 2017/00526; A61B 17/04; A61B 2090/508; A61B 17/29; A61B 17/56; A61B 17/08;
(Continued)

(56) References Cited

U.S. PATENT DOCUMENTS 5,298,012 A 3/1994 Handlos
5,415,651 A 5/1995 Schmieding
(Continued)

FOREIGN PATENT DOCUMENTS

| EP | 1297798 A2 | 4/2003 |
|---|---|---|
| EP | 2772193 A1 | 9/2014 |
| EP | 2923672 A1 | 9/2015 |

OTHER PUBLICATIONS

Arthrex, Inc.; Arthrex SpeedWhip Technique with FiberLoop; Jun. 11, 2010; retrieved from the Internet: <https://www.arthrex.com/resources/animation/sjjf3PkEEeCRTQBQVoRHOw/speedwhip-technique-with-fiberloop>; 5 pages.
(Continued)

*Primary Examiner* — Robert A Lynch
(74) *Attorney, Agent, or Firm* — Barclay Damon LLP

(57) ABSTRACT

A medical holding system and method are disclosed herein. The medical holding system, in an embodiment, includes a retainer and a pivot device having a plurality of arms. Each of the arms is configured to be engaged with the retainer. The medical holding system also includes a grasper configured to be coupled to the pivot device. The grasper is configured to grasp a portion of an implantable element, and the pivot device is configured to be pivoted relative to the retainer.

23 Claims, 103 Drawing Sheets

Related U.S. Application Data

(60) Provisional application No. 62/658,053, filed on Apr. 16, 2018.

(51) Int. Cl.
  *A61B 17/28* (2006.01)
  *A61B 17/00* (2006.01)

(58) Field of Classification Search
  CPC ............... A61B 17/32; A61B 17/3468; A61B 2017/00477; A61B 2017/00075; A61B 2017/3492; A61B 2017/00039; A61B 90/00; A61B 90/57; A61B 2090/571; A61B 17/06061; A61B 17/8869; A61B 2017/0496; A61L 2430/10
  USPC ............................................ 623/13.11, 13.12
  See application file for complete search history.

(56) References Cited

U.S. PATENT DOCUMENTS

| | | | |
|---|---|---|---|
| 5,683,400 | A | 11/1997 | McGuire |
| 6,001,106 | A | 12/1999 | Ryan et al. |
| 6,547,778 | B1 | 4/2003 | Sklar et al. |
| 7,118,578 | B2 | 10/2006 | West, Jr. et al. |
| 8,298,284 | B2 | 10/2012 | Cassani |
| 8,439,976 | B2 | 5/2013 | Albertorio et al. |
| 2002/0040240 | A1 | 4/2002 | Heckele et al. |
| 2003/0065247 | A1* | 4/2003 | Yap ........................... A61F 2/08 600/36 |
| 2005/0065533 | A1 | 3/2005 | Magen et al. |
| 2011/0287403 | A1 | 11/2011 | Ciccone, II et al. |
| 2016/0008123 | A1 | 1/2016 | Woodruff et al. |
| 2018/0013252 | A1 | 1/2018 | Moser |
| 2018/0050407 | A1 | 2/2018 | Richards |
| 2019/0314141 | A1 | 10/2019 | Lissy |

OTHER PUBLICATIONS

Arthrex, Inc.; Arthrex SpeedWhip Video; Aug. 14, 2017; retrieved from the Internet: <https://www.youtube.com/watch?v=SFfkNRac2_U>; 7 pages.

Plasma Engineer; Something Surprising Blog; Feynman's Shaft Passer; Nov. 9, 2011; retrieved from the Internet: <http://somethingsurprising.blogspot.com/2011/11/feynmans-shaft-passer-in-reality.html>; 4 pages.

Arthrex, Inc.; GraftPro™, Graft Preparation System; On or before Dec. 31, 2016; 4 pages.

Wikipedia; Shaft Passer by Wilipedia, Dec. 5, 2017; retrieved from the Internet: <https://en.wikipedia.org/wiki/Shaft_passer>; 4 pages.

Arthrex, Inc.; SpeedWhip™ Technique with FiberLoop® and TigerLoop®; On or before Dec. 31, 2011; 1 page.

Vunoo; Printable Cable Passer; Nov. 30, 2013; retrieved from the Internet: <https://www.thingiverse.com/make:55132>; 2 pages.

Arthrex, Inc.;Anthrex Stands; On or before Apr. 3, 2020; 3 pages.

PCT/US2019/027614; filed Apr. 16, 2019; International Search Report and Written Opinion; dated Jul. 10, 2019; 11 pages.

PCT/US2019/027614; International Filing Date Apr. 16, 2019; International Preliminary Report on Patentability; dated Oct. 29, 2020 (10 pages).

PCT/US2021/026969; filed Apr. 13, 2021; International Search Report and Written Opinion; dated Jul. 12, 2021 (17 pages).

EP Application No. 19788911; filed Apr. 16, 2019; Extended Search Report; dated Dec. 20, 2021 (9 pages).

* cited by examiner

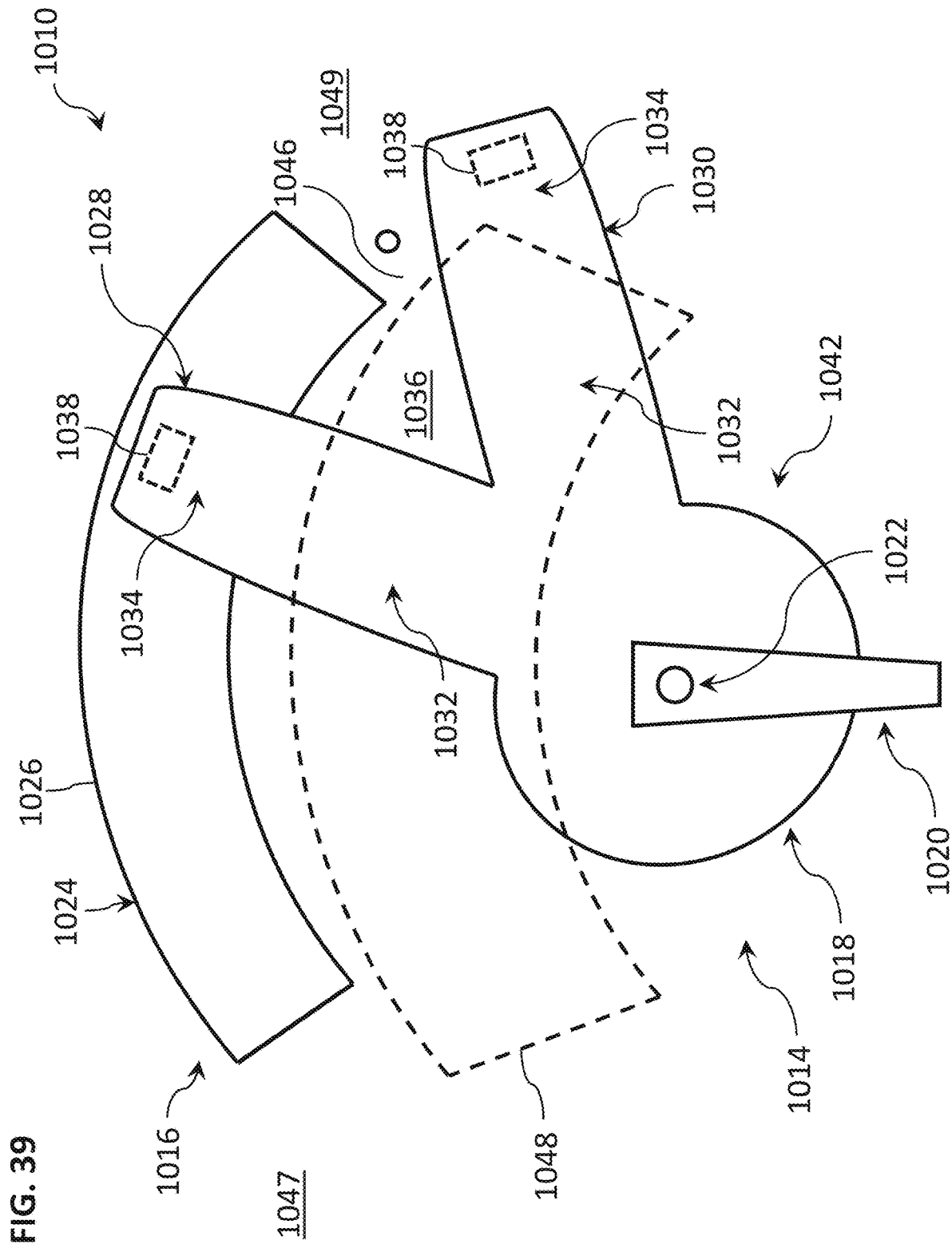

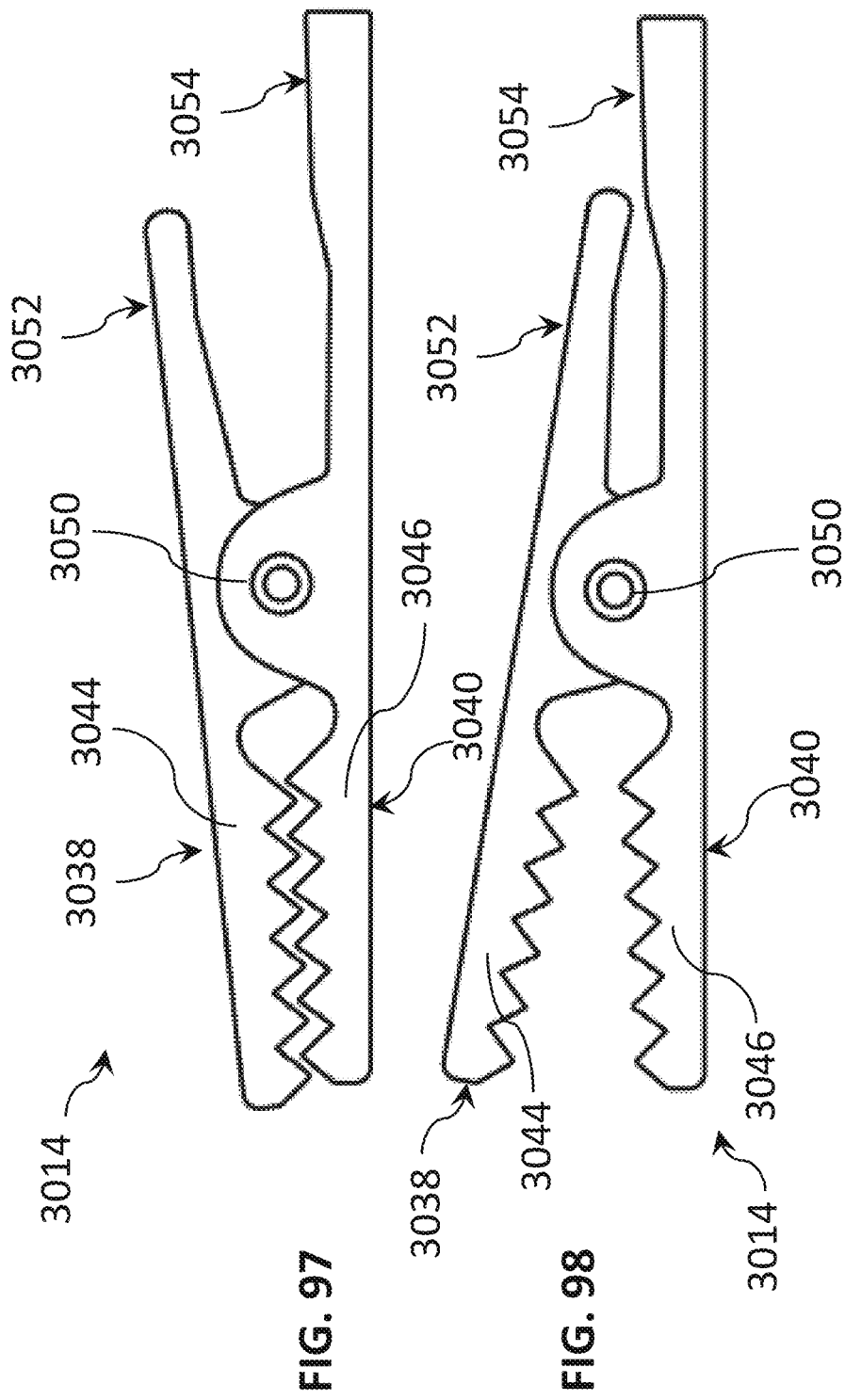

PIVOT-BASED MEDICAL HOLDING SYSTEM AND METHOD

CROSS-REFERENCE TO RELATED APPLICATIONS

This application is a continuation-in-part of, and claims the benefit and priority of, U.S. patent application Ser. No. 16/385,427 filed on Apr. 16, 2019, which, in turn, is a non-provisional of, and claims the benefit and priority of, U.S. Provisional Patent Application No. 62/658,053 filed on Apr. 16, 2018. The entire contents of such applications are hereby incorporated herein by reference.

BACKGROUND

In certain surgical procedures, the surgeon inserts or implants a graft into the surgical site of the patient. Depending upon the type of surgery, the graft can be tissue excised from the patient or tissue supplied from a donor. In some cases, the graft must be prepared or treated before the surgery. In surgeries involving the repair or replacement of tendons or ligaments, the graft can include a substitute tendon or substitute ligament.

As illustrated in FIGS. 1-2, there are known graft preparation stations 10, 12 designed to hold one or more grafts 14, 15. Each of these stations 10, 12 has one or more left posts 16, 17 and one or more right posts 18, 19. To suspend the graft 14, the user can couple ropes 20, 22 to the left and right posts 17, 19, respectively. To suspend the graft 15, the user can couple the graft 15 directly to the left post 16, and the user can use rope 23 to couple the graft 15 to the right post 18.

Consequently, as illustrated in FIG. 2, there is an uninterrupted, continuous line 26 (whether a line of graft by itself or a line made of graft and rope) extending between the posts 16, 18 or between posts 17, 19. This continuous line 26 acts as a barrier that restricts the types of graft preparation methods that can be employed. For example, this continuous line 26 prevents the user from using a loop-based suturing method, such as the FiberLoop® and TigerLoop® suturing methods published by Arthrex, Inc. As illustrated in FIG. 3, a loop-based suturing method can involve the use of a needle 28 connected to a loop of rope or a looped rope 30. According to this suturing method, the user must periodically pass the looped rope 30 over the end of the graft 14 to be treated. However, the continuous line 26 prevents this passage, and, therefore, the known graft preparation stations 10, 12 impede, or are incompatible with, the use of loop-based suturing methods.

Because of this problem, clinicians have had to resort to a relatively complex, labor intensive process for the use of loop-based suturing methods. The labor intensive process requires at least two people, typically a surgeon and a physician assistant or other clinical assistant. For example, as shown in FIGS. 4-9, the labor intensive process involves the following steps:

(a) a surgeon 32 locks a surgical clamp 34 onto the treatable end 36 of the graft 38, as shown in FIG. 4;
(b) the assistant 40 holds the surgical clamp 34, as shown in FIG. 4, using the assistant's upper hand 42;
(c) after the surgeon 32 passes the needle (not shown) through the treatable end 36 of the graft 38, the surgeon 32 moves the looped rope 30 beyond the clamp handles 46, as shown in FIG. 4;
(d) the assistant 40 then moves the surgical clamp 34 upward, partially through the opening 41 defined by the looped rope 30, as shown in FIG. 4;
(e) as the surgeon 32 moves the looped rope 30 upward, the upper hand 42 of the assistant 40 releases the surgical clamp 34, and the lower hand 48 of the assistant 40 grasps the surgical clamp 34, as shown in FIG. 5;
(f) the assistant 40 then clears away the upper hand 42, enabling the surgeon 32 to pass the looped rope 30 over the surgical clamp 34, as shown in FIG. 6,
(g) the surgeon 32 then proceeds to suture the treatable end 36, as shown in FIGS. 7-9, by passing the needle 28 through the treatable end 36; and
(h) the assistant 40 and surgeon 32 repeat the foregoing steps (b) through (g) multiple times to fully suture the treatable end 36.

This labor intensive process can be prone to error, is tedious, is time consuming and is complex, resulting in fatigue of the surgeon and clinical assistant. These factors can expose the surgeon and assistant to heightened risks of graft preparation errors, deficiencies in the graft preparation, needle pricks and injuries, and other disadvantages.

The foregoing background describes some, but not necessarily all, of the problems, disadvantages, shortcomings and challenges related to the preparation of implantable elements.

SUMMARY

The medical holding system, in an embodiment, includes a holder and a support device. The holder includes a grasper and a coupler. The grasper is configured to be coupled to an implantable element. The implantable element includes a first element end configured to be suspended by a first upright support. The first upright support is configured to be supported by a support surface. The implantable element also includes a second element end. The grasper is configured to be secured to the second element end of the implantable element. The coupler includes a coupler portion. The support device is configured to be coupled to the support surface. The support device includes a second upright support. The second upright support includes a release interface.

The coupler portion and the release interface are configured to cooperate with each other so that coupler portion is configured to be transitioned from an engagement condition to a disengagement condition and back to the engagement condition. In the engagement condition, the coupler portion is engaged with the release interface to keep the implantable element suspended above the support surface when the implantable element is subject to a suturing force that acts downward toward the support surface. In the disengagement condition, the coupler portion is disengaged from the release interface in response to a pass-through force, thereby forming a passageway between the support device and the second element end. The passageway is configured to receive a cord segment of a medical looped cord. After the cord segment passes through the passageway, the coupler portion is configured to transition back to the engagement condition. The coupler portion and the release interface are configured to keep the implantable element suspended above the support surface throughout the engagement and disengagement conditions.

In another embodiment, the medical holding system includes a holder and a support device. The holder includes a grasper and a coupler. The grasper is configured to be coupled to an end of an implantable element when the implantable element includes an opposing end coupled to an upright support. The coupler includes a coupler portion. The support device includes a release interface. The support device is configured to be supported by a support surface. The holder and the support device are configured to cooperate with each other so that the coupler portion is configured to transition from an engagement condition to a disengagement condition and back to the engagement condition. In the engagement condition, the coupler portion is engaged with the release interface. In the disengagement condition, the coupler portion is disengaged from the release interface in response to a pass-through force, thereby forming a passageway between the support device and the end of the implantable element. The passageway is configured to receive a cord segment of a medical cord. The holder and the support device are configured to keep the implantable element suspended above the support surface throughout the engagement and disengagement conditions.

The medical holding system is configured to be manufactured according to a manufacturing method. In an embodiment, the manufacturing method includes: configuring, structuring or fabricating a holder. The configuring, structuring or fabricating of the holder includes configuring, structuring or fabricating a grasper to be coupled to an end of an implantable element when the implantable element includes an opposing end coupled to an upright support. The configuring, structuring or fabricating of the holder also includes configuring, structuring or fabricating a coupler to include a coupler portion. The manufacturing method also includes configuring, structuring or fabricating a support device to include a release interface and to be supported by a support surface. Also, the manufacturing method includes configuring, structuring or fabricating the holder and the support device to cooperate with each other so that the coupler portion is operable to transition from an engagement condition to a disengagement condition and back to the engagement condition. In the engagement condition, the coupler portion is engaged with the release interface. In the disengagement condition, the coupler portion is disengaged from the release interface in response to a pass-through force, thereby forming a passageway between the support device and the end of the implantable element. The passageway is configured to receive a cord segment of a medical cord. The holder and the support device are configured to keep the implantable element suspended above the support surface throughout the engagement and disengagement conditions.

In an embodiment, the medical holding system includes: (a) a retainer defining a retainer interface; (b) a pivot device having a plurality of arms; and (c) a grasper coupled to the pivot device. The grasper is configured to grasp an implantable element. Each of the arms has a first arm portion and a second arm portion. Each of the second arm portions has an arm interface configured to mate with the retainer interface. The first arm portions are separated by a cord transport space. The pivot device is configured to be pivoted, relative to the retainer, between an entry position and an outlet position. In the entry position, there is an entry space between the retainer and one of the second arm portions so that a cord segment of a medical cord is moveable through the entry space to the cord transport space. In the outlet position, there is an outlet space between the retainer and one of the second arm portions so that the cord segment is moveable from the cord transport space to the outlet space. The pivoting of the pivot device causes the cord transport space to move along a cord passageway extending from the entry space to the outlet space. At least one of the arm interfaces remains mated with the retainer interface during the pivoting of the pivot device between the entry position and the outlet position.

In another embodiment, the medical holding system includes: (a) a retainer; (b) a pivot device having a plurality of arms; and (c) a grasper configured to be coupled to the pivot device. Each of the arms has a first arm portion and a second arm portion. Each of the second arm portions is configured to be engaged with the retainer. The grasper is configured to grasp a portion of an implantable element. The pivot device is configured to be pivoted relative to the retainer.

In yet another embodiment, a method for manufacturing a medical holding system includes the following steps performed in any order: configuring a retainer; configuring a pivot device to have a plurality of arms so that: (a) each of the arms has a first arm portion and a second arm portion; and (b) each of the second arm portions is configured to be engaged with the retainer; configuring a grasper to be coupled to the pivot device; configuring the grasper to grasp a portion of an implantable element; and configuring the pivot device to be pivoted relative to the retainer.

Additional features and advantages of the present disclosure are described in, and will be apparent from, the following Brief Description of the Drawings and Detailed Description.

BRIEF DESCRIPTION OF THE DRAWINGS

FIG. 39 is a top, schematic view of the medical holding system of FIG. 36, illustrating the pivot device in an outlet position.

FIG. 97 is a side elevation view of an embodiment of the cord management device of FIG. 95, illustrating another embodiment of a clip of such cord management device wherein the jaws of such clip are closed.

FIG. 98 is a side elevation view of the clip of FIG. 97, illustrating the jaws of such clip in an open position.

DETAILED DESCRIPTION

Figure 1:
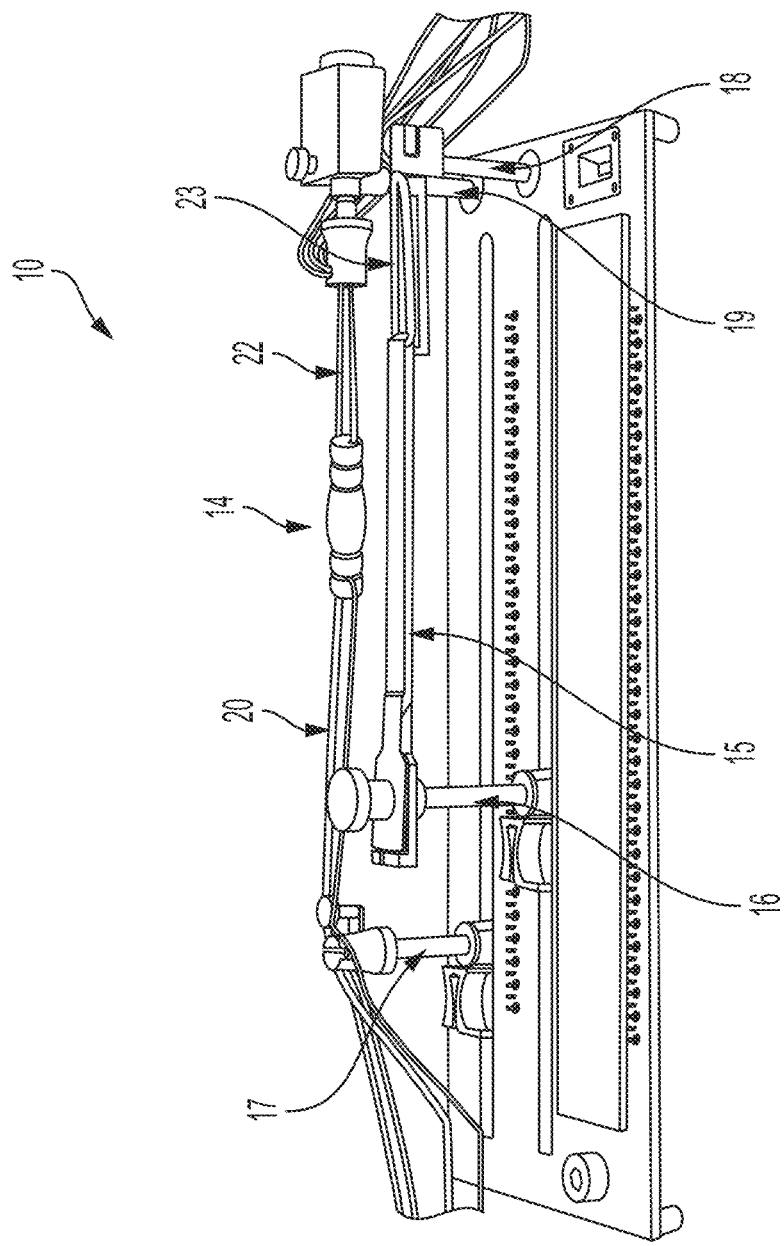
FIG. 1 is an isometric view of a prior art graft preparation station.
Figure 2:
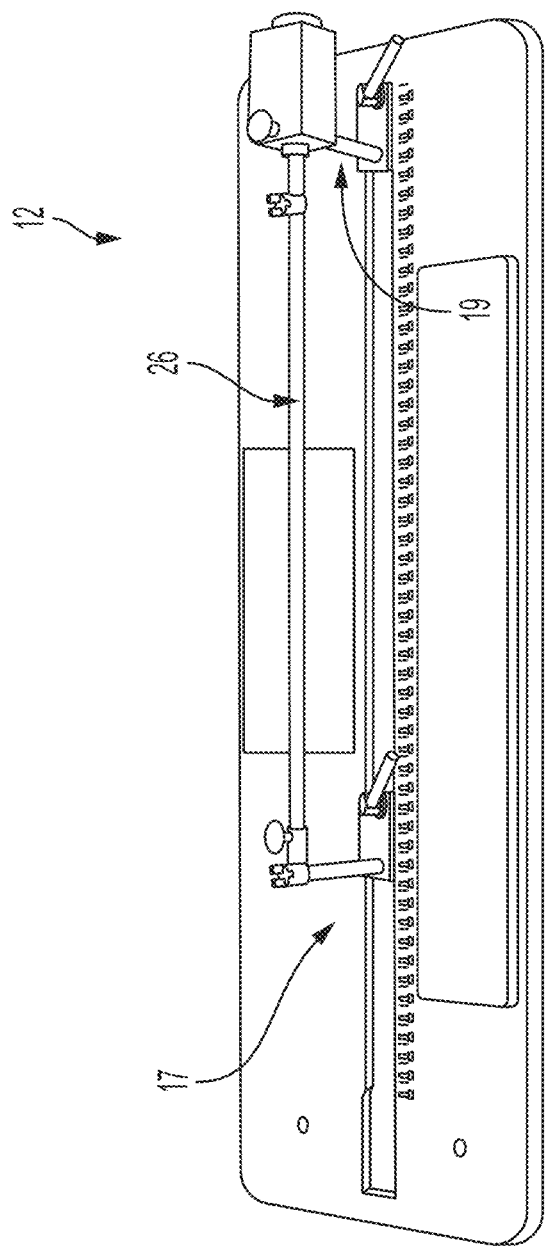
FIG. 2 is an isometric view of another prior art graft preparation station.
Figure 3:
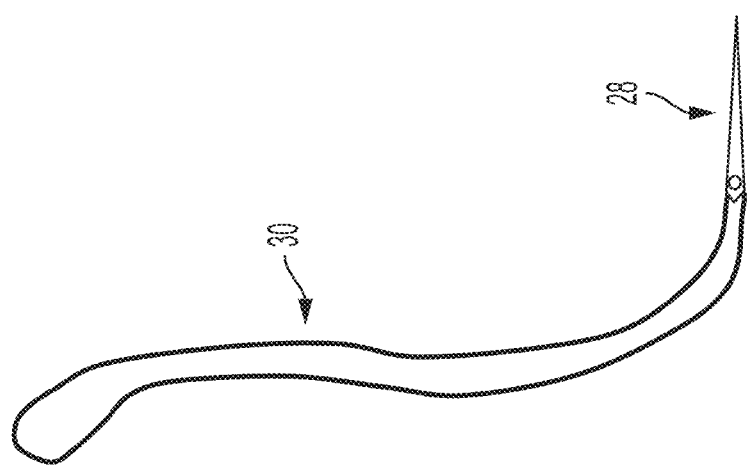
FIG. 3 is a top view of a prior art looped rope and needle.
Figure 4:
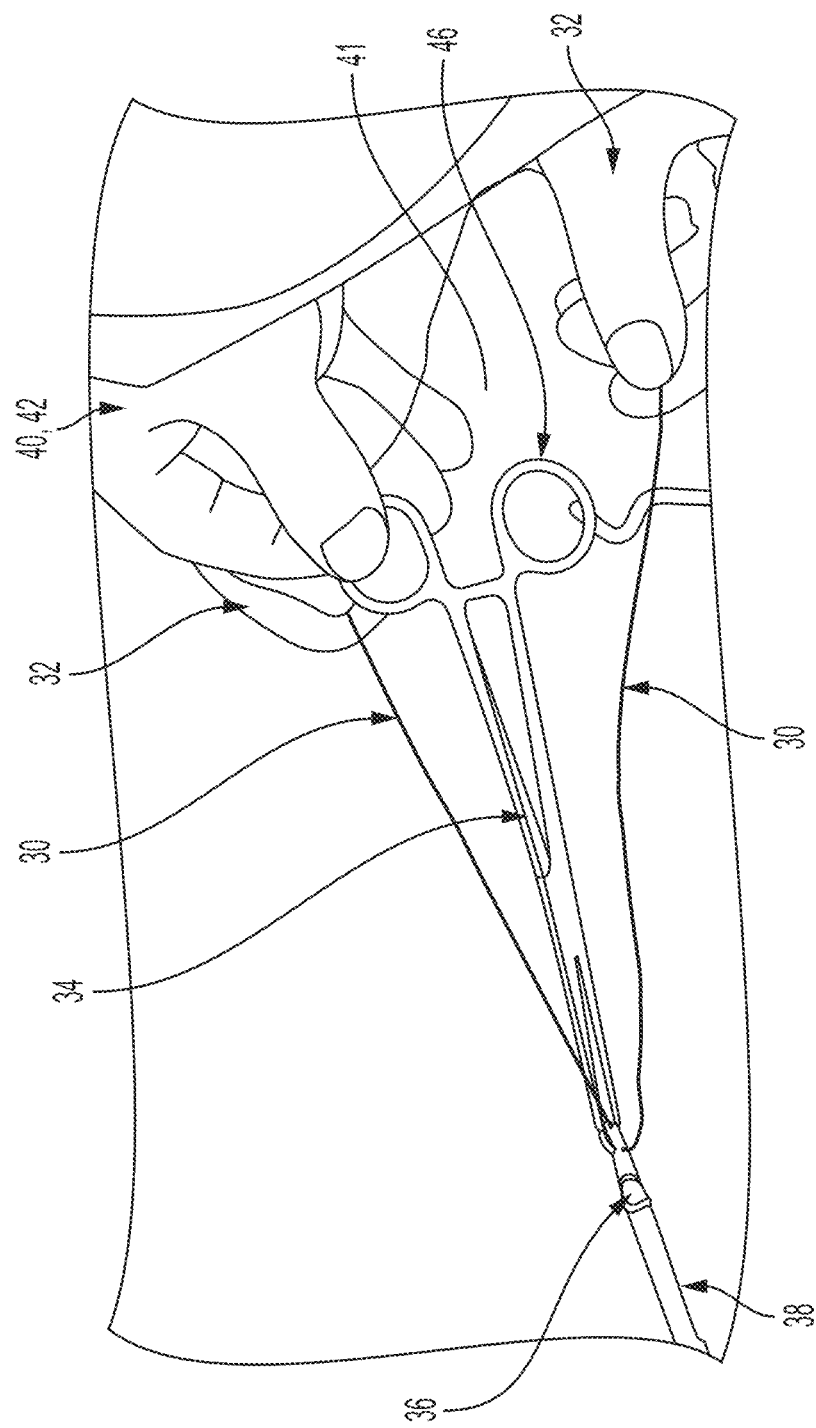
FIG. 4 is an isometric view of a prior art looped rope, as held in the first step of an example of a prior art labor intensive process for the use of a loop-based suturing method.
Figure 5:
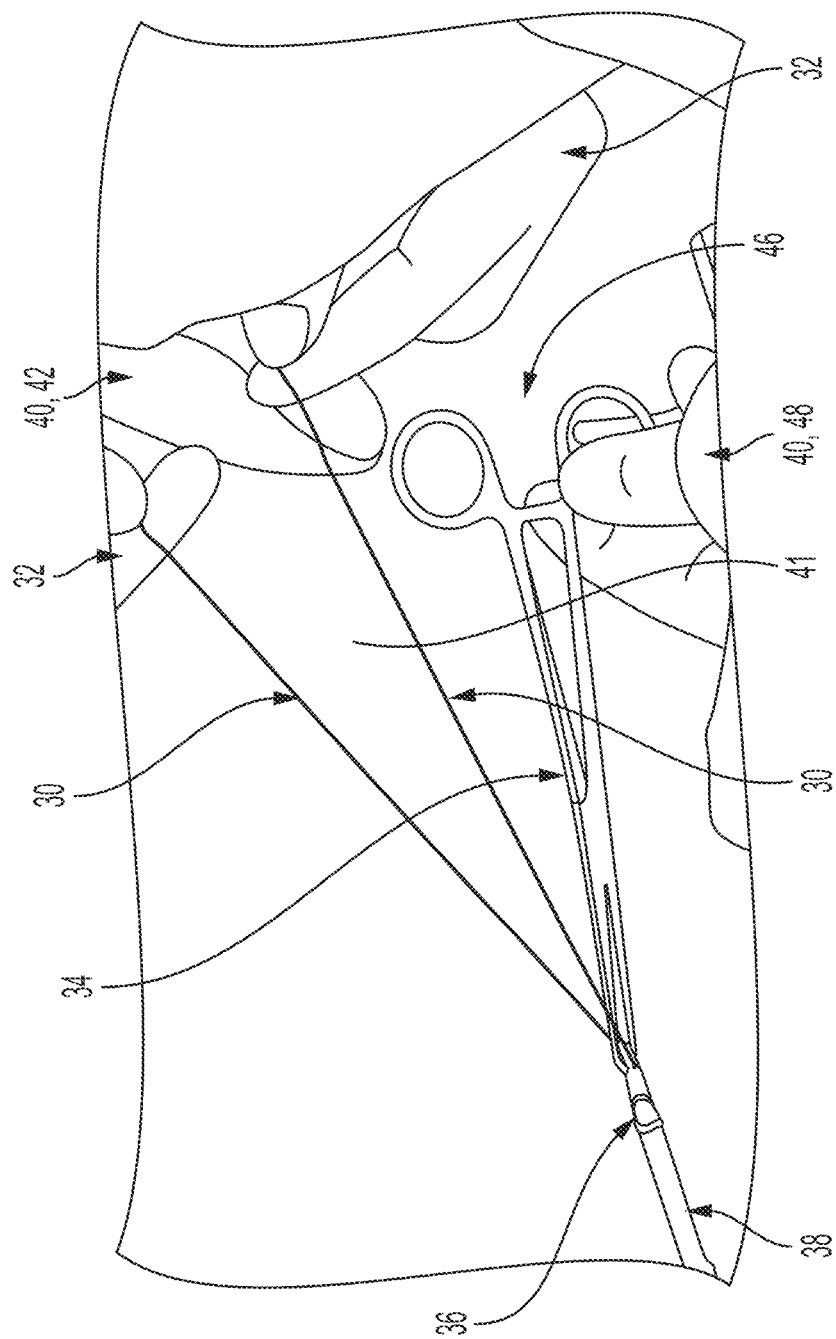
FIG. 5 is an isometric view of the prior art looped rope of FIG. 4, illustrating the second step of the example of the prior art labor intensive process for the use of the loop-based suturing method.
Figure 6:
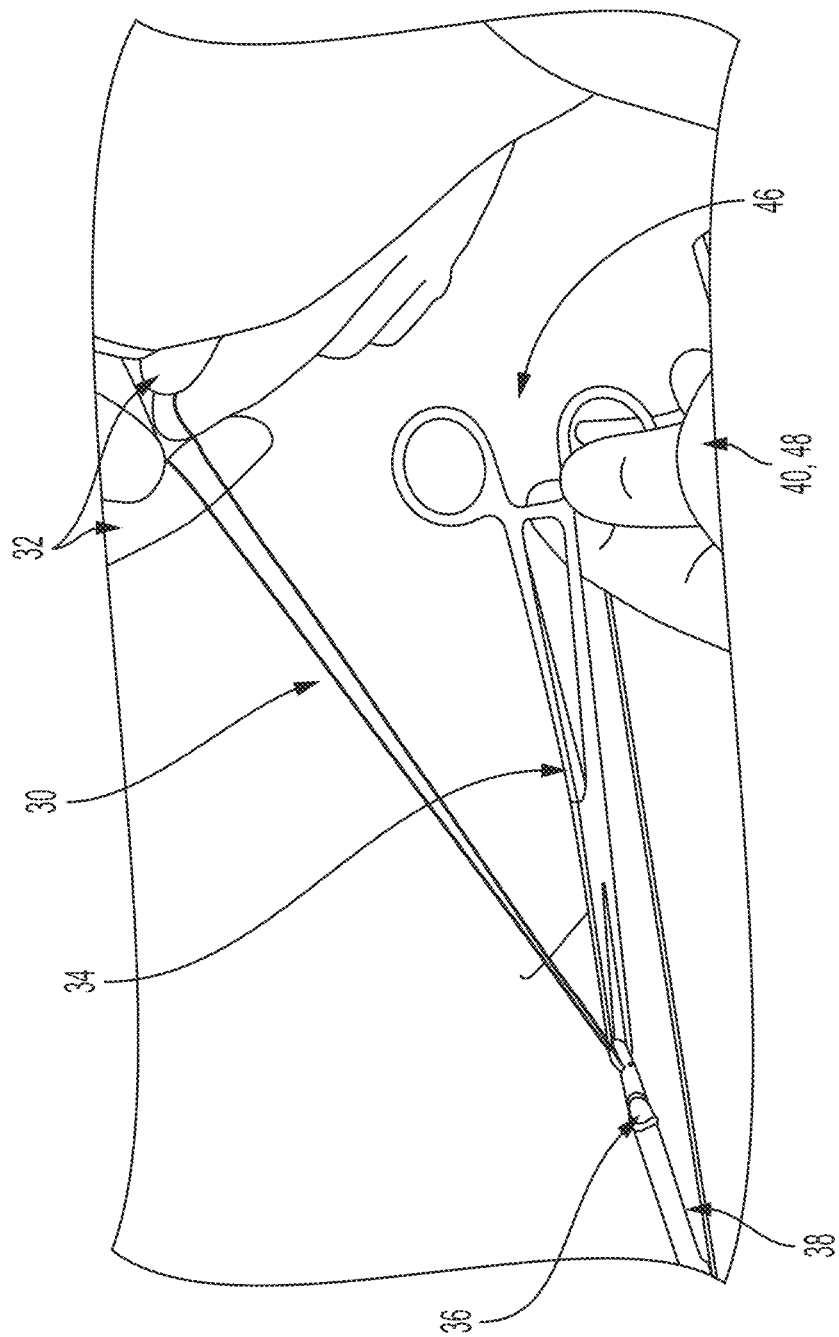
FIG. 6 is an isometric view of the prior art looped rope of FIG. 4, illustrating the third step of the example of the prior art labor intensive process for the use of the loop-based suturing method.
Figure 7:
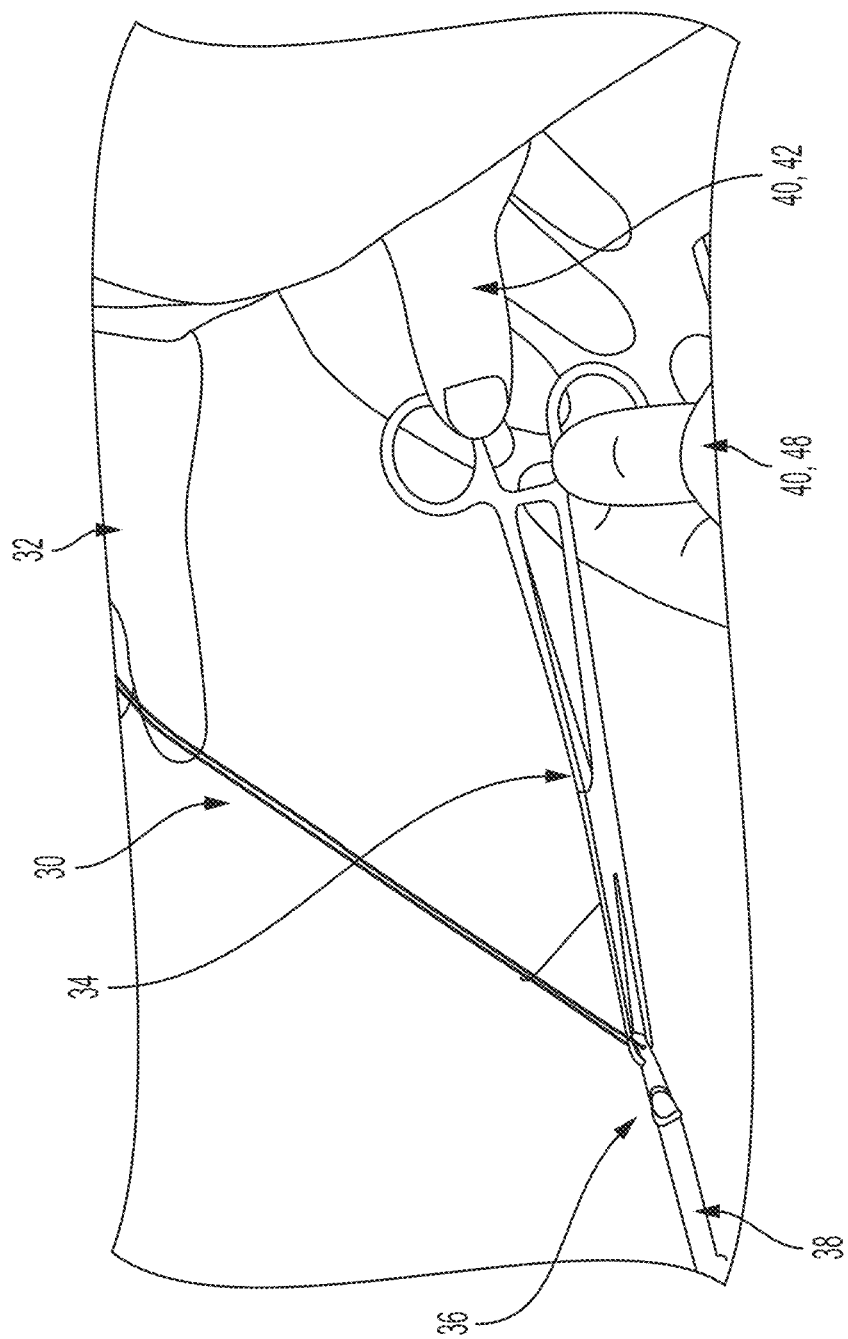
FIG. 7 is an isometric view of the prior art looped rope of FIG. 4, illustrating the fourth step of the example of the prior art labor intensive process for the use of the loop-based suturing method.
Figure 8:
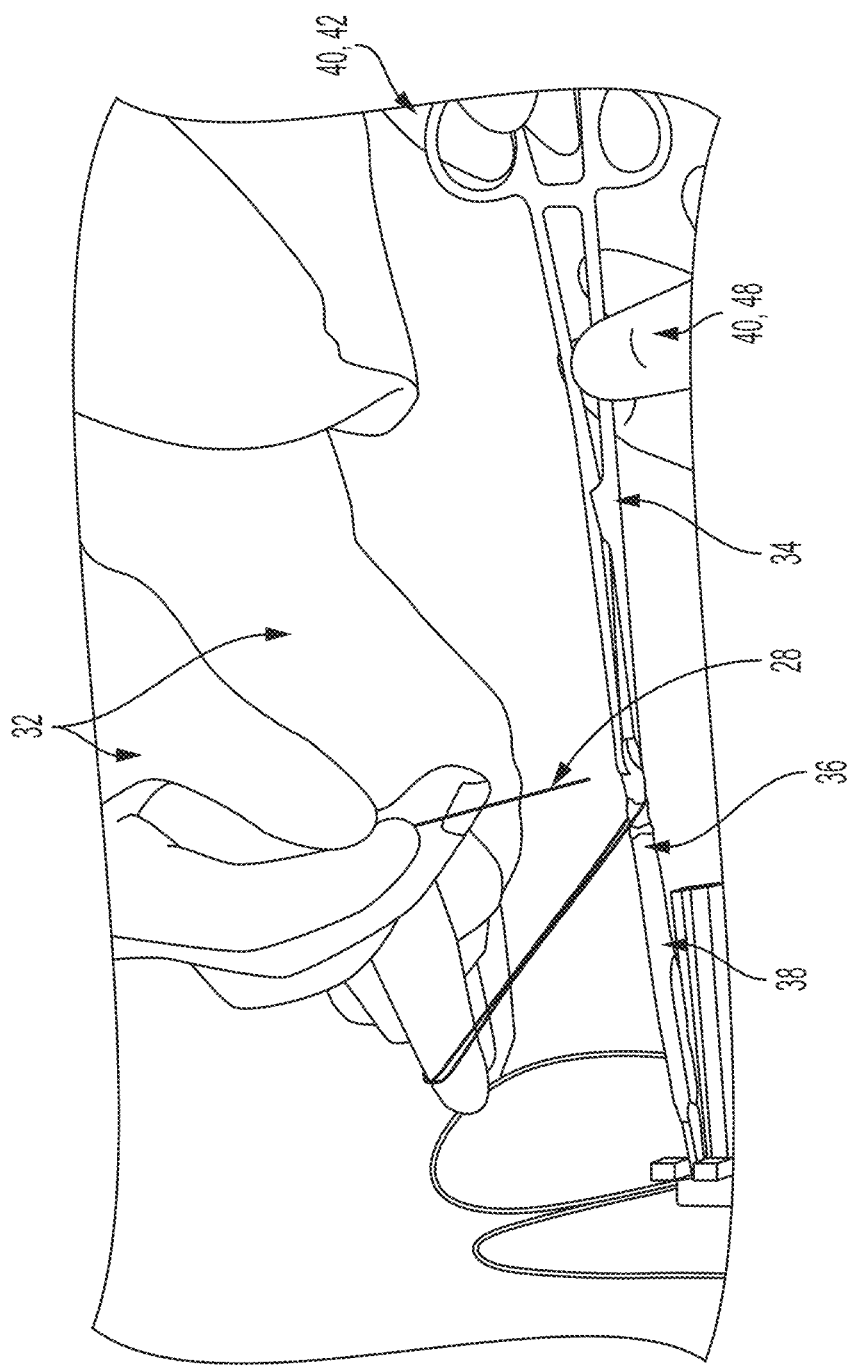
FIG. 8 is an isometric view of the prior art looped rope of FIG. 4, illustrating the fifth step of the example of the prior art labor intensive process for the use of the loop-based suturing method.
Figure 9:
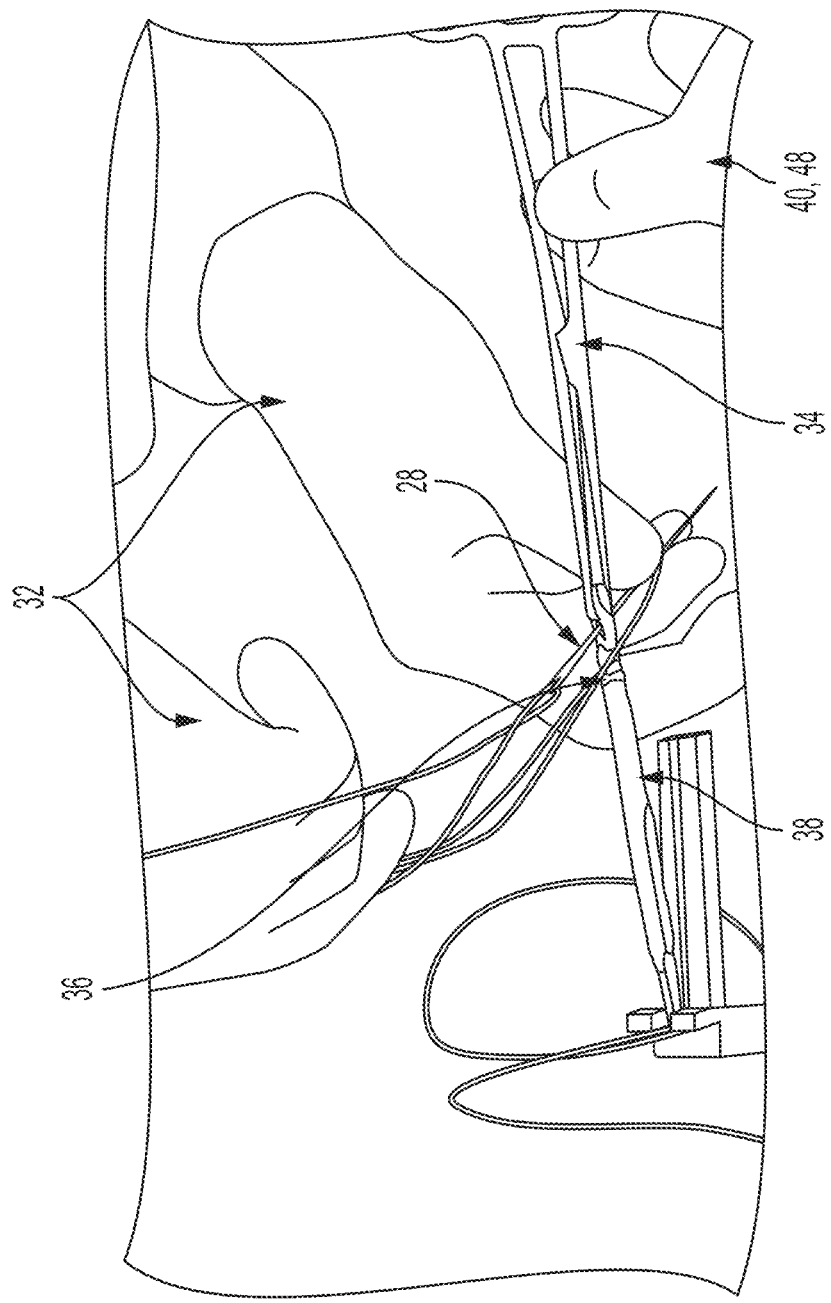
FIG. 9 is an isometric view of the prior art looped rope of FIG. 4, illustrating the sixth step of the example of the prior art labor intensive process for the use of the loop-based suturing method.
Figure 10:
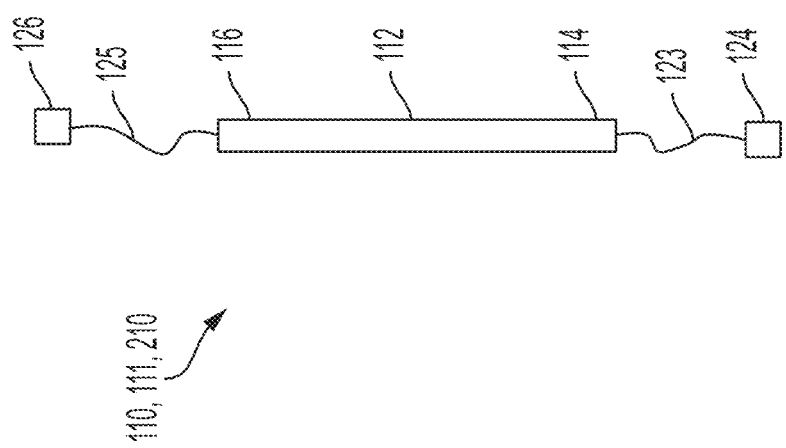
FIG. 10 is a top view of an embodiment of an implantable element.

Referring to FIG. 10, an implantable element 110 can include a graft of biological tissue excised from a patient or a graft of biological tissue supplied by a donor. For example, the implantable element 110 can include a portion of a tendon or a portion of a ligament. It should be understood, however, that the implantable element 110 can include any item suitable to be implanted or otherwise surgically coupled to a subject, such as a human or other animal undergoing medical treatment. Depending on the embodiment, the implantable element 110 can be natural or artificial, constructed of biological tissue (soft or hard) or constructed of a synthetic or non-biological material, such as a natural or synthetic rubber or any other suitable polymer, whether elastic, pierceable, flexible, pliable, deformable, semi-rigid or rigid.

Figure 11:
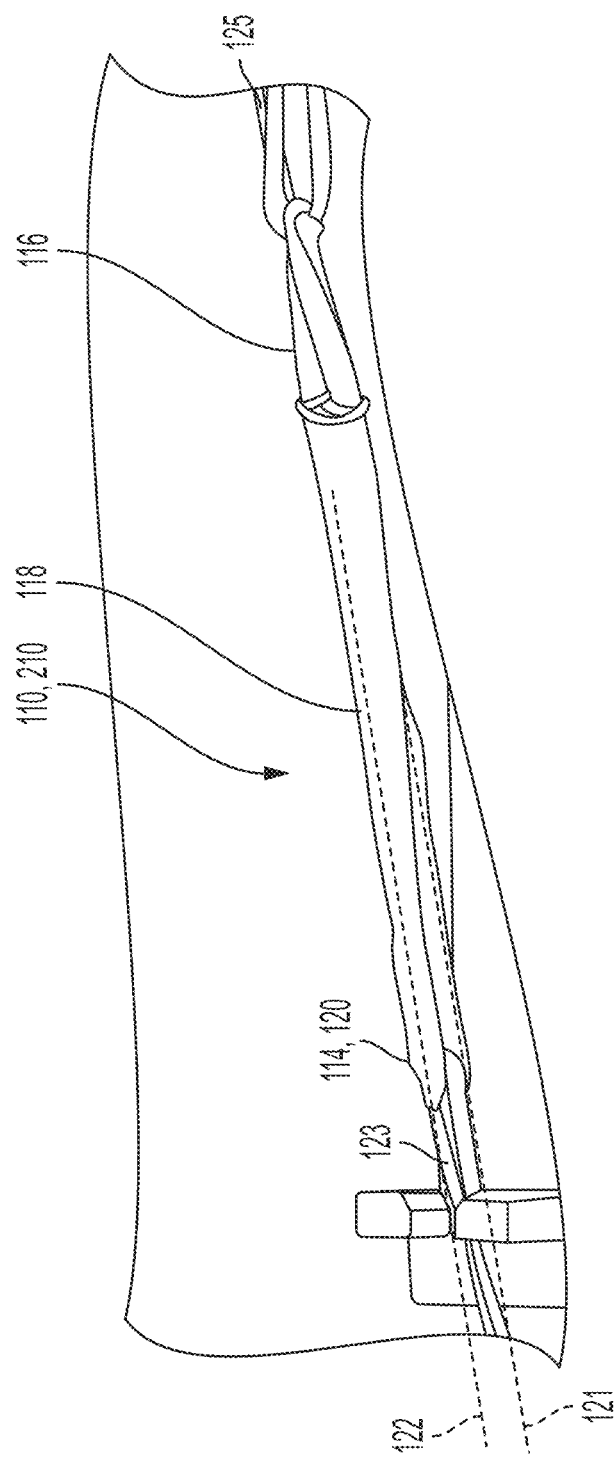
FIG. 11 is an isometric view of another embodiment of an implantable element.

In an embodiment, the implantable element 110 is a single-plane, implantable element 111 having: (a) an elongated body 112 extending along a single plane, which extends along a single longitudinal axis; (b) a first element end 114; and (c) a second element end 116. Alternatively, as illustrated in FIG. 11, the implantable element 110 can be a multi-plane, implantable element 210 having a body 118 that includes a single strip folded onto itself, forming a fold 120. Body 118 extends along multiple planes, which, in turn, extend along a plurality of longitudinal axes 121, 122.

A surgeon or other clinician can use a preoperative, pass-through preparation method to prepare the implantable element 110 to be secured to the surgical site of the subject. In an embodiment, the pass-through preparation method involves a loop-based suturing method, including, but not limited to, the FiberLoop® and TigerLoop® suturing methods published by Arthrex, Inc.

As illustrated in FIGS. 10-11, the pass-through preparation method for the implantable element 110 involves securing a plurality of harnesses, threads, ropes, cables or cords 123, 125 to the first and second element ends 114, 116, respectively. Depending on the type of surgery, the surgeon can install fasteners 124, 126 (e.g., medical screws or pins) to secure the cords 123, 125 to the subject's bone or otherwise within the surgical site.

Figure 12:
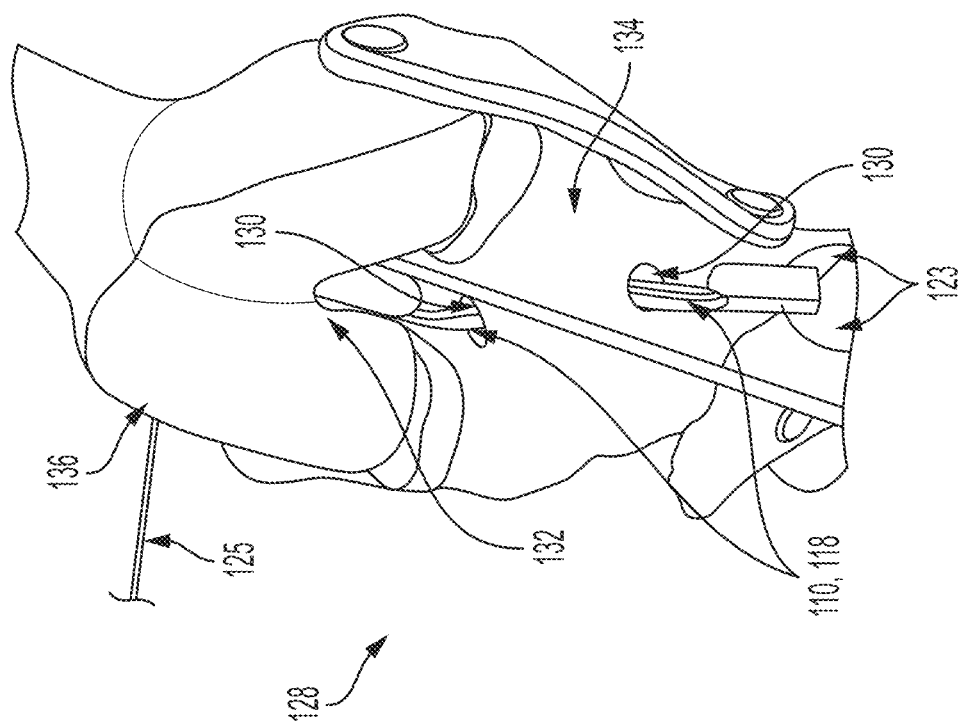
FIG. 12 is an isometric view of a knee site, illustrating an example of the implanting of an implantable element into the knee site.
Figure 13:
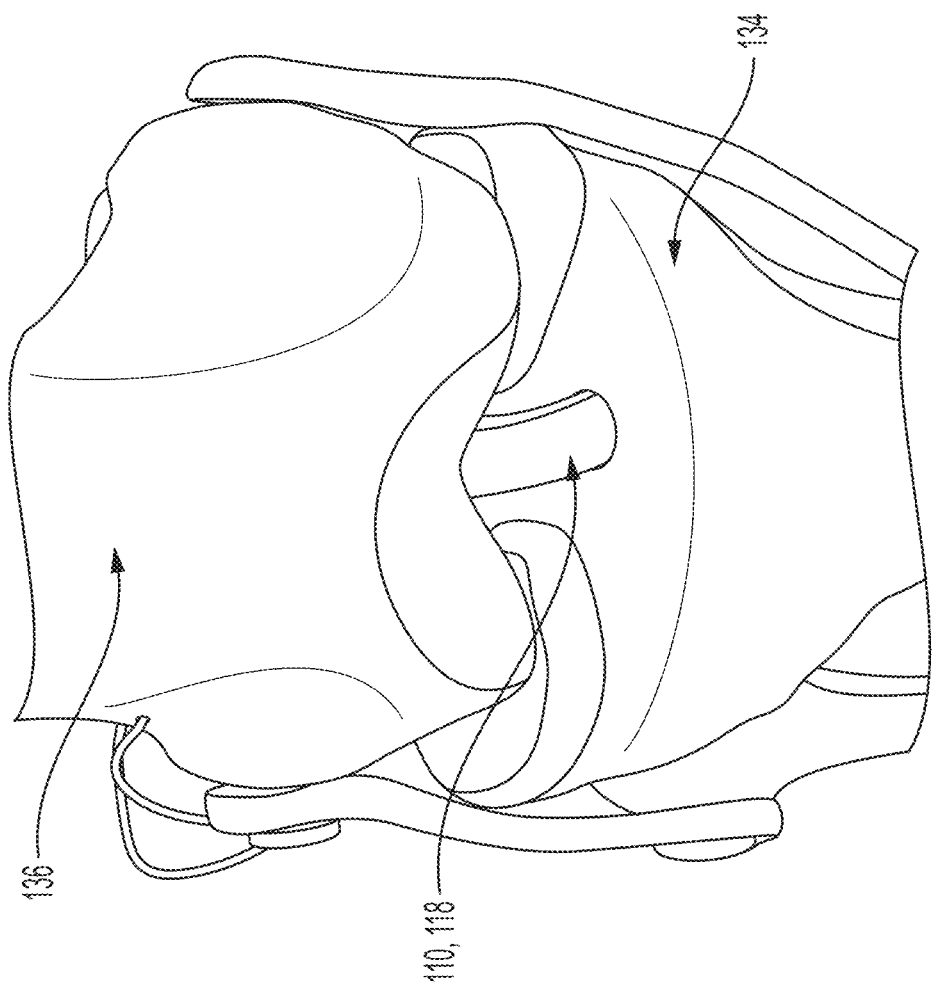
FIG. 13 is an enlarged isometric view of the knee site of FIG. 12, illustrating the implanting of the implantable element into the knee site.

In the example shown in FIG. 12, the implantable element 110 includes a tendon portion that has been prepared for ligament reconstruction within the knee site 128 of a subject. In this example, the subject's anterior cruciate ligament ("ACL") has been torn through injury and surgically removed. First, the surgeon secures the cords 123, 125 to the implantable element 110 according to the pass-through preparation method described below. Next, for the ACL reconstruction surgery, the surgeon drills tunnels 130, 132 in the subject's tibia 134 and femur 136, respectively. Then, the surgeon inserts the implantable element 110 into the tunnels 130, 132. After inserted and properly placed and tensioned, the surgeon binds the cords 125, 123 to tunnels 130, 132 by screwing fasteners (not shown) into the interior surfaces of the tunnels 130, 132. This results in the reconstructed ACL, as shown in FIG. 13.

Figure 14:
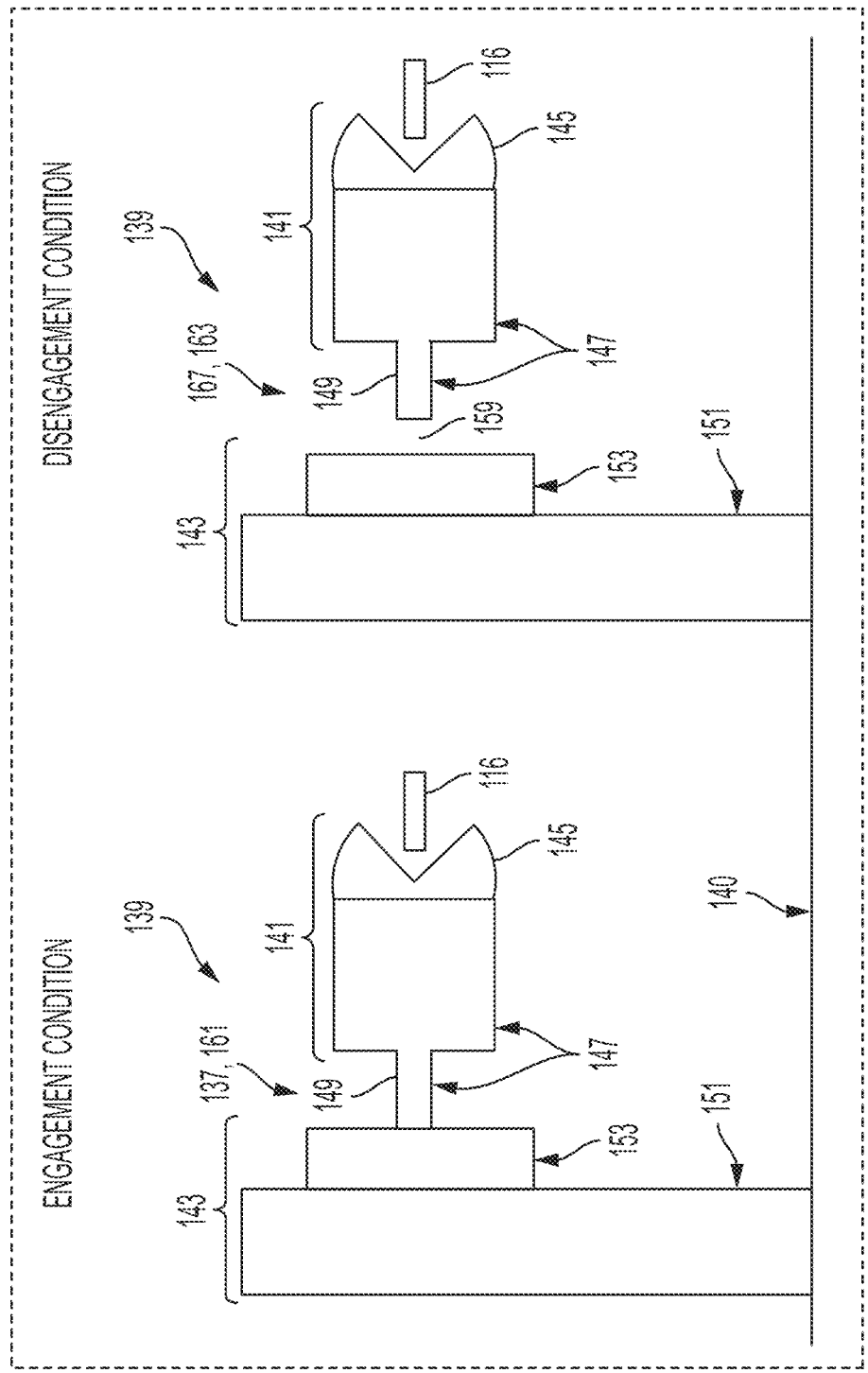
FIG. 14 is a schematic diagram of an embodiment of a medical holding system, illustrating the transition of the coupler portion from an engagement condition to a disengagement position.
Figure 15:
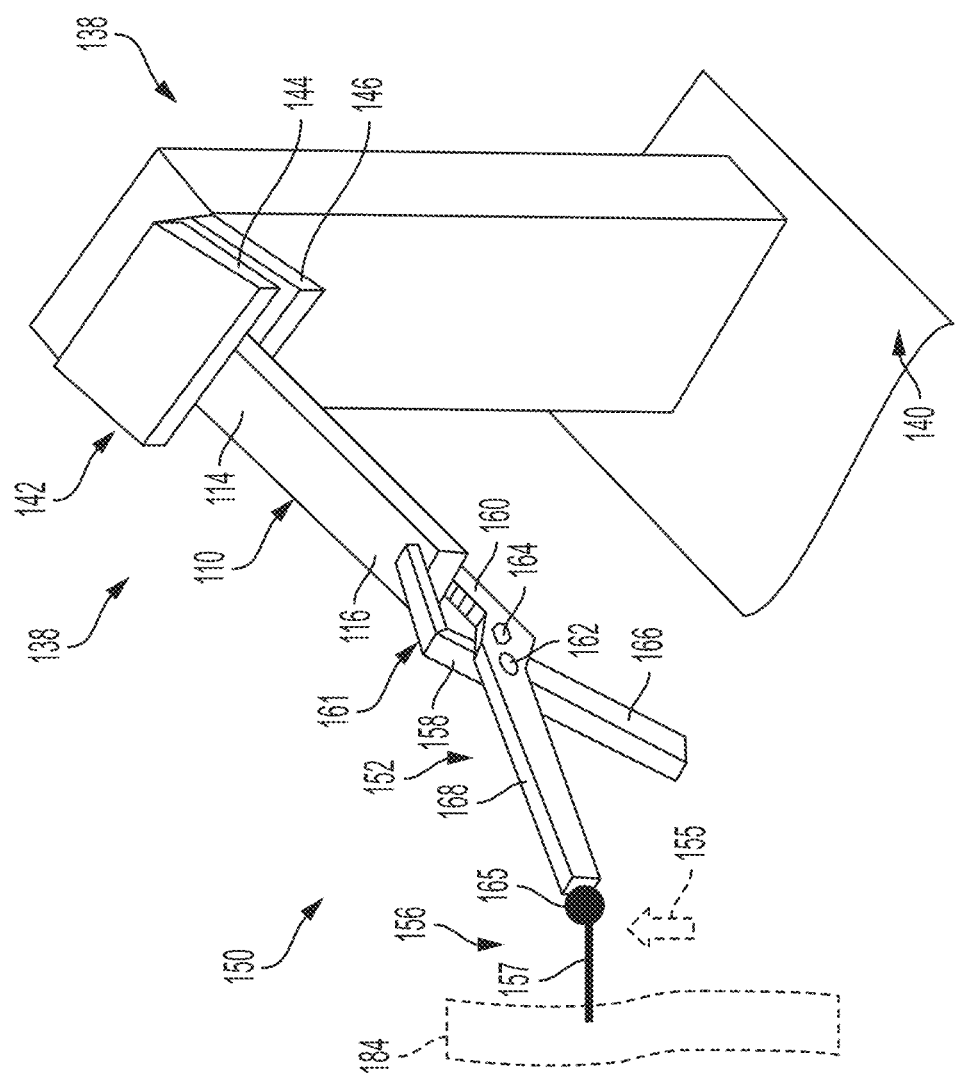
FIG. 15 is an isometric view of an embodiment of a medical holding system, illustrating the system's grasping of the end of an implantable element.

Referring to FIGS. 14-15, in an embodiment, the pass-through preparation method includes or incorporates the steps of a loop-based suturing method. This pass-through preparation method can be conducted by a single user, such as a single surgeon. To setup for this pass-through preparation method, the user uses a mount or hanger 138 (FIG. 15) to suspend the first element end 114 of the implantable element 110 above a support surface 140. In the embodiment shown in FIG. 15, the hanger 138 is an upright having a coupler configured to clamp or otherwise compress the first element end 114. To generate compression force on the first element end 114, the coupler 142 can sandwich the first element end 114 between a plurality of clamping members 144, 146, at least one of which is configured to move relative to the other. In an embodiment, the coupler 142 includes a fastener, such as a screw having a knob, that passes through threaded portions of the clamping members 144, 146. By rotating such fastener, the user can clamp or unclamp the first element end 114. It should be appreciated that any device or mechanism can be used to support, hang or suspend the first element end 114, including, but not limited to, a hook device, a holder or a clamping mechanism having one or more springs generating a predisposed clamping effect, pivot members, bolts, screws, pins or other fasteners.

Next, the user uses the medical holding assembly or medical holding system 139 (FIG. 14) or 150 (FIG. 15) to hold the second element end 116 while implementing the pass-through preparation method. The second element end 116 can be a free end or a medically-treatable end to be medically prepared or treated.

As illustrated in FIG. 14, in an embodiment, the medical holding system 139 includes: (a) a holder 141 configured to grasp or hold the second element end 116; and (b) a support device 143 configured to cooperate with the holder 141 to suspend the second element end 116 above the support surface 140. The holder 141 includes a grasper 145 configured to grasp and secure the second element end 116. The holder 141 also includes a coupler 147. The coupler 147 includes at least one coupler portion 149 configured to be reversibly coupled to the support device 143. The support device 143 includes an upright support 151 and a release interface 153 coupled to the upright support 151.

The holder 141 and the support device 143 are structured or configured to cooperate with each other so that the coupler portion 149 is configured to reversibly engage with the release interface 153. The cooperation between the holder 141 and the support device 143 can be mechanical, magnetic, electromechanical, electromagnetic or any other suitable form of cooperation.

The coupler portion 149 and the release interface 153 are configured to cooperate with each other so that coupler portion 149 is configured to be transitioned from an engagement condition 137 to a disengagement condition 167 and back to the engagement condition 137. In the engagement condition 137, the coupler portion 149 is engaged with the release interface 153 to keep the implantable element 110 suspended above the support surface 140 when the implantable element 110 is subject to a suturing force that acts downward toward the support surface 140. In the disengagement condition 167, the coupler portion 149 is temporarily disengaged from the release interface 153 in response to a pass-through force, thereby forming a passageway 159 between the support device 143 and the second element end 116. The passageway 159 is configured to receive a cord segment of a medical looped cord, as described below. After the cord segment passes through the passageway 159, the coupler portion 149 is configured or predisposed to transition back to the engagement condition 137. The coupler portion 149 and the release interface 153 are configured to keep the implantable element 110 suspended above the support surface 140 throughout the engagement and disengagement conditions 137, 167.

In an embodiment, the coupler portion 149 is configured to move between closed and open positions 161, 163 relative to the support device 143. In the closed position 161, the coupler portion 149 is engaged and in physical contact with the release interface 153, causing the passageway 159 to be closed. In the open position 163, the coupler portion 149 is disengaged and physically removed from the release interface 153, causing the passageway 159 to be temporarily opened.

In an embodiment, the pass-through force is an upward user force provided by the user. For example, the user can push or tap the coupler 147 or coupler portion 149 by using the user's finger, a taut segment of the looped cord, or the suturing needle. The coupler portion 147 and the release interface 153 are configured to keep the implantable element 110 suspended above the support surface 140 throughout the engagement and disengagement conditions 137, 167 without relying or depending on the continuation of such upward user force or any other user force. In a series of repeated transitions between the engagement and disengagement conditions 137, 167, the passageway 159 repeatedly transitions between closed and open. Each opening of the passageway 159 enables the user to pass the medical cord between the support device 143 and the second element end 116 while keeping the implantable element 110 from falling to the support surface 140.

In the embodiment illustrated in FIG. 15, the medical holding system 150 includes: (a) a holder 152 configured to hold the second element end 116; and (b) a support device 154 (FIG. 21) configured to cooperate with the holder 152 to suspend the second element end 116 above the support surface 140. To best illustrate the operation of the pass-through preparation method in this embodiment, the support device 154 is omitted from FIGS. 15-20. It should be understood that the support device 154 (FIGS. 21-23) generates an upward support force 155 during the pass-through preparation method. Depending on the embodiment, the support force 155 can vary during the pass-through preparation method.

As shown in FIG. 15, the user secures the holder 152 to the second element end 116. In an embodiment, the holder 152 includes: (a) a grasper 161 configured to be attached to the second element end 116; and (b) a coupler 156 connected to and extending from the grasper 161. In an embodiment, the grasper 161 includes: (a) a plurality of jaws 158, 160 moveable relative to each other; (b) a pivot member 162 configured to pivotally couple the jaws 158, 160 together; (c) a position lock 164 configured to lock or secure the jaws 158, 160 in a desired, fixed position relative to each other; and (d) a plurality of handles or extensions 166, 168 extending from the jaws 158, 160, respectively. In such embodiment, the coupler 156 extends from one or both of the extensions 166, 168. As described below, in an embodiment, the coupler 156 includes a support engager or coupler portion 157 coupled to a connector 165. Depending on the embodiment, the connector 165 can include a joint (e.g., a ball joint or other type of joint), hinge, rotary or pivot member.

Figure 16:
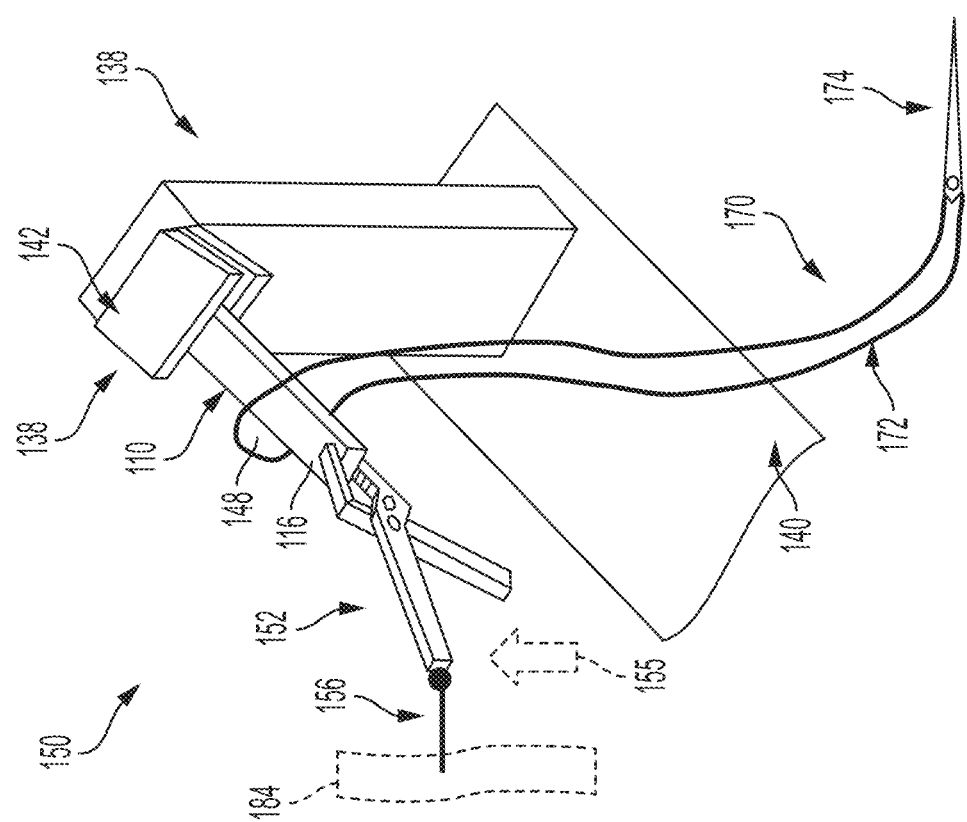
FIG. 16 is an isometric view of the medical holding system of FIG. 15, illustrating a looped cord that is looped around the end of the implantable element.

Referring to FIG. 16, before or after the user secures the holder 152 to the second element end 116, the user inserts the second element end 116 through the loop opening 148 defined by a cord assembly 170. In an embodiment, the cord assembly 170 includes a looped cord 172 and a piercer or needle 174. Depending on the embodiment, the looped cord 172 can include a ring, hoop or loop of any rope, thread, wire, belt, cable or other cord. The looped cord 172 can be constructed of any suitable, flexible material, including, but not limited to, polymer, natural or synthetic fibers, natural or synthetic rubber, or flexible metal.

The assembly process for the cord assembly 170 begins with a single cord having two free ends. The assembler passes one of the free ends through the eye of the needle 174. Next, the assembler mechanically bonds, fuses, ties or otherwise connects such free end to the other free end of the cord to form the looped cord 172. The needle 174 is free to slidably engage with the looped cord 172.

Figure 17:
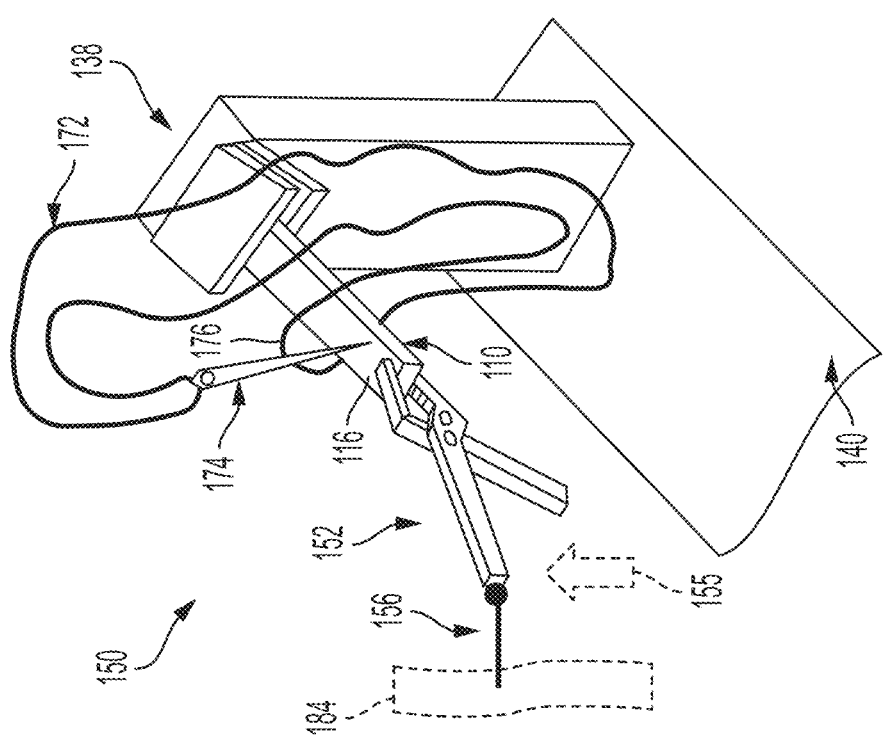
FIG. 17 is an isometric view of the medical holding system of FIG. 15, illustrating the first piercing of the end of the implantable element at a location in front of the loop.
Figure 18:
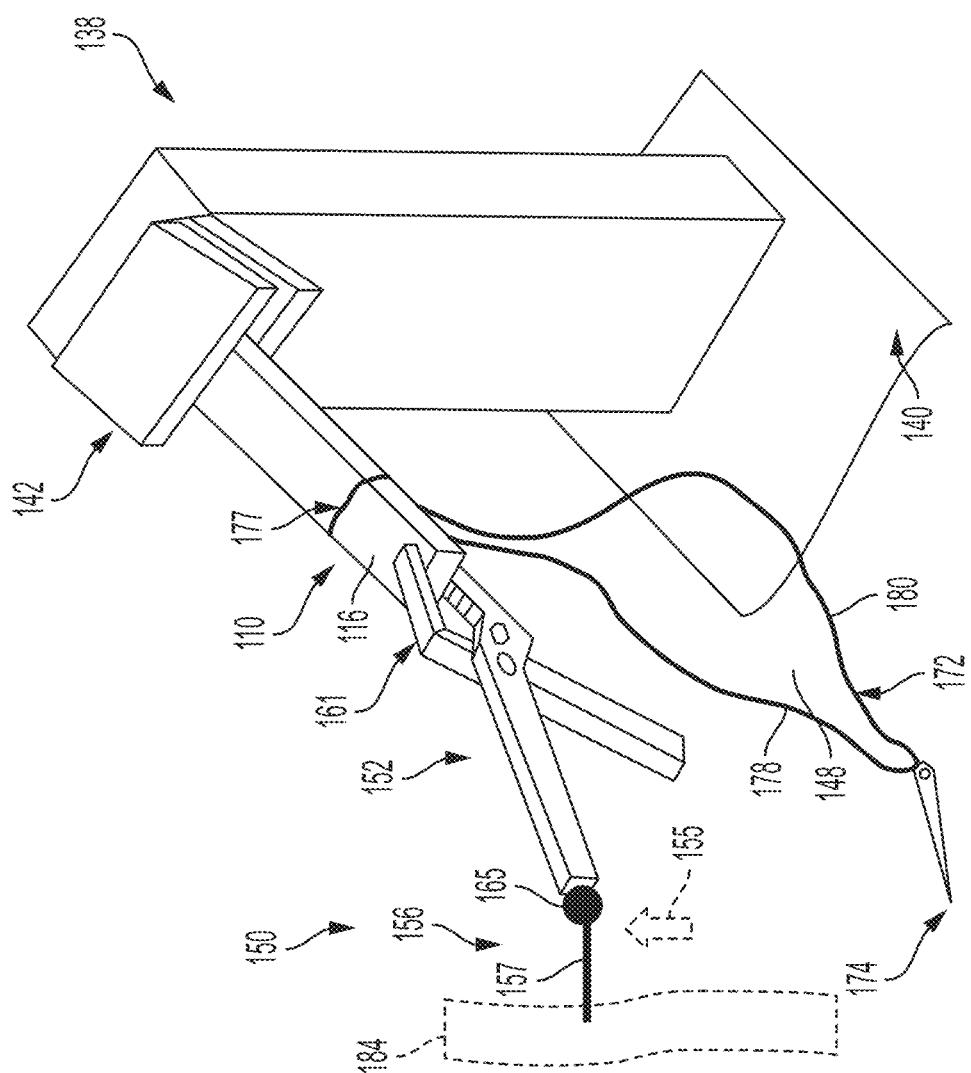
FIG. 18 is an isometric view of the medical holding system of FIG. 15, illustrating the first suture line resulting from the first piercing step.
Figure 19:
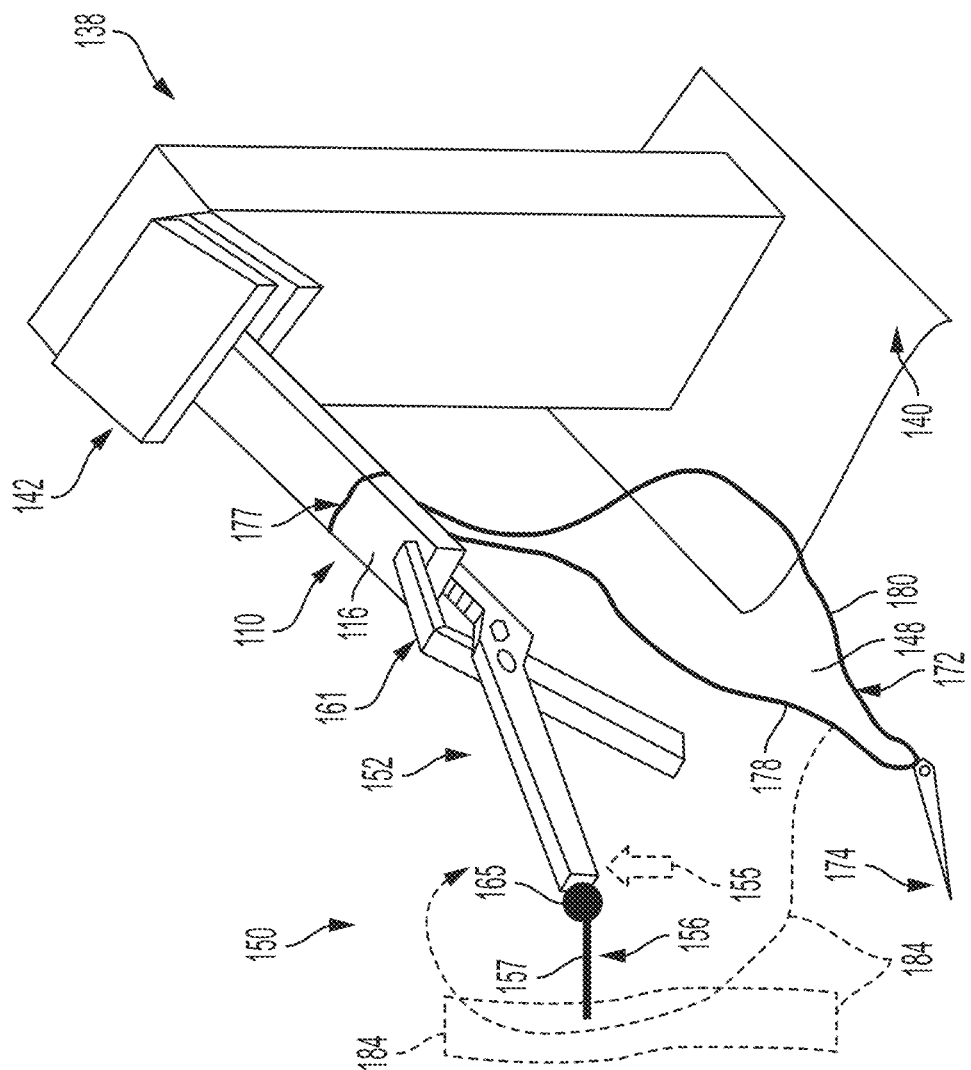
FIG. 19 is an isometric view of the medical holding system of FIG. 15, illustrating the formation of a passageway that receives a segment of the cord to enable a pass-through of the cord segment.
Figure 20:
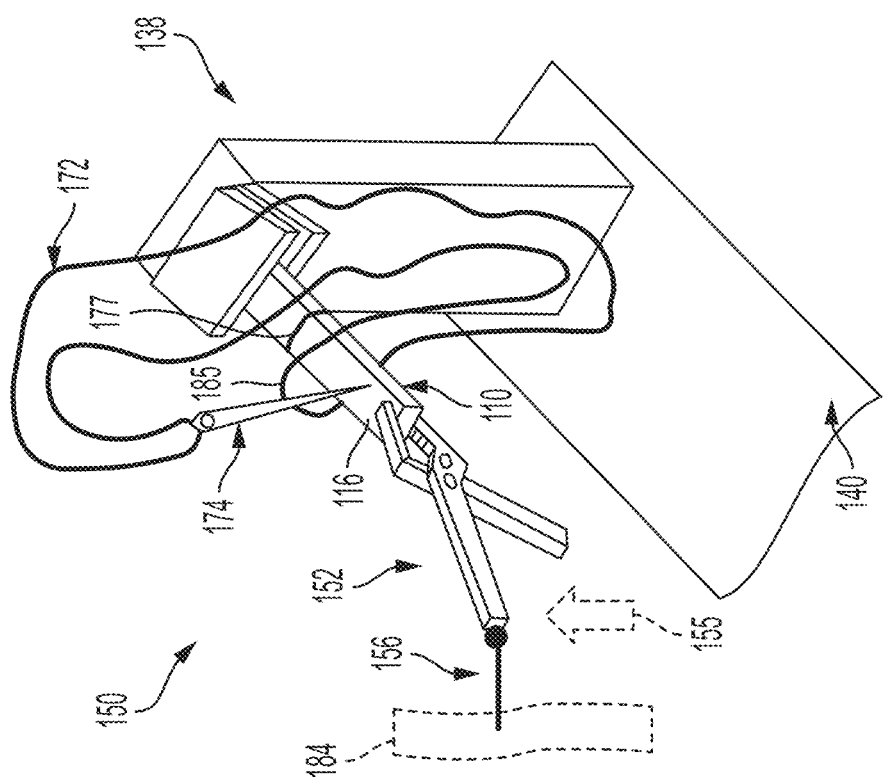
FIG. 20 is an isometric view of the medical holding system of FIG. 15, illustrating the second piercing of the end of the implantable element at a location in front of the first suture line.

Referring to FIG. 17, next, the user pierces the second element end 116 and passes the needle 174 entirely through the second element end 116. As shown, the piercing occurs in front of the loop section 176. This results in an initial suture line 177, as shown in FIG. 18. As illustrated in FIGS. 18-19, the user next spreads the loop segments 178, 180 apart to form the loop opening 148. The user moves the loop segment 178 upward through the passageway 184 while passing the holder 152 through the loop opening 148. Next, as illustrated in FIG. 20, the user forms another loop section 185 around the second element end 116, and the user pierces the second element end 116 and passes the needle 174 entirely through the second element end 116. As part of the pass-through preparation method, the user repeats the steps illustrated in FIGS. 17-20 until establishing a desired number of suture lines in the second element end 116. This results in a looped cord 172 that is firmly secured to the second element end 116. The user may cut the looped cord 172, remove the needle 174, and use the two segments of the cut looped cord 172 to secure the implantable element 110 within a surgical site as described above. It should be appreciated that the user can perform the same pass-through preparation method on the first element end 114.

Figure 21:
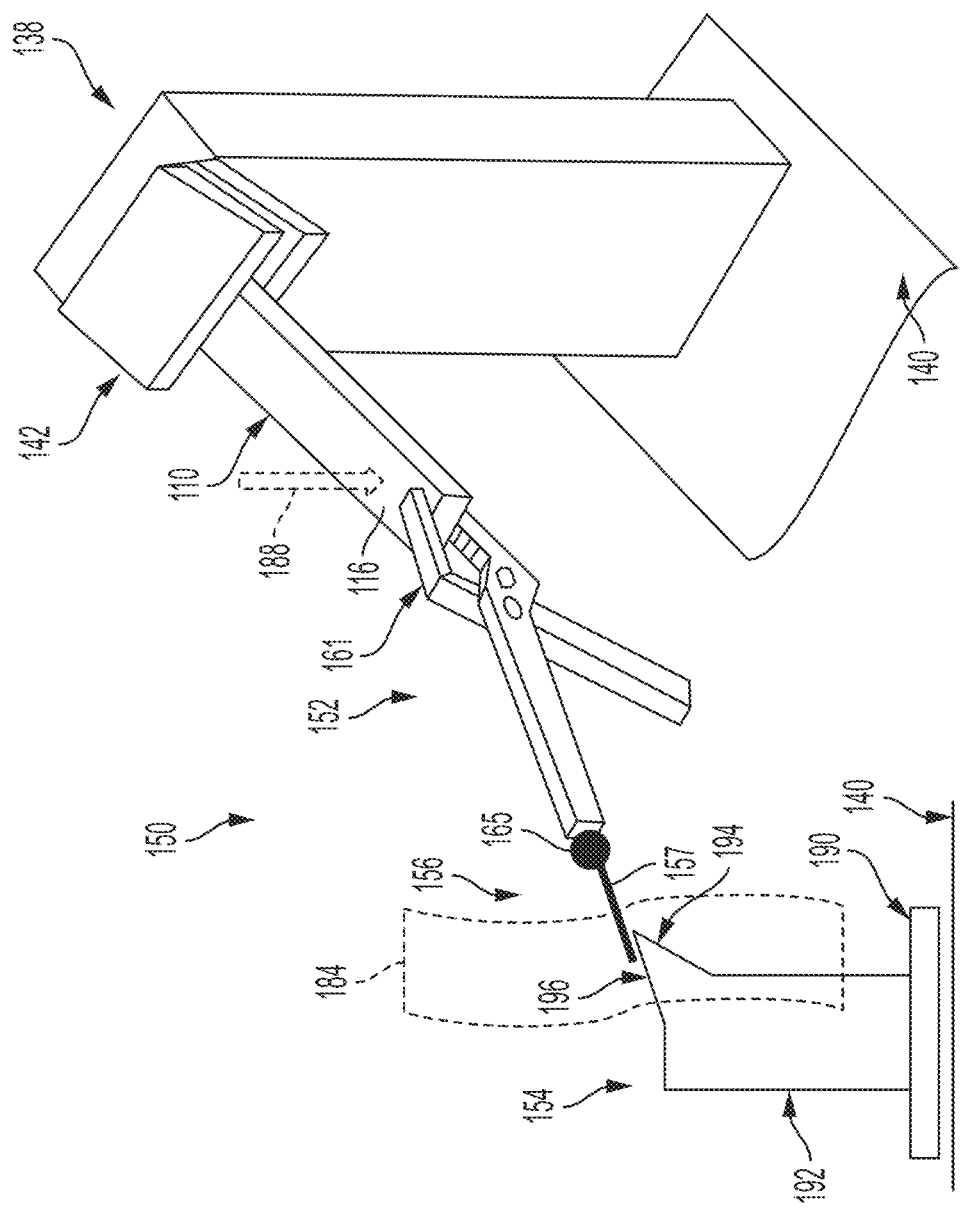
FIG. 21 is an isometric view of the medical holding system of FIG. 15, illustrating the cooperation between the coupler and the support device when the coupler portion is in a closed position.
Figure 22:
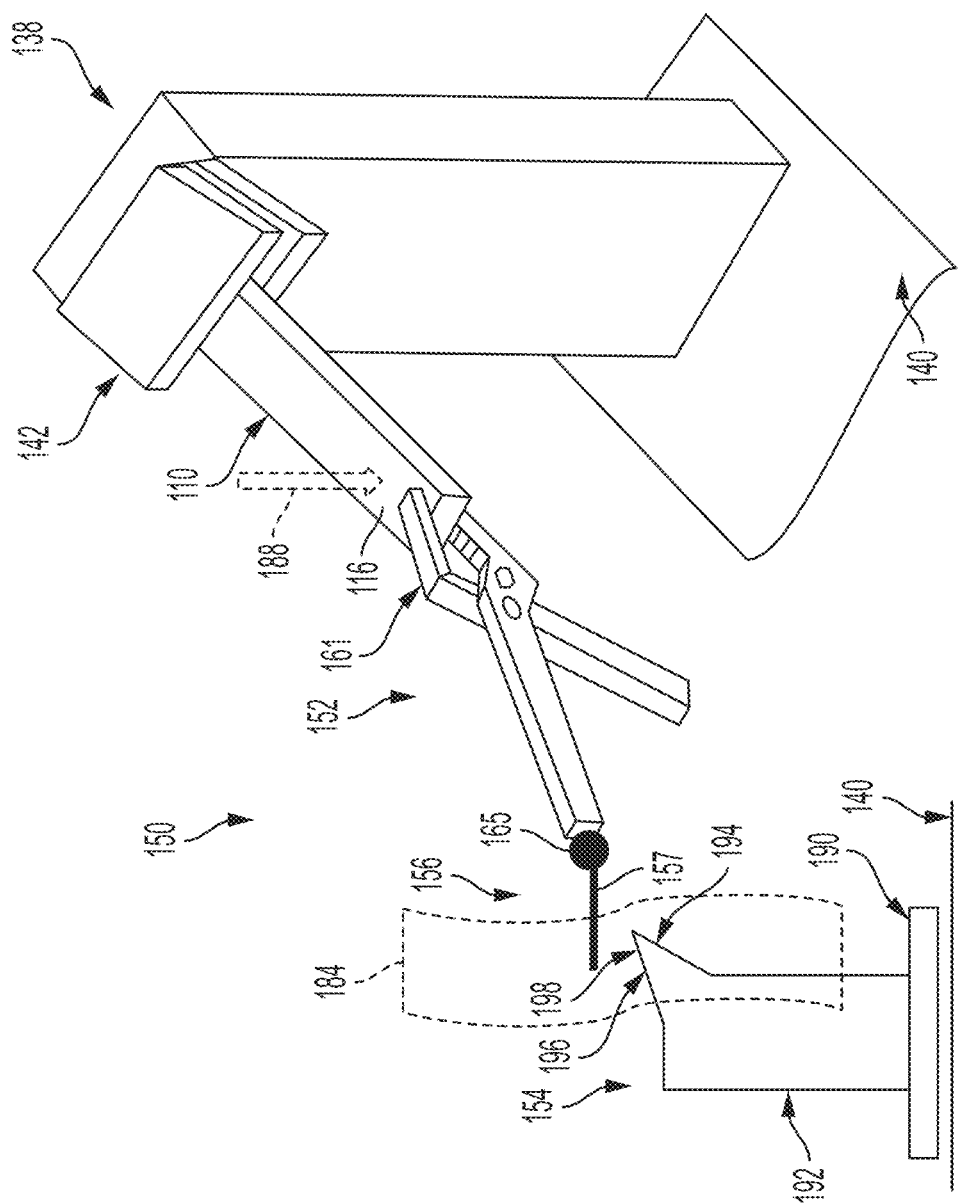
FIG. 22 is an isometric view of the medical holding system of FIG. 15, illustrating the cooperation between the coupler and the support device when the coupler portion is in an open position.

As illustrated in FIGS. 21-22, the support device 154 of the medical holding system 150 generates the upward support force 155 described above. Accordingly, the support device 154 prevents the second element end 116 from falling or dropping to the support surface 140 during the pass-through preparation method. In other words, the support device 154, in cooperation with the hanger 138, keeps the implantable element 110 suspended despite the downward piercing force 188.

In an embodiment, the support device 154 includes: (a) a base 190 defining one or more holes (not shown) configured to receive one or more fasteners (not shown) to removably mount the base 190 to the support surface 140; (b) an upright portion or support body 192 extending upward from the base 190; and (c) a support member 194 coupled to, extending from, or otherwise supported by the support body 192.

The support member 194, in an embodiment, includes a release interface 196 and a stopper 198. In an embodiment, the release interface 196 is the surface portion of the support member 194 that is positioned to make physical contact with the coupler portion 157 of the coupler 156. In an embodiment, the stopper 198 is a portion of the release interface 196 that is configured to stop or prevent the coupler portion 157 from falling to the support surface 140. In the embodiment shown in FIGS. 21-22, the release interface 196 is the same as the stopper 198. In another embodiment, the release interface 196 includes any structure, material or characteristic configured to urge the coupler portion 157 into reversible engagement with the support member 194.

For example, in an embodiment, the release interface 196 and the coupler portion 157 are structured or configured to be magnetically attracted to each other. In an embodiment, the release interface 196 includes a magnetic characteristic operable to magnetically attract the coupler portion 157 to the support member 194. In such embodiment, the coupler portion 157 and the release interface 196 include a suitable combination of metallic or magnetic characteristics. One or each of the coupler portion 157 and the release interface 196 can include a magnet or a magnetizable element configured to be magnetized, including, but not limited to, an electromagnet. In the case of an electromagnet, the medical holding system 150 includes: (a) a coil of wire surrounding a core of ferromagnetic material, such as steel; (b) an electrical circuit operatively coupled to the coil; and (c) an electrical power cord or battery power source operatively coupled to the electrical circuit.

In an embodiment, the medical holding system 150 includes a magnetic shield configured and arranged to block any level of undesirable amount of magnetic fields generated by the coil of wire, electromagnet, magnets or other magnetic field generators of the medical holding system 150. The magnetic shield can be constructed of: (a) sheet metal, metal screen, metal foam, copper, nickel and any other suitable conductive material; and (b) a grounding connector operable to electrically ground the magnetic field generator to the chassis or housing of the medical holding system 150, to the support surface 140, or otherwise to earth ground. Accordingly, the magnetic shield can reduce risks of the medical holding system 150 creating electrical interference with electrical hospital equipment or electrical medical devices implanted in subjects.

Figure 23:
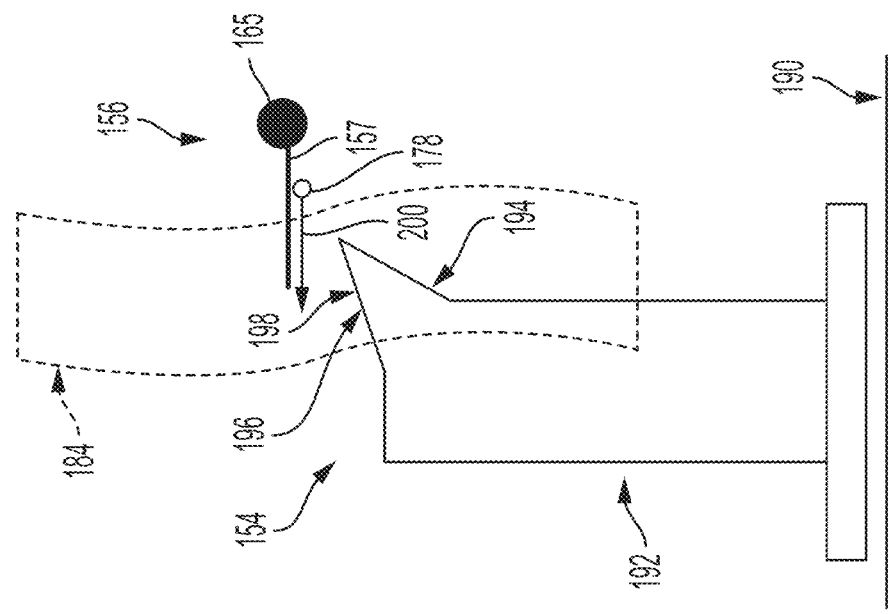
FIG. 23 is an enlarged, side elevation view of the medical holding system of FIG. 15, illustrating the coupler portion in the open position.

With continued reference to FIGS. 21-23, the coupler portion 157 and the release interface 196 are configured to cooperate with each other so that the coupler portion 157 is predisposed to remain engaged with the release interface 196. During the engagement, the second element end 116 remains suspended above the support surface 140 when the implantable element 110 is subject to the downward piercing force 188. The predisposition of engagement can be due to gravity (a combination of the weight of the holder 152 and the weight of the implantable element 110) and the piercing force 188. Alternatively, as described above, the predisposition of engagement can be due to a magnetic attraction, spring-based mechanism or other phenomena.

When the user is ready to pass the loop segment 178 (FIG. 19) through the passageway 184, as described above, the user can apply an upward pass-through force to the coupler portion 157. In response, the coupler portion 157 disengages the release interface 196, thereby forming the passageway 184 between the support device 154 and the second element end 116. The passageway 184 is configured to receive the loop segment 178.

Referring to FIG. 23, the user can generate the upward, pass-through force in various ways and methods. For example, the user can stretch the loop segment 178 of the looped cord 172 so that the cord segment or loop segment 178 is relatively tight. Next, the user can drag the loop segment 178 in the rearward direction 200 until clearing the coupler portion 157 and reaching the passageway 184. Alternatively, the user can push the needle 174 (FIG. 19) upward against the coupler portion 157 until the needle 174 (and loop segment 178) reach the passageway 184. Also, the user can tap or press the user's finger upward against the coupler portion 157 while slipping the loop segment 178 beyond the coupler portion 157 until the loop segment 178 reaches the passageway 184. In either method, a single user can repeatedly and periodically move the loop segment 178 into the passageway 184 with relative ease and quickness.

Because the coupler portion 157 is predisposed to be engaged with the release interface 196, the coupler portion 157 re-engages the release interface 196 after the loop segment 178 passes into the passageway 184. In this way, the coupler portion 157 is operable as a gate configured to be periodically opened, providing temporary access to the passageway 184. Consequently, the implantable element 110 remains suspended above the support surface 154 while the user periodically passes the loop segment 178 through the passageway 184 during the pass-through preparation method.

In an embodiment, the medical holding system 150 enables a single user to conveniently perform the pass-through preparation method. Depending on the embodiment, the medical holding system 150 can produce a threshold level of tension in the implantable element 110 during the pass-through preparation method. This threshold level of tension can be equal to, substantially equal to, or correspond with, the indwelling tension that the surgeon will set for the implantable element 110 when implanting the implantable element 110 in the subject. Depending on the embodiment, the tension during the pass-through preparation method can decrease during the formation of the passageway 184, and the tension can then return to the threshold tension by the time the needle 174 pierces the implantable element 110. Accordingly, the construction of the stitching or suturing in the second element end 116 can provide strength that is sufficient to withstand the indwelling tension of the implantable element 110 when implanted in the subject.

Figure 24:
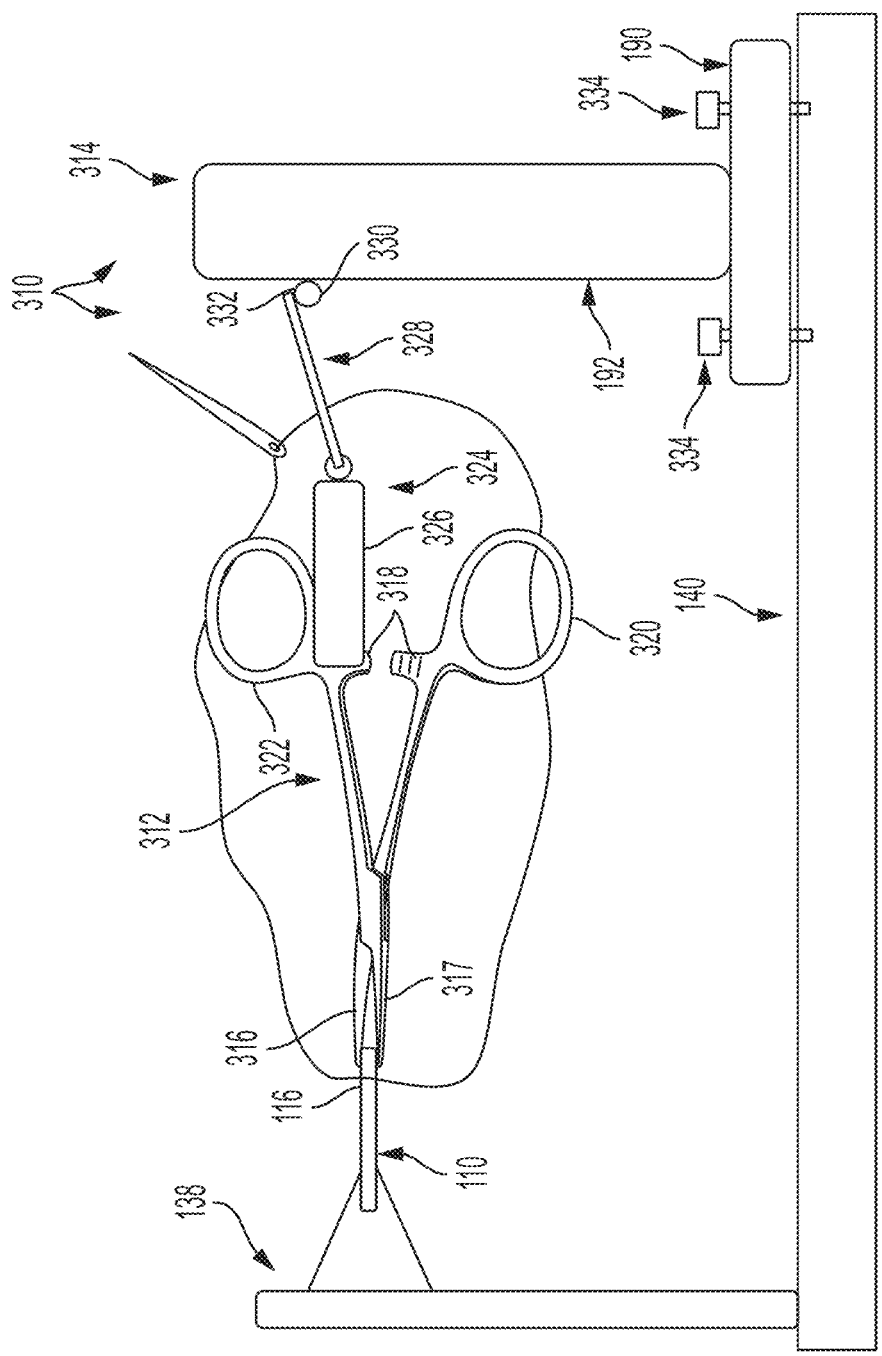
FIG. 24 is a side elevation view of another embodiment of a medical holding system, illustrating the coupler portion in a closed position.

In an embodiment illustrated in FIG. 24, the medical holding system 310 includes the same structure, parts, elements and functionality as medical holding system 150 except that the medical holding system 310 includes holder 312 and support device 314. Holder 312 includes: (a) a plurality of jaws 316, 317 pivotally coupled together; (b) a position lock 318 configured to reversibly lock the jaws 316, 317 in a desired position when the jaws 316 are clamped onto the second element end 116; (c) a plurality of handles 320, 322; and (d) a coupler 324 connected to the handle 322. The coupler 324 includes a connector 326 attached to the handle 320, and a coupler portion 328 coupled to the connector 326. Depending on the embodiment, the connector 326 can include a joint (e.g., ball joint), hinge, rotary or pivot member.

Figure 25:
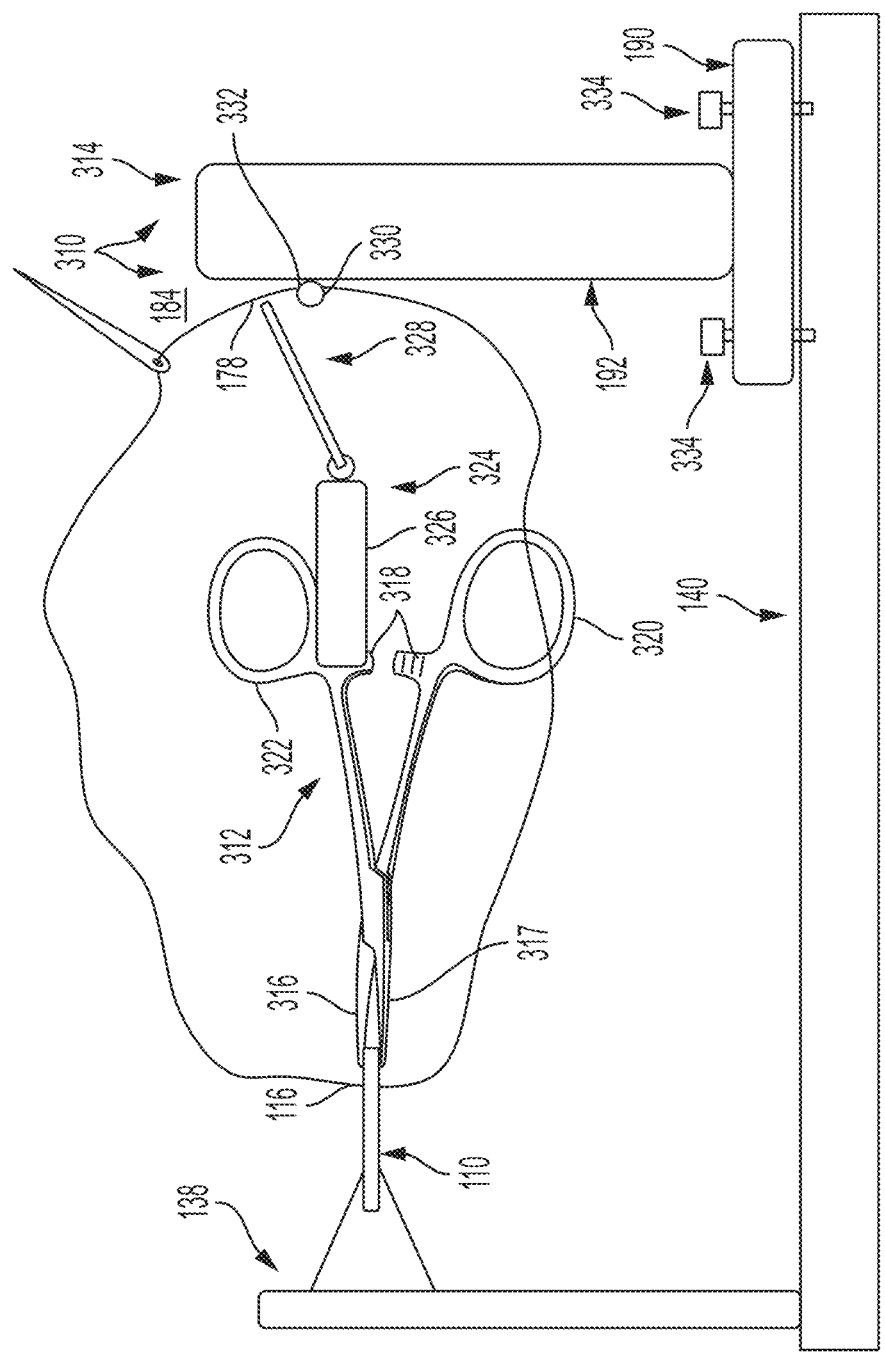
FIG. 25 is a side elevation view of the medical holding system of FIG. 24, illustrating the coupler portion in an open position.

The support device 314 includes: (a) a support member 330 having a release interface 332; and (b) a plurality of fasteners 334 configured to be inserted through the base 190 and screwed into the support surface 140. The release interface 332 is configured to be magnetically attracted to the coupler portion 328. As illustrated in FIG. 25, during the pass-through preparation method, the user periodically passes the cord segment or loop segment 178 of the looped cord 172 between the coupler portion 328 and the support member 330 until the loop segment 178 reaches the passageway 184. During the passage, the user generates an upward force on the coupler portion 328 that overcomes the magnetic force of attraction between the coupler portion 328 and the release interface 332. The periodic passages enable the user to conveniently perform the pass-through preparation method.

Figure 26:
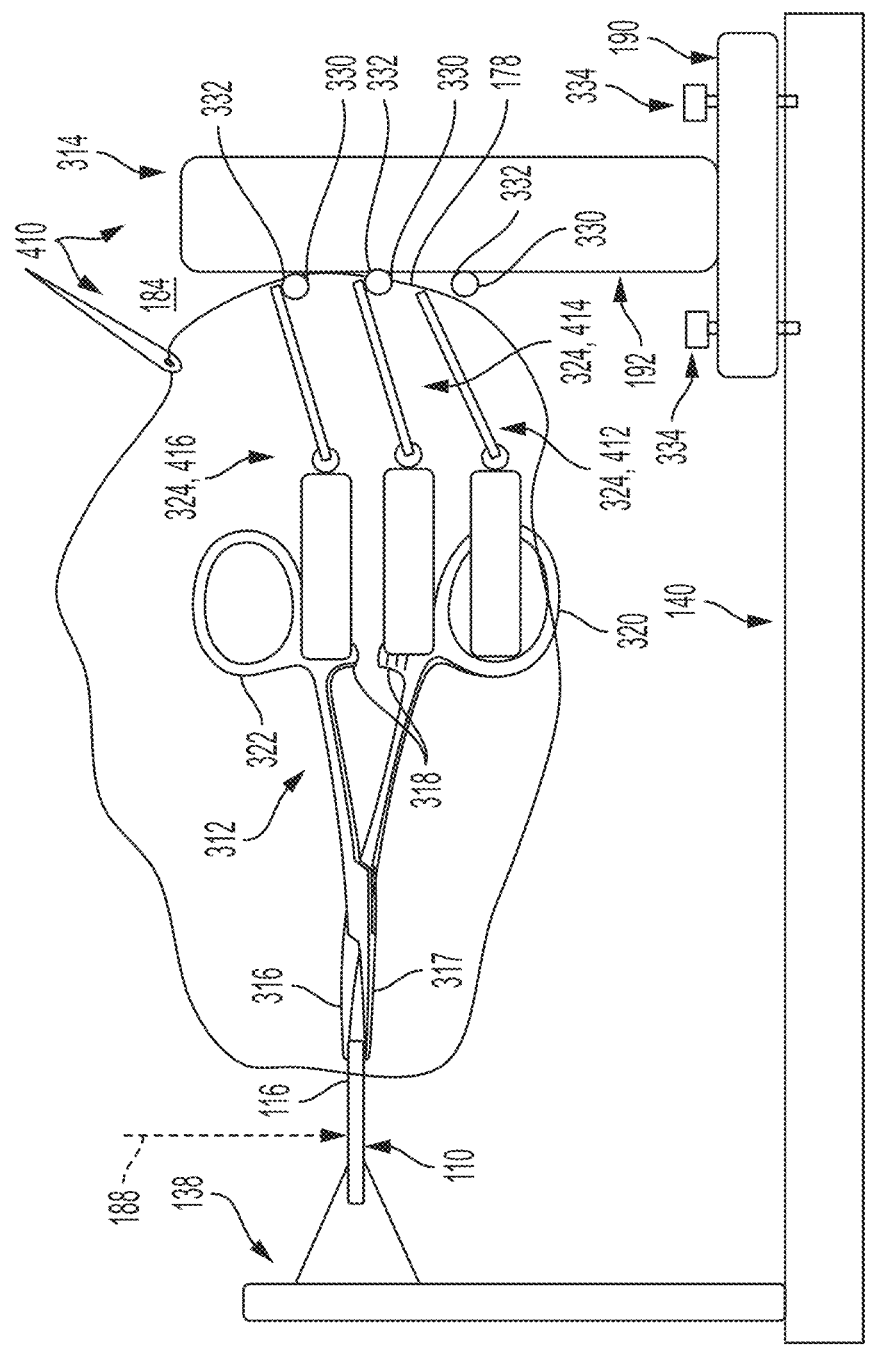
FIG. 26 is a side elevation view of yet another embodiment of a medical holding system, illustrating an example of a bottom coupler portion in an open position and two other coupler portions in closed positions.

In an embodiment illustrated in FIG. 26, the medical holding system 410 includes the same structure, parts, elements and functionality as medical holding system 310 except that the medical holding system 410 includes: (a) a plurality of couplers 324; and (b) a plurality of support members 330, each of which has a release interface 332. Based on this arrangement, the medical holding system 410 provides a series of gates 412, 414, 416 that are vertically stacked. In an embodiment, at all times during the pass-through preparation method, at least one of the gates 412, 414, 416 is closed, while one or more of the other gates 412, 414, 416 can be in an open position. This ensures that, at all times, the support device 314 is physically supporting the second element end 116.

In operation of one example, as illustrated in FIG. 26: (a) the user first passes the cord segment or loop segment 178 through gate 412; (b) then, gate 412 closes due to a magnetic force; (c) then, the user passes the loop segment 178 through gate 414; (d) then, gate 414 closes due to a magnetic force; and (e) then, the user passes the loop segment 178 through gate 416 to proceed with suturing the second element end 116. In this example, at all times during the pass-through preparation method, two of the gates 412, 414, 416 are closed. The number of gates in the medical holding system 410 can be adjusted based on the piercing force 188 necessary to pierce the applicable implantable element 110. For example, a relatively soft implantable element 110, suitable for a relatively low piercing force 188, can be sutured with the use of two gates, and a relatively hard implantable element 110, requiring a relatively high piercing force 188, can be sutured with the use of five gates.

Figure 27:
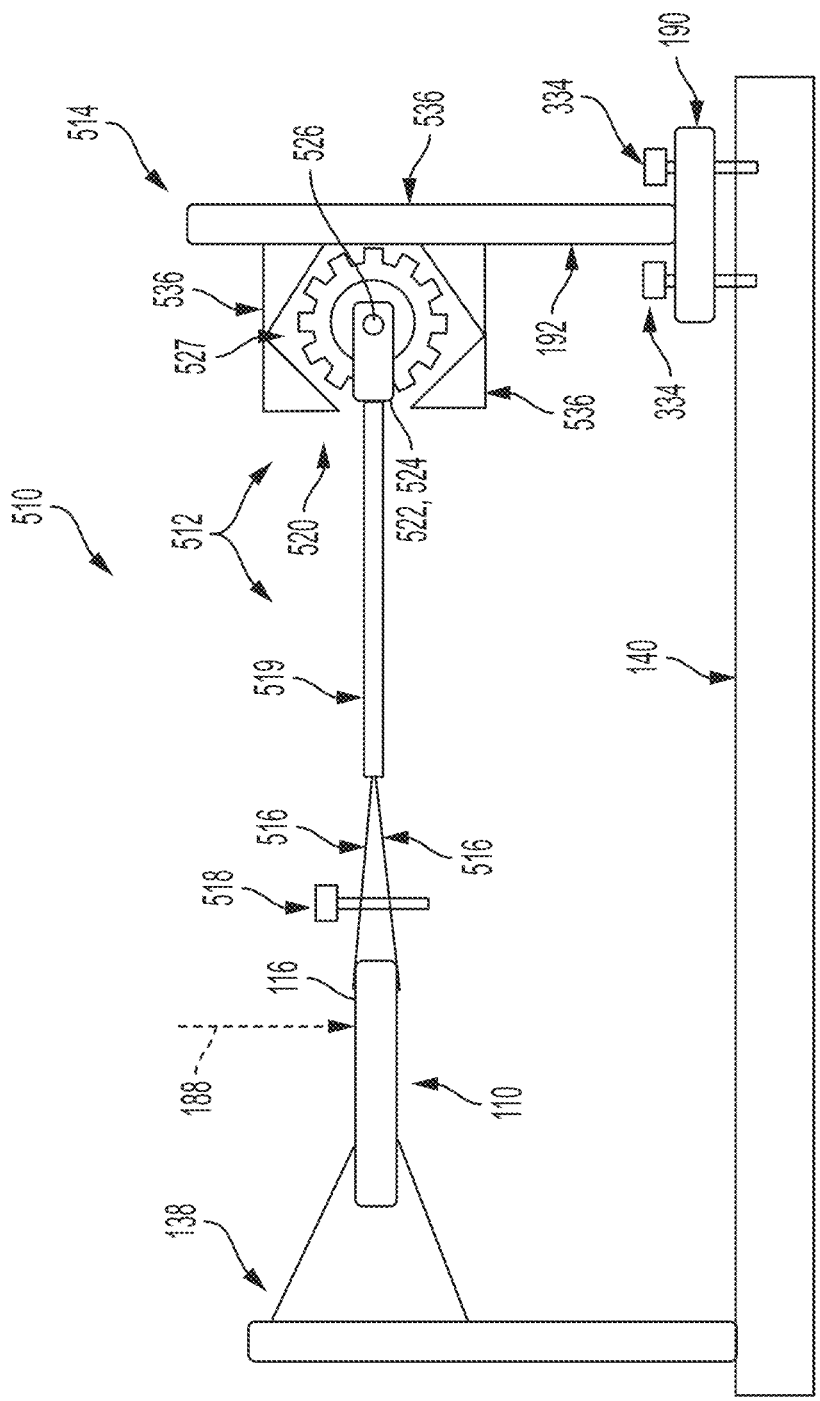
FIG. 27 is a side elevation view of still another embodiment of a medical holding system, illustrating the multiple coupler portions of a rotary coupler.
Figure 28:
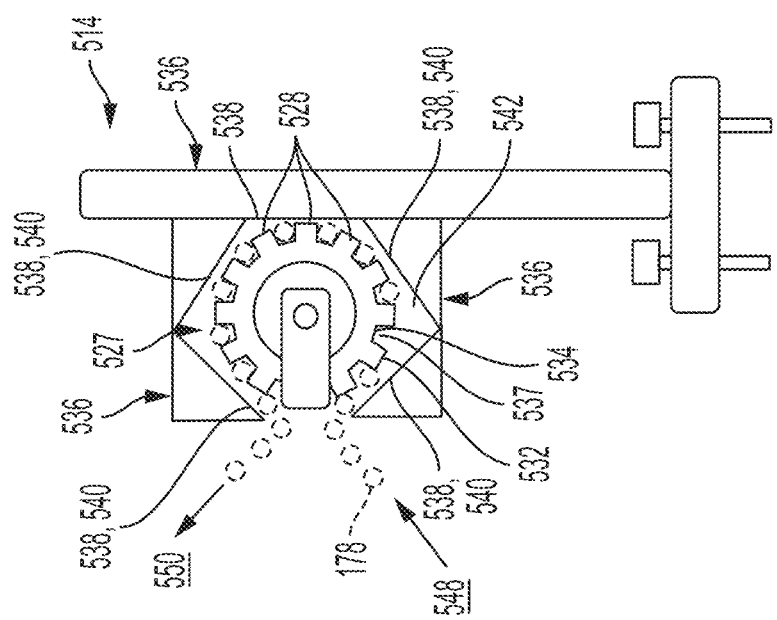
FIG. 28 is an enlarged side elevation view of the coupler of the medical holding system of FIG. 27, illustrating the coupler portions spaced apart by valley spaces.

In an embodiment illustrated in FIGS. 27-28, the medical holding system 510 includes the same structure, parts, elements and functionality as medical holding system 150 except that the medical holding system 510 includes holder 512 and support device 514. Holder 512 includes: (a) a plurality of jaws 516 configured to be clamped or squeezed onto the second element end 116; (b) a fastener 518 (e.g., a screw or bolt) configured to draw the jaws 516 together and secure the jaws 516 in a position that compresses the second element end 116; (c) a rigid extension or arm 519 extending from the jaws 516; (d) a coupler 520 attached to the arm 519.

Depending on the embodiment, the fastener 518 can include a screw having a grasp or knob to facilitate rotation by the user's hand. In this embodiment, the coupler 520 includes a connector 522 having a yoke or fork-shaped frame 524, and a shaft 526 coupled to the fork-shaped frame 524. The coupler 520 also includes a wheel, disk, gear or rotor 527 that is rotatable relative to the support device 514. In the embodiment shown, the rotor 527 is rotatably coupled to the shaft 526. The rotor 527 includes a plurality of coupler portions 528 that are spaced apart from each other. As shown in FIG. 28, each coupler portion 528 is a protrusion, tooth or projection extending from the rotor 527, providing the rotor 527 with a forming a gear configuration. In this embodiment, each coupler portion 528 has a peak surface 532. In between each coupler portion 528 is a valley surface 534. Depending on the embodiment, the rotor 527 can have a compliant, flexible or deformable surface or characteristic. For example, the coupler portions 528, peak surfaces 532 and valley surfaces 534 can be constructed of an elastic or rubber (natural or synthetic) material.

Also, in this embodiment, the support device 514 includes a support member 536 having a release interface 538 and a stopper 540. In the embodiment shown, the support member 536 has a substantially C-shaped, side profile that defines a passageway 542. In this embodiment, the release interface 538 may or may not be configured to be magnetically attracted to the rotor 527.

In an embodiment, the release interface 538 defines a slot configured to receive the peak surface 532 of each one of the coupler portions 528. For example, the slot can have a T-shape that conforms to (and is slightly larger than) a T-shaped peak surface 432. In this way, each peak surface 432 serves as a male element. The slot of the release interface 538 serves as a female element configured to receive and mate with the male elements. As the rotor 527 rotates, the coupler portions 528 travel along an arc and slide within such slot. While within such slot, the release interface 538 restrains the movement of the coupler portions 528 to a circular path of movement, preventing the rotor 527 from decoupling from the support device 514.

As illustrated in FIGS. 27-28, during the pass-through preparation method, in order to pass a cord segment or loop segment 178 of the looped cord 172 between the coupler portions 528 and the support member 536, the user routes the loop segment 178 around the rotor 527, through the C-shaped or arc-shaped passageway 542. The valley space 537 between each coupler portion 528 includes at least part of the passageway 542. In this process, the loop segment 178 fits at least partially within one of the valley spaces 537 while pushing against one of the peak surfaces 532. It should be understood that the cord segment or loop segment 178 can pass by coupler portion 528 to coupler portion 528, sequentially moving from valley space 537 to valley space 537 while traveling through the passageway 542. Alternatively, the user can initially position the loop segment 178 in a first one of the valley spaces 537. The loop segment 178 can remain in the first valley space 537 while traveling entirely through the passageway 542.

In either case, the user can pull the loop segment 178 from the entry space 548 to the outlet space 550 to fully pass the loop segment 178 through the passageway 542. The periodic pass-through cycles enable the user to conveniently perform the pass-through preparation method. During and after the periodic pass-through cycles, the release interface 538 or stopper 540 retains the rotor 527 within the passageway 542, stopping the rotor 527 from falling to the support surface 140, despite the downward piercing force 188.

Figure 29:
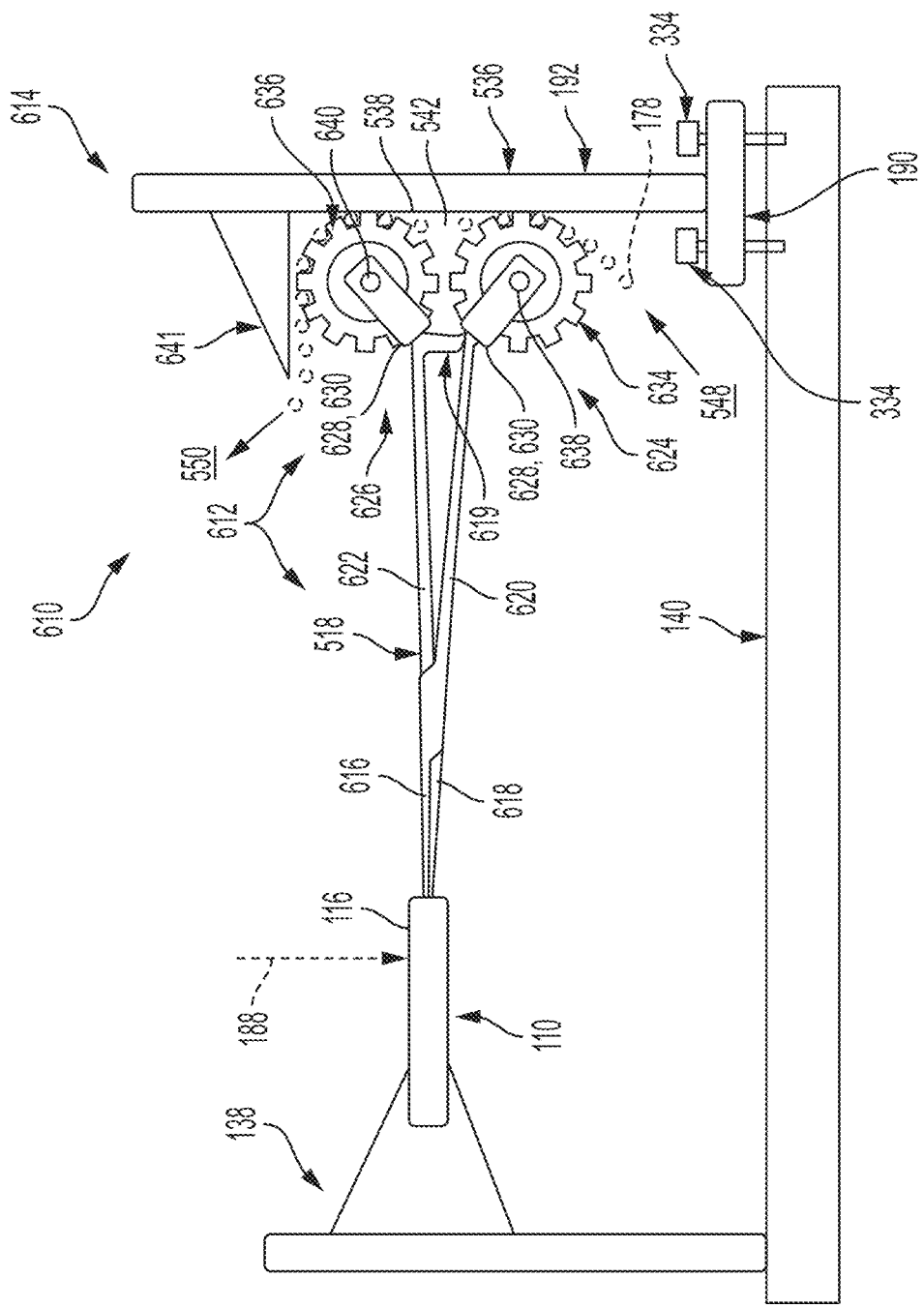
FIG. 29 is a side elevation view of another embodiment of a medical holding system, illustrating a lower rotary coupler, an upper rotary coupler, and the multiple coupler portions of the lower and upper rotary couplers.

In an embodiment illustrated in FIG. 29, the medical holding system 610 includes the same structure, parts, elements and functionality as medical holding system 310 except that the medical holding system 610 includes holder 612 and support device 614. Holder 612 includes: (a) a plurality of jaws 616, 618 pivotally coupled to each other; (b) a position lock 619 configured to secure the jaws 616, 618 in a fixed position that compresses the second element end 116; (c) a plurality of handles 620, 622 connected to the the jaws 616, 618, respectively; and (d) a plurality of couplers 624, 626 attached to the handles 620, 622, respectively. Each of the couplers 624, 626 includes a connector 628 having a yoke or fork-shaped frame 630, and shafts 638, 640, each of which is coupled to one of the fork-shaped frames 630. The couplers 624, 626 include wheels or rotors 634, 636. Rotors 634, 636 are rotatably coupled to shafts 638, 640, respectively.

Each of the rotors 634, 636 has the same structure, elements, configuration and functionality as rotor 527 described above with respect to FIG. 28. However, in this embodiment, each of the rotors 634, 636 is configured to be magnetically attracted to the release interface 538 of the support body 192. For example, each of the rotors 634, 636 can include a metallic material configured to be attracted to a release interface 538 that is magnetic or magnetized. In another example, the release interface 538 of the support body 192 can include a metallic material configured to be attracted to the rotors 634, 636, each of which is magnetic or magnetized. In yet another example, the rotors 634, 636 and the release interface 538 can all be magnetic or magnetized to generate an enhanced magnetic attraction force between the rotors 634, 636 and the support body 192.

During the pass-through preparation method, to pass a loop segment 178 between the holder 612 and support device 614, the user routes the loop segment 178 around and behind rotor 634 and then around and behind rotor 636. Referring to FIG. 29, while traveling behind each of the rotors 634, 636, the loop segment 178 fits at least partially within one of the valley space 537 while pushing against the adjacent coupler portion 528. It should be understood that the loop segment 178 can switch from coupler portion 528 to coupler portion 528 while traveling through the passageway 542, or the loop segment 178 can remain in the same valley space 537 of each of the rotors 634, 636. In use, the user pulls the loop segment 178 from the entry space 548 to the outlet space 550 to fully pass the loop segment 178 through the passageway 542. The periodic pass-through cycles enable the user to conveniently perform the pass-through preparation method.

In an embodiment, the support device 614 has a stopper 641, which may or may not be magnetically attracted to the rotors 634, 636. During the periodic passages of the loop segment 178, the stopper 641 retains the rotors 634, 636 engaged with the support body 192. In particular, the stopper 641 prevents the upward force of the loop segment 178 from causing the rotors 634, 636 to fully slide upward and off of the support body 192. During and after the periodic passages of the loop segment 178, the magnetic forces between the rotors 634, 636 and the support body 192 keep the rotors 634, 636 engaged with the support body 192. This prevents the second element end 116 from falling to the support surface 140 despite the downward piercing force 188.

Figure 30:
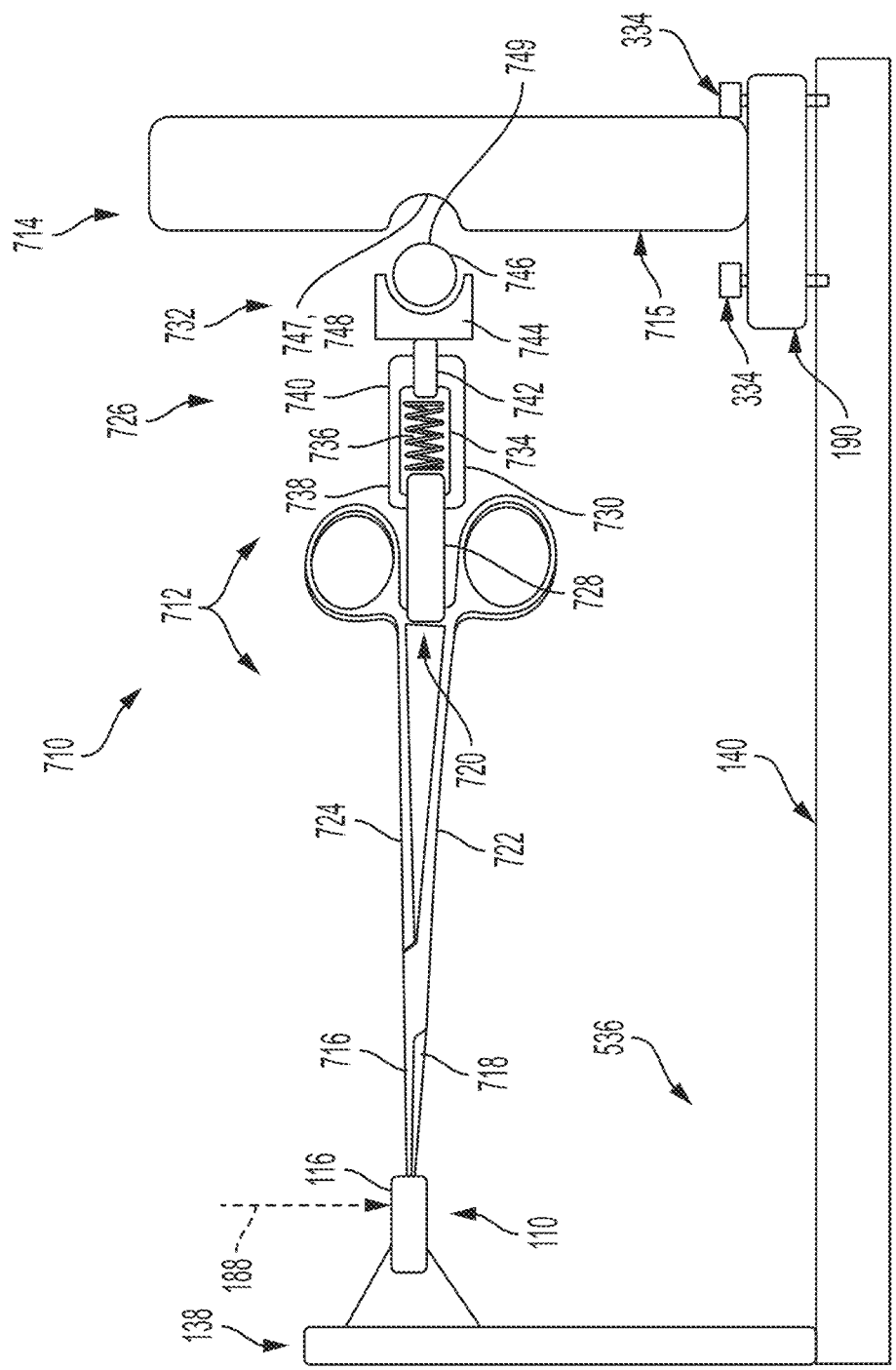
FIG. 30 is a side elevation view of another embodiment of a medical holding system, illustrating a ball-shaped coupler portion uninstalled from a socket of a support device.
Figure 31:
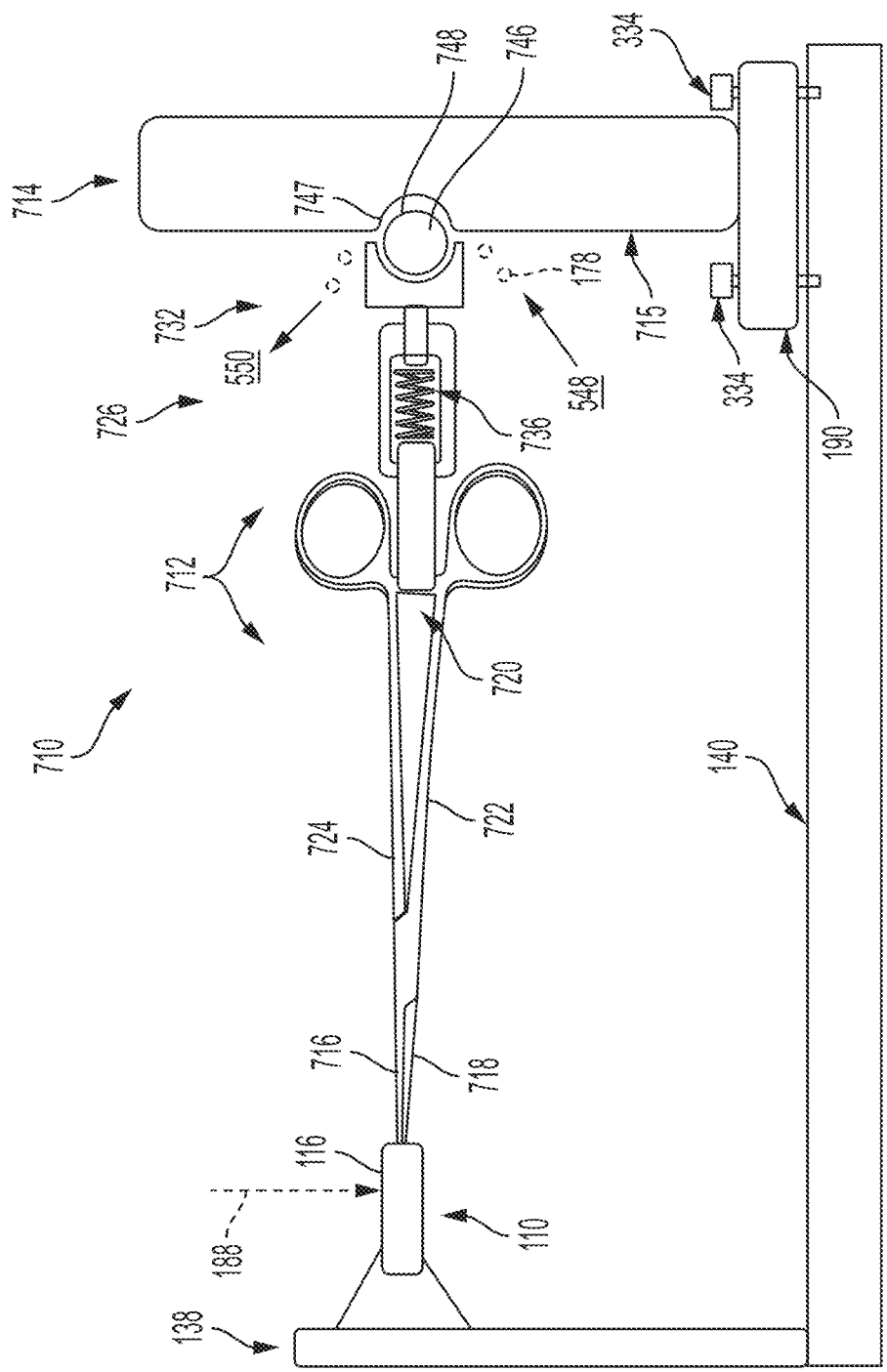
FIG. 31 is a side elevation view of the medical holding system of FIG. 30, illustrating the ball-shaped coupler portion engaged with the socket-shaped release interface of the support device.

In an embodiment illustrated in FIGS. 30-31, the medical holding system 710 includes the same structure, parts, elements and functionality as medical holding system 310 except that the medical holding system 710 includes holder 712, support device 714 and support body 715. Holder 712 includes: (a) a plurality of jaws 716, 718 pivotally coupled to each other; (b) a position lock 720 configured to secure the jaws 716, 718 in a fixed position that compresses the second element end 116; (c) a plurality of handles 722, 724 connected to the the jaws 716, 718, respectively; and (d) a coupler 726 connected to the position lock 720.

In the embodiment shown, the coupler 726 includes: (a) a rod or arm 728; (b) a housing 730 configured to receive an end of the arm 728; and (c) a coupler assembly 732. The housing 730 has a retainer 734 configured to hold a biasing member or spring 736. The housing 730 also has a first housing end 738 defining a opening (not shown) configured to receive the arm 728, and the housing 730 has a second housing end 740 defining an opening (not shown) configured to receive an arm 742 of the coupler assembly 732.

The coupler assembly 732 includes: (a) a socket 744; (b) a coupler portion 746 held by the socket 744; and (c) the arm 742 extending from the socket 744. In the embodiment shown, the coupler portion 746 is a joint member. The coupler portion 746 can be a metallic or magnetized ball, or a disk, gear, wheel, rotor or other suitable type of articulating element.

The support body 715 has the same structure, elements and functionality as support body 192 except that support body 715 includes a release interface 747. The release interface 747 defines a socket, slot, groove, recess or cavity 748. The cavity 748 is concave and has an arc shape or partial spherical shape. The cavity 748 is configured to partially receive the coupler portion 746.

In this embodiment, the coupler portion 746 is configured to be magnetically attracted to the support body 715. For example, the coupler portion 746 can include a metallic material configured to be attracted to the support body 715 that is magnetic or magnetized. In another example, the support body 715 can include a metallic material configured to be attracted to the coupler portion 746, which is magnetic or magnetized. In yet another example, the coupler portion 746 and the support body 715 can each be magnetic or magnetized to generate an enhanced magnetic attraction force between the coupler portion 746 and the support body 715.

In the setup stage, the user brings the coupler portion 746 into contact with the support body 715 so that the coupler portion 746 partially fits within the cavity 748, as shown in FIG. 31. The magnetic force between the coupler portion 746 and the support body 715 secures the coupler portion 746 partially within the cavity 748.

During the periodic passages of the loop segment 178 during the pass-through preparation method, the coupler portion 746 remains partially within the cavity 748 and engaged with the support body 715. In particular, the release interface 747, serving as a stopper, prevents the upward force of the loop segment 178 from causing the coupler portion 746 to fully slide upward and off of the support body 715. During and after the periodic passages of the loop segment 178, the magnetic force between the coupler portion 746 and the support body 715 keep the coupler portion 746 engaged with the support body 715. This prevents the second element end 116 from falling to the support surface 140 despite the downward piercing force 188. Each time the users passes the loop segment 178 along the rear side 749 (FIG. 30) of the coupler portion 746, the spring 736 flexes (compresses) to facilitate the passage of the loop segment 178.

Figure 33:
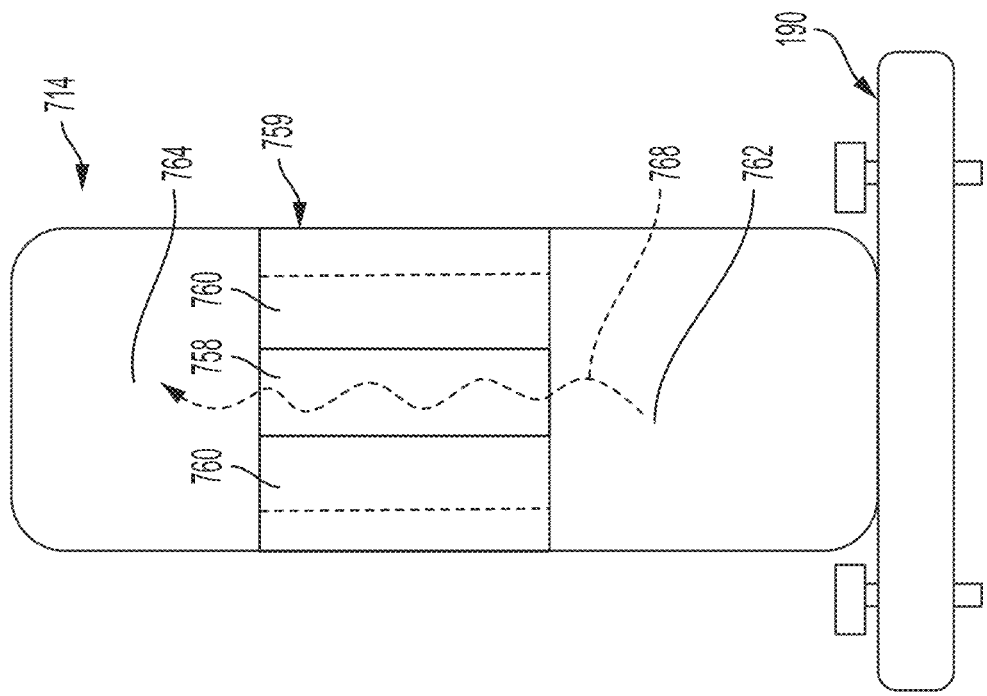
FIG. 33 is a side elevation view of an embodiment of a support device configured for an embodiment of the medical holding system of FIG. 30.
Figure 32:
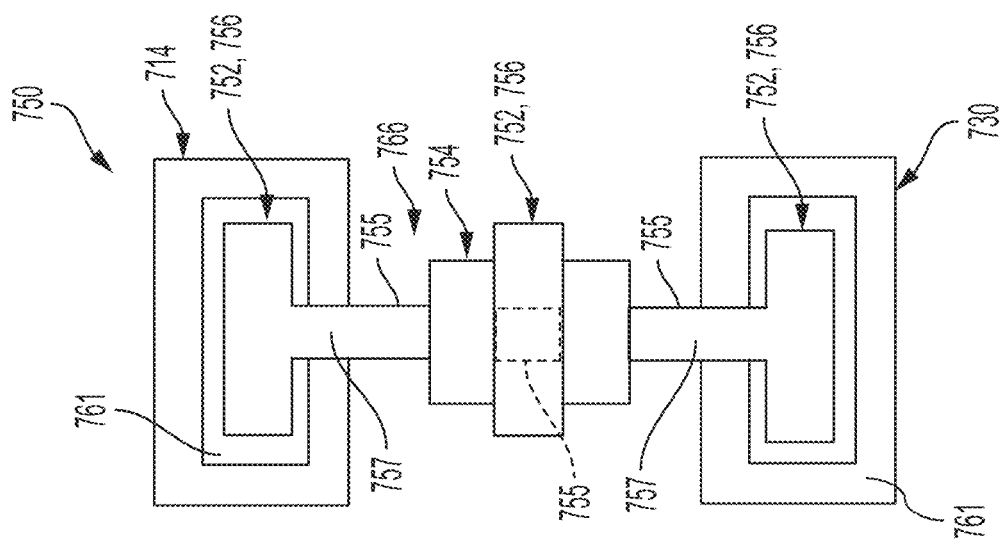
FIG. 32 is a side elevation view of an embodiment of a coupler assembly configured for an embodiment of the medical holding system of FIG. 30.

In another embodiment illustrated in FIGS. 32-33, the coupler 726 includes a coupler assembly 750 in place of the coupler assembly 732. The coupler assembly 750 includes a wheel or rotor that has a plurality of coupler portions 752 that radially extend from the central hub or central portion 754 of the coupler assembly 750. In this example, there are four coupler portions 752, three of which are shown in FIG. 32. The coupler portions 752 are separated by equal angles. Each coupler portion 752 has a neck or extension 755 and a head or retainer member 756. In the example shown, each coupler portion 752 has a T-shape.

The housing 730 defines a first arc-shaped or C-shaped slot 757 configured to receive the extensions 755. The housing 730 also defines a second arc-shaped or C-shaped slot 761 configured to receive the retainer members 756. The first C-shaped slot 757 is narrower than the second C-shaped slot 761. As a result, once a coupler portion 752 rotates within the slots 757, 761, such coupler portion 752 is slidably mated and interlocked with the housing 730. The interlocking enables such coupler portion 752 to slide within the housing 730 while retaining and coupling such coupler portion 752 to the housing 730.

Likewise, the release interface 759 of the support device 714 defines a first arc-shaped or C-shaped slot 758 configured to receive the extensions 755. The release interface 759 also defines a second arc-shaped or C-shaped slot 760 configured to receive the retainer members 756. The first C-shaped slot 758 is narrower than the second C-shaped slot 760. As a result, once a coupler portion 752 rotates within the slots 758, 760, such coupler portion 752 is slidably mated and interlocked with the housing 730. The interlocking enables such coupler portion 752 to slide within the housing 730 while retaining and coupling such coupler portion 752 to the support device 714.

In this embodiment, the coupler assembly 750 is positioned between the C-shaped portions of the housing 730 and support device 714. The C-shaped portions of the housing 730 and support device 714 are spaced apart so that there is a lower entry space 762 (FIG. 33) and an upper outlet space 764 (FIG. 33) between such C-shaped portions. When pushed, the central portion 754 is configured to rotate relative to the housing 730 and support device 714. The user can insert the loop segment 178 into a dwelling space 766 (FIG. 32) between two of the extensions 755 and then pull the loop segment 178 upward against a first one of the extensions 752. This causes the central portion 754 to rotate relative to the housing 730 and the support device 714. Eventually, the first extension 752 reaches the upper outlet space 764 and disengages from the release interface 759. This causes the loop segment 178 to fully pass the through the passageway 768. In this example, the passageway 768 includes the space along the arc-shaped path of the first extension 752. At all times during the rotation of the central portion 754, at least one retainer member 756 remains mated with, and slidably interlocked with, the housing 730, and at least one retainer member 756 remains mated with, and slidably interlocked with, the release interface 759. Accordingly, during the rotation action, the support device 714 keeps the implantable element 110 from falling to the support surface 140. The periodic pass-through cycles enable the user to conveniently perform the pass-through preparation method.

Figure 34:
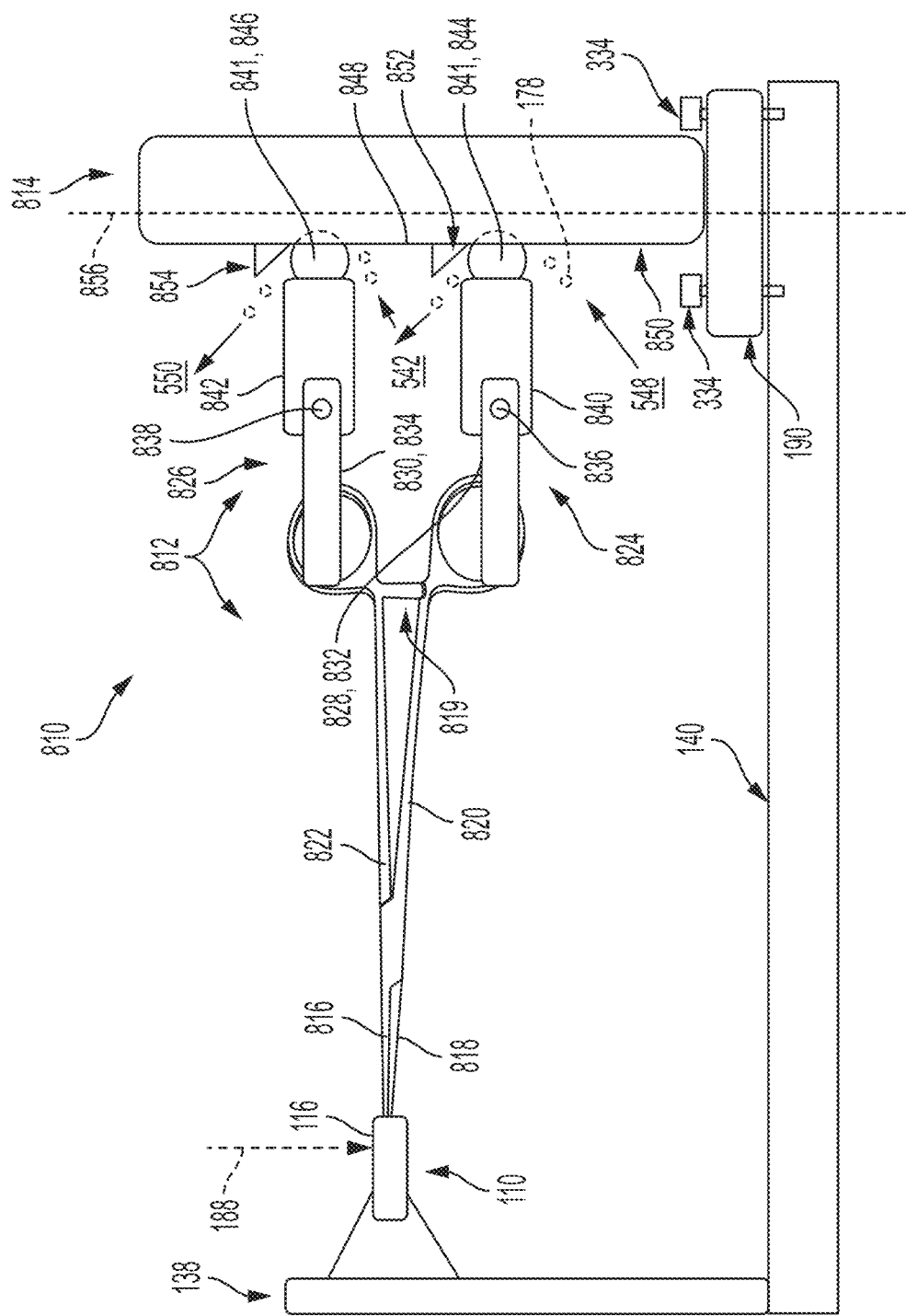
FIG. 34 is a side elevation view of another embodiment of a medical holding system, illustrating a lower rotary coupler that fits within a valley of the support device, an upper rotary coupler that fits within the valley, and the coupler portions of the lower and upper rotary couplers.

In an embodiment illustrated in FIG. 34, the medical holding system 810 includes the same structure, parts, elements and functionality as medical holding system 310 except that the medical holding system 810 includes holder 812 and support device 814. Holder 812 includes: (a) a plurality of jaws 816, 818 pivotally coupled to each other; (b) a position lock 819 configured to secure the jaws 816, 818 in a fixed position that compresses the second element end 116; (c) a plurality of handles 820, 822 connected to the the jaws 816, 818, respectively; and (d) a plurality of couplers 824, 826 attached to the handles 820, 822, respectively.

Couplers 824, 826 include: (a) connectors 828, 830 having yokes or fork-shaped frames 832, 834, respectively; (b) shafts 836, 838 coupled to the fork-shaped frames 832, 834, respectively; (c) housings 840, 842 coupled to the frames 832, 834, respectively; and (d) coupler portions 841, 842 coupled to the housings 840, 842. Depending on the embodiment, the each of the coupler portions 841, 842 can include a pivot member, ball, wheel, disk, gear or rotor. In the embodiment shown, the coupler portions 841, 842 include balls 844, 846, respectively. Balls 844, 846 are rotatably mounted within sockets (not shown) defined by the housings 840, 842, respectively. In this embodiment, each of the balls 844, 846 is configured to be magnetically attracted to the release interface 848 of the support body 850. For example, each of the balls 844, 846 can include a metallic material configured to be attracted to the release interface 848 that is magnetic or magnetized. In another example, the release interface 848 of the support body 850 can include a metallic material configured to be attracted to the balls 844, 846, each of which is magnetic or magnetized. In yet another example, the balls 844, 846 and the release interface 848 can all be magnetic or magnetized to generate an enhanced magnetic attraction force between the balls 844, 846 and the support body 850.

In the embodiment shown, the support body 850 includes the release interface 848 and a plurality of stoppers 852, 854. The release interface 848 defines a longitudinal valley extending along the longitudinal axis 856. A portion of each of the balls 844, 846 fits within such valley. The concave shape of the valley enhances the magnetic forces between the balls 844, 846 and the release interface 848.

During the pass-through preparation method, to pass a loop segment 178 between the holder 812 and support device 814, the user routes the loop segment 178 around and behind ball 844 and then around and behind ball 846. The user pulls the loop segment 178 from the entry space 548 to the outlet space 550 to fully pass the loop segment 178 through the passageway 542. The periodic pass-through cycles enable the user to conveniently perform the pass-through preparation method.

It should be understood that the stoppers 852, 854 may or may not be magnetically attracted to the balls 844, 846. During the periodic pass-through cycles of the loop segment 178, the stoppers 852, 854 retain the balls 844, 846 in engagement with the support body 850. In particular, the stopper 852 prevents the upward force of the loop segment 178 from causing the ball 844 to fully slide upward and off of the support body 850, and the stopper 854 prevents the upward force of the loop segment 178 from causing the ball 846 to fully slide upward and off of the support body 850. During and after the periodic passages of the loop segment 178, the magnetic forces between the balls 844, 846 and the support body 850 keep the balls 844, 846 engaged with the support body 850. This prevents the second element end 116 from falling to the support surface 140 despite the downward piercing force 188.

Figure 35:
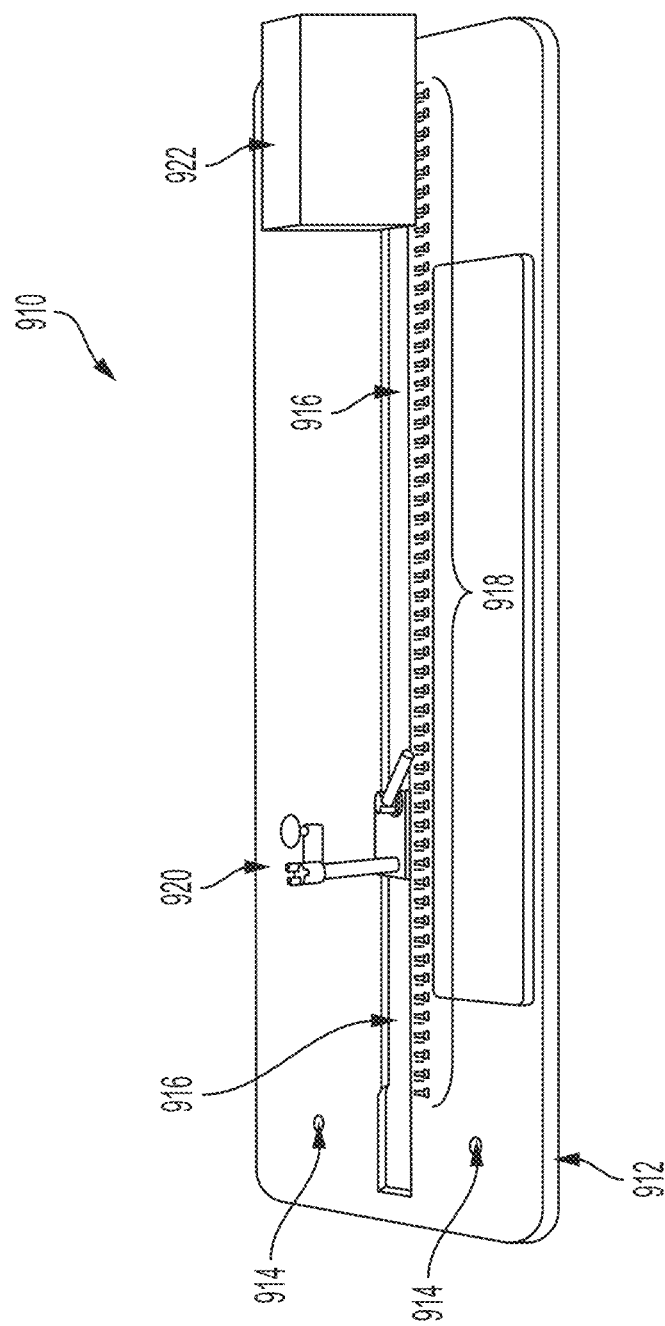
FIG. 35 is an isometric view of an embodiment of an implant preparation station or implant preparation device.
Figure 36:
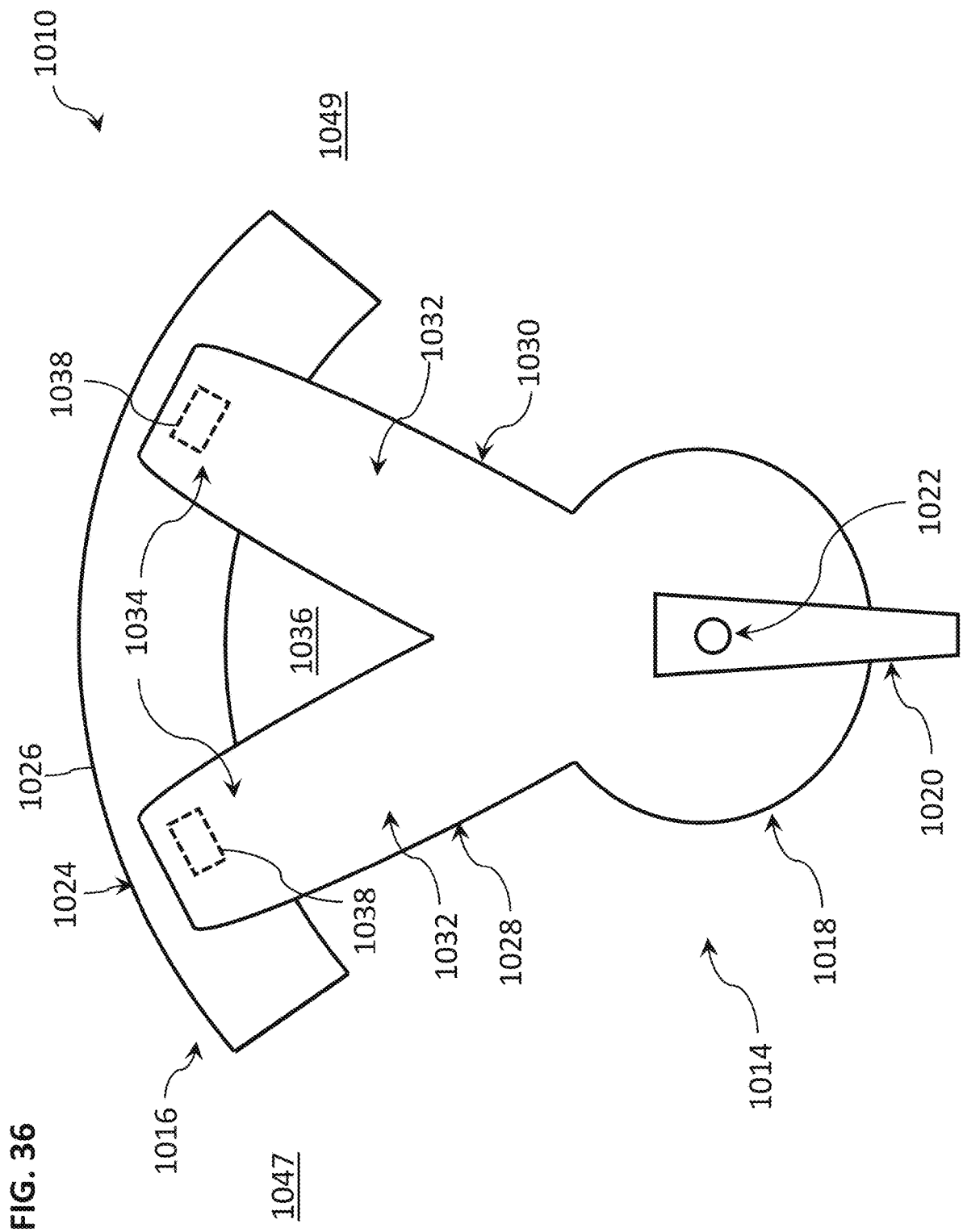
FIG. 36 is a top, schematic view of an embodiment of a medical holding system.

Referring to FIG. 35, in an embodiment, an implant preparation station or implant preparation device 910 includes: (a) a base or support surface 912 defining a plurality of mounting holes 914 and a longitudinal adjustment valley, groove or track 916; (b) a plurality of measurement markings 918 displayed or otherwise visible adjacent to the track 916; (c) a hanger 920 adjustably coupled to the track 916; and (d) a support device 922 adjustably coupled to the track 916. Depending on the embodiment, the support device 922 can include support device 143, 154, 314, 514, 614, 714, 814 or 922 or any suitable combination thereof. The user can secure the first element end 114 (FIG. 10) to the hanger 920. Next, the user can clamp a holder 141, 152, 312, 512, 612, 712 or 812 (or any suitable combination thereof) onto the second element end 116 (FIG. 10) of an implantable element 110. Next, the user can reversibly couple the applicable holder to the support device 922 according to one of the methods described above. Then, the user can perform the pass-through preparation method, which involves making periodic passes between the support device 922 and such holder which, depending on the embodiment, may be holder 141, 152, 312, 512, 612, 712 or 812 or any suitable combination thereof.

In another embodiment illustrated in FIGS. 36 to 39, the medical holding system 1010 includes a support device (not shown) and a holder 1014 configured to be coupled to the support device. The support device includes a retainer 1016. The holder 1014 includes a pivot device 1018, a grasper 1020, and a pivot member 1022 that pivotally couples the grasper 1020 to the pivot device 1018.

The retainer 1016, in an embodiment, includes a retainer interface 1024 that has an arc shape 1026. The pivot device 1018 has a plurality of arms 1028, 1030. Each of the arms 1028, 1030 has: (a) a proximal or first arm portion 1032; and (b) a distal or second arm portion 1034 that is connected to or extends from one of the first arm portions 1032. The first arm portions 1032 of the arms 1028, 1030 are at least partially separated from each other by a cord transport space 1036.

The second arm portion 1034 of each of the arms 1028, 1030 has an arm interface 1038. Each of the arm interfaces 1038 is configured to dynamically, slideably or otherwise moveably interlock with, inter-fit with, mate with or otherwise engage with the retainer interface 1024.

Figure 37:
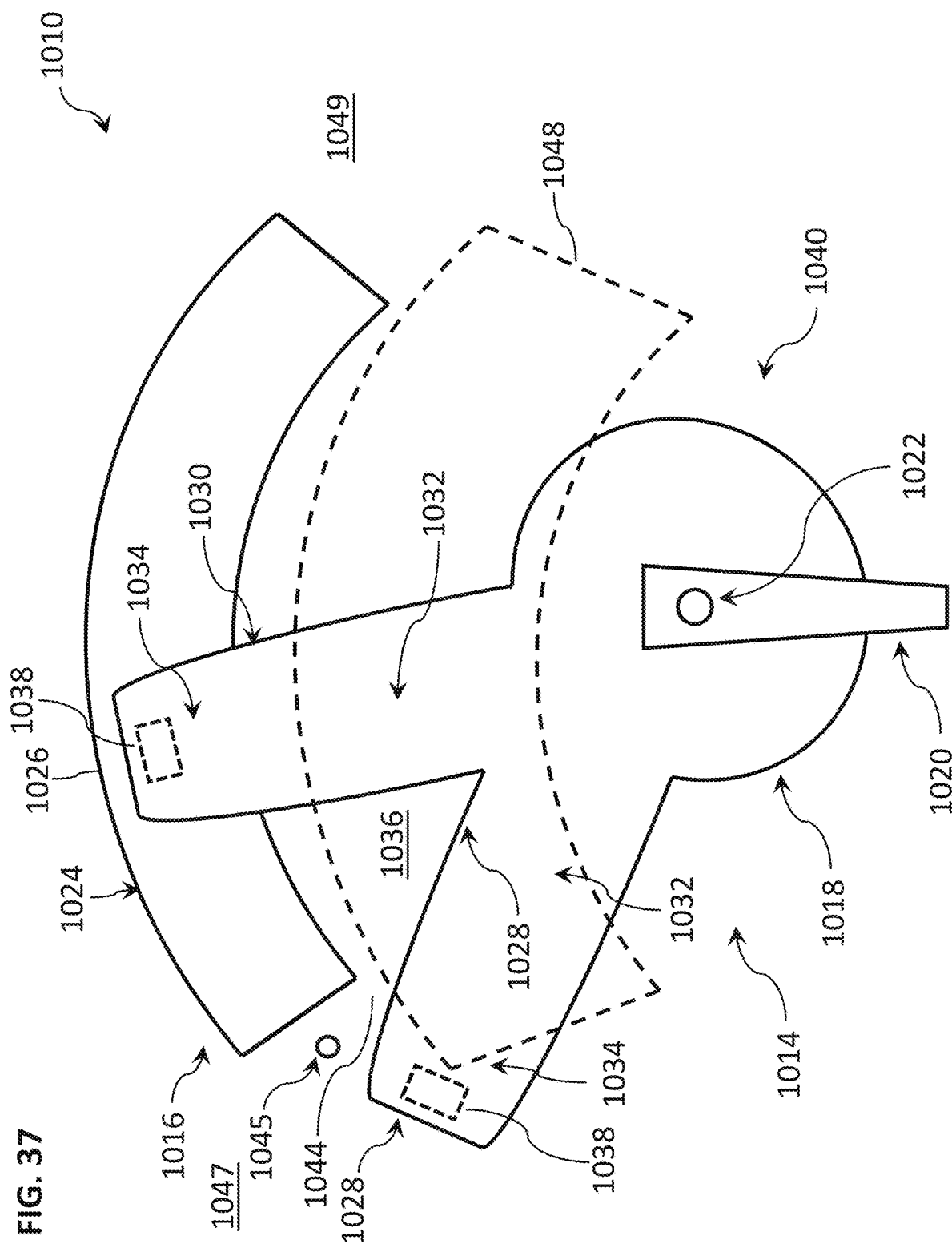
FIG. 37 is a top, schematic view of the medical holding system of FIG. 36, illustrating the pivot device in an entry position.
Figure 38:
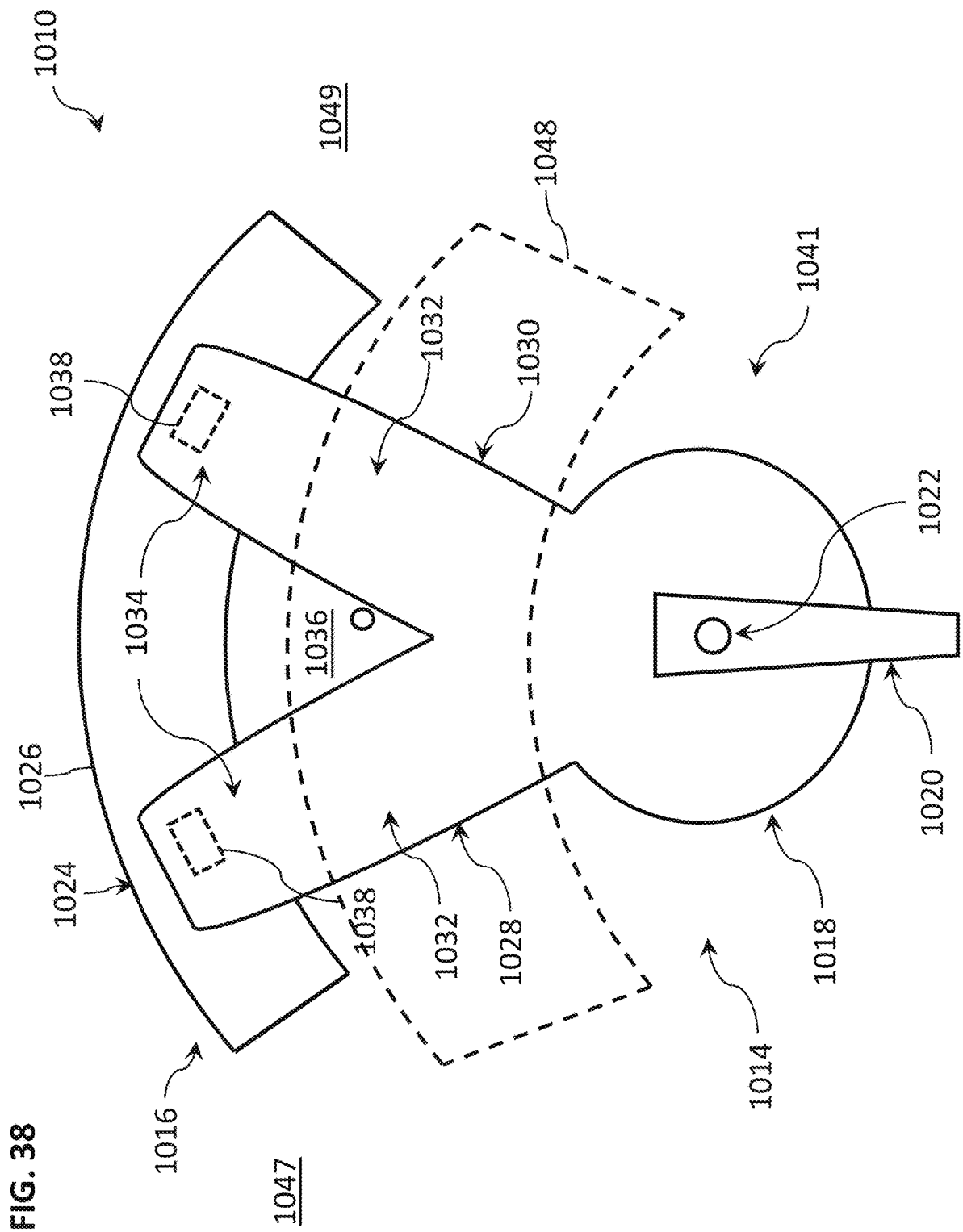
FIG. 38 is a top, schematic view of the medical holding system of FIG. 36, illustrating the pivot device in an intermediate position.

The pivot device 1018 is pivotal, relative to the retainer 1016, between a loading or entry position 1040, shown in FIG. 37, an intermediate position 1041, shown in FIG. 38, and an off-loading or outlet position 1042, shown in FIG. 39.

In the entry position 1040, there is an entry space 1044 between arm 1028 and the retainer 1016. This enables a user to move the cord segment or loop segment 1045 from a first environmental space 1047, through the entry space 1044, and into the cord transport space 1036. In the outlet position 1042 shown in FIG. 39, there is an outlet space 1046 between arm 1030 and the retainer 1016. This enables the user to move the cord segment or loop segment 1045 from the cord transport space 1036 through the outlet space 1046 and to a second environmental space 1049. The arm interface 1038 of at least one of the arms 1028, 1030 remains engaged with the retainer interface 1024 during the pivoting of the pivot device 1018 between the entry position 1040 and the outlet position 1042.

In operation of one example, the user attaches the grasper 1020 to a portion or second element end 116 (FIG. 15) of an implantable element 110 (FIG. 15). Next, as shown in FIG. 37, the user moves the loop segment 1045 from the first environmental space 1047, through the entry space 1044, and then into the cord transport space 1036. Then, as shown in FIG. 38, the user pulls the loop segment 1045 to the right, causing the pivot device 1018 to pivot clockwise. During the clockwise pivoting, the cord transport space 1036, the loop segment 1045, and the first arm portion 1032 of each of the arms 1028, 1030 collectively move along a pass-through path or arc-shaped passageway 1048. Eventually, as shown in FIG. 39, the pivoting forms the outlet space 1046, which enables the user to move the loop segment 1045 from the cord transport space 1036, through the outlet space 1046 and then to the second environmental space 1049. In this pass-through process, the user has passed the loop segment 1045 from the entry space 1044 to the outlet space 1046 while at least one of the arms 1028, 1030 remained engaged with the retainer interface 1024. As described below, this enables the user to suture the second element end 116 while at least the following two conditions are present: (a) the grasper 1020 remains clamped onto the second element end 116; and (b) the pivot device 1018 remains at least partially engaged with the retainer interface 1024.

To repeat this operation, the user can reset the pivot device 1018 by pushing the pivot device 1018 to move counterclockwise until the entry space 1044 is re-formed between the arm 1028 and the retainer 1016. Alternatively, the medical holding system 1010 can include a reset device that automatically returns the pivot device 1018 to the entry position 1040. Depending on the embodiment, the reset device can include a biasing device (e.g., a spring), earth magnet, electromagnet, solenoid, pump, motor or any other suitable electromechanical device.

In the embodiment illustrated in FIGS. 36-39, the pivot device 1018 is operable to pivot clockwise less than three hundred sixty degrees and counterclockwise less than three hundred sixty degrees. It should be appreciated that, depending on the embodiment, the pivot device 1018 can have three, four or more arms equally spaced apart about a three hundred sixty degree circle. In such embodiment, the pivot device 1018 can continuously pivot or rotate three hundred sixty degrees. The user can insert the loop segment 1045 into the cord transport space 1036 between any two of such arms to move the loop segment 1045 along the passageway 1048.

Figure 40A:
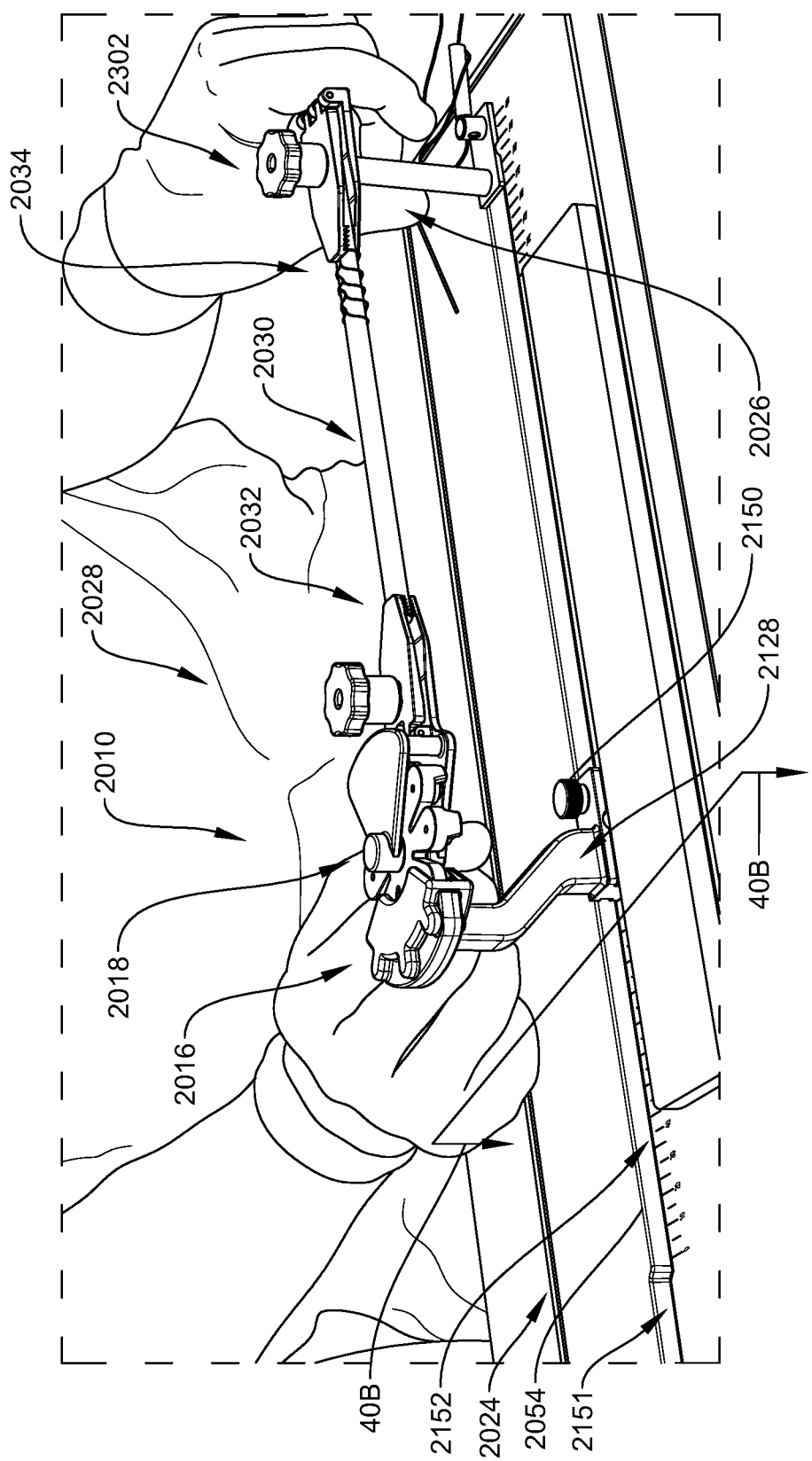
FIG. 40A is a right side, top isometric view of an embodiment of a medical preparation station having an embodiment of a medical holding system.

In an embodiment illustrated in FIG. 40A, the medical holding system 2010 is usable in conjunction with a panel, working surface, support surface or support structure 2024 as well as a mount or hanger 2026 attachable to the support structure 2024. The combination of the medical holding system 2010, the support structure 2024 and the hanger 2026 constitutes a medical preparation station 2028 usable to medically prepare an implantable element 2030. The implantable element 2030 has a first element portion 2032 and a second element portion 2034. As described below, the medical preparation station 2028 is operable to suspend the implantable element 2030 above the support structure 2024 while the user (e.g., surgeon, clinician or other person) medically prepares the implantable element 2030.

Referring to FIGS. 41-46, the medical holding system 2010 includes a support device 2012 and a holder 2014 configured to be coupled to the support device 2012. In an embodiment, the support device 2012 includes a retainer 2016 and an upright support 2116. The holder 2014 includes a pivot device 2018, a grasper 2020, and a pivot member 2022 that pivotally couples the grasper 2020 to the pivot device 2018.

Figure 48:
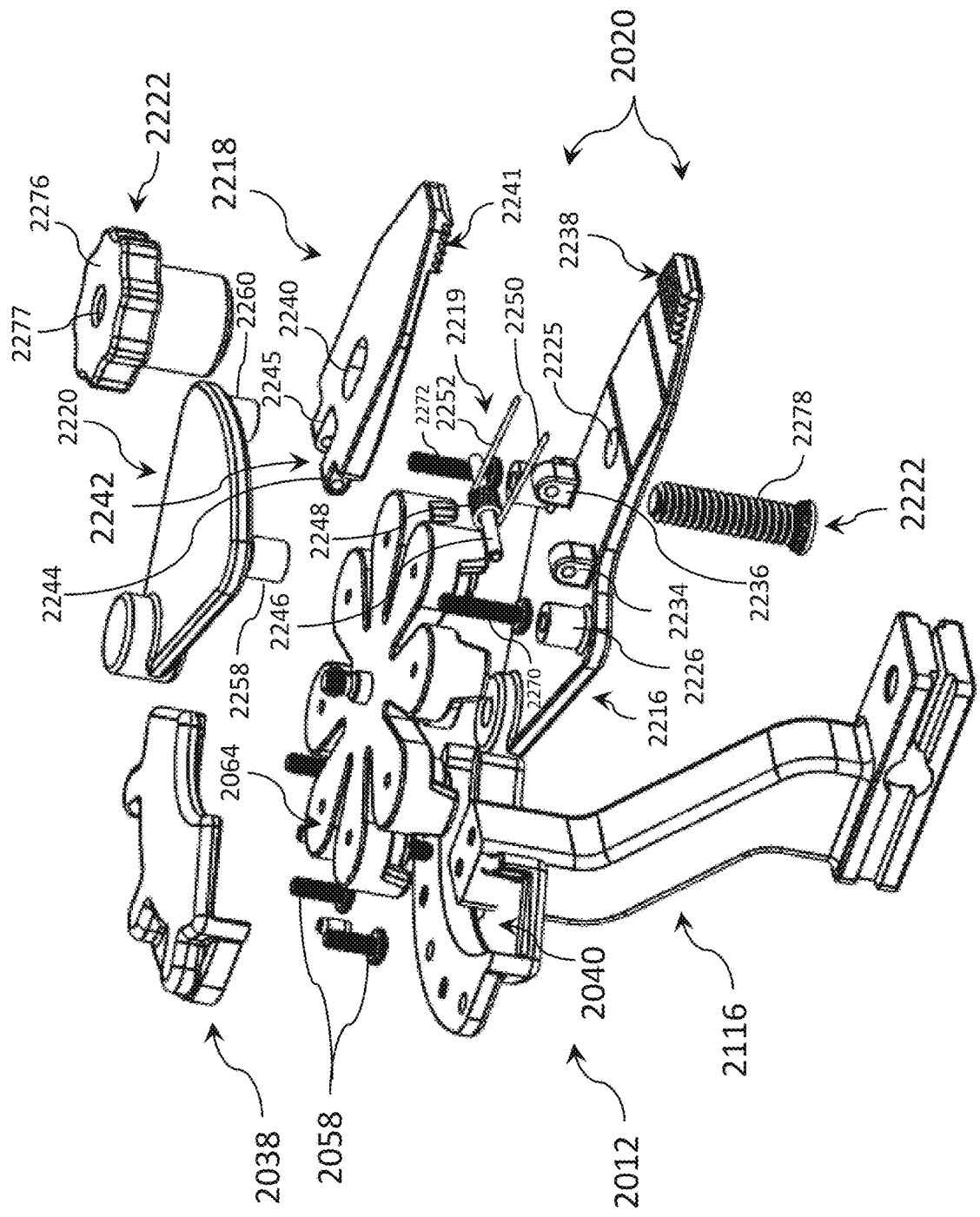
FIG. 48 is a right, isometric, exploded view of the medical holding system of FIG. 43, illustrating the rotor separated from the retainer and the grasper.
Figure 49:
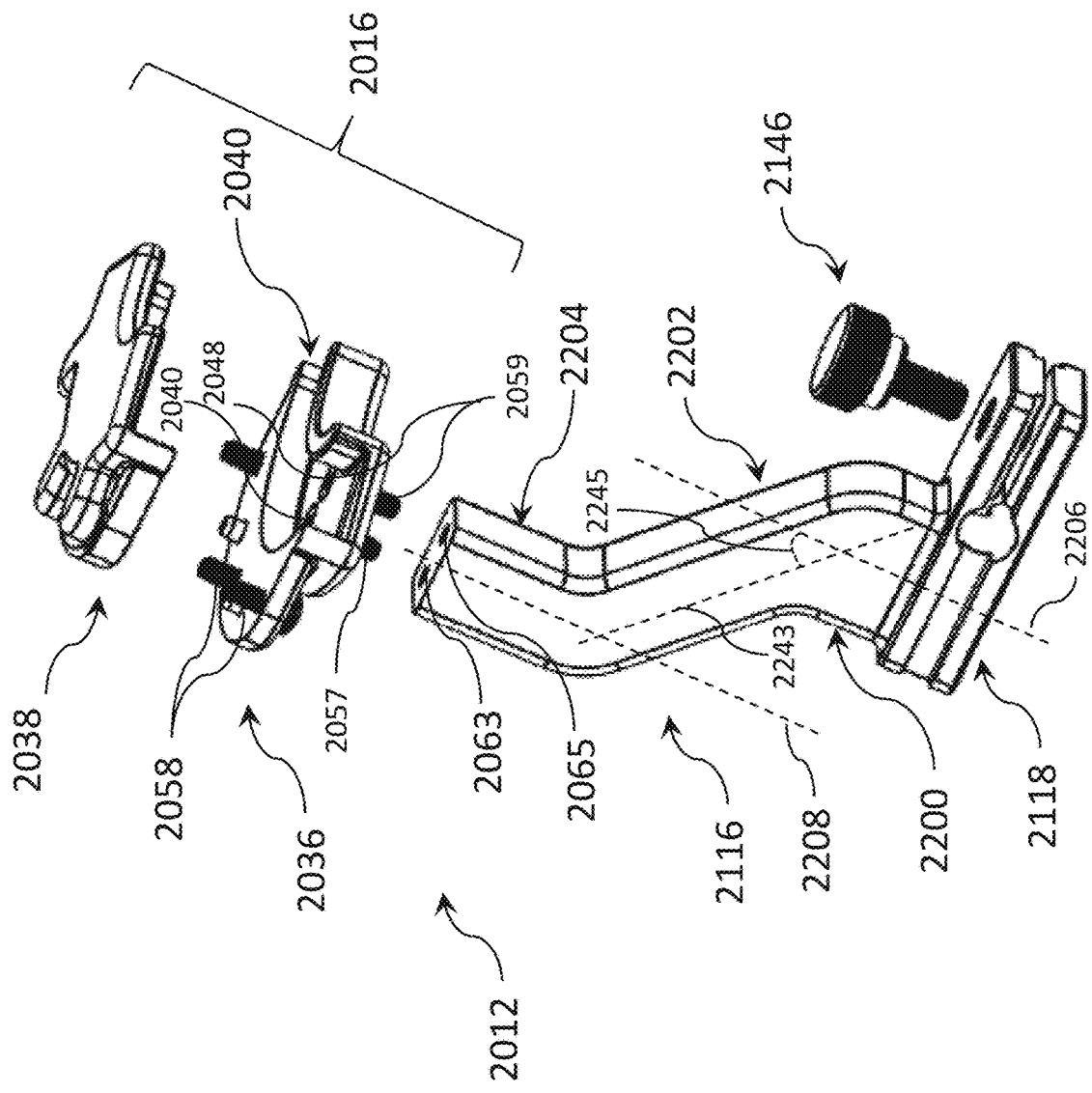
FIG. 49 is a right, isometric, exploded view of the medical holding system of FIG. 43, illustrating the retainer separated from the support device.
Figure 50:
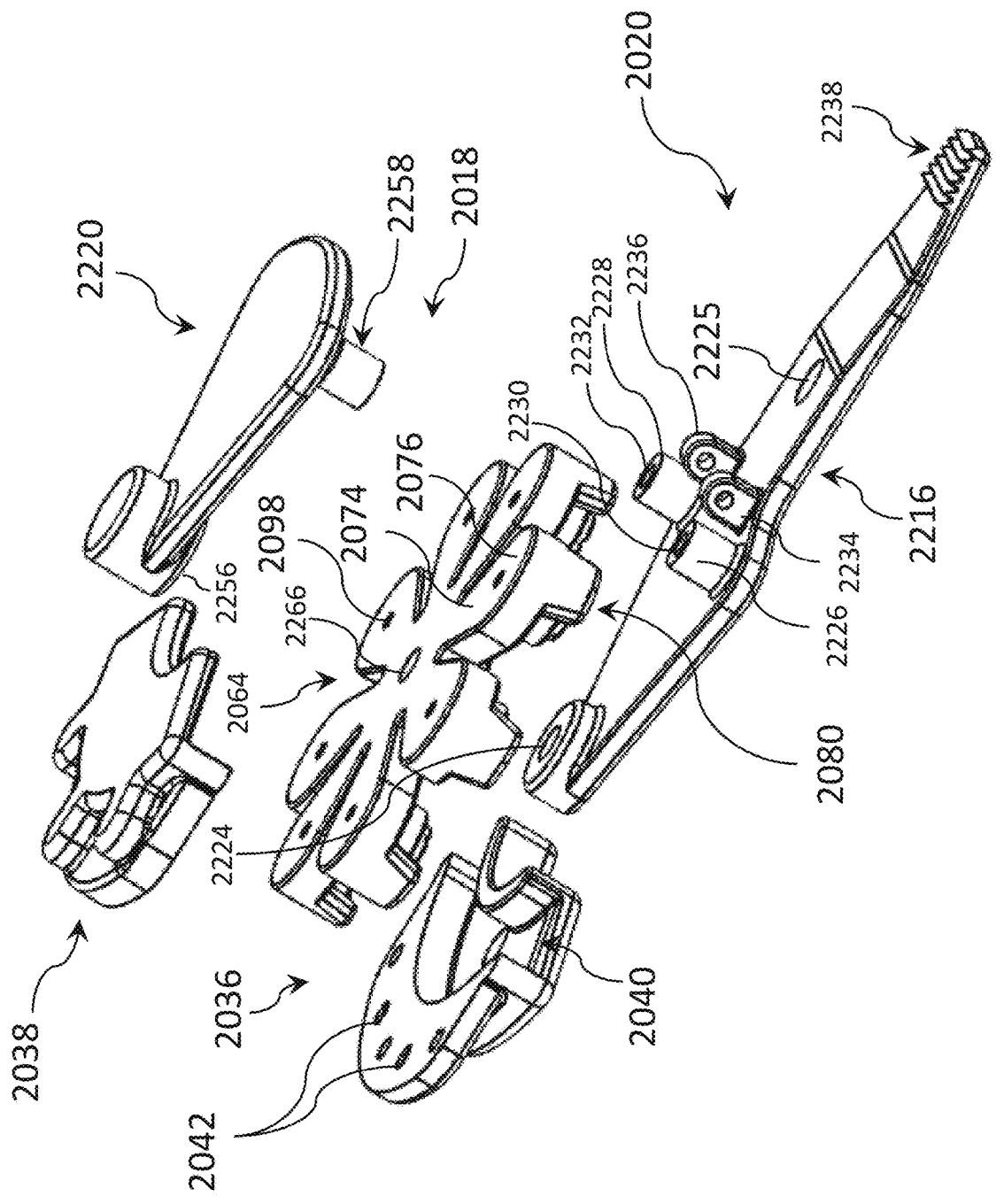
FIG. 50 is a right, isometric, exploded view of the medical holding system of FIG. 43, illustrating the rotor and the separate components of the retainer and holder.
Figure 51:
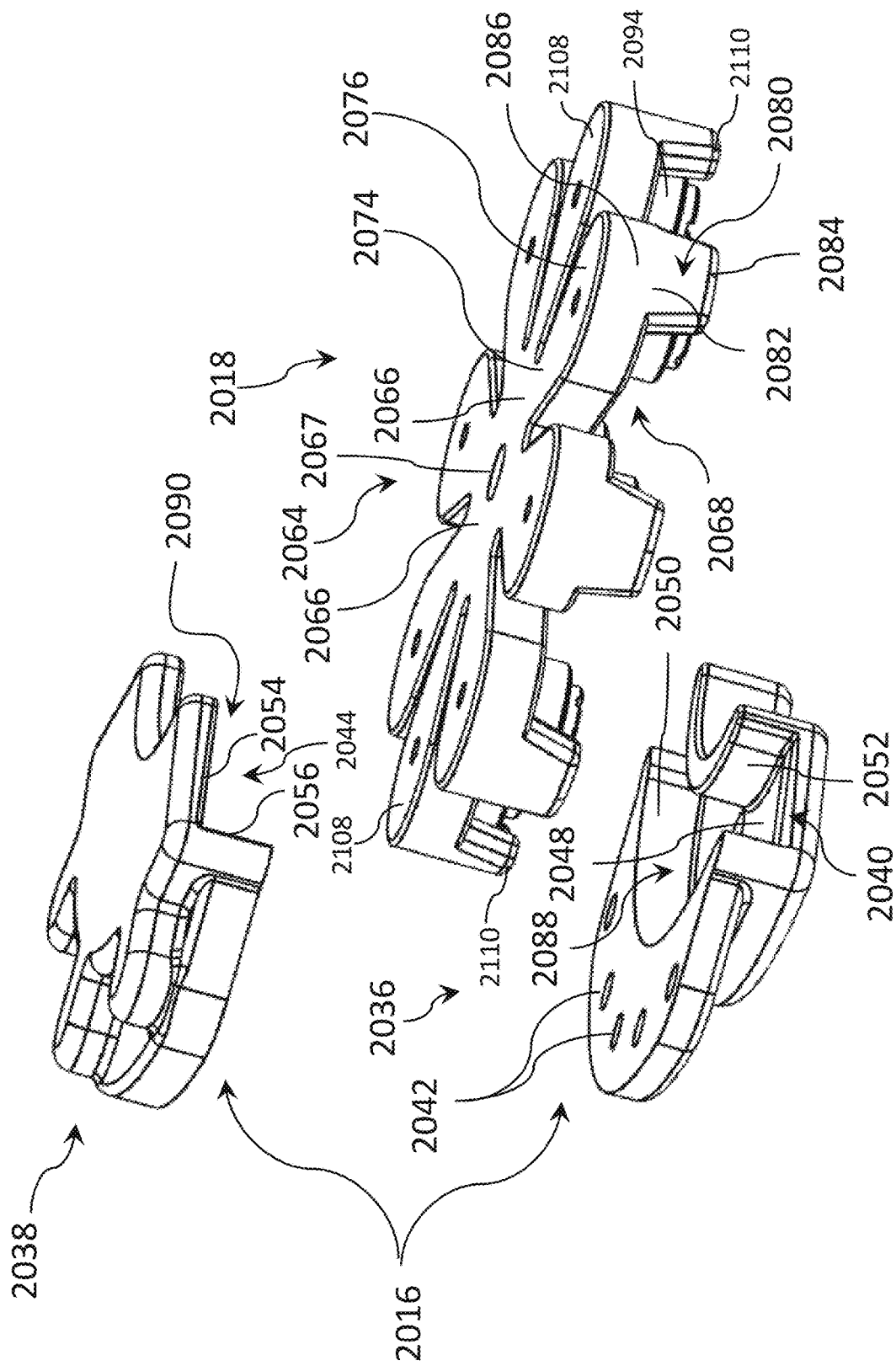
FIG. 51 is a top, right, isometric, exploded view of the medical holding system of FIG. 43, illustrating the rotor separated from the top and bottom retainer portions.
Figure 52:
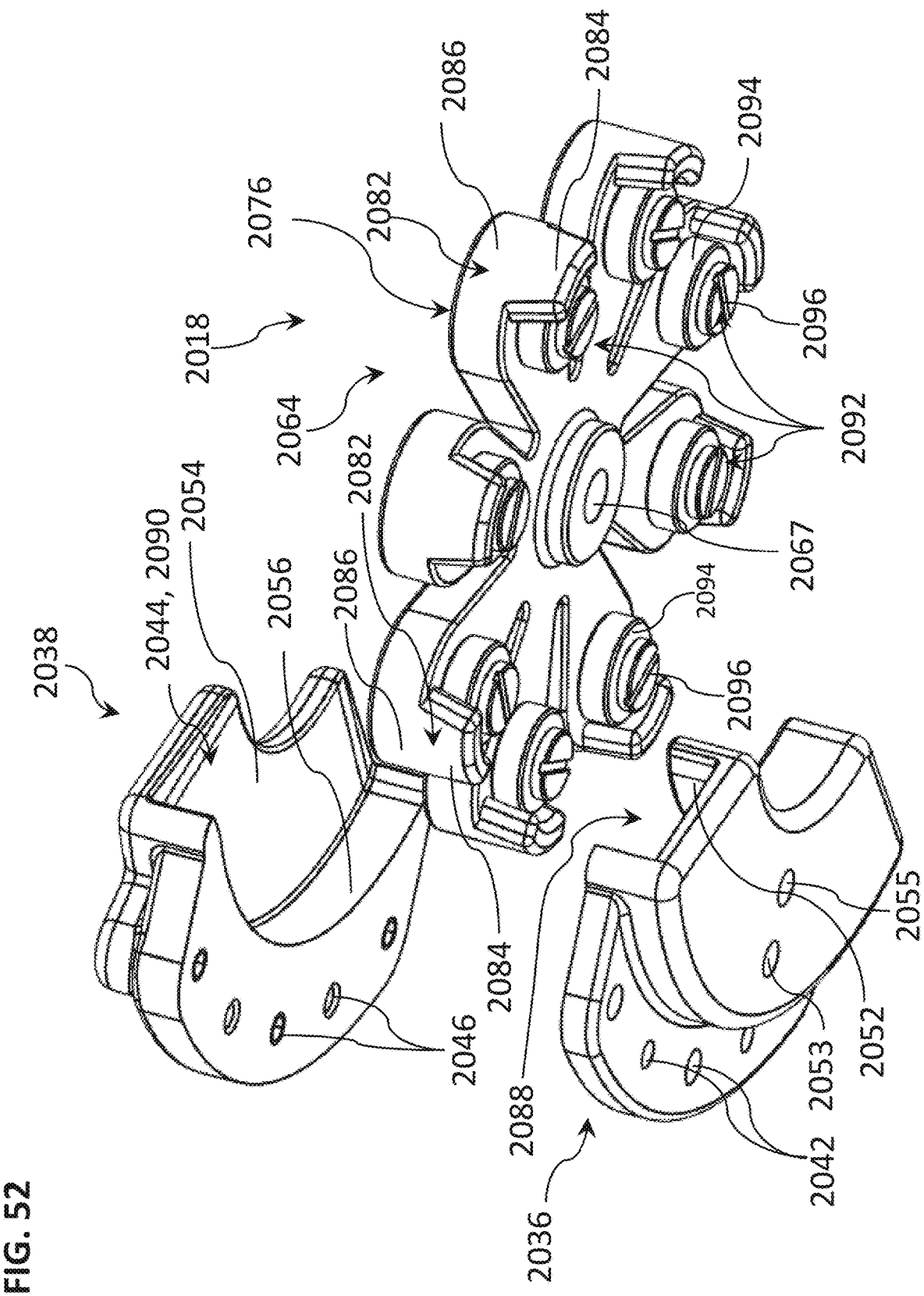
FIG. 52 is a bottom, right, isometric, exploded view of the medical holding system of FIG. 43, illustrating the rotor separated from the top and bottom retainer portions.

Referring to FIGS. 47-54, the retainer 2016, in an embodiment, includes a bottom retainer portion 2036 and a top retainer portion 2038. The bottom retainer portion 2036 has a bottom retainer interface 2040. As shown in FIGS. 50-51, the bottom retainer portion 2036 defines a plurality of pilot, lower fastening openings 2042. As shown in FIG. 52, the top retainer portion 2038 has a top retainer interface 2044, and the top retainer portion 2038 defines a plurality of threaded, upper fastening openings 2046.

Figure 53:
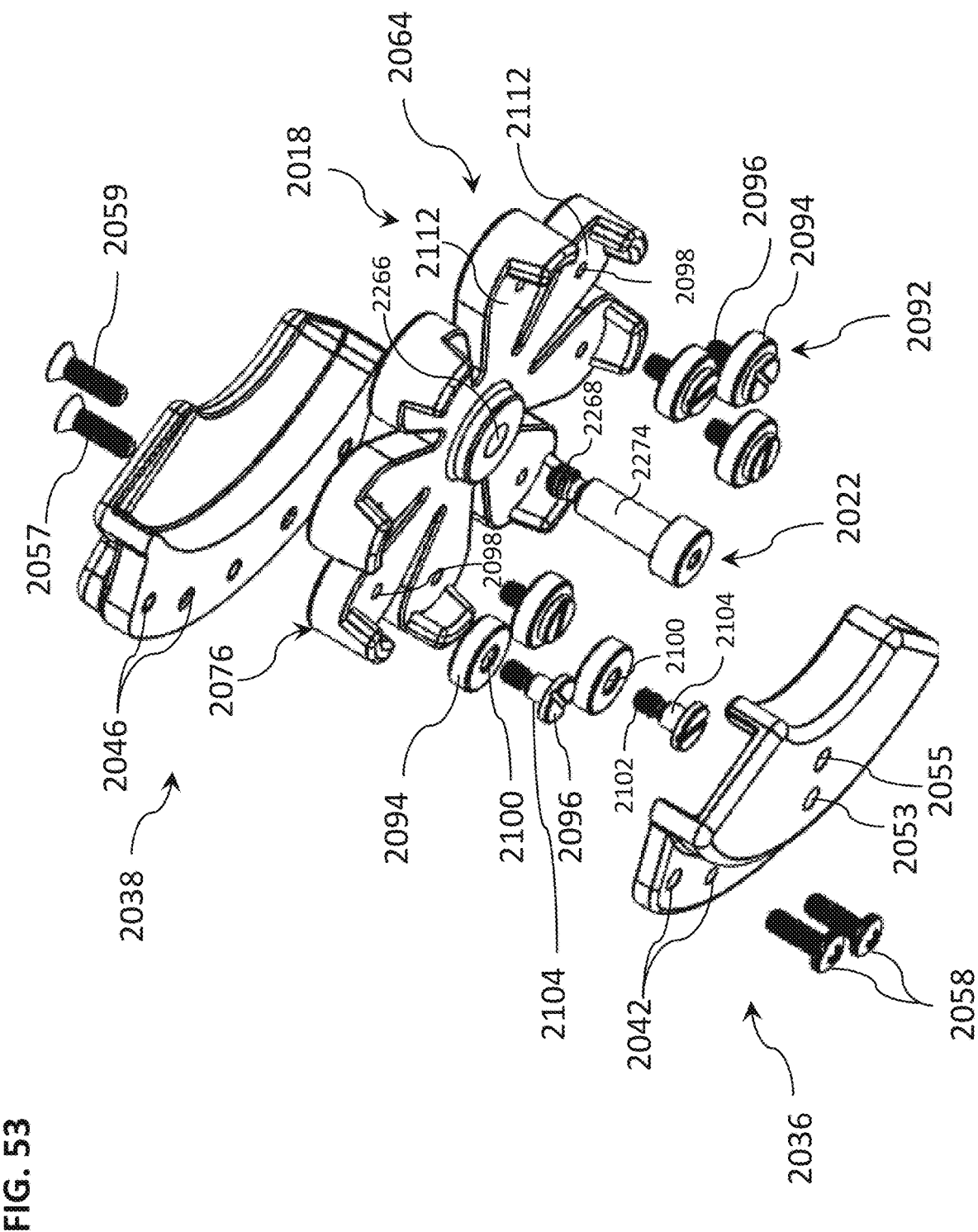
FIG. 53 is a bottom, right, isometric, exploded view of the medical holding system of FIG. 43, illustrating the pivot member, rollers and rotor separated from the top and bottom retainer portions.

As shown in FIG. 51, the bottom retainer interface 2040 includes a floor or bottom retainer surface 2048 and a plurality of bottom side retainer surfaces 2050, 2052 that extend from the bottom retainer surface 2048. As shown in FIG. 53, the bottom retainer surface 2048 defines a plurality of support mount openings 2053, 2055 configured to receive a plurality of support fasteners 2057, 2059, respectively.

Referring to FIG. 49, in an embodiment, each of the mount openings 2053, 2055 is countersunk so that the heads of the support fasteners 2057, 2059 do not interfere with the rotor 2064. After inserting the support fasteners 2057, 2059 through the bottom retainer surface 2048, the assembler can insert the support fasteners 2057, 2059 into the threaded support openings 2063, 2065, respectively. Then, the assembler can rotate and tighten the support fasteners 2057, 2059 to secure the bottom retainer portion 2036 to the upright support 2116.

As shown in FIG. 49, the retainer 2016 also has a plurality of retainer fasteners 2058. Depending on the embodiment, the retainer fasteners 2058 can include threaded screws, threaded bolts, pins or other suitable connectors. An assembler can insert the retainer fasteners 2058 through the lower fastening openings 2042 and into the upper fastening openings 2046. By screwing the retainer fasteners 2058 into the bottom retainer portion 2036, the assembler can unite the bottom and top retainer portions 2036, 2038.

Figure 54:
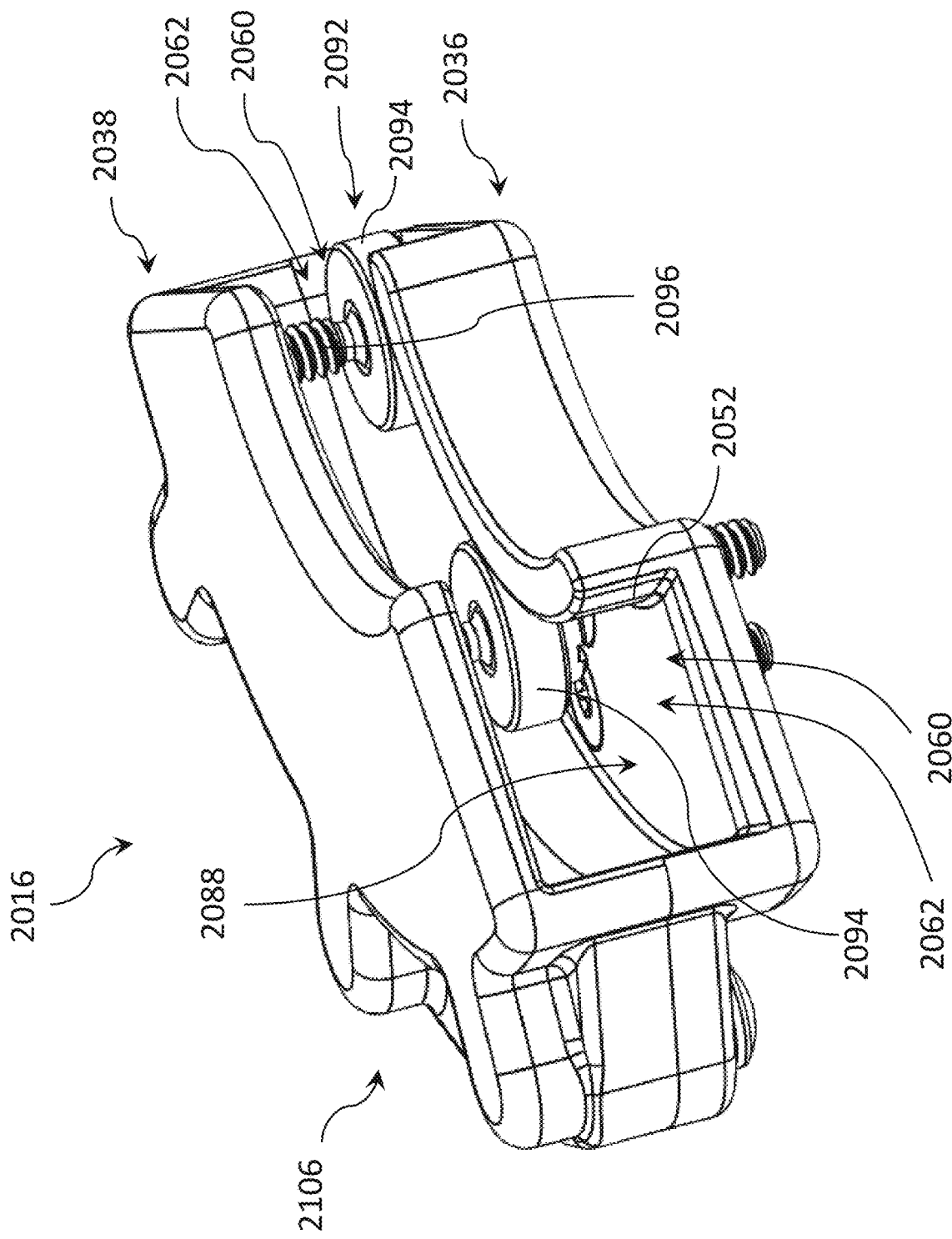
FIG. 54 is a right isometric view of the retainer of the medical holding system of FIG. 43.

As shown in FIGS. 51-52, the top retainer interface 2044 includes a ceiling or top retainer surface 2054 and a top side retainer surface 2056 extending from the top retainer surface 2054. Referring to FIG. 54, when the bottom and top retainer portions 2036, 2038 are united, the bottom and top retainer portions 2036, 2038 collectively define a retainer channel 2060. The retainer channel 2060 has an arc shape 2062.

Figure 55:
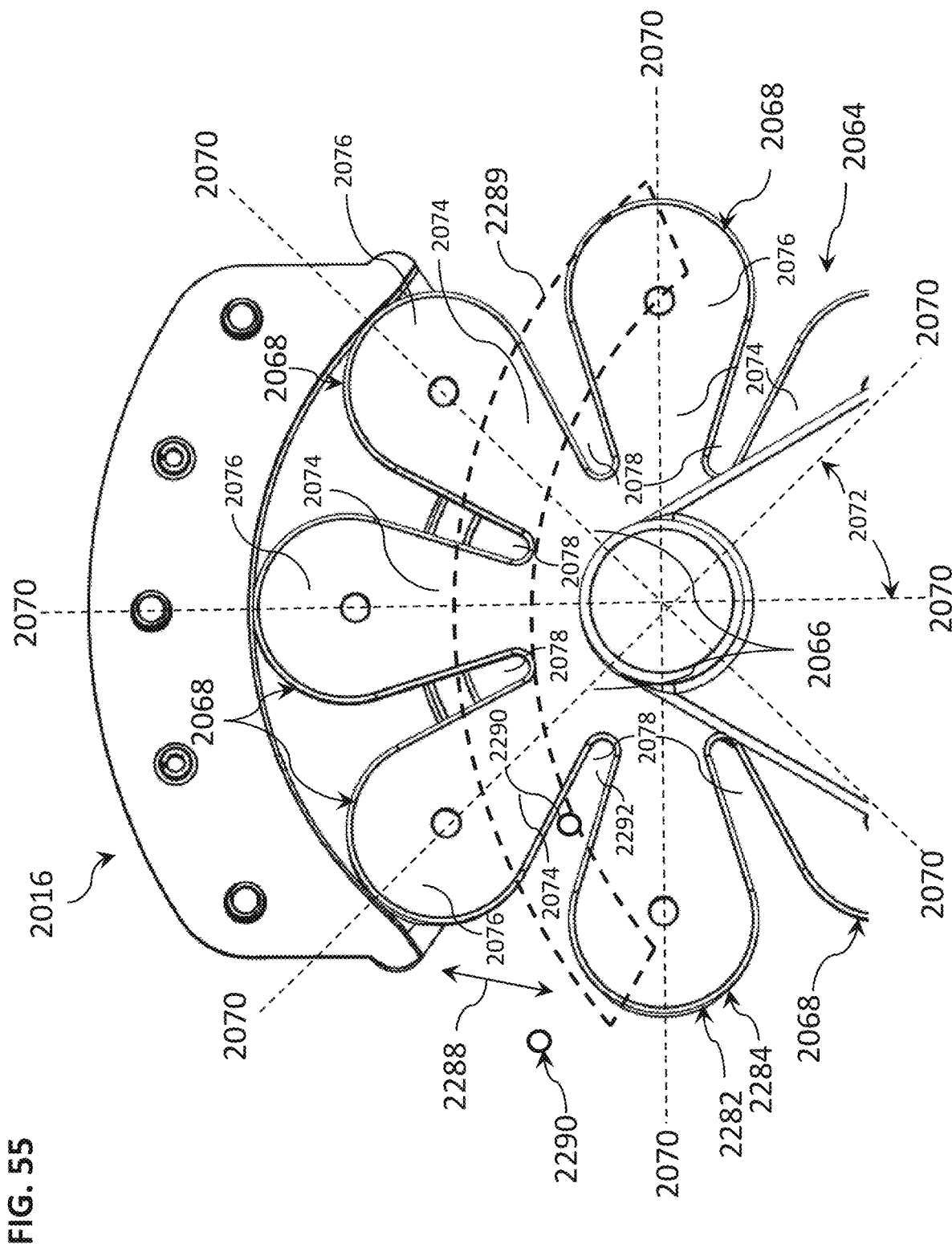
FIG. 55 is a top view of the medical holding system of FIG. 43, illustrating the rotor, illustrating an entry space.
Figure 56:
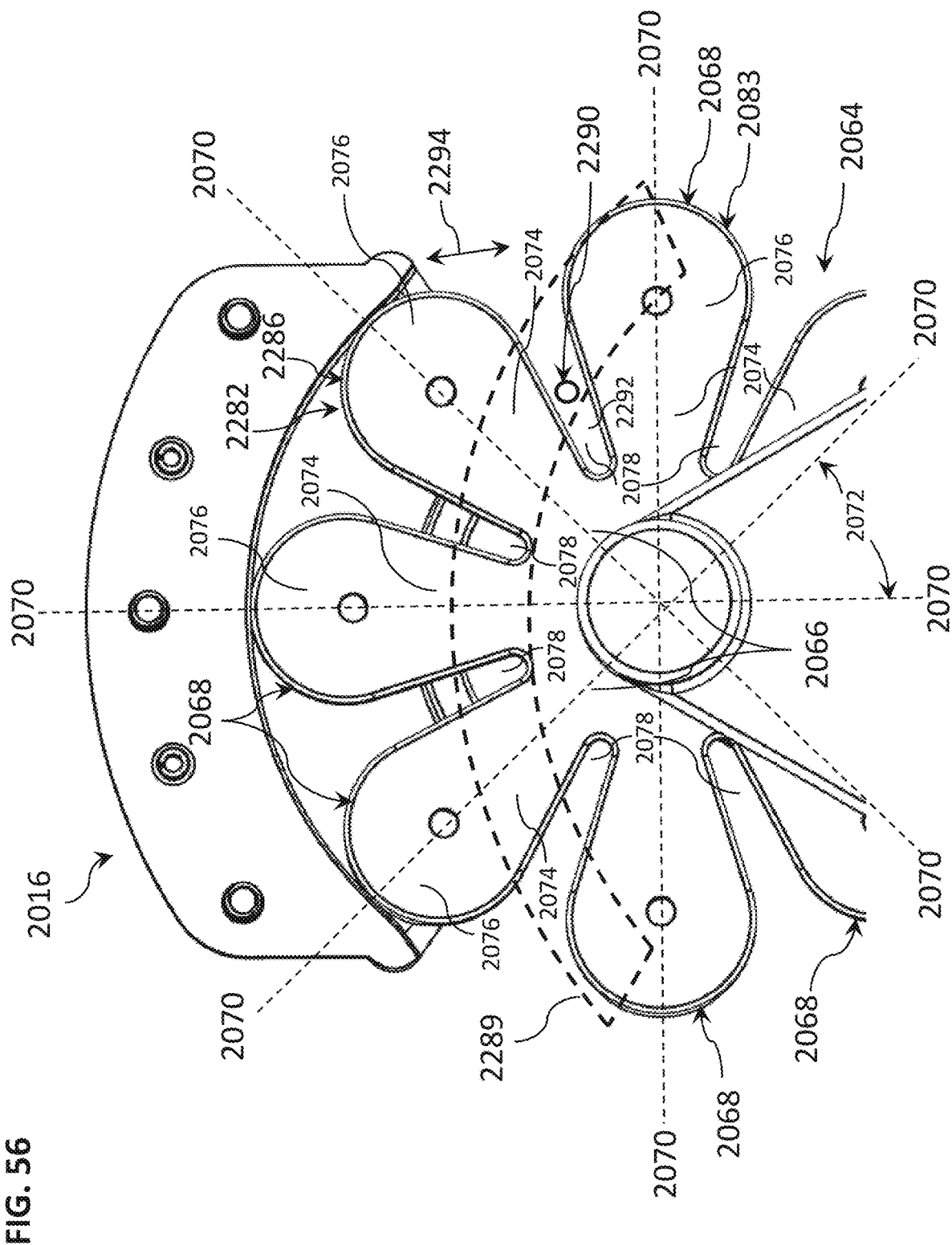
FIG. 56 is a top view of the medical holding system of FIG. 43, illustrating the rotor, illustrating an outlet space.

Referring to FIGS. 55-56, in the embodiment shown, the pivot device 2018 includes a rotor 2064. The rotor 2064 has a central rotor portion 2066 and a plurality of arms 2068 extending from the central rotor portion 2066. The rotor 2064 also defines a central opening 2266 (shown in FIG. 53) positioned in the center of the central rotor portion 2066. In this embodiment, there are eight arms 2068. Each of the arms 2068 radially extends from the central rotor portion 2066 along a radial axis 2070. Each pair of radial axes 2070 are separated by angle 2072. In this embodiment, the angles 2072 are the same, and the rotor 2064 is symmetric relative to a vertical plane extending through the center of the central rotor portion 2066. It should be appreciated, however, that the rotor 2064 can have more than or less than eight arms 2068, and the angles 2070 can be identical or they can differ from each other.

Each of the arms 2068 has: (a) a proximal or first arm portion 2074; and (b) a distal or second arm portion 2076 that is connected to or extends from the first arm portion 2074. The first arm portions 2074 of the arms 2068 are at least partially separated by a cord transport space 2078. In this embodiment, the cord transport space 2078 has a U-shape.

Referring to FIG. 51, the second arm portion 2076 of each of the arms 2068 has an arm interface 2080. The arm interface 2080 is configured to interlock with, inter-fit with, mate with otherwise engage with the bottom and top interfaces 2040, 2044 of the retainer 2016. Each of the arm interfaces 2080 has an arm guide 2082. The arm guide 2082 has a lower guide portion 2084 and an upper guide portion 2086. The lower guide portion 2084 is configured to point downward and fit, at least partially, into the lower cavity 2088 of the retainer channel 2060 shown in FIG. 54. In particular, the bottom retainer surface 2048 and bottom side retainer surfaces 2050, 2052 define a female shape of the lower cavity 2088. The lower guide portion 2084 defines a male shape so that the lower guide portion 2084 is configured to mate with the lower cavity 2088 in a male-female relationship.

With continued reference to FIG. 51, the upper guide portion 2086 is configured to extend and fit into the upper cavity 2090 of the retainer channel 2060 shown in FIG. 54. In particular, the top retainer surface 2054 and top side retainer surface 2056 define a female shape of the upper cavity 2090. The upper guide portion 2086 defines a male shape so that the upper guide portion 2086 is configured to mate with the upper cavity 2090 in a male-female relationship.

Also, referring to FIG. 52, the second arm portion 2076 of each of the arms 2068 has a friction reducer 2092. Depending on the embodiment, the friction reducer 2092 can include a layer, sheet or other member constructed of a material that has a friction reduction characteristic or a relatively low coefficient of friction, including, but not limited to, graphite, nylon, an acetal plastic, Teflon™, or a polymer having a PFTE (Polytetrafluoroethylene) additive or graphite additive. Such member can be non-moveably secured, fixed or attached to the arm guide 2082 or any other part of the second arm portion 2076, or such member can be unitarily incorporated into the arm guide 2082. Alternatively, the friction reducer 2092 can include a motion interface device, including, but not limited to, a bearing, wheel, ball, roller or other type of part that is configured to spin, roll, rotate or otherwise move relative to the second arm portion 2076.

In the illustrated embodiment, the friction reducer 2092 includes a roller 2094 and a roller pivot member 2096. Referring to FIG. 53, each of the rollers 2094, configured as a wheel or ring, has a circular shape that defines a central opening 2100 configured to receive one of the roller pivot members 2096. Each of the second arm portions 2076 defines an arm opening 2098 configured to at least partially receive the roller pivot member 2096.

As illustrated in FIG. 53, an assembler can install a roller 2094 on a second arm portion 2076 by inserting the roller pivot member 2096 through the central opening 2100 and then inserting the roller pivot member 2096 into the arm opening 2098. The fastening end 2102 of the roller pivot member 2096 has a threaded surface, and the second arm portion 2076 has an inner threaded surface that defines the arm opening 2098. The pivot portion 2104 of the roller pivot member 2096 has a relatively smooth outer surface and a diameter that is greater than, and blocks entry into, the arm opening 2096. The pivot portion 2104 has a length so that, when the roller pivot member 2096 is fully screwed into the arm opening 2098, there is a gap between the roller 2094 and the associated second arm portion 2076. This gap enables the roller 2094 to freely rotate relative to the second arm portion 2076.

Referring to FIG. 52, when installed on the associated second arm portion 2076, the roller 2094 is positioned adjacent to, and radially inward from, the associated arm guide 2082. Put another way, the roller 2094 on the second arm portion 2076 is positioned closer to the central opening 2067 than the arm guide 2082 on the same second arm portion 2076. With the rollers 2094 installed on the arms 2068, an assembler can insert one, two or three of the second arm portions 2076 into the lower cavity 2088 of the bottom retainer portion 2036. Next, the assembler can place the top retainer portion 2038 so as to cover such second arm portions 2076.

Next, referring to FIG. 53, the assembler can insert each of the retainer fasteners 2058 through one of the lower fastening openings 2042 and then into the associated upper fastener opening 2046. The assembler can then screw the retainer fasteners 2058 until the top retainer portion 2038 is securely compressed with the bottom retainer portion 2036.

In this compressed or trapping position or trapping arrangement 2106, shown in FIG. 54, the bottom and top retainer portions 2036, 2038 surround and entrap the one, two or three of the second arm portions 2076 that the assembler inserted into the lower cavity 2088. In the trapping arrangement 2106, the retainer 2016 vertically restrains the rotor 2064, and the retainer 2016 radially restrains the rotor 2064. Despite and during this vertical and radial restraining, the retainer 2016 enables the rotor 2064 to be pivoted or rotated relative to the retainer 2016.

Referring to FIG. 51, for the vertical restraining, each second arm portion 2076 has a top arm surface 2108 slightly spaced apart from the top retainer surface 2054. The lower guide portion 2084 has a guide end 2110 that abuts and makes contact with the bottom retainer surface 2048. Therefore, the arm guide 2082 of each arm 2068, when located within the retainer 2016, has a limited degree of translational freedom along a vertical axis 2114 shown in FIG. 41.

With continued reference to FIG. 51, for the radial restraining, the lower guide portion 2084 of each arm 2068 located within the retainer 2016 is positioned so as to be slightly spaced apart from both the bottom outer side retainer surface 2050 and the top side retainer surface 2056. The second arm portion 2076 defines a recessed space 2112 adjacent to, and radially inward from, the lower guide portion 2084, as shown in FIG. 53. The roller 2094 is positioned within the recessed space 2112. The guide end 2110 extends downward further than the roller 2094. This spaces the roller 2094 apart from the bottom retainer surface 2048. The lower guide portion 2084 and roller 2094 are positioned on the associated arm 2068 such that the roller 2094 is in contact or engaged (constantly, periodically or intermittently) with the bottom inner side retainer surface 2050 while there is a relatively small gap between: (a) the lower guide portion 2084; and (b) the united bottom outer side retainer surface 2050 and the top side retainer surface 2056. Therefore, the arm guide 2082 and roller 2094 of each arm 2068, when located within the retainer 2016, have a limited degree of translational freedom along a radial axis 2070 shown in FIGS. 41 and 55.

Figure 57A:
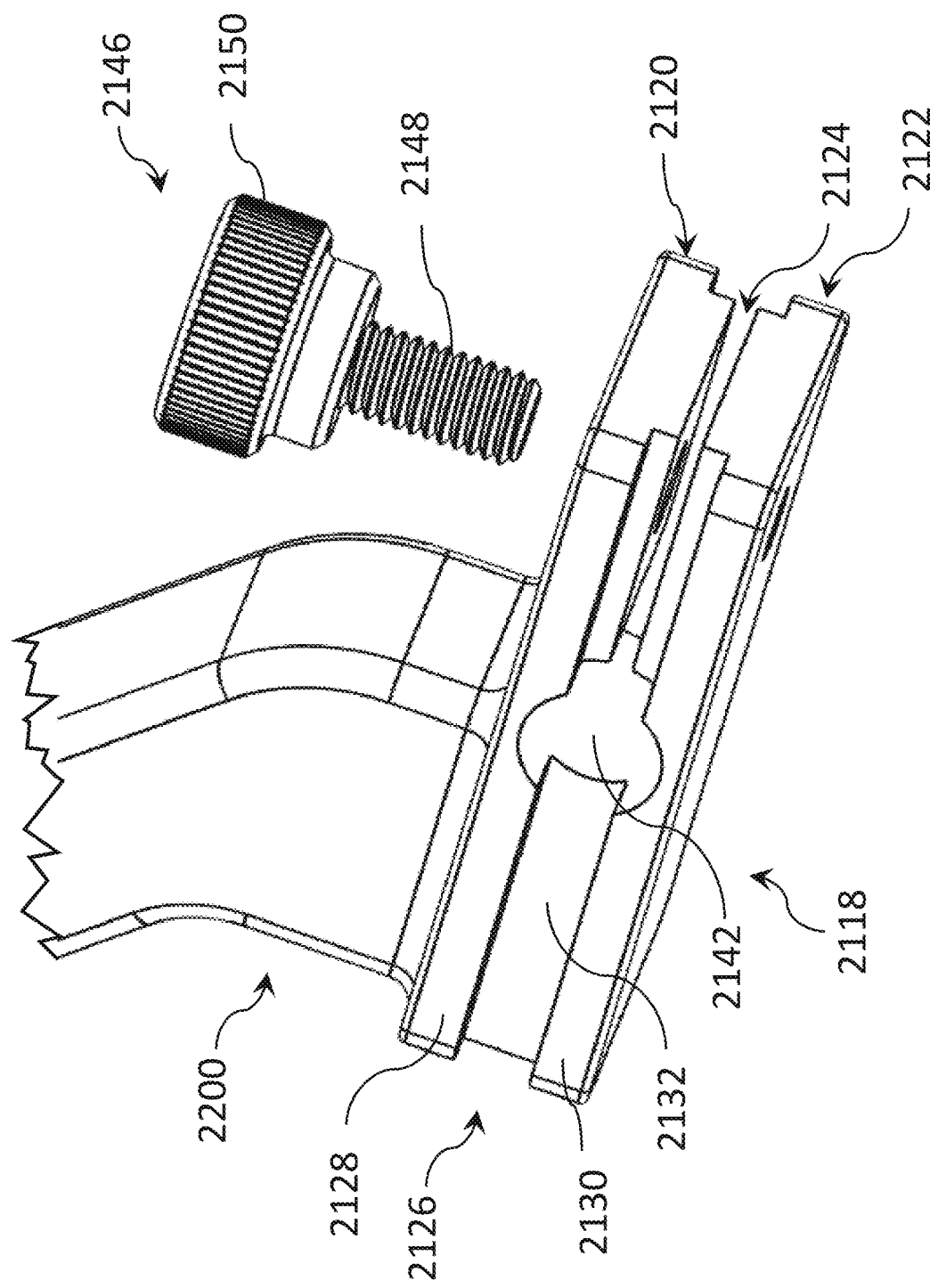
FIG. 57A is a fragmentary, right isometric view of the lower body portion of the upright support of the medical holding system of FIG. 43.
Figure 57B:
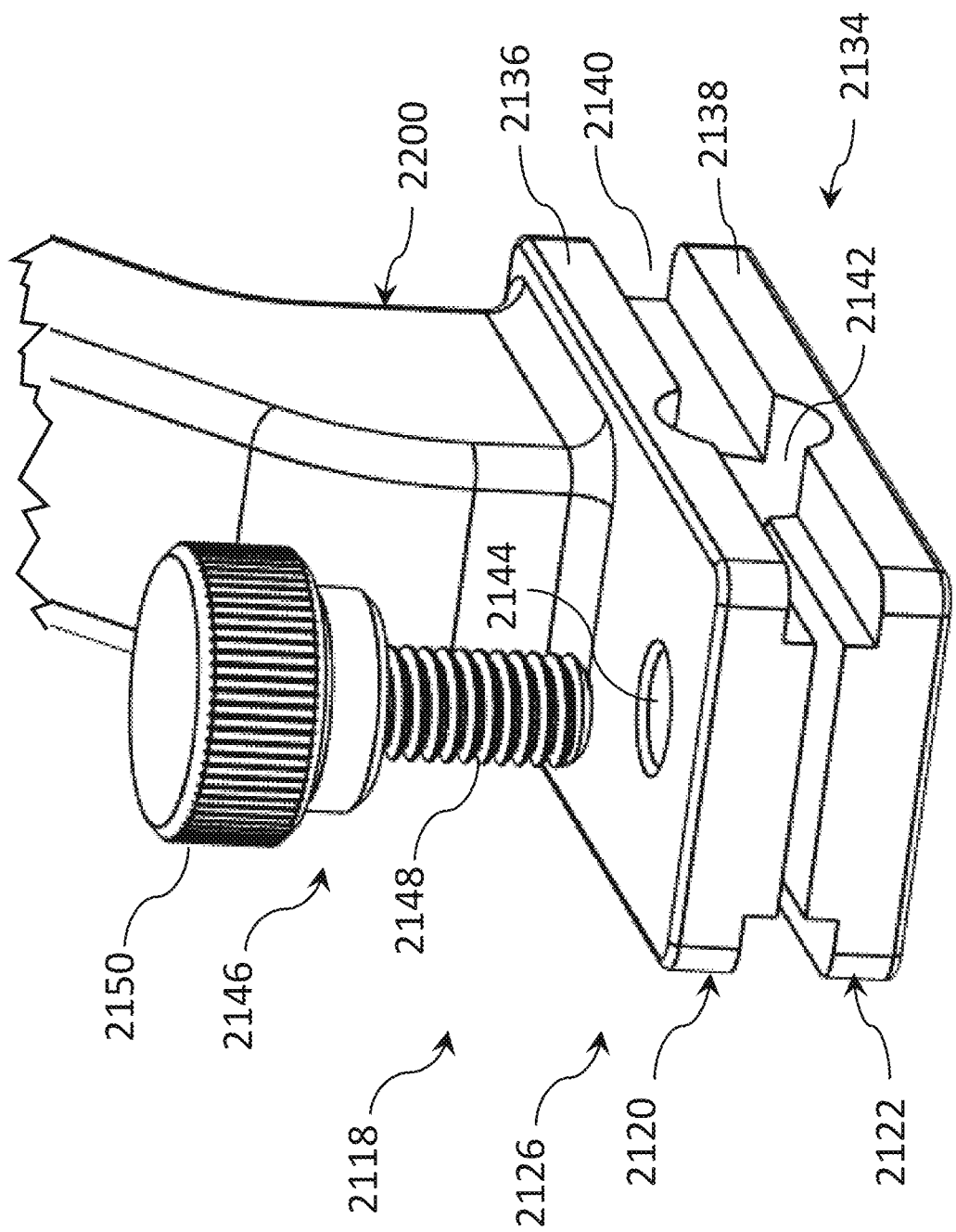
FIG. 57B is a fragmentary, top isometric view of lower body portion of the upright support of the medical preparation station of FIG. 43.

Referring to FIGS. 49 and 57A-57B, the support device 2012 includes an upright support 2116. The upright support 2116 has a mount or foot 2118, a lower body portion 2200 extending upward from the foot 2118, an intermediate or transition body portion 2202 extending upward from the lower body portion 2200, and an extension or neck 2204 extending upward from the transition body portion 2202.

As illustrated in FIG. 57A, the foot 2118 includes an upper foot portion 2120 and a lower foot portion 2122 spaced apart from the upper foot portion 2120 by a flex gap 2124. The side 2126 of the foot 2118 has a plurality of side guides 2128, 2130 that define a recessed side slot 2132. As illustrated in FIG. 57B, the opposite side 2134 of the foot 2118 has a plurality of side guides 2136, 2138 that define a recessed side slot 2140. Also, the foot 2118 defines a channel 2142 that extends entirely from the side 2126 through the side 2134. The channel 2142 is configured to receive or cooperate with a part or component of the preparation station 2028 or support structure 2024.

Figure 40B:
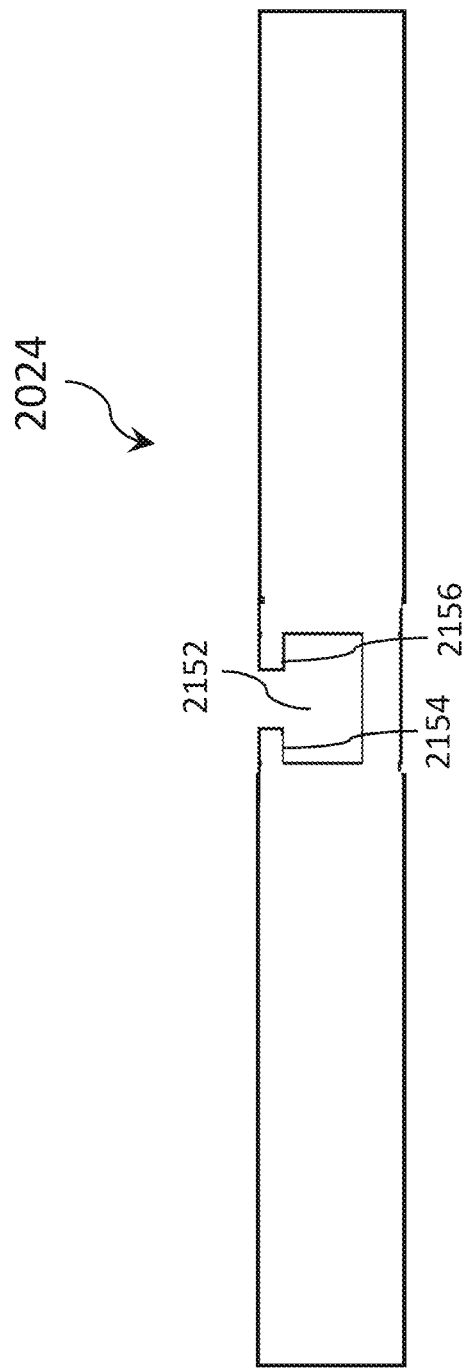
FIG. 40B is a cross-sectional view of the support structure of the medical preparation station of FIG. 40A illustrating the track, taken substantially along line 40B-40B of FIG. 40A.
Figure 41:
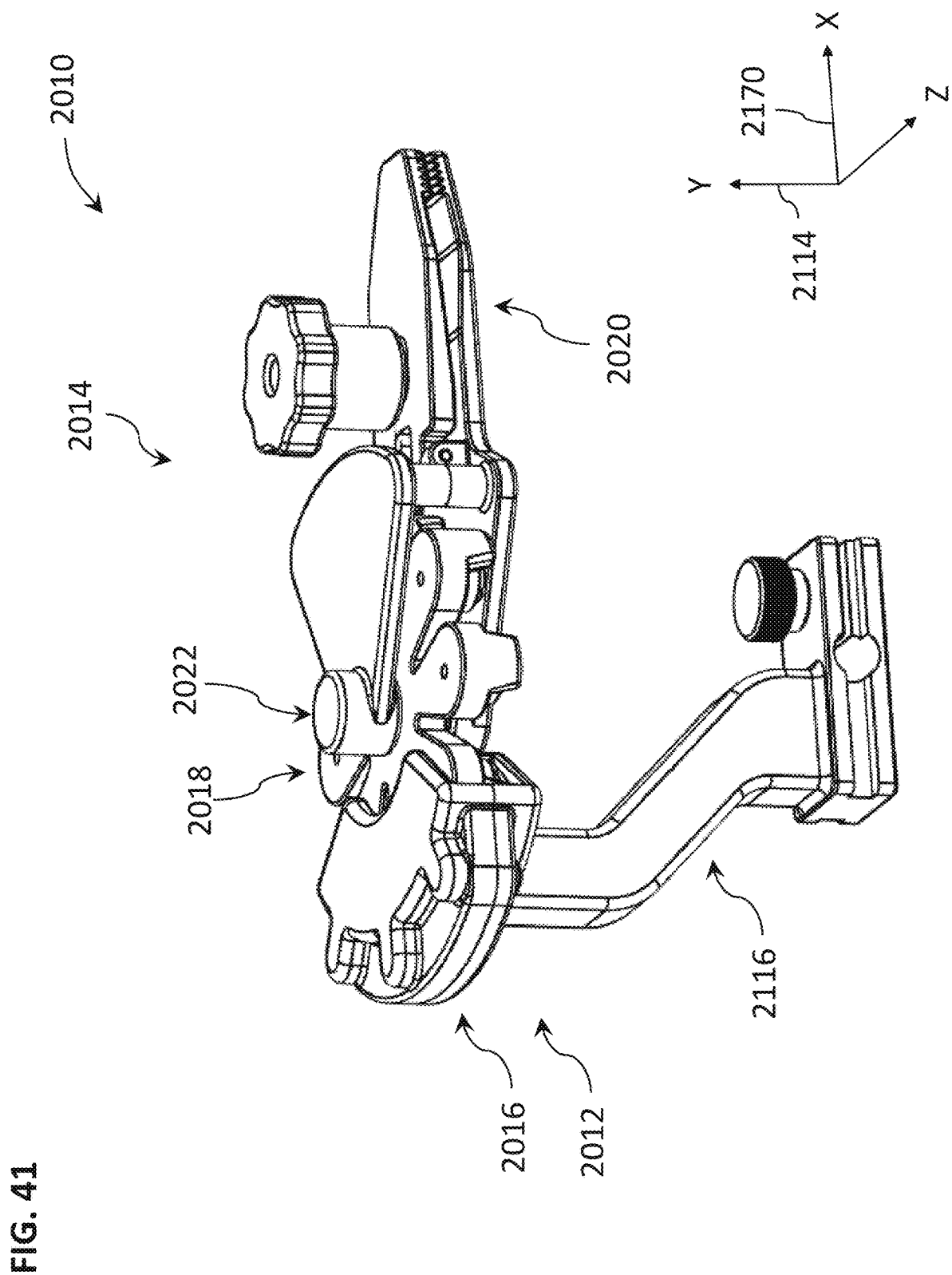
FIG. 41 is a right side, isometric view of the medical holding system of FIG. 40A.
Figure 42:
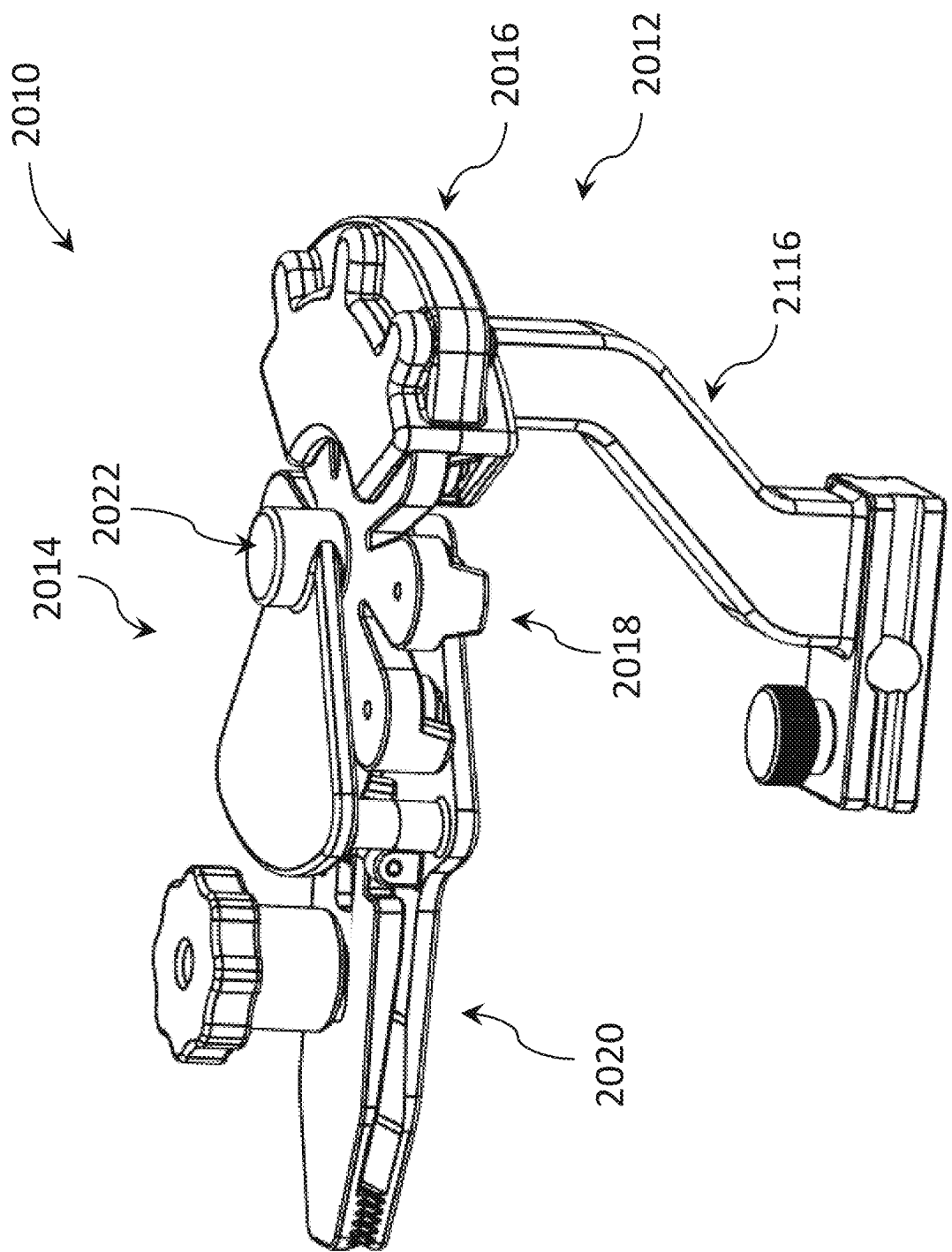
FIG. 42 is a left side, isometric view of the medical holding system of FIG. 40A.
Figure 43:
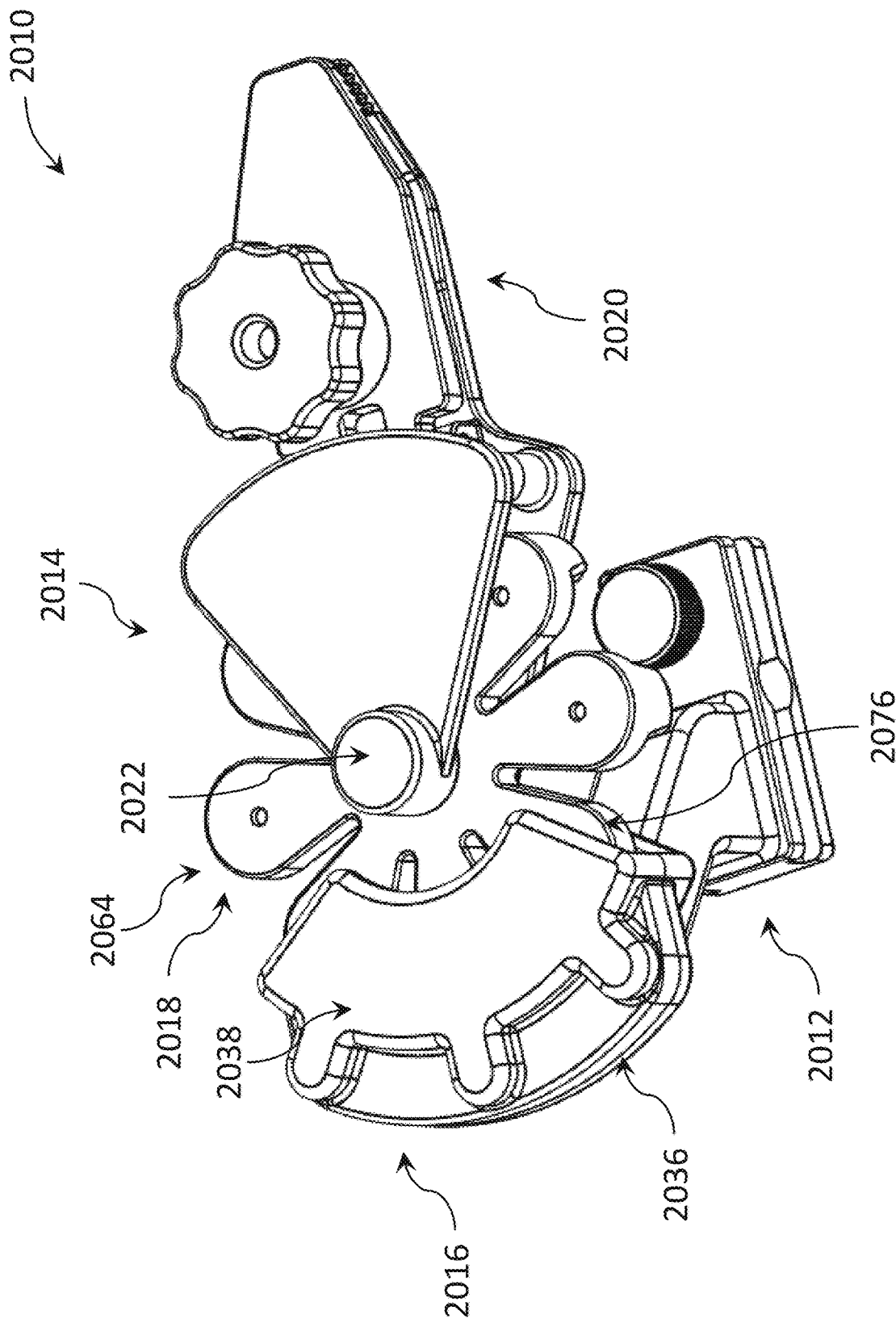
FIG. 43 is a top right, isometric view of the medical holding system of FIG. 43.
Figure 44:
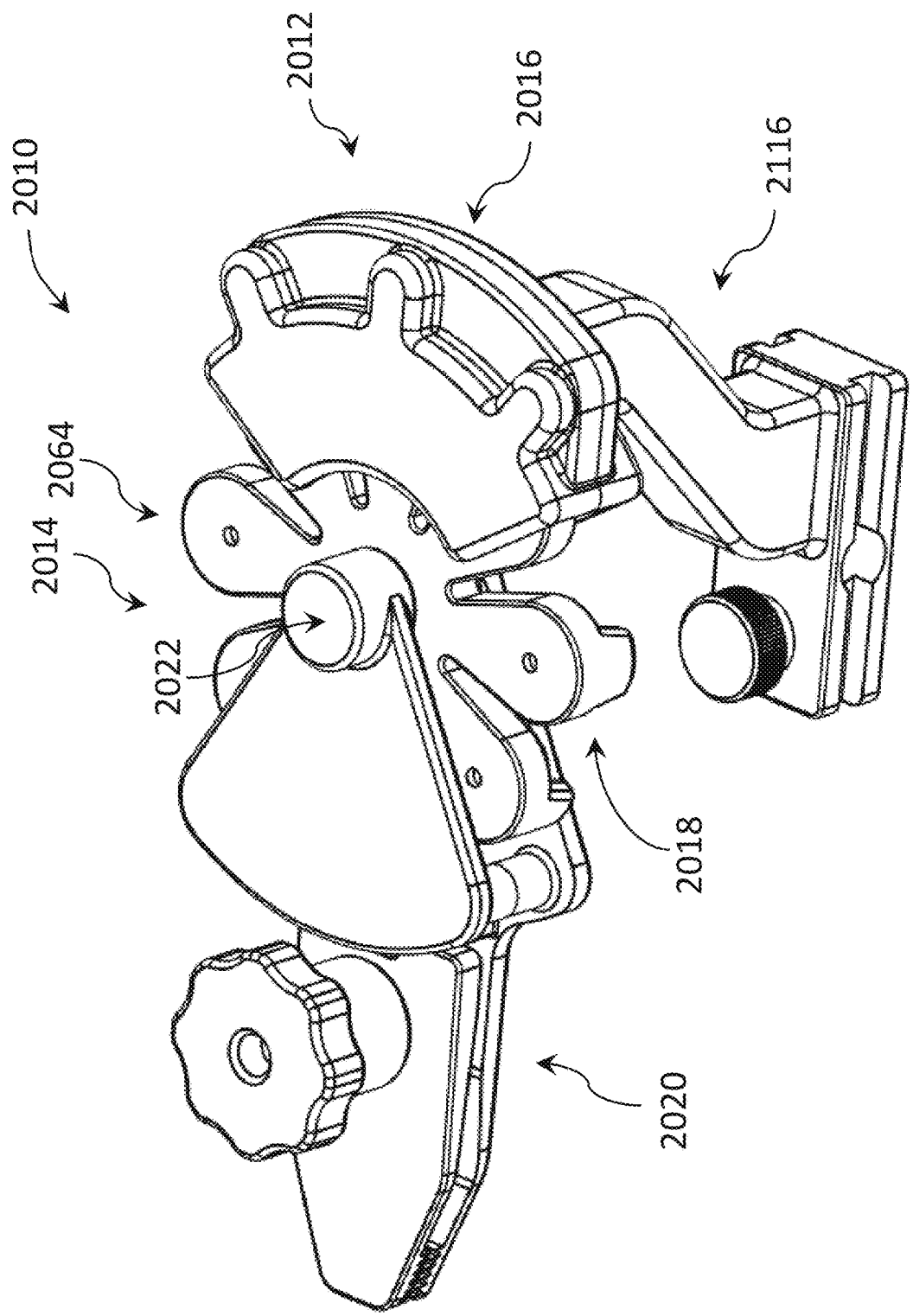
FIG. 44 is a top, left isometric view of the medical holding system of FIG. 43.
Figure 45:
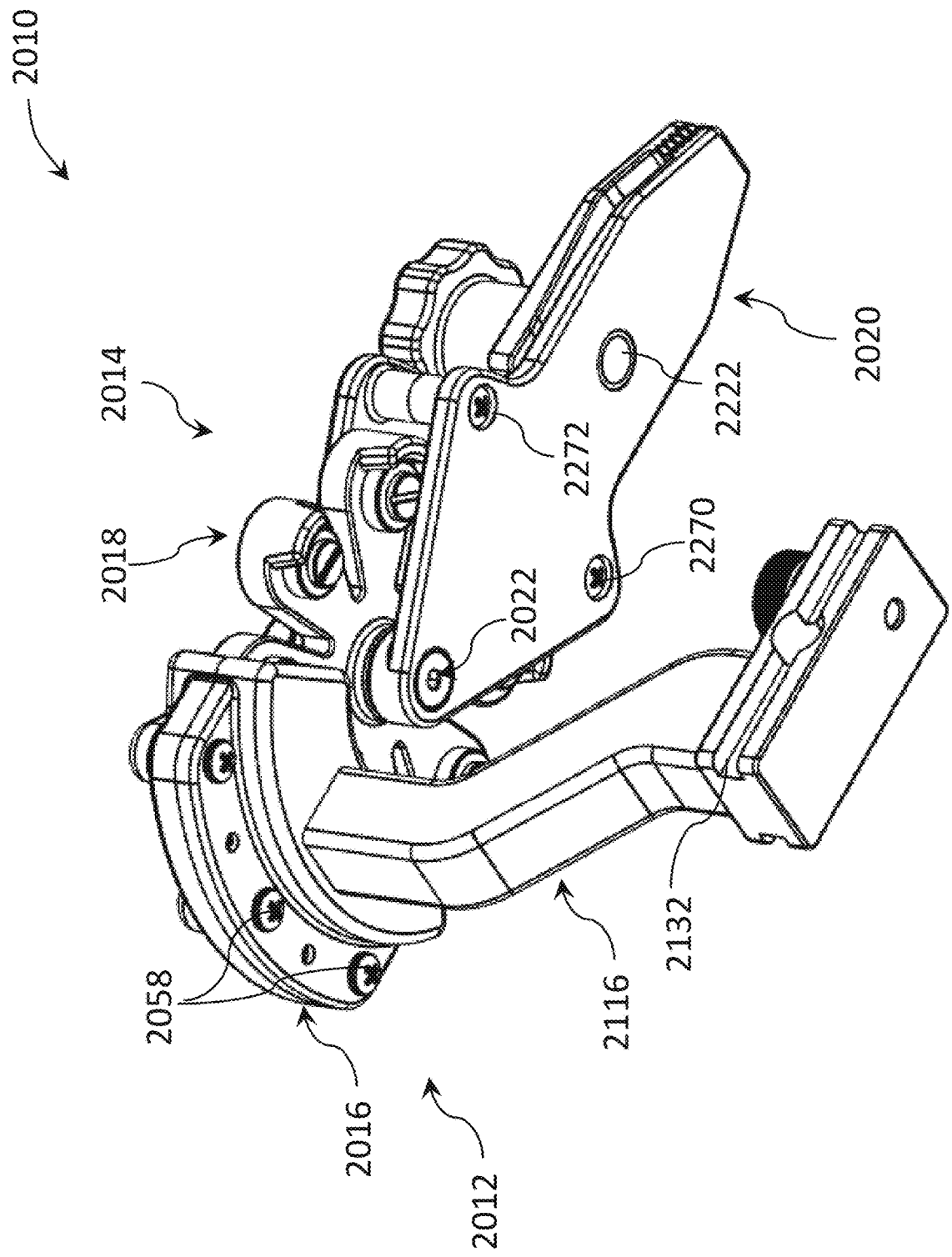
FIG. 45 is a bottom, right isometric view of the medical holding system of FIG. 43.
Figure 46:
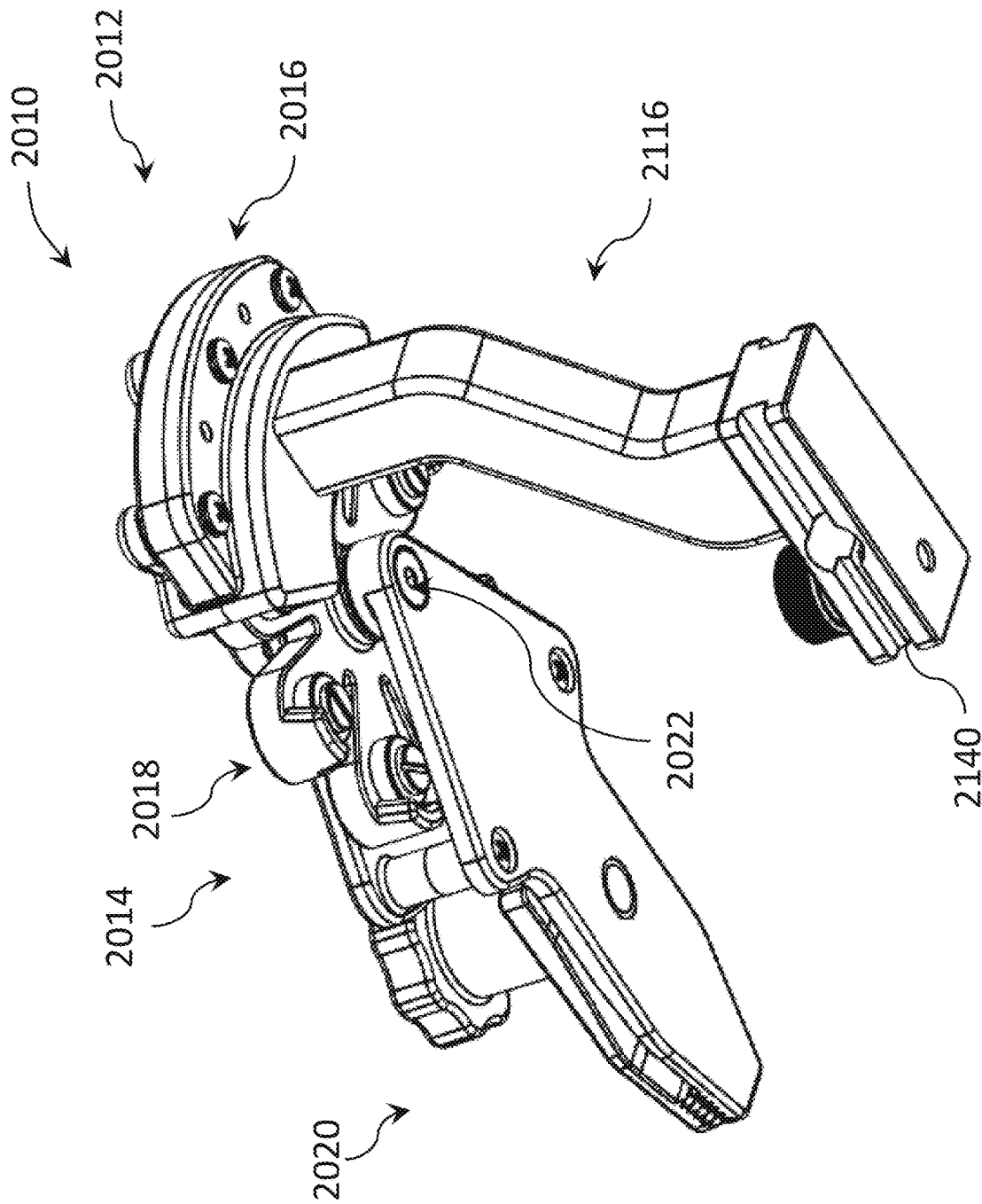
FIG. 46 is a bottom, left isometric view of the medical holding system of FIG. 43.

The foot 2118 also defines a threaded foot securement opening 2144 that extends through the upper and lower foot portions 2120, 2122. The foot 2118 includes a foot securement device 2146 having a threaded section 2148 and a foot grasp or foot knob 2150. The foot 2118 is configured to be slideably engaged with the support structure 2024. Referring to FIGS. 40A-40B, the support structure 2024 defines: (a) an entry valley 2151 configured and sized to receive the upper and lower foot portions 2120, 2122; and (b) a valley or track 2152 configured to at least partially receive the lower foot portion 2122. The track 2152 has a width that is less than the width of the entry valley 2151. The support structure 2024 has a plurality of linear notches or edges 2154, 2156 protruding from the side walls that at least partially define the track 2152.

An assembler or user can insert the upper and lower foot portions 2120, 2122 into the entry valley 2151 of the support structure 2024. Next, referring to FIGS. 40A, 40B and 57B, the assembler or user can slide the foot 2118 so that the side slots 2132, 2140 receive the edges 2154, 2156, respectively. Once the assembler or user positions the foot 2118 at the desired location, the assembler or user can rotate the foot knob 2150. The rotation of the foot knob 2150 causes the upper and lower foot portions 2120, 2122 to flex and move toward each other, narrowing the flex gap 2124, clamping onto, and compressing, the edges 2154, 2156. Once the foot knob 2150 is fully tightened, the foot 2118 will be secured to the support structure 2024.

As shown in FIG. 49, the lower body portion 2200 extends along a front vertical axis 2206, and the neck 2204 extends along a rearward vertical axis 2208. The transition body portion 2202 is slanted, extending along a slanted axis 2243 at an angle 2245 to transition the upright support 2116 from the front vertical axis 2206 to the rearward vertical axis 2208. As described below, the transition body portion 2202 functions as an adapter for the station 2028 by locating the grasper 2020 at a rearward distance from the first element portion 2032, shown in FIG. 40A, as if the retainer 2016 and pivot device 2018 were not present.

Figure 58A:
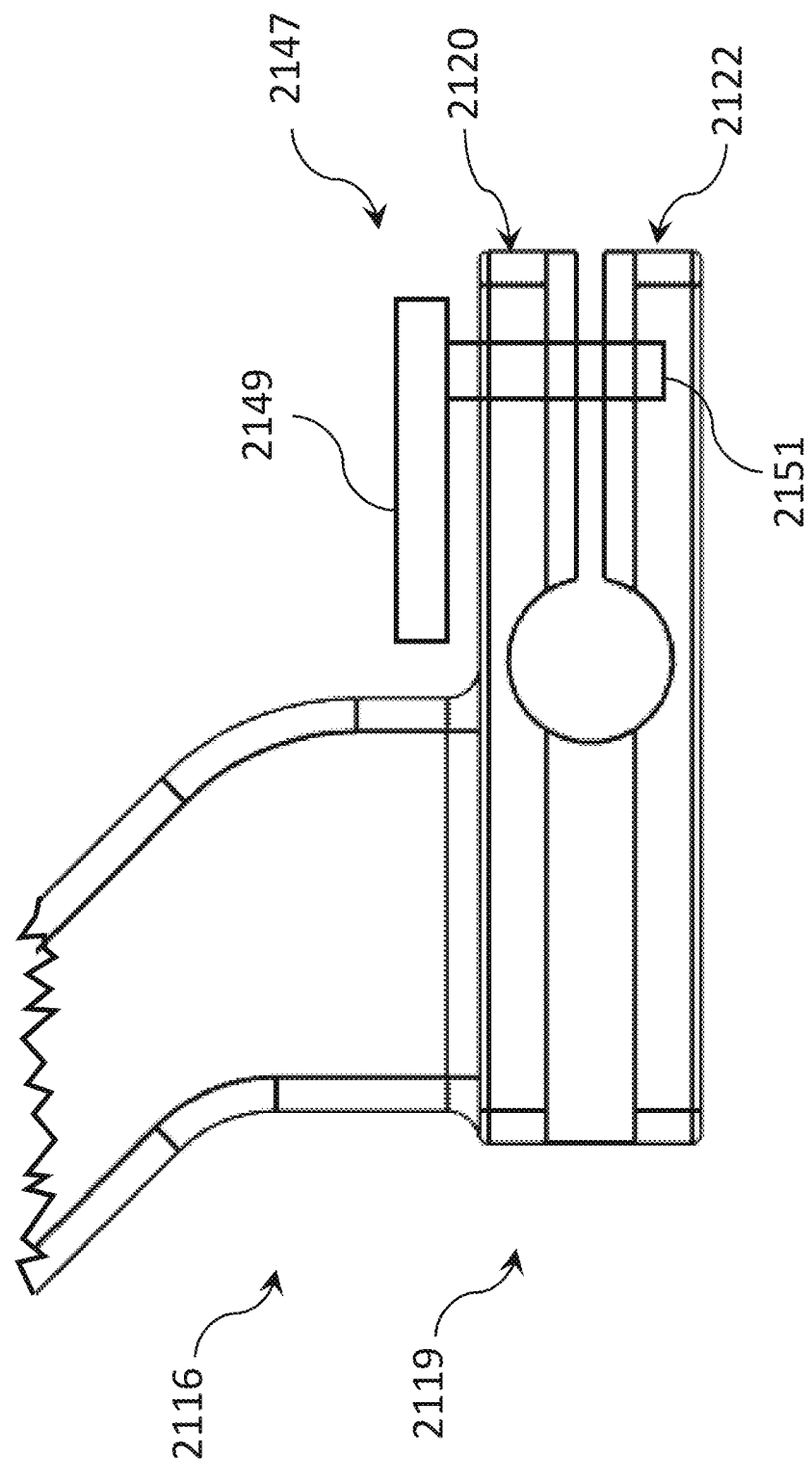
FIG. 58A is a fragmentary, side elevation view of an embodiment of an upright support that is usable as part of the medical holding system of FIG. 43.
Figure 58B:
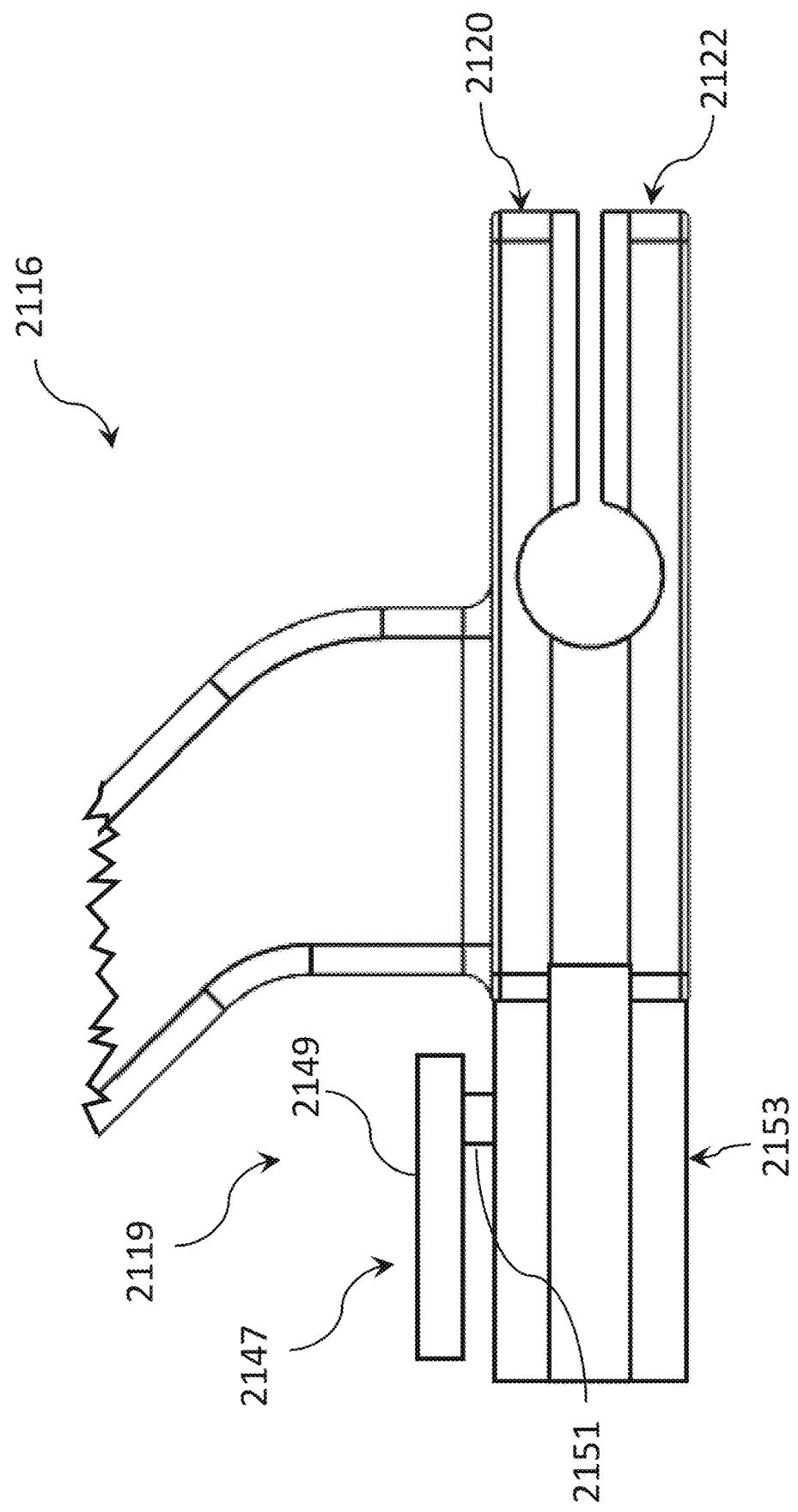
FIG. 58B is a fragmentary, side elevation view of another embodiment of an upright support that is usable as part of the medical holding system of FIG. 43.

Referring to FIGS. 58A-58B, in an embodiment, the upright support 2116 has a mount or foot 2119. The foot 2119 has the same structure, characteristics, shape, configuration and function as the foot 2118 except the foot 2119 has a securement device 2147 instead of the securement device 2146. The securement device 2147 includes: (a) a latch, lever or securement arm 2149; and (b) a shaft, pin or drive member 2151 coupled to the securement arm 2149. Depending on the embodiment, the drive member 2151 can include a threaded portion, a cam-shaped portion, a gear or any other structure configured to spread apart the upper and lower foot portions 2120, 2122 to fixedly secure the foot 2119 to the support structure 2024. In operation, the user pivots or rotates the securement arm 2149 relative to the upright support 2116. The pivoting action can include a movement through a range of less than ninety degrees, less than one hundred eighty degrees or less than three hundred sixty degrees. After moving the securement arm 2149 to a secure or lock position, the foot 2119 is secured to the support structure 2024. In the embodiment shown in FIG. 58B, the securement device 2147 is coupled to a rear portion 2153 of the foot 2119. In this position, the securement device 2147 functions the same as described above with respect to FIG. 58A. In another embodiment, the securement device 2147 is moveable between a plurality of up and down positions along a vertical axis. In response to an upward pull on the securement arm 2149, the drive member 2151 enables the foot 2119 to slide or move relative to the support structure 2024. In response to a downward push on the securement arm 2149, the drive member 2151 secures the foot 2119 at a desired location relative to the support structure 2024.

Figure 58C:
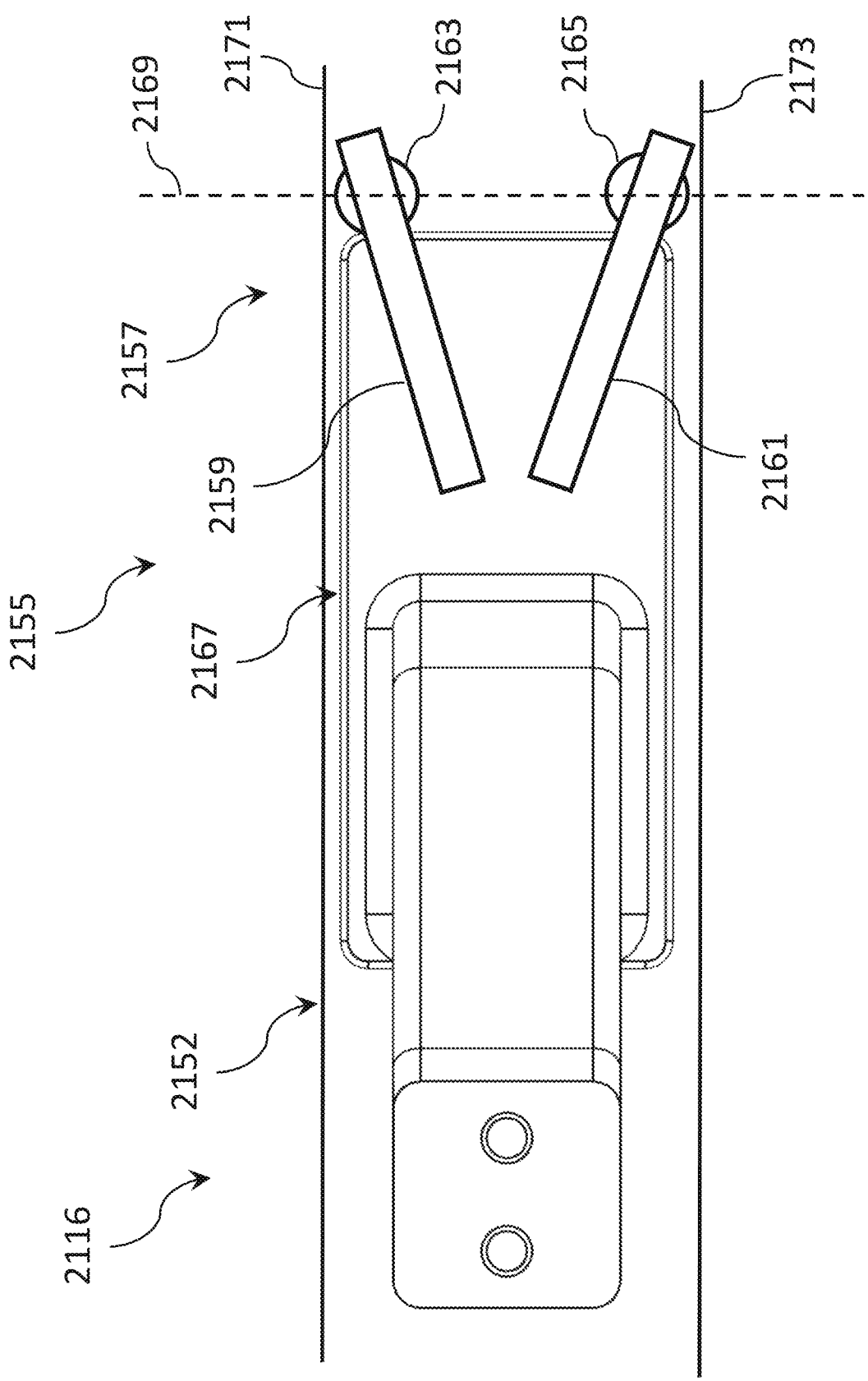
FIG. 58C is a top view of yet another embodiment of an upright support that is usable as part of the medical holding system of FIG. 43.

Referring to FIG. 58C, in an embodiment, the upright support 2116 has a mount or foot 2155. The foot 2155 has the same structure, characteristics, shape, configuration and function as the foot 2118 except the foot 2155 has a securement device 2157 instead of the securement device 2146. The securement device 2157 includes: (a) a plurality of latches, levers or securement arms 2159, 2161; and (b) a plurality of bumpers, rollers, brakes or engagers 2163, 2165 coupled to the securement arms 2159, 2161, respectively. Each of the engagers 2163, 2165 is moveably coupled to the body 2167 of the foot 2155. In an embodiment, each of the engagers 2163, 2165 is at least partially moveable along a lateral axis 2169 from an inward position to an outward position. The outward position of engager 2163 is closer to side 2171 of track 2152 than the inward position of engager 2163. Likewise, the outward position of engager 2165 is closer to side 2173 of track 2152 than the inward position of engager 2165. In operation, the user pivots each of the securement arms 2159, 2161 relative to the body 2167, which causes the engagers 2163, 2165 to move, respectively, from the inward positions to the outward positions. When the engagers 2163, 2165 are in the inward positions, the user can slides the foot 2155 within the track 2152 relative to the support structure 2024. When the engagers 2163, 2165 are in the outward positions, the foot 2155 has a fixed, secured position relative to the support structure 2024. In such secured position, the engagers 2163, 2165 apply a securing force to the sides 2171, 2173, respectively, of the track 2152.

Figure 47:
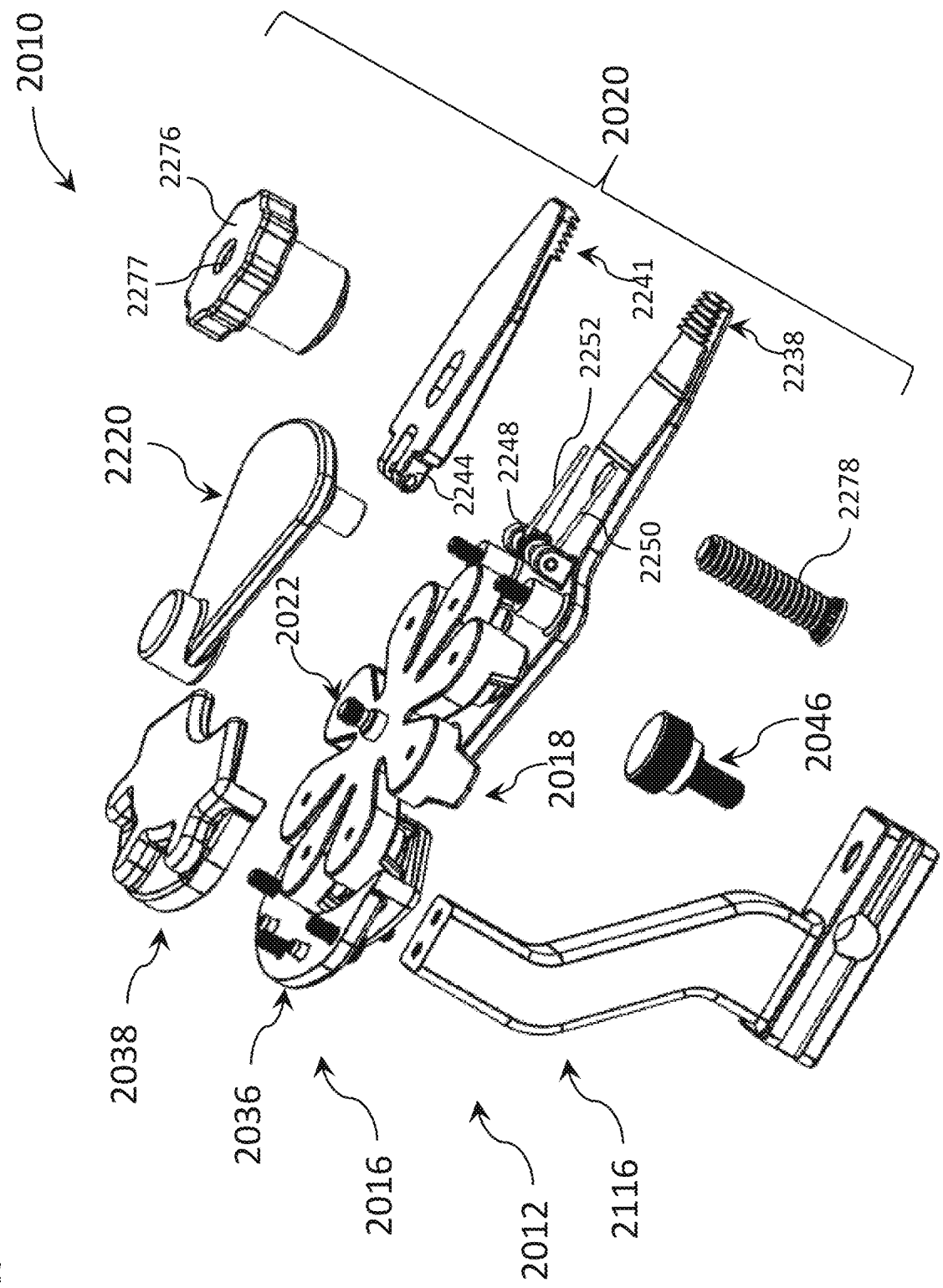
FIG. 47 is a right, isometric, exploded view of the medical holding system of FIG. 43.

As indicated above, the holder 2014 includes the grasper 2020. Referring to FIGS. 47, 48 and 50, the grasper 2020 includes: (a) a grasper base 2216; (b) a jaw 2218 pivotally coupled to the grasper base 2216; (c) a grasper biaser or biasing device 2219 coupled to the grasper base 2216 and the jaw 2218; (d) a grasper coupler 2220 configured to couple the grasper base 2216 to the rotor 2064; and (e) an adjustable lock, compressor or securement device 2222 coupled to the jaw 2218 and the grasper base 2216.

As shown in FIG. 50, the grasper base 2216 defines a pivot opening 2224 and a lower securement opening 2225. The grasper base 2216 includes a plurality of standoffs or spacers 2226, 2228 that define a plurality of openings 2230, 2232, respectively. The grasper base 2216 also has a plurality of jaw mounts 2234, 2236 and a lower gripper 2238. The lower gripper 2238 has a friction-enhanced surface, such as a plurality of ridges or traction members.

Referring to FIGS. 47-48, the jaw 2218 defines an upper securement opening 2240. The jaw 2218 has an upper gripper 2241. The upper gripper 2241 has a friction-enhanced surface, such as a plurality of ridges or traction members. Also, the jaw 2218 has a pivot portion 2242 that defines a plurality of jaw couplers 2244, 2245 that are spaced apart from each other.

The biasing device 2219 includes a plurality of biasing legs 2250, 2252 and a biasing member 2248 configured to be coupled to the biasing legs 2250, 2252. In the illustrated embodiment, the biasing member 2248 is a torsion spring having a cylindrical spring coil that receives the jaw pivot member 2246. However, it should be appreciated that, depending on the embodiment, the biasing member 2248 can be or include any suitable type of spring (e.g., a compression, extension or spiral spring) or biasing mechanism.

Figure 60:
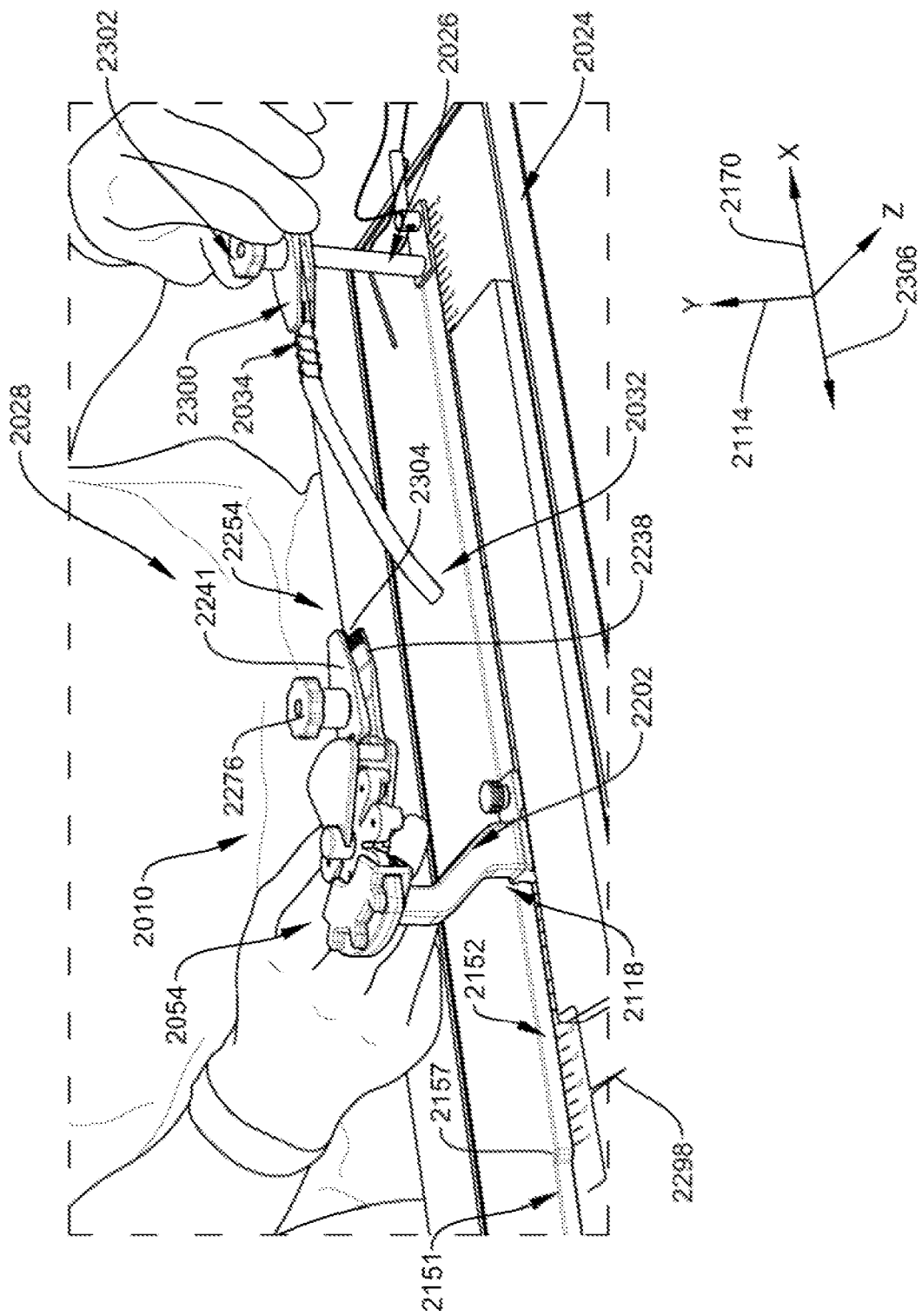
FIG. 60 is a top isometric view of the medical preparation station of FIG. 40A, illustrating the user rotating the hanger knob while the mouth of the holder has a predisposed, open position.

The assembler can insert the jaw pivot member 2246 through the jaw mounts 2234, jaw couplers 2244, 2245 and biasing member 2248, as illustrated in FIG. 48. The biasing legs 2250, 2252 of the biasing member 2248 engage and apply biasing forces to the grasper base 2216 and jaw 2218, respectively. Such biasing forces urge the grasper base 2216 apart from the jaw 2218 to cause the jaw 2218 to have a predisposed, open position 2254, as shown in FIG. 60. The predisposed, open position 2254 makes it easier for the user to insert the first element portion 2032 into the mouth 2304 of the jaw 2218 and grasper base 2216.

Figure 59:
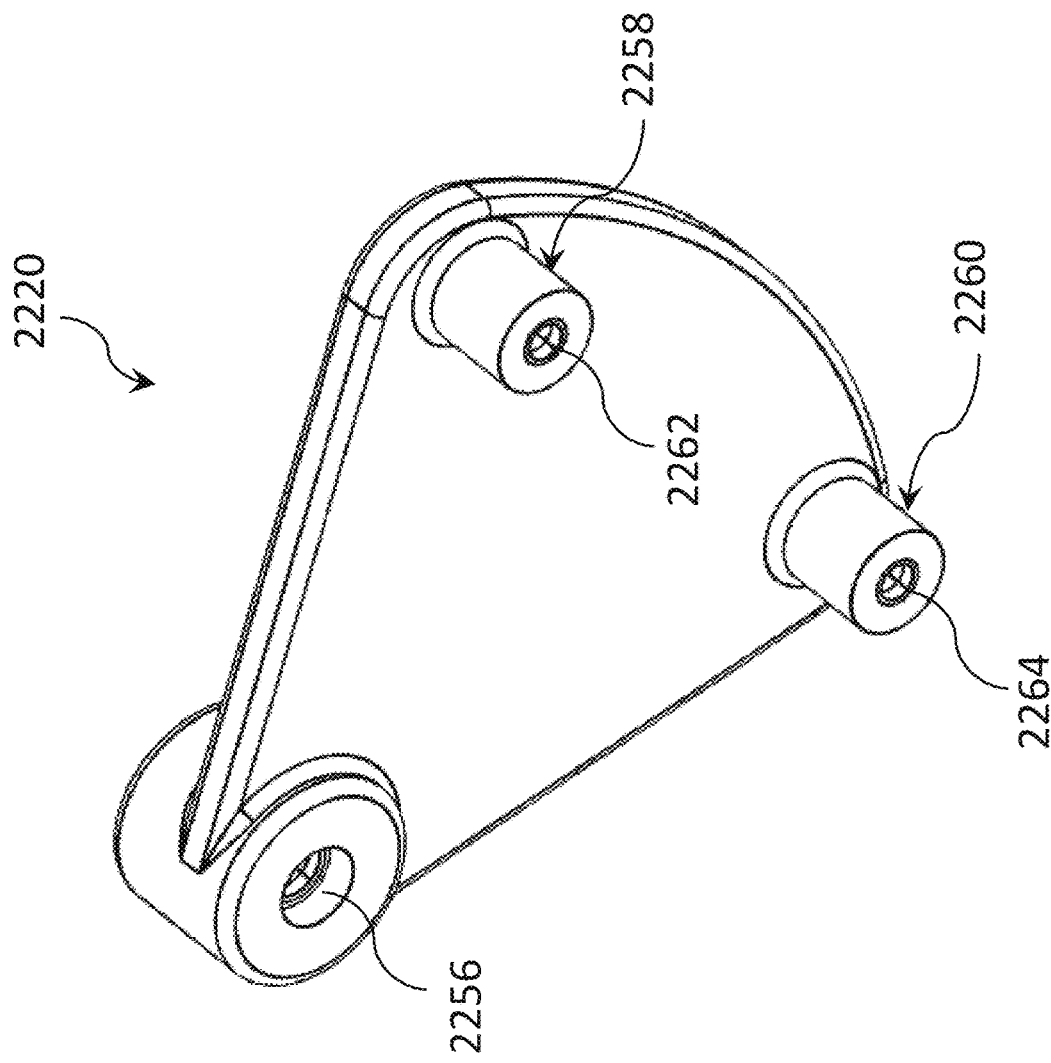
FIG. 59 is a top view of the retainer and rotor of the medical holding system of FIG. 43, illustrating the rotor or arm pair in the entry position.

Referring to FIGS. 53 and 59, the grasper coupler 2220 defines a threaded coupler opening 2256 configured to receive, and threadably mate with, the pivot member 2022. The grasper coupler 2220 includes a plurality of coupler standoffs or coupler spacers 2258, 2260 which define a plurality of threaded coupler openings 2262, 2264, respectively. Referring to FIGS. 47 and 50, to couple the grasper 2020 to the pivot device 2018, an assembler can perform the following steps: (a) insert the pivot member 2022 through the pivot opening 2224 of the grasper base 2216, then insert the pivot member 2022 through the central opening 2266 of the rotor 2064, then screw the threaded section 2268 of the pivot member 2022 (shown in FIG. 53) into the threaded coupler opening 2256; (b) insert a plurality of grasper fasteners 2270, 2272 (shown in FIG. 48) through the openings 2230, 2232, respectively, of the grasper base 2216, then insert the threaded fasteners 2270, 2272 into the coupler openings 2262, 2264, respectively, of the grasper coupler 2220; and (c) rotate the pivot member 2022 and fasteners 2270, 2272 until fully tightening the grasper coupler 2220 onto the grasper base 2216.

When united, the grasper coupler 2220 and grasper base 2216 partially surround and sandwich the rotor 2064. The grasper coupler 2220 and grasper base 2216 are positioned a designated distance apart from each other to avoid restricting the rotation of the rotor 2064. The spacer section 2274 of the pivot member 2022, shown in FIG. 53, has a diameter less than the diameter of the central opening 2266 but greater than the diameter of the coupler opening 2256 shown in FIG. 59. Accordingly, the interference of the spacer section 2274 with the grasper coupler 2220 determines such designated distance. Likewise, the interference of the spacers 2226, 2228 with the coupler spacers 2258, 2260, respectively, determines such designated distance.

Once the grasper 2020 is connected to the rotor 2064, the grasper 2020 is pivotal about the pivot member 2022 so that the grasper 2020 is pivotal relative to the rotor 2064. This enables the angle of the grasper 2020 to adjust to, and align with, the axis that extends through the implantable element 2030. Such dynamic adjustment reduces binding and bending of the implantable element 2030, which aids the user in establishing and maintaining consistent tension in the implantable element 2030 that is uniformly (or substantially uniformly) distributed along the entire length of the implantable element 2030.

Referring to FIG. 48, the securement device 2222 includes a handle or grasp knob 2276 that defines a threaded opening 2277 configured to receive, and threadably mate with, a securement fastener 2278. An assembler can insert the securement fastener 2278 through the lower securement opening 2225, then through the upper securement opening 2240, and then into the threaded opening 2277 in the grasp knob 2276. Referring to FIG. 60, in use, the jaw 2241 has the predisposed, open position 2254 as result of the biasing device 2219. The user can, therefore, easily insert the first element portion 2032 into the mouth 2304 of the jaw 2218 and grasper base 2216. Next, the user can rotate the grasp knob 2276 to clamp the lower and upper grippers 2238, 2241 onto the first element portion 2032, generating a compression force acting on the first element portion 2032.

Referring to FIGS. 55-56, the rotor 2064 is pivotal or rotatable through three hundred and sixty degrees relative to the retainer 2016. As a result, arm 2282, for example, is moveable between a loading or entry position 2284, shown in FIG. 55, and an off-loading or outlet position 2286, shown in FIG. 56. In the entry position 2284, there is an entry space 2288 between the arm 2282 and the retainer 2016. This enables the user to move the cord segment or loop segment 2290 through the entry space 2288 to the cord transport space 2292. In this embodiment, the cord transport space 2292 has a U-shape.

As shown in FIG. 56, in the outlet position 2286, there is an outlet space 2294 between the arm 2283 and the retainer 2016. This enables the user to move the cord segment or loop segment 2290 from the cord transport space 2292 through the outlet space 2294. In this embodiment, the arm interfaces 2080 of at least two of the arms 2068 remain engaged with the retainer 2016 as the arm 2282 moves, pivots or rotates from the entry position 2284 to the outlet position 2286.

Since, in this embodiment, all of the arms 2068 are identical to the arm 2282, each of the arms 2068 is operational the same as the arm 2282. This enables the user to conveniently select any one of the selectable cord transport spaces 2078 for insertion of the loop segment 2290. For example, as the user continuously rotates the rotor 2064 clockwise, each of the arms 2068 moves from the entry position 2284, along the passageway 2289, to the outlet position 2286. This provides the user with an improved ease of use, facilitating the rapid and recurring passage of the loop segment 2290 through the entry space 2288, along the passageway 2289, through the outlet space 2294.

It should be appreciated that the user can pass the loop segment 2290 clockwise from the entry space 2288 to the an outlet space 2294, or the user can pass the loop segment 2290 counterclockwise from the outlet space 2294 to the entry space 2288. In this way, the rotor 2064 enables bidirectional passage of the loop segment 2290 from one side of the retainer 2016 to the other side of the retainer 2016.

Referring to FIG. 60, in an embodiment, the support structure 2024 has a plurality of measurement or position markings 2298 displayed along the entry valley 2151 and track 2152. Initially, the user inserts the foot 2118 into the entry valley 2151. If the user decides to position the foot 2118 at the beginning point 2157 of the track 2152 to accommodate a relatively long implantable element (not shown), the length of the retainer 2016 and rotor 2064, extending along the X-axis 2170, could position the grippers 2238, 2241 too close to such implantable element, resulting in undesirable slack in such implantable element. To alleviate or overcome this disadvantage, the transition body portion 2202 locates the retainer 2016 and rotor 2064 in a rearward direction 2306, rearward of the foot 2118.

Figure 61:
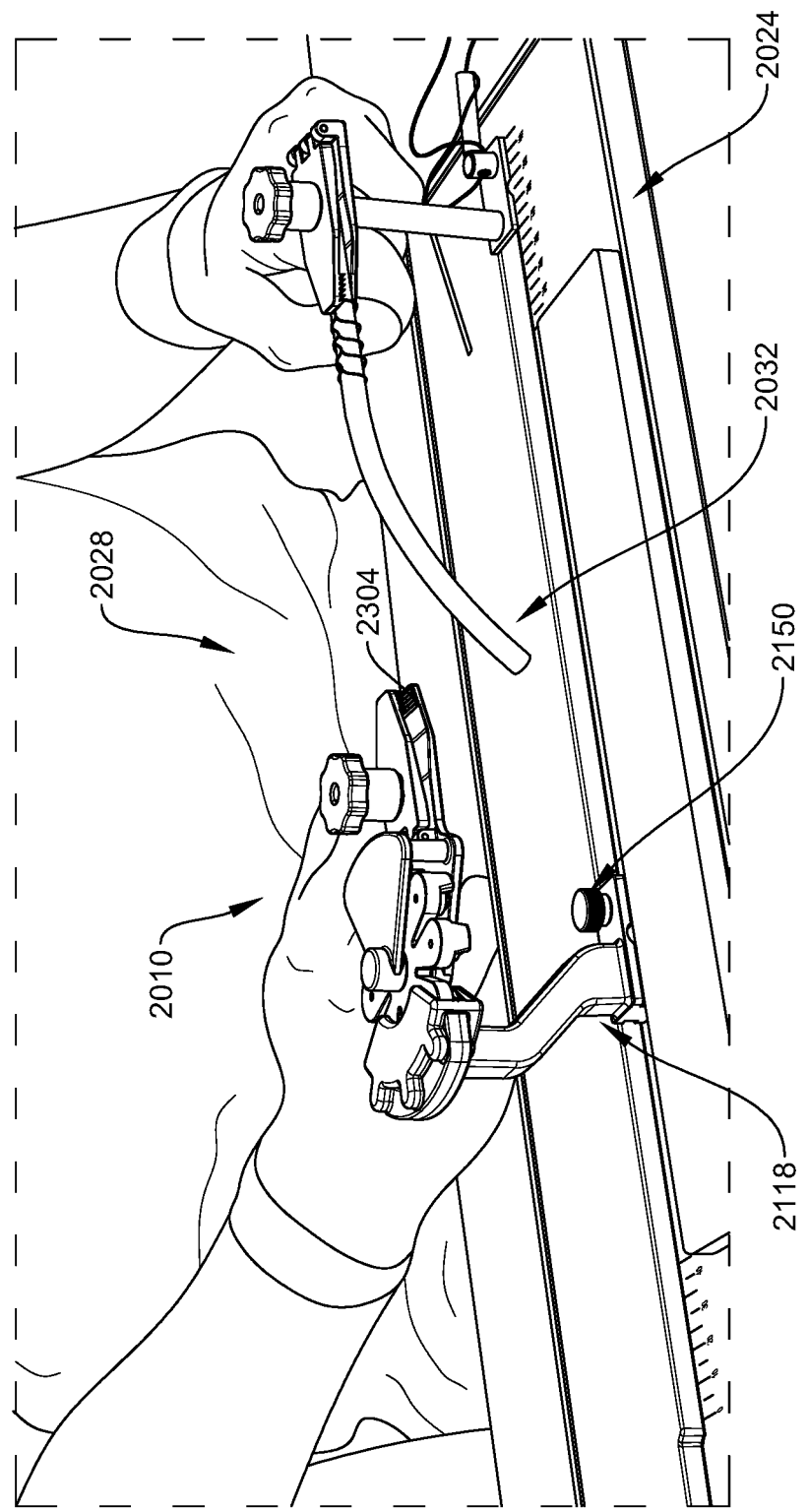
FIG. 61 is a top, right isometric view of the medical preparation station of FIG. 40A, illustrating the second element portion of the implantable element secured to the hanger and the open mouth of the holder ready to receive the first element portion of the implantable element.
Figure 62:
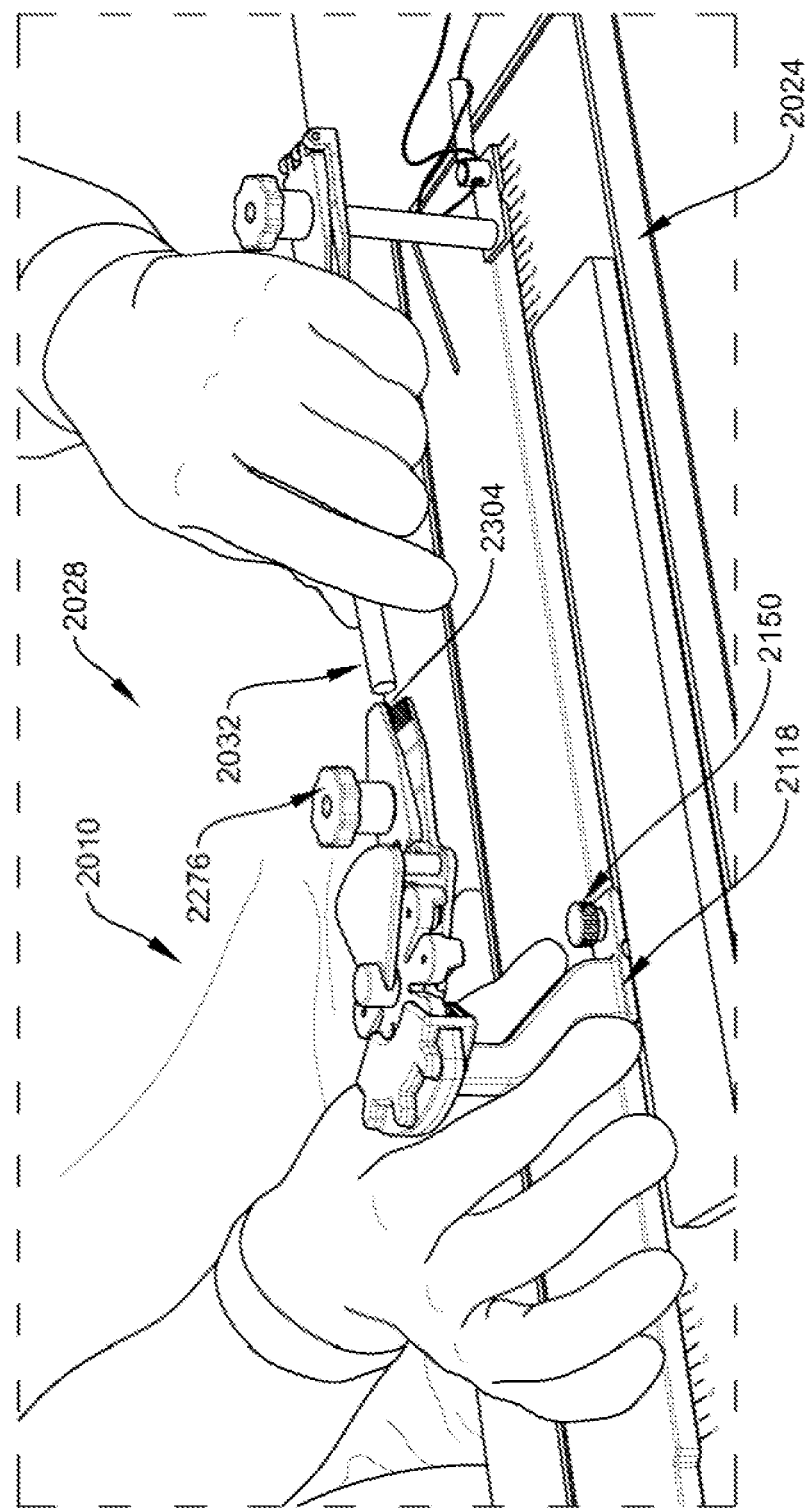
FIG. 62 is a top, right isometric view of the medical preparation station of FIG. 40A, illustrating the user inserting the first element portion of the implantable element into the open mouth of the holder.
Figure 63:
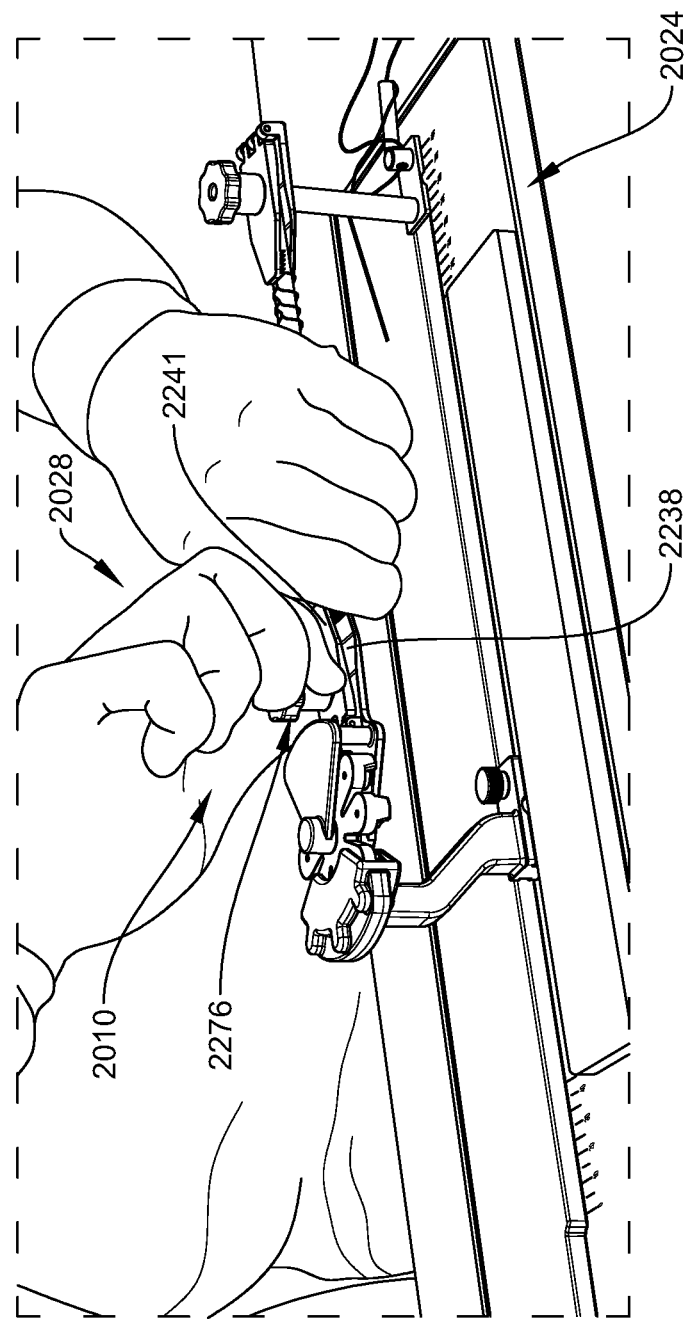
FIG. 63 is a top, right isometric view of the medical preparation station of FIG. 40A, illustrating the user rotating the grasp knob to clamp onto, and secure, the first element portion.

In the example shown in FIG. 60, the user has inserted the second element portion 2034 into the hanger jaws 2300 of the hanger 2026, and the user has tightened the hanger knob 2302 to securely clamp the second element portion 2034. At this stage, as shown in FIG. 61, the user is now ready to slide the foot 2118 to a position within reach of the first element portion 2032. As shown in FIGS. 62-63, the user slides the foot 2118 forward until reaching the first element portion 2032, inserts the first element portion 2032 into the mouth 2304 and tightens the grasp knob 2276 until the grippers 2238, 2241 securely hold the first element portion 2032.

Figure 64:
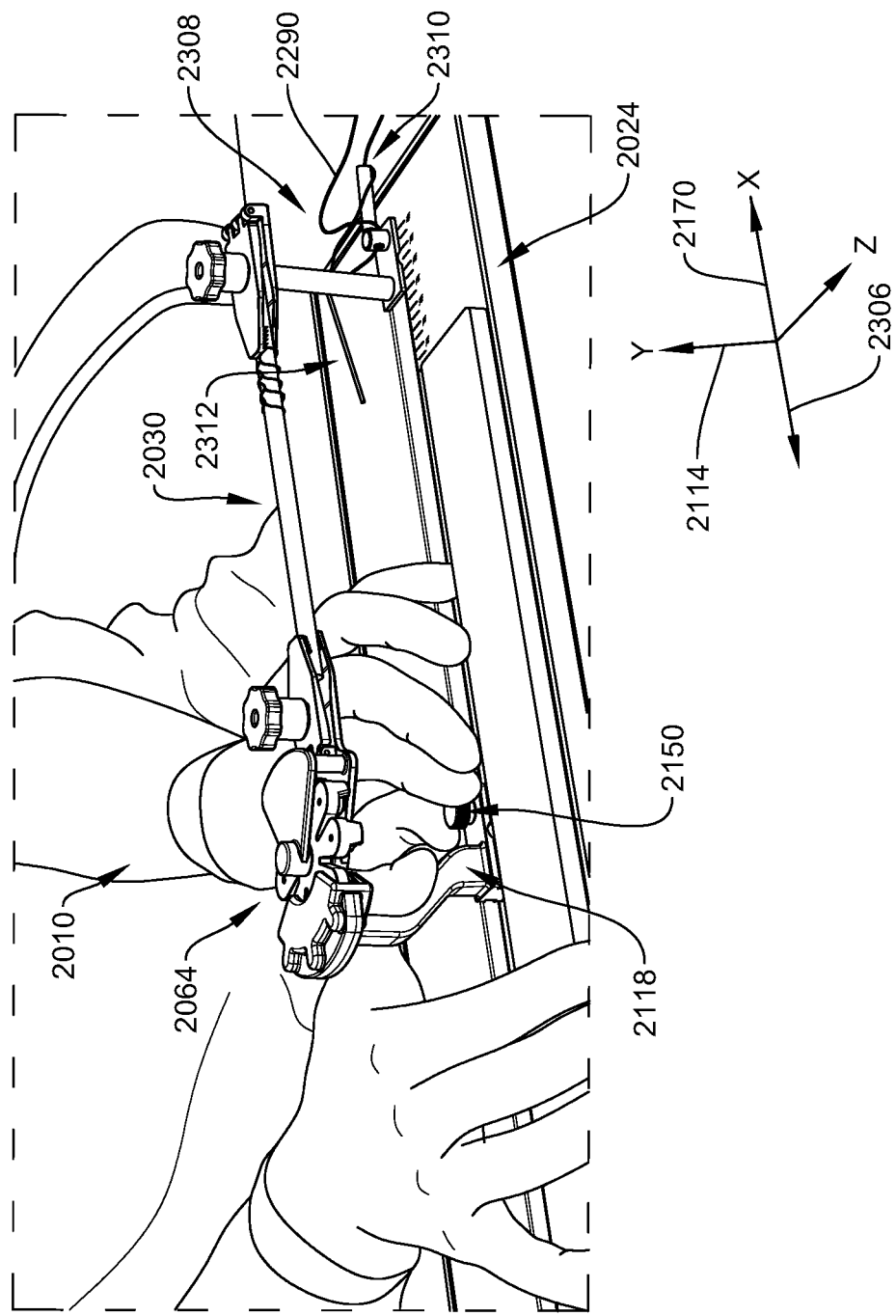
FIG. 64 is a top, right isometric view of the medical preparation station of FIG. 40A, illustrating the user sliding the foot rearward, reaching a desired tension in the implantable element, and rotating the foot knob to fix or set the position of the foot relative to the support structure.

Next, as illustrated in FIG. 64, the user slides the foot 2118 in the rearward direction 2306. In doing so, the user establishes a desired or suitable level of tension in the implantable element 2030. Once the user reaches such tension level, the user tightens the foot knob 2150 to fix, set or secure the position of the foot 2118 relative to the support structure 2024. As described below, during the periodic passage of the loop segment 2290 through the rotor 2064, the medical holding system 2010 maintains a suitable degree of tension in the implantable element 2030. Such tension is equal to or substantially equal to the initial tension level established when the user initially tightens the foot knob 2150.

Figure 65:
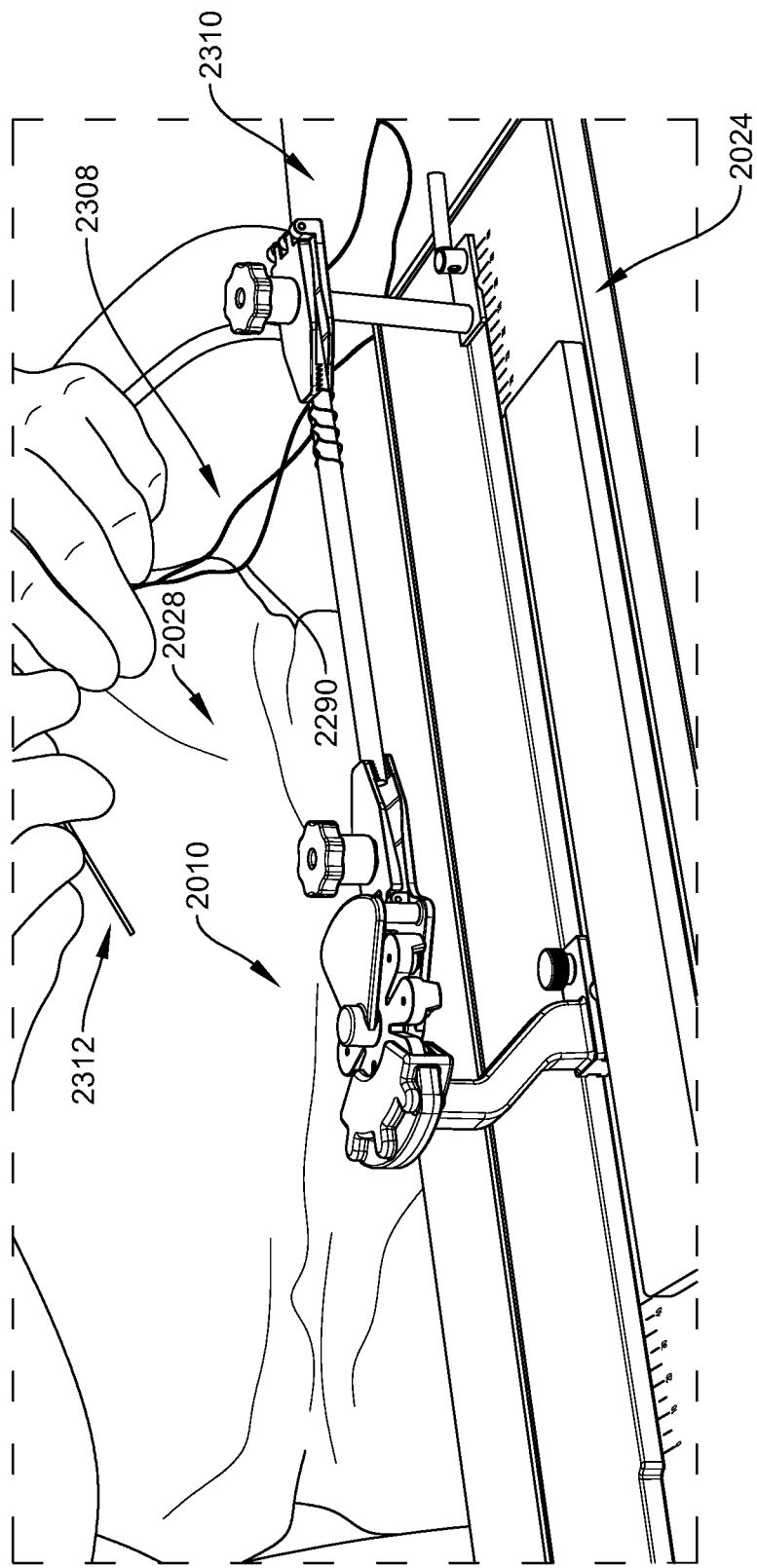
FIG. 65 is a top, right isometric view of the medical preparation station of FIG. 40A, illustrating the user picking-up the cord assembly, including the needle.

Referring to FIGS. 64-65, for a loop-based suturing method, the loop segment 2290 is a section of a cord assembly 2308. The cord assembly 2308, like the cord assembly 170, includes a looped cord 2310 and a piercer or needle 2312. In an embodiment, the cord assembly 2308 has the same structure, shape, characteristics and function as the cord assembly 170 described above.

Figure 66:
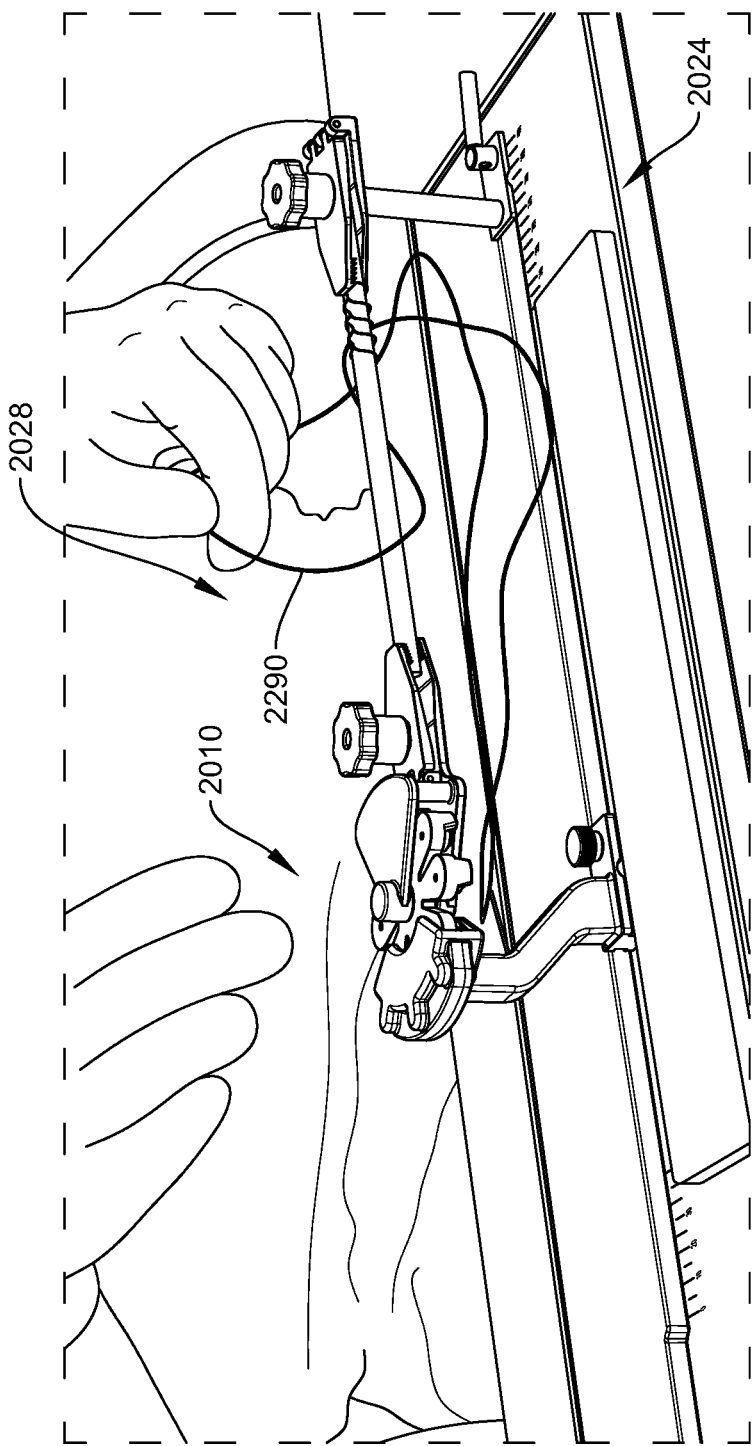
FIG. 66 is a top, right isometric view of the medical preparation station of FIG. 40A, illustrating the user holding a loop segment of the cord assembly.
Figure 67:
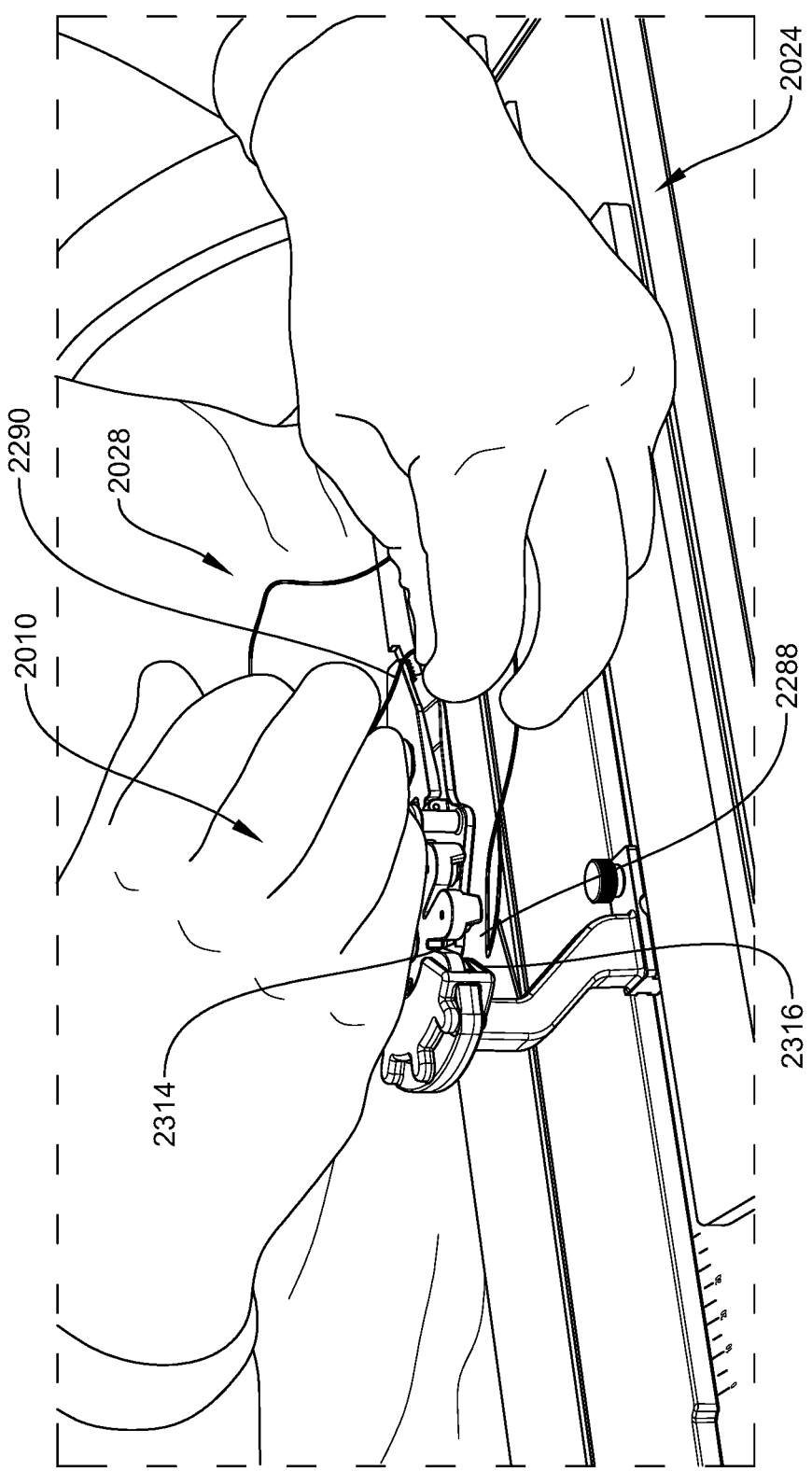
FIG. 67 is a top, right isometric view of the medical preparation station of FIG. 40A, illustrating the user moving the loop segment toward the entry space.
Figure 68:
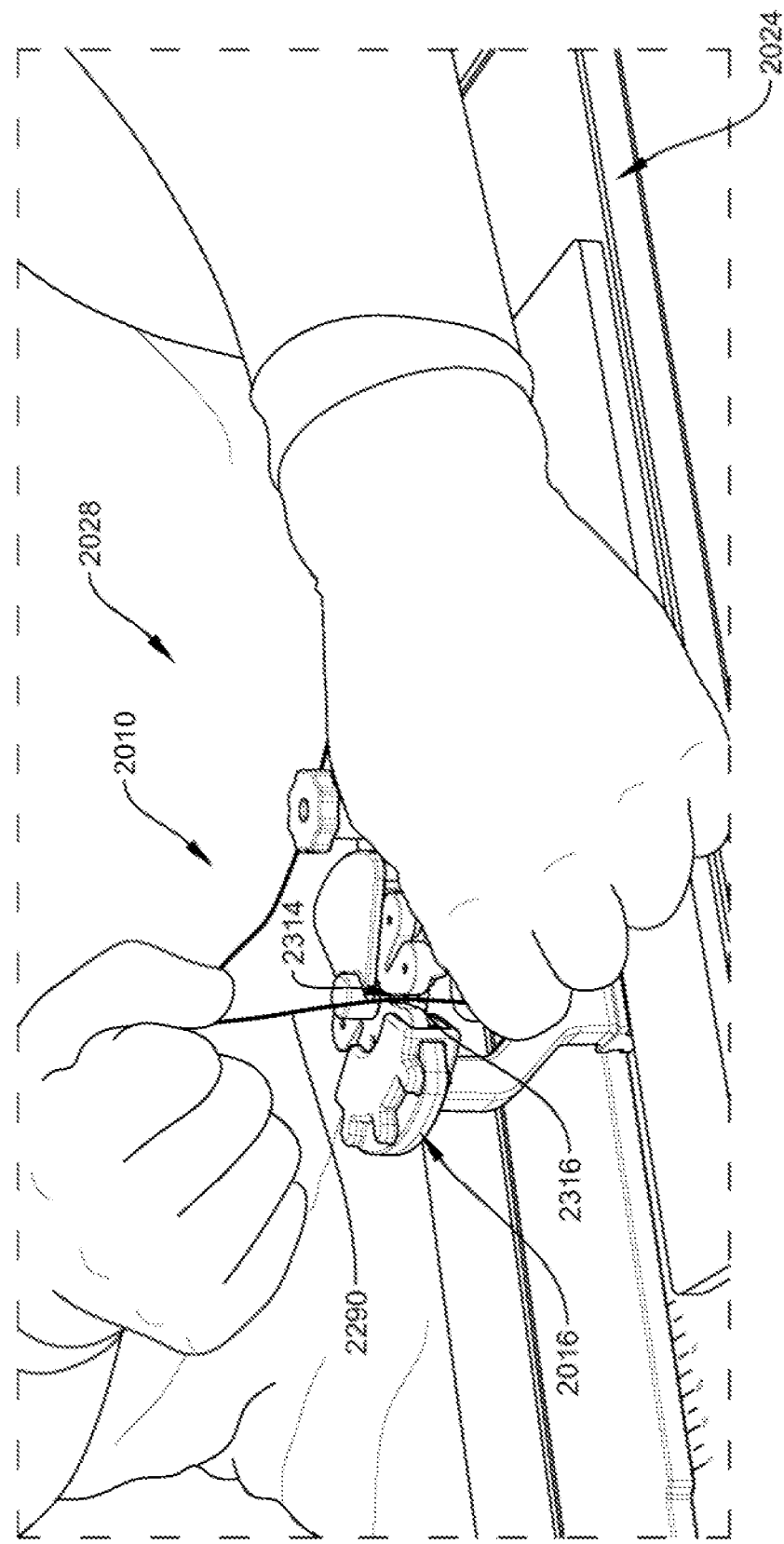
FIG. 68 is a top, right isometric view of the medical preparation station of FIG. 40A, illustrating the user moving the loop segment from the first environmental space, through the entry space and into one of the cord transport spaces.
Figure 69:
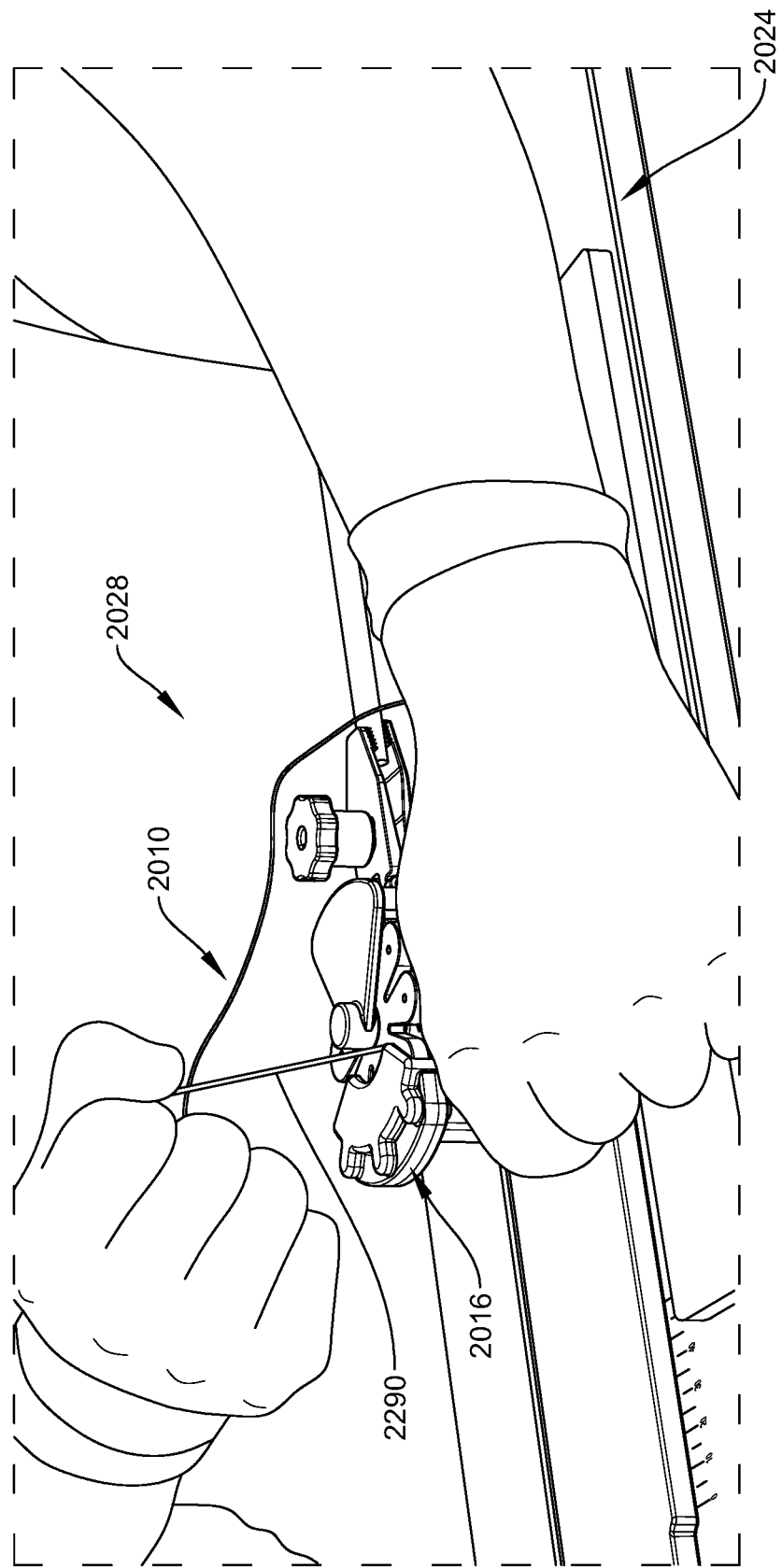
FIG. 69 is a top, right isometric view of the medical preparation station of FIG. 40A, illustrating the user pulling the loop segment, causing the rotor to rotate while the cord segment remains within one of the cord transport spaces.
Figure 70:
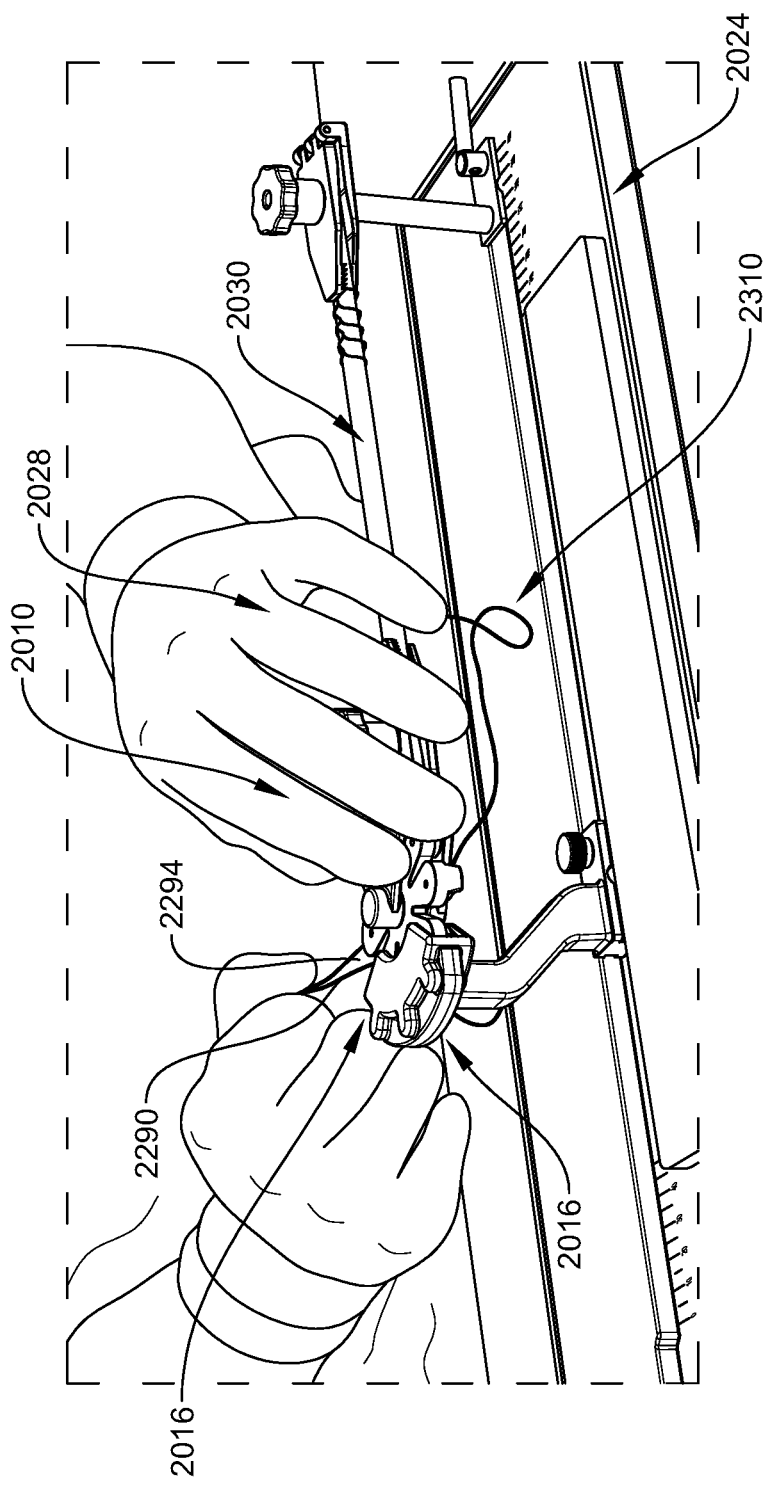
FIG. 70 is a top, right isometric view of the medical preparation station of FIG. 40A, illustrating the user moving the loop segment from the cord transport space, through the outlet space and to the second environmental space.
Figure 71:
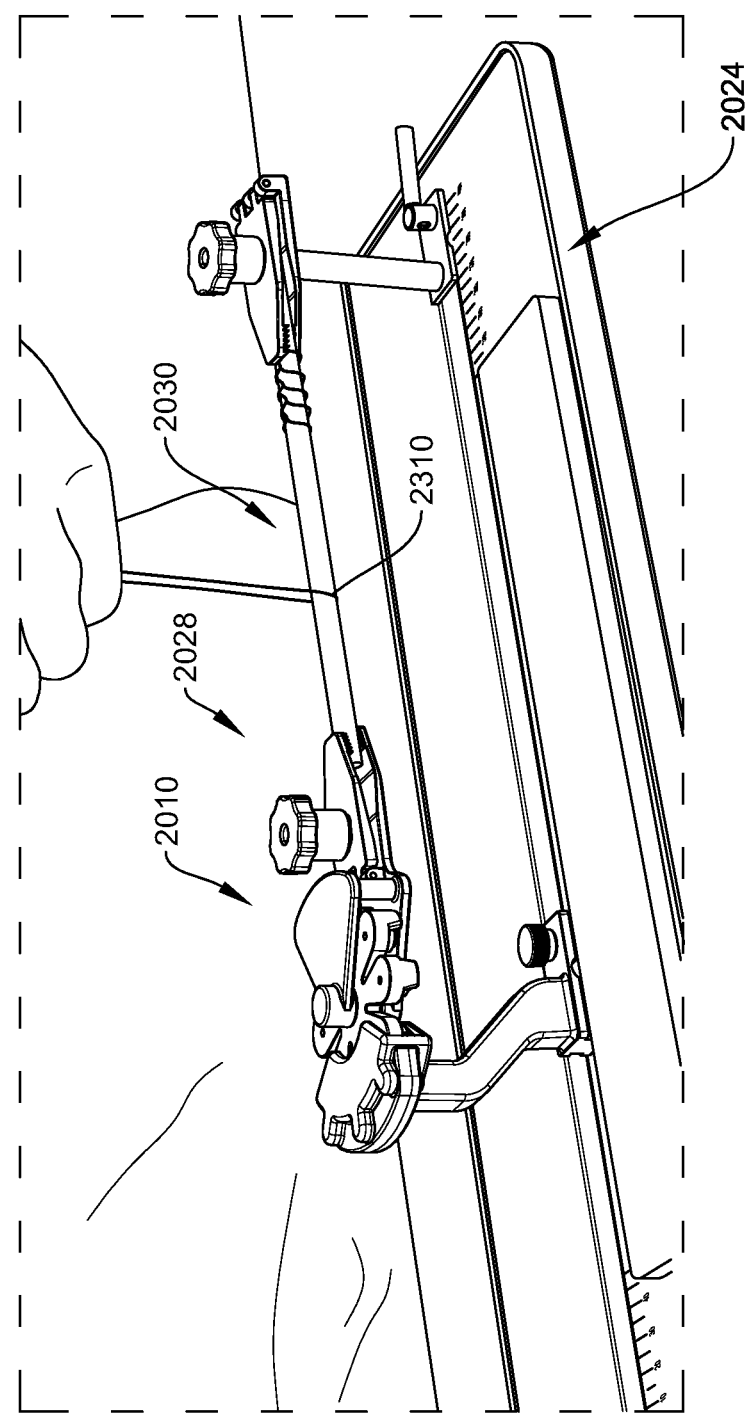
FIG. 71 is a top, right isometric view of the medical preparation station of FIG. 40A, illustrating the looped cord encircling the implantable element after the user completed a first pass-through step.

As shown in FIG. 65, the user picks-up the cord assembly 2308. As shown in FIGS. 66-67, the user then moves the loop segment 2290 from the entry space 2288 into one of the cord transport spaces 2314. As shown in FIG. 68, the user then pulls the loop segment 2290 toward the user. In doing so, the loop segment 2290 forces the arm 2316 to rotate, which, in turn, causes the entire rotor 2064 to rotate. As shown in FIG. 69, the loop segment 2290 remains in the cord transport space 2314 during this rotation. While within the cord transport space 2314, the loop segment 2290 slides past the retainer 2016 until the cord transport space 2314 is aligned with the outlet space 2294, as shown in FIG. 70. At this stage, the user has completed a first pass-through step, resulting in the looped cord 2310 being looped around the implantable element 2030, as shown in FIG. 71.

Figure 72:
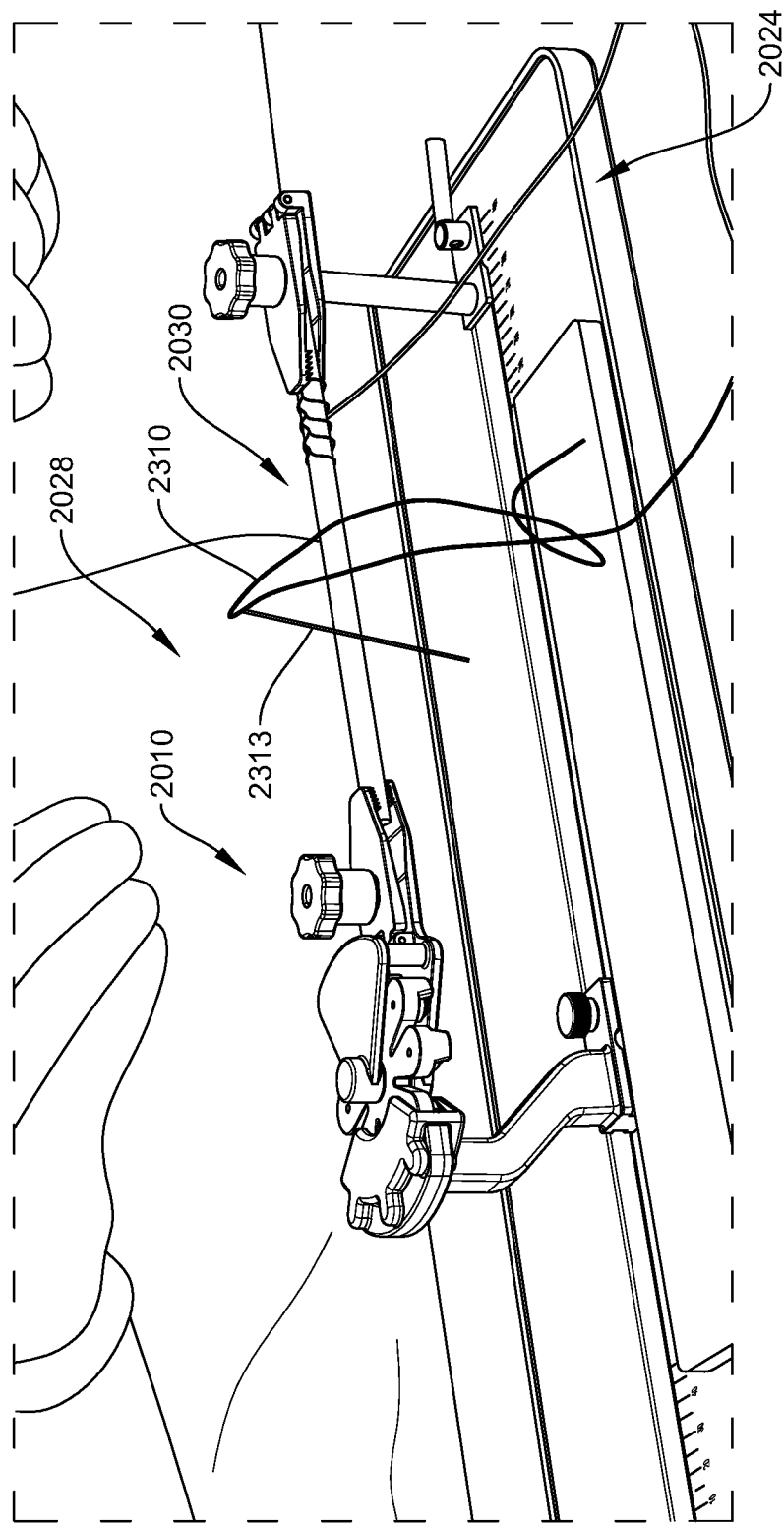
FIG. 72 is a top, right isometric view of the medical preparation station of FIG. 40A, illustrating the user piercing the implantable element while the looped cord encircles the implantable element.
Figure 73:
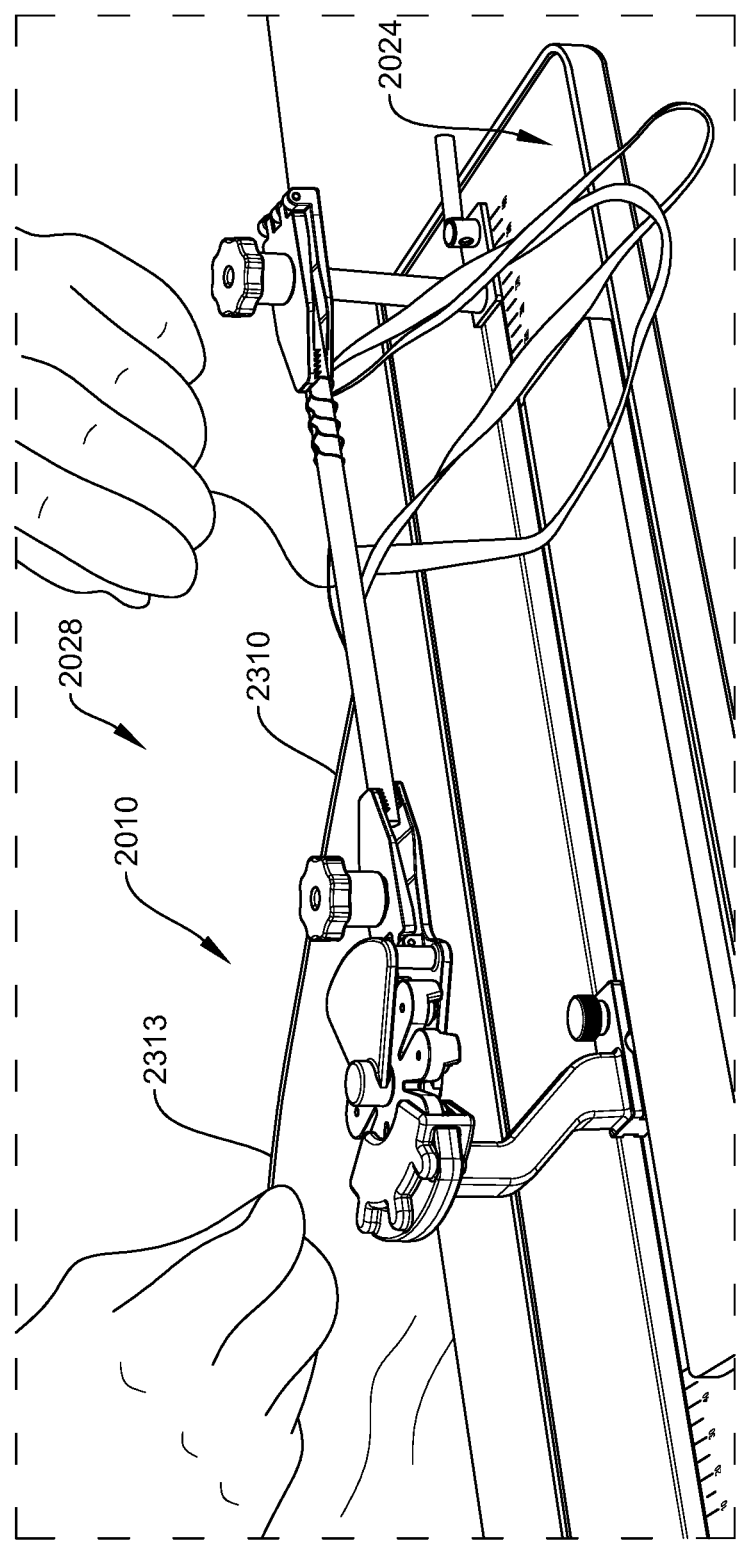
FIG. 73 is a top, right isometric view of the medical preparation station of FIG. 40A, illustrating the user pulling the looped cord through the pierced implantable element.
Figure 74:
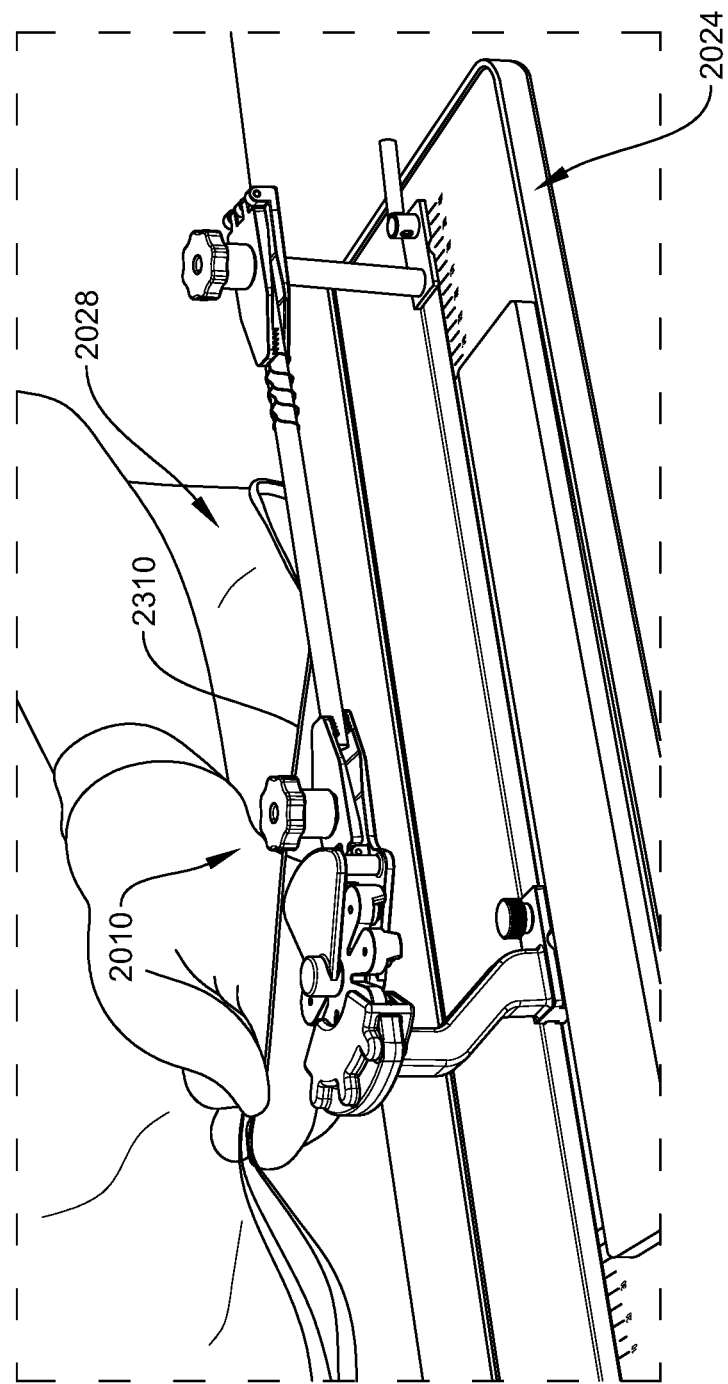
FIG. 74 is a top, right isometric view of the medical preparation station of FIG. 40A, illustrating the user completing the pulling of the looped cord through the pierced implantable element.
Figure 75:
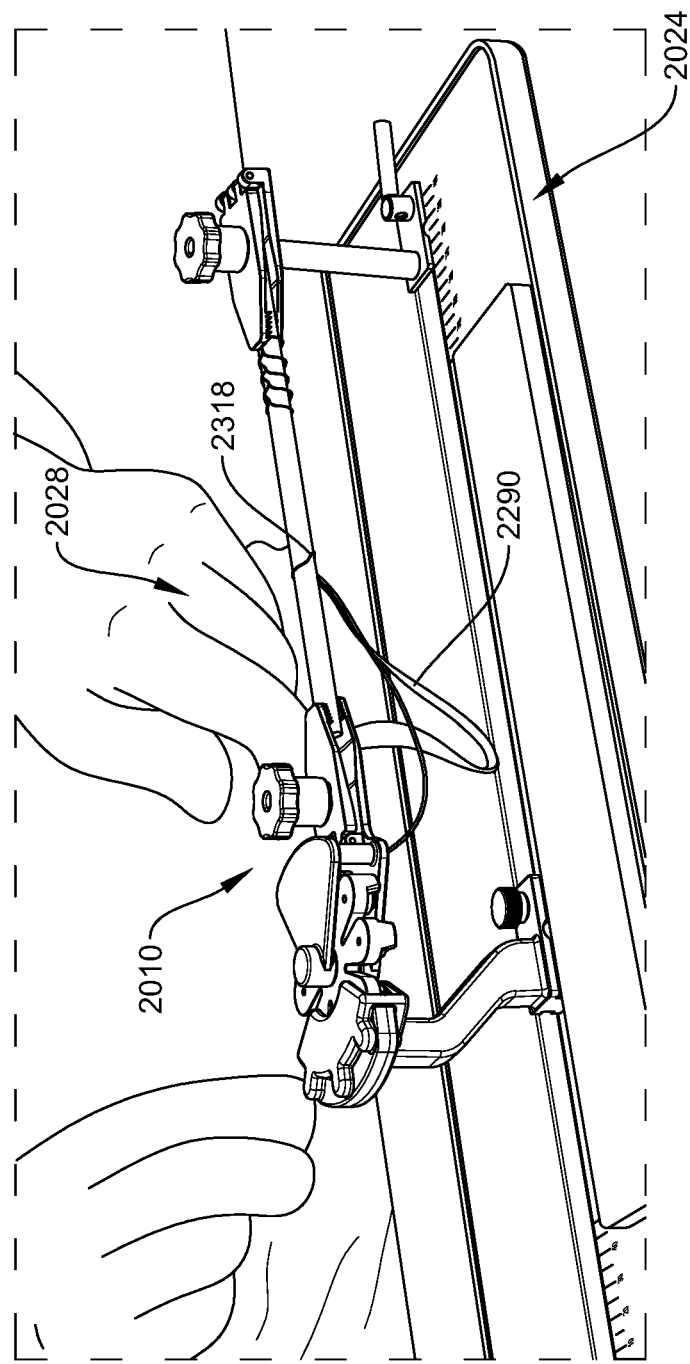
FIG. 75 is a top, right isometric view of the medical preparation station of FIG. 40A, illustrating the first stitch formed following the first pass-through step.

As shown in FIG. 72, while the looped cord 2310 encircles the implantable element 2030, the user pierces the implantable element 2030 with the needle 2313. The user then pulls the looped cord 2310 through the implantable element 2030, as shown in FIGS. 73-75 until establishing a relatively tight, first suture line or first stitch 2318.

Figure 76:
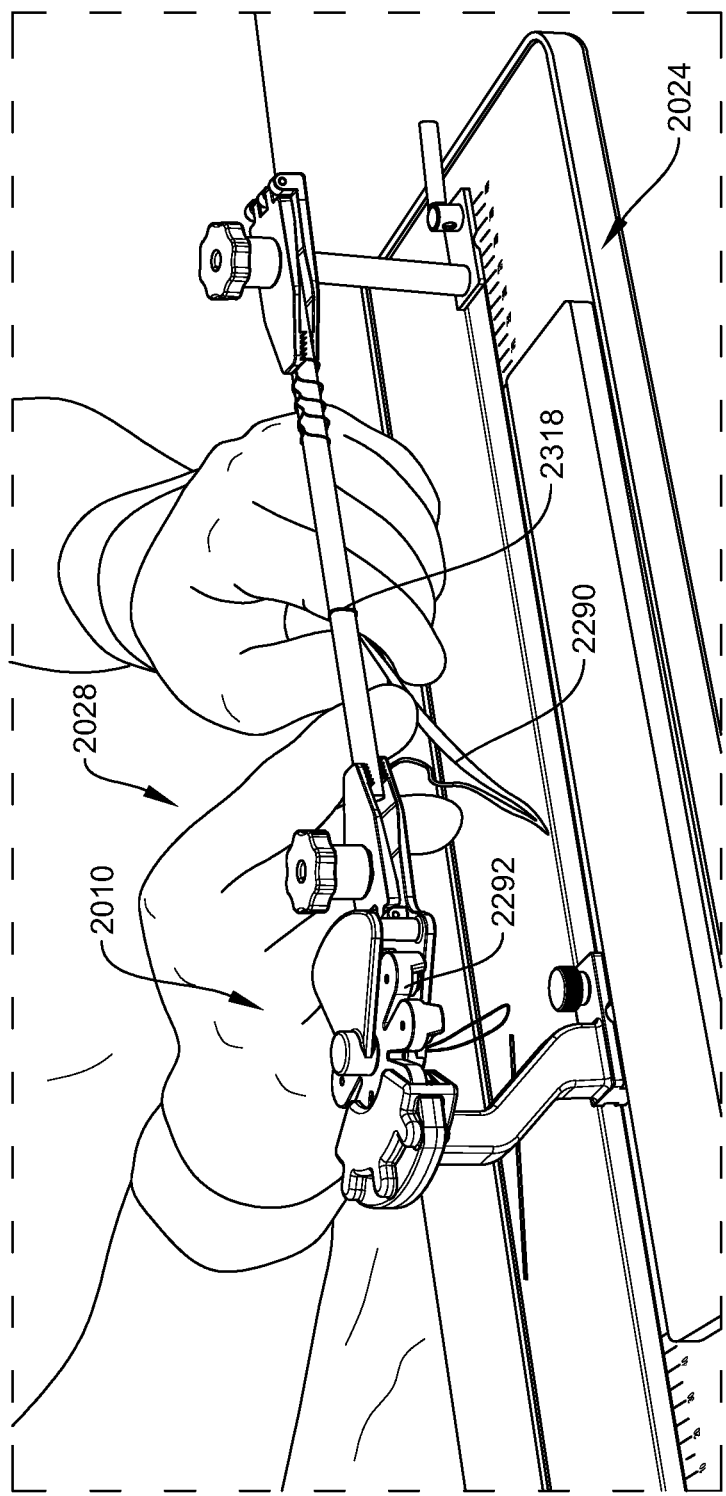
FIG. 76 is a top, right isometric view of the medical preparation station of FIG. 40A, illustrating the user holding the loop segment of the cord assembly to begin a second pass-through step.
Figure 77:
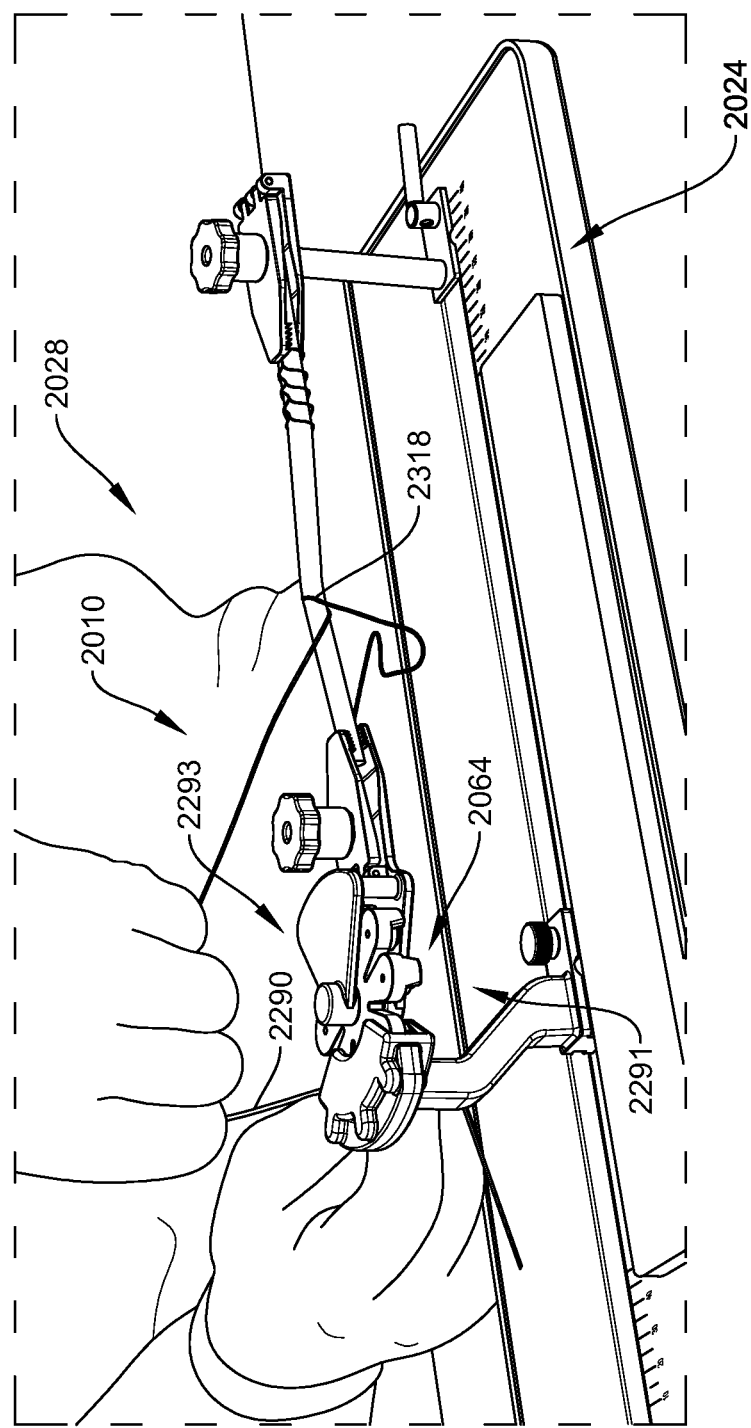
FIG. 77 is a top, right isometric view of the medical preparation station of FIG. 40A, illustrating the user: (a) moving the loop segment from the first environmental space, through the entry space and into one of the cord transport spaces; (b) pulling the loop segment, causing the rotor to rotate while the cord segment remains within one of the cord transport spaces; and (c) moving the loop segment from the cord transport space, through the outlet space and to the second environmental space.

Next, referring to FIGS. 76-77, the user begins a second pass-through step by grasping the loop segment 2290, inserting the loop segment 2290 into one of the cord transport spaces 2292 of the rotor 2064, and pulling the loop segment 2290 until such cord transport space 2292 moves from being aligned with a first environmental space 2291 to being aligned with a second environmental space 2293. At this stage, the user has completed the second pass-through step.

Figure 78:
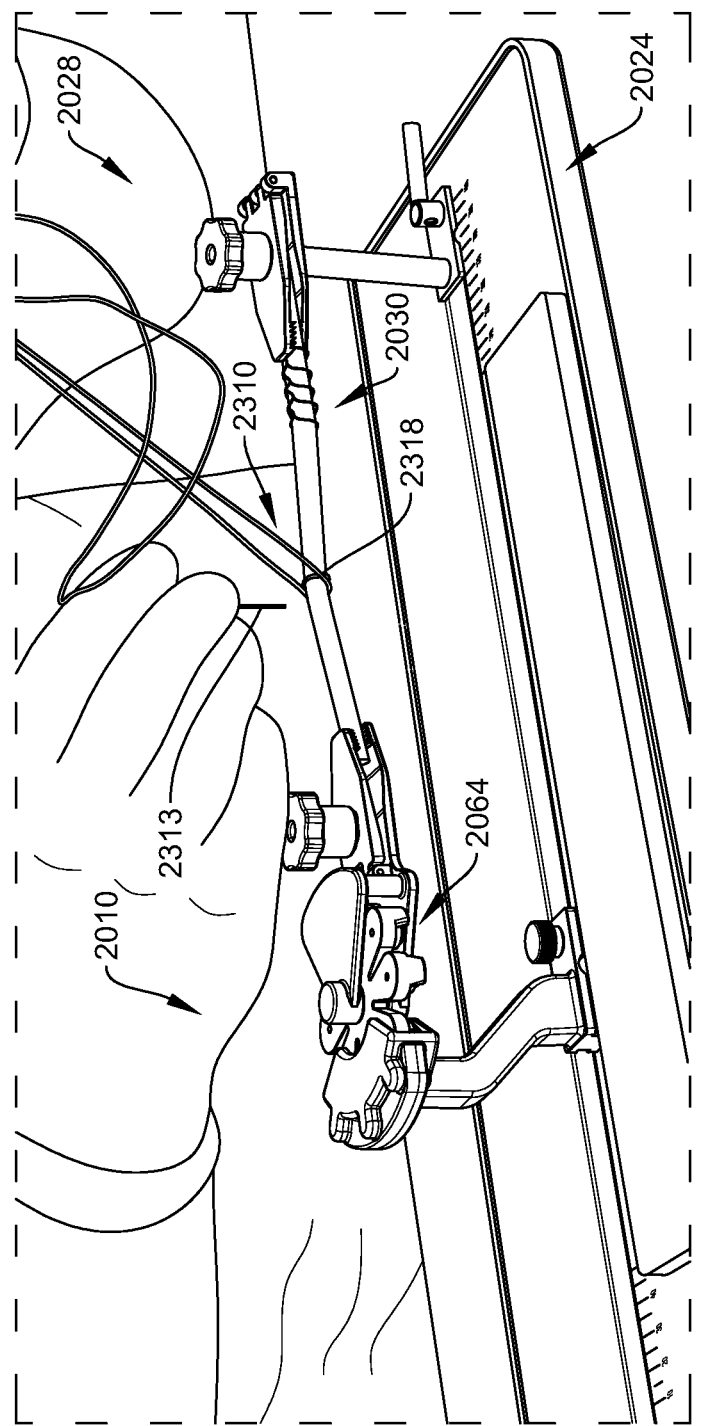
FIG. 78 is a top, right isometric view of the medical preparation station of FIG. 40A, illustrating the user beginning to pierce the implantable element while the looped cord encircles the implantable element.
Figure 79:
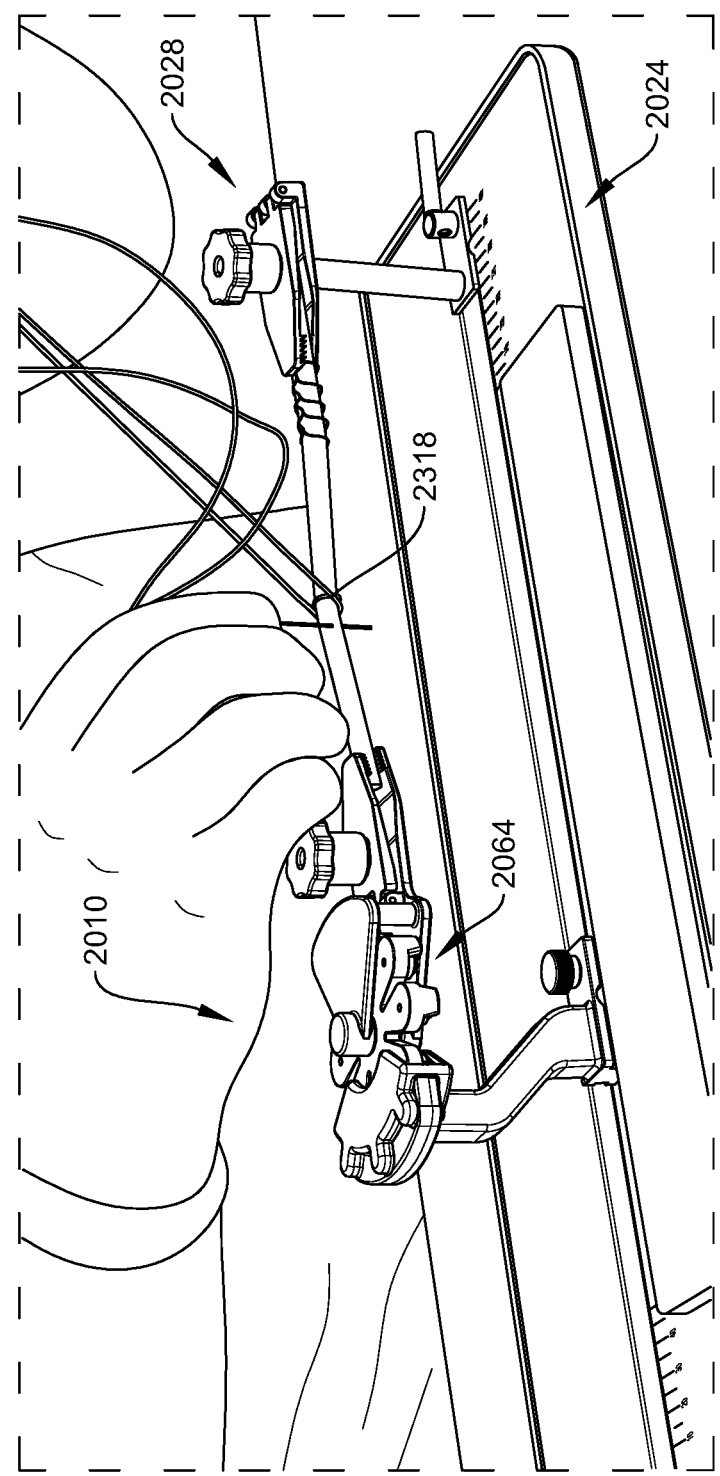
FIG. 79 is a top, right isometric view of the medical preparation station of FIG. 40A, illustrating the user piercing the implantable element while the looped cord encircles the implantable element.
Figure 80:
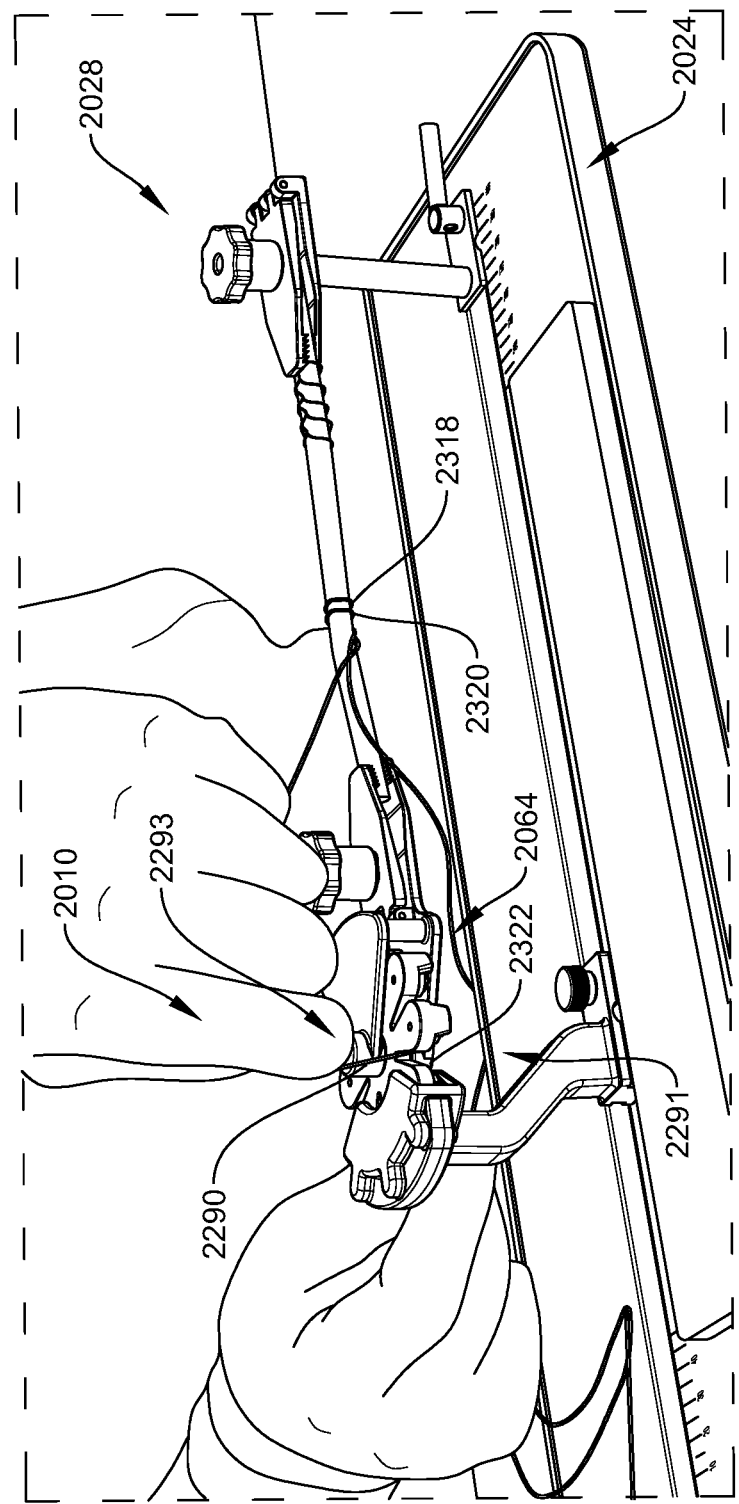
FIG. 80 is a top, right isometric view of the medical preparation station of FIG. 40A, illustrating the second stitch formed following the second pass-through step.
Figure 81:
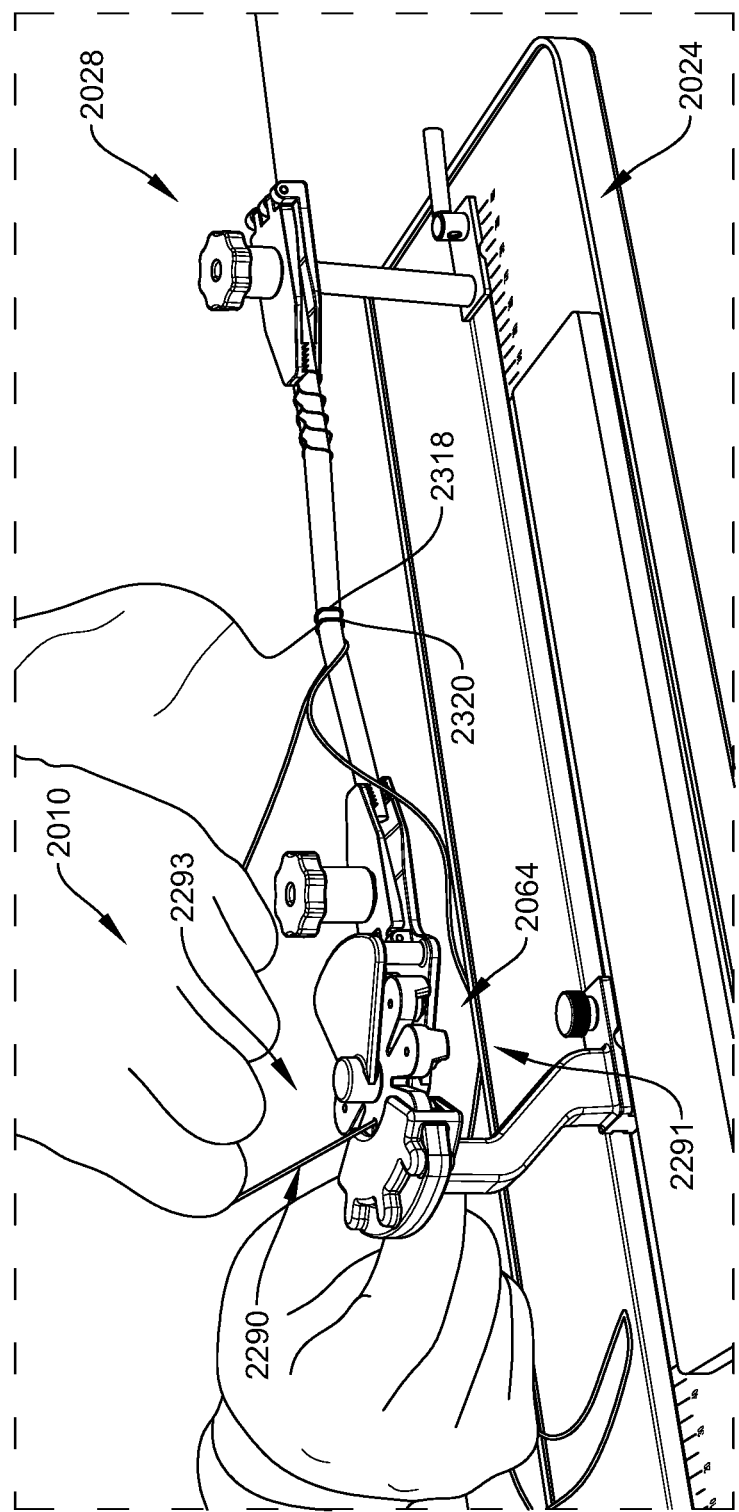
FIG. 81 is a top, right isometric view of the medical preparation station of FIG. 40A, illustrating the user performing a third pass-through step by: (a) moving the loop segment from the first environmental space, through the entry space and into one of the cord transport spaces; (b) pulling the loop segment, causing the rotor to rotate while the cord segment remains within one of the cord transport spaces; and (c) moving the loop segment from the cord transport space, through the outlet space and to the second environmental space.

As shown in FIGS. 78-79, the user, again, proceeds to pierce the implantable element 2030 with the needle 2313. After pulling the looped cord 2310 through the implantable element 2030 establishing a relatively tight, second suture line or second stitch 2320, shown in FIG. 80, the user begins a third pass-through step. As shown in FIG. 80, the user grasps the loop segment 2290, inserts the loop segment 2290 into a cord transport space 2322 of the rotor 2064, and pulls the loop segment 2290 until the cord transport space 2322 moves from being aligned with the first environmental space 2291 to being aligned with the second environmental space 2293, as shown in FIG. 81. At this stage, the user has completed the third pass-through step.

Figure 82:
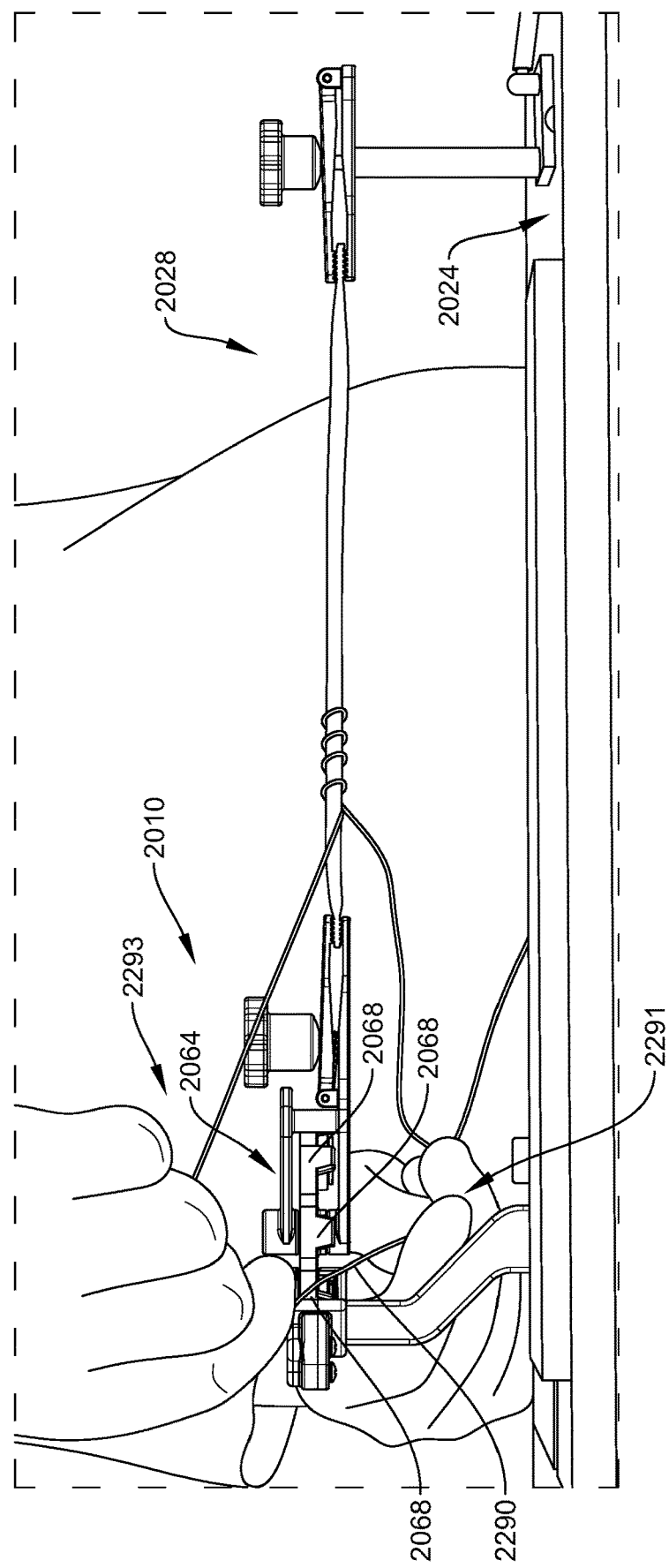
FIG. 82 is a right side elevation view of the medical preparation station of FIG. 40A, illustrating the user inserting the loop segment between a user-selected one of the pairs of the arms of the rotor.
Figure 83:
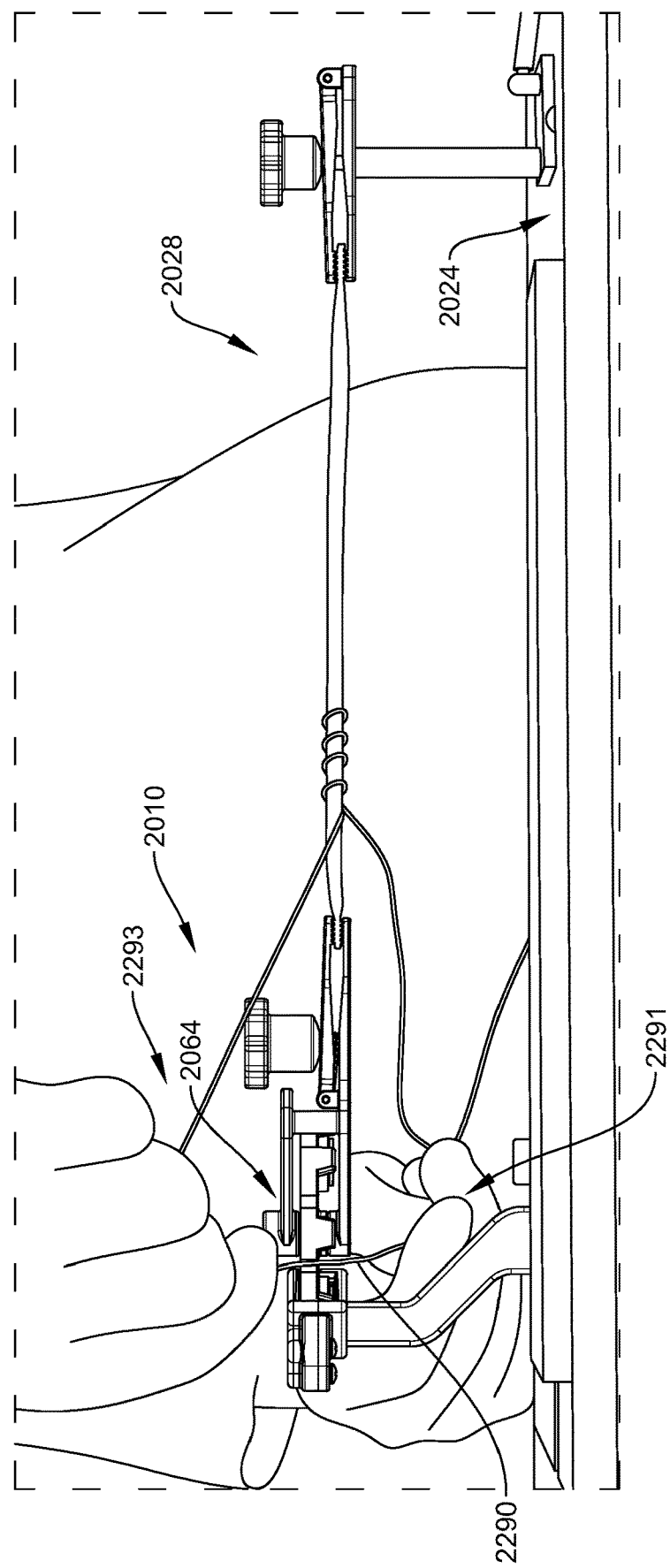
FIG. 83 is a right side elevation view of the medical preparation station of FIG. 40A, illustrating the user pulling the loop segment, causing the rotor to rotate.
Figure 84:
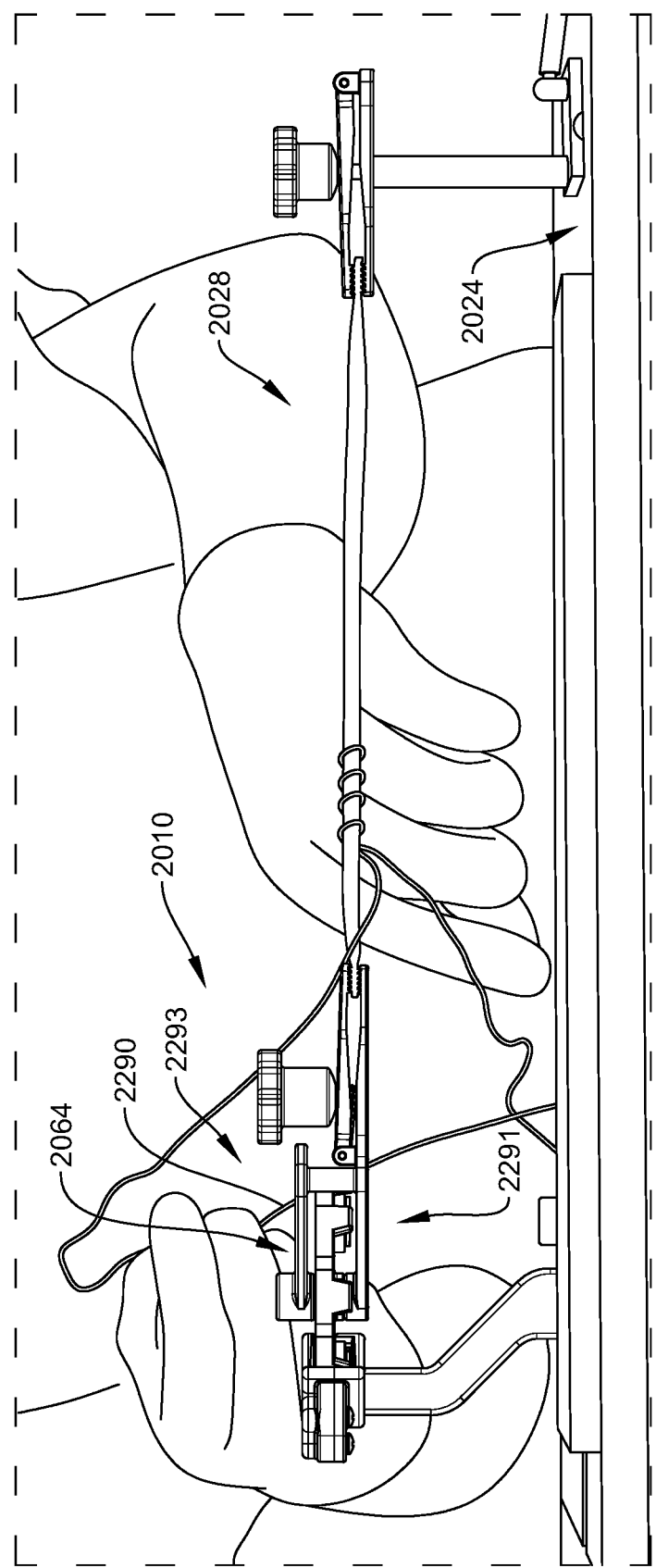
FIG. 84 is a right side elevation view of the medical preparation station of FIG. 40A, illustrating the user moving the loop segment from the cord transport space, through the outlet space and to the second environmental space.

As illustrated in FIGS. 82-84, the rotor 2064 is configured to enable the user to conveniently insert the loop segment 2290 between any pair of the arms 2068, moving the loop segment 2290 from the first environmental space 2291, which is furthest from the user, to the second environmental space 2293, which is closest to the user.

Figure 85:
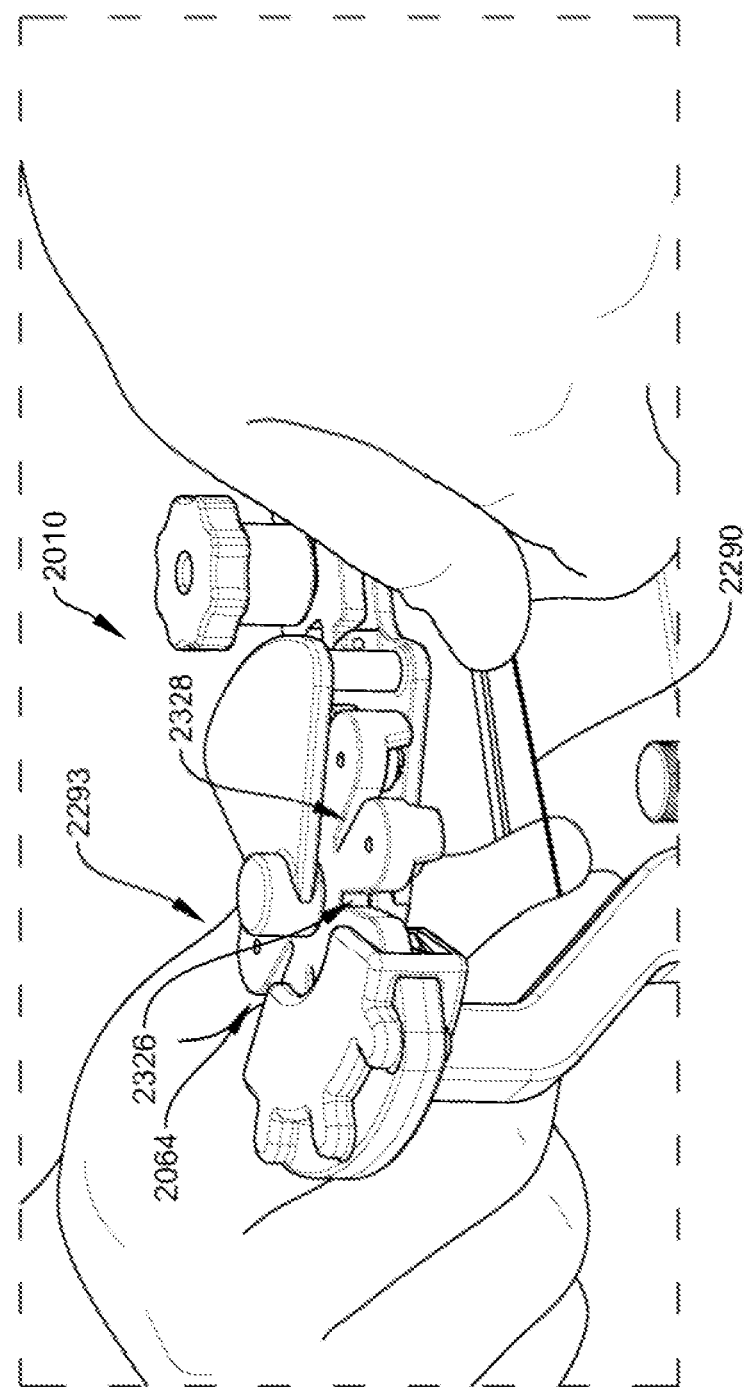
FIG. 85 is a right side elevation view of the medical preparation station of FIG. 40A, illustrating the user inserting the loop segment between a user-selected one of the pairs of the arms of the rotor.
Figure 86:
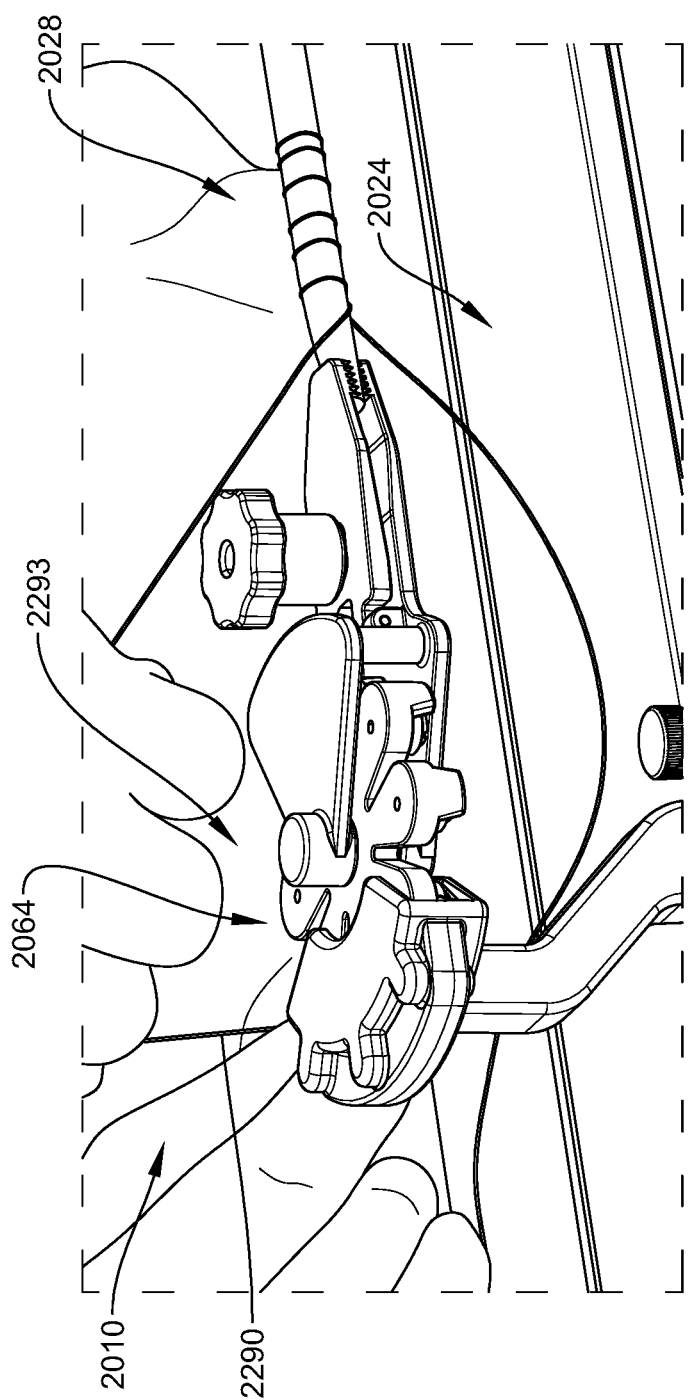
FIG. 86 is a right side elevation view of the medical preparation station of FIG. 40A, illustrating the user moving the loop segment from the cord transport space, through the outlet space and to the second environmental space.

As illustrated in FIG. 85, the user has the option of selecting the cord transport space 2326 or the cord transport space 2328 for insertion of the loop segment 2290. After inserting the loop segment 2290 into cord transport space 2326 or 2328, the user easily pulls the loop segment 2290 toward the user. In response, the rotor 2064 rotates, moving the loop segment 2290 into alignment with the second environmental space 2293. The user can then easily move the loop segment 2290 from the rotor 2064 to the second environmental space 2293, as shown in FIG. 86.

Figure 87:
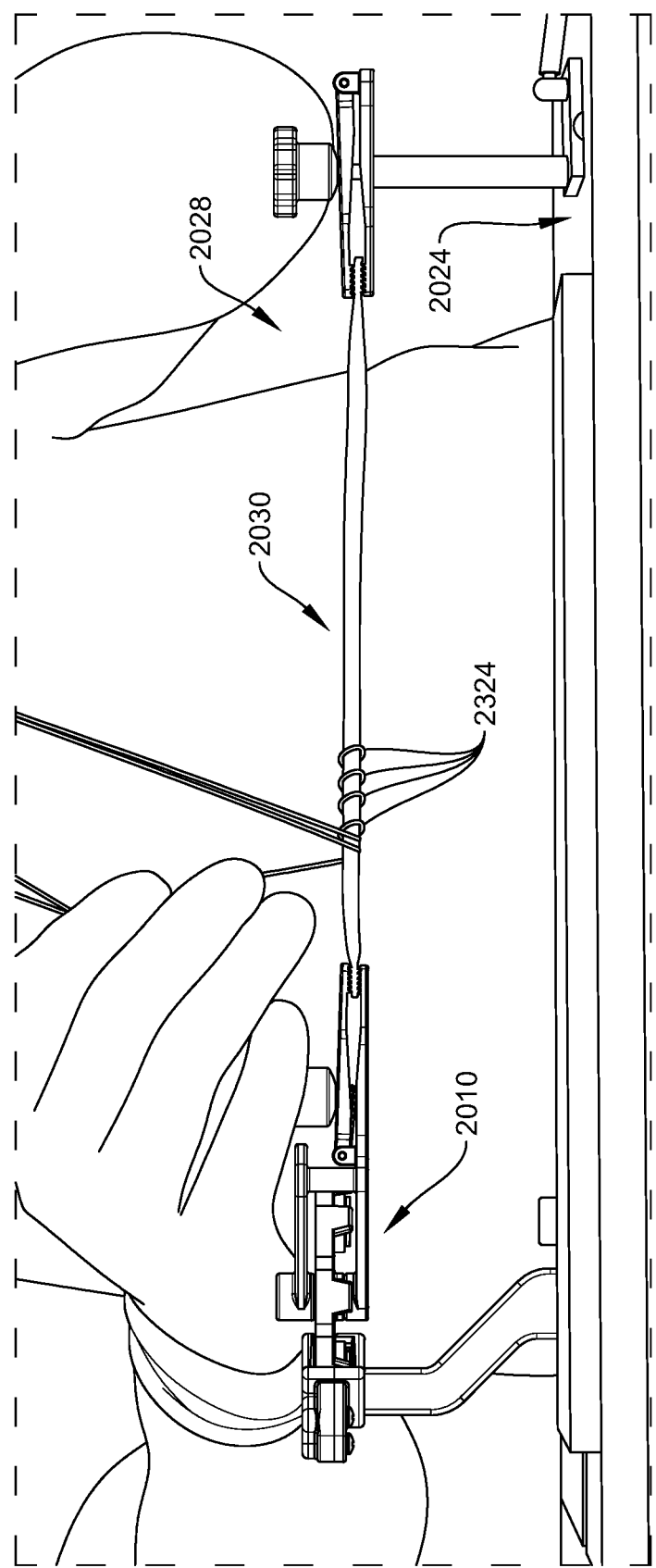
FIG. 87 is a right side elevation view of the medical preparation station of FIG. 40A, illustrating a series of four stitches formed in the implantable element as a result of a series of four pass-through steps based on the use of the medical holding system.

As illustrated in FIG. 87, the user has prepared the implantable element 2030 with a series of stitches 2324 by completing a series of the pass-through steps described above.

Figure 88:
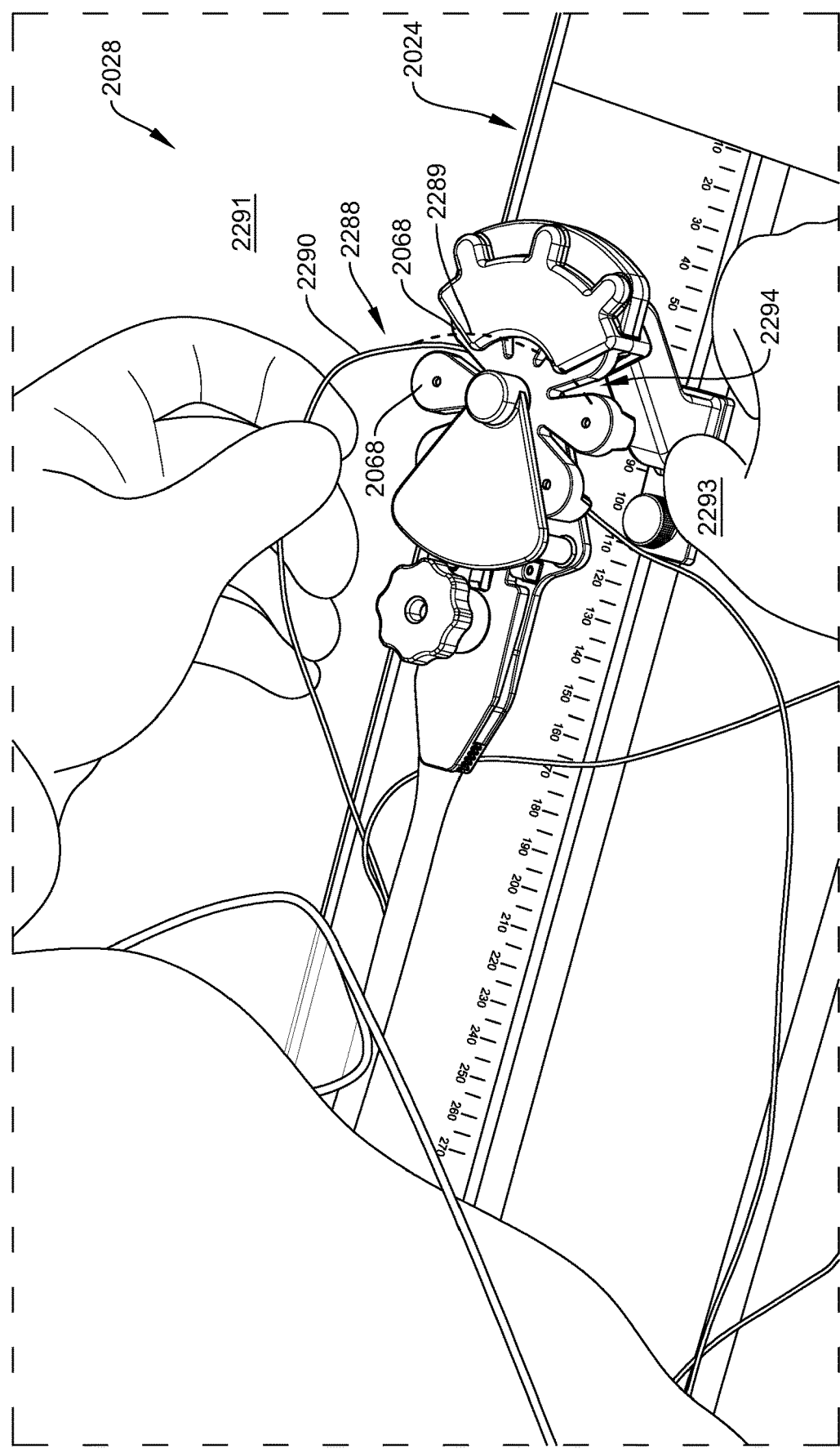
FIG. 88 is a top, left isometric view of the medical preparation station of FIG. 40A, illustrating the user inserting the loop segment between a user-selected one of the pairs of the arms of the rotor.
Figure 89:
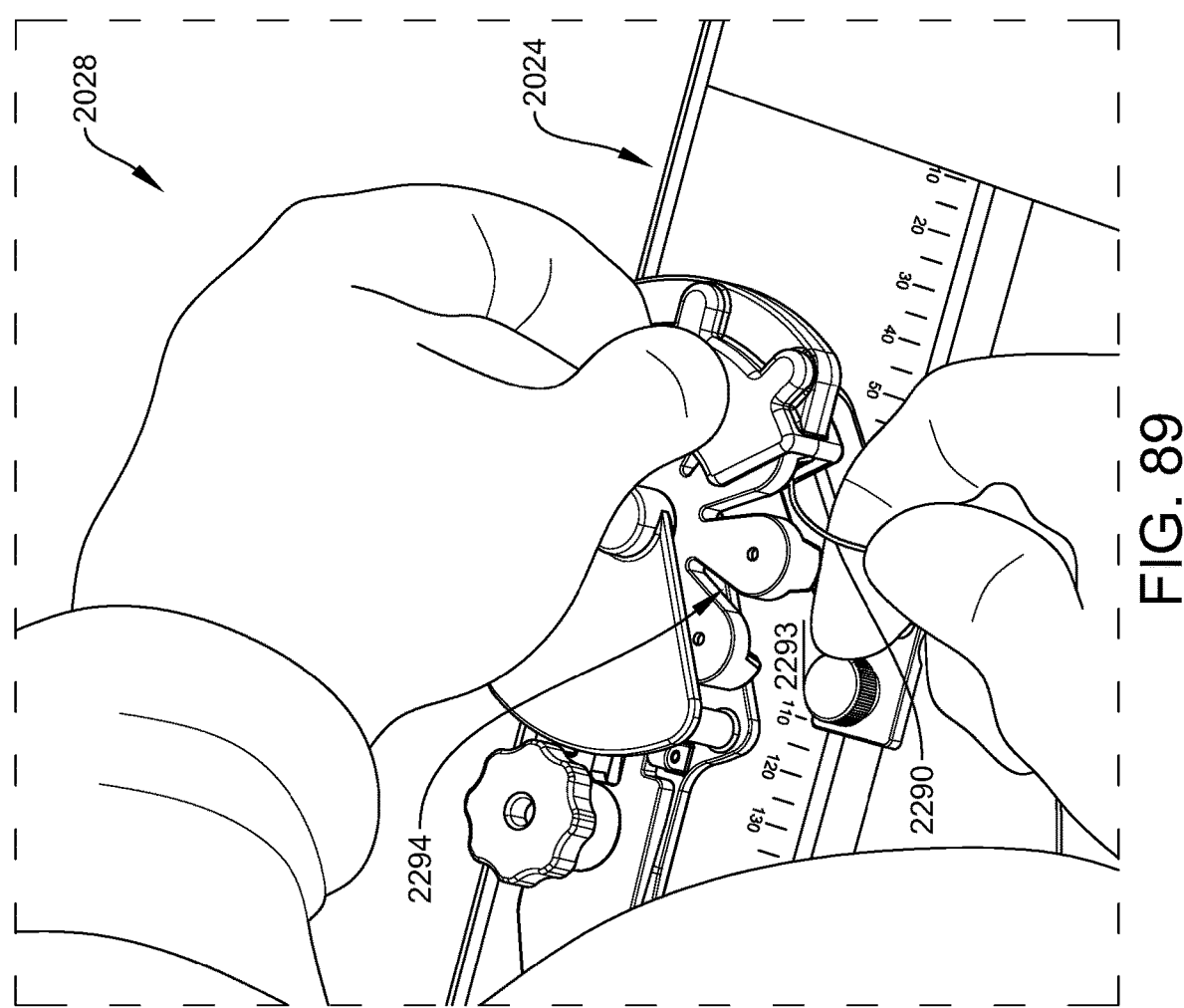
FIG. 89 is a top, left isometric view of the medical preparation station of FIG. 40A, illustrating the user moving the loop segment from the cord transport space, through the outlet space and to the second environmental space.

As illustrated in FIGS. 88-89, the loop segment 2290 is moveable from the first environmental space 2291, through the entry space 2288, to a position between a pair of the arms 2068. The user can then pull the loop segment 2290 along the passageway 2289 and eventually move the loop segment 2290 from between the arms 2068, through the outlet space 2294, and to second environmental space 2293.

Figure 90:
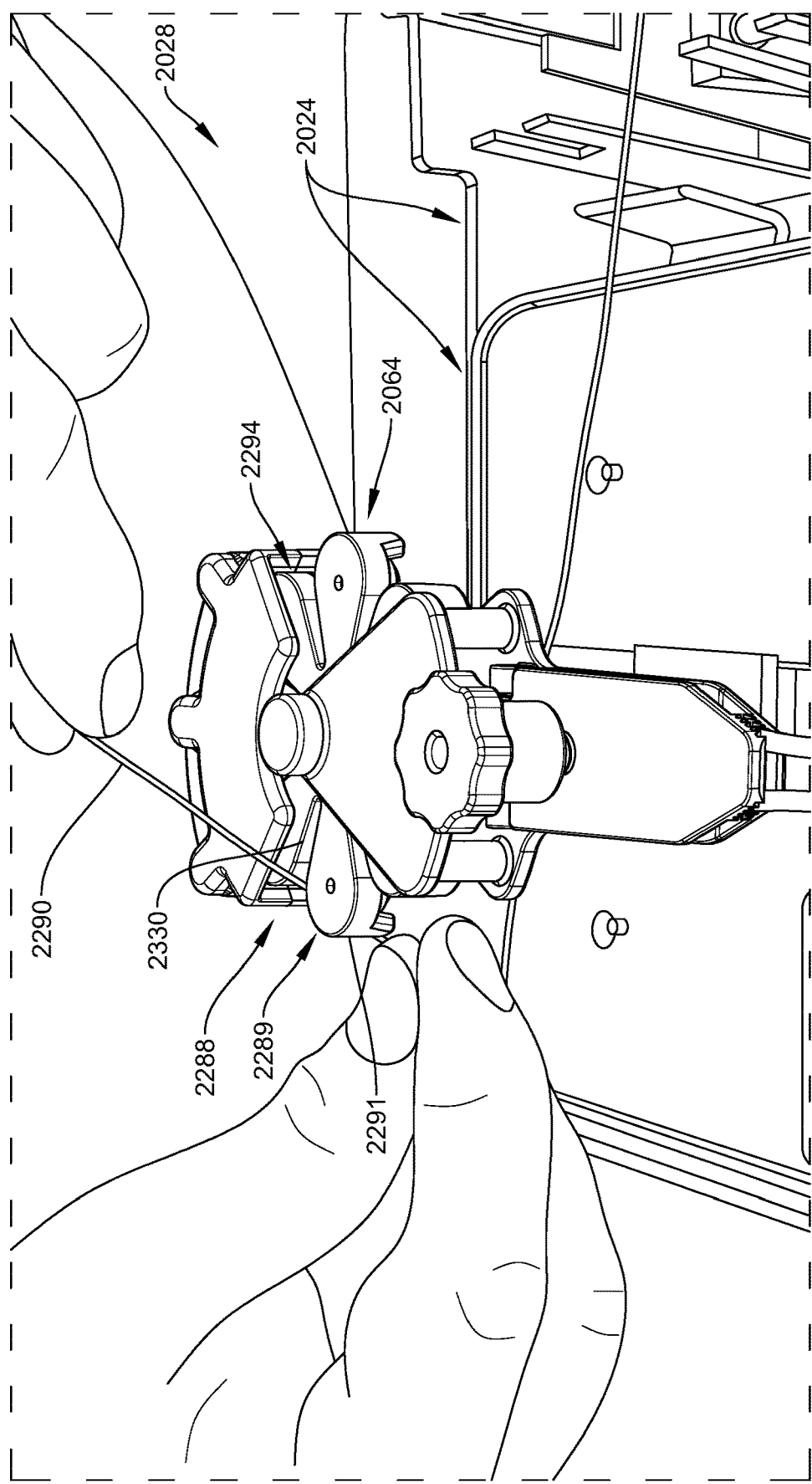
FIG. 90 is a front isometric view of the medical preparation station of FIG. 40A, illustrating the user moving the loop segment from the first environmental space, through the entry space, and into one of the cord transport spaces.
Figure 91:
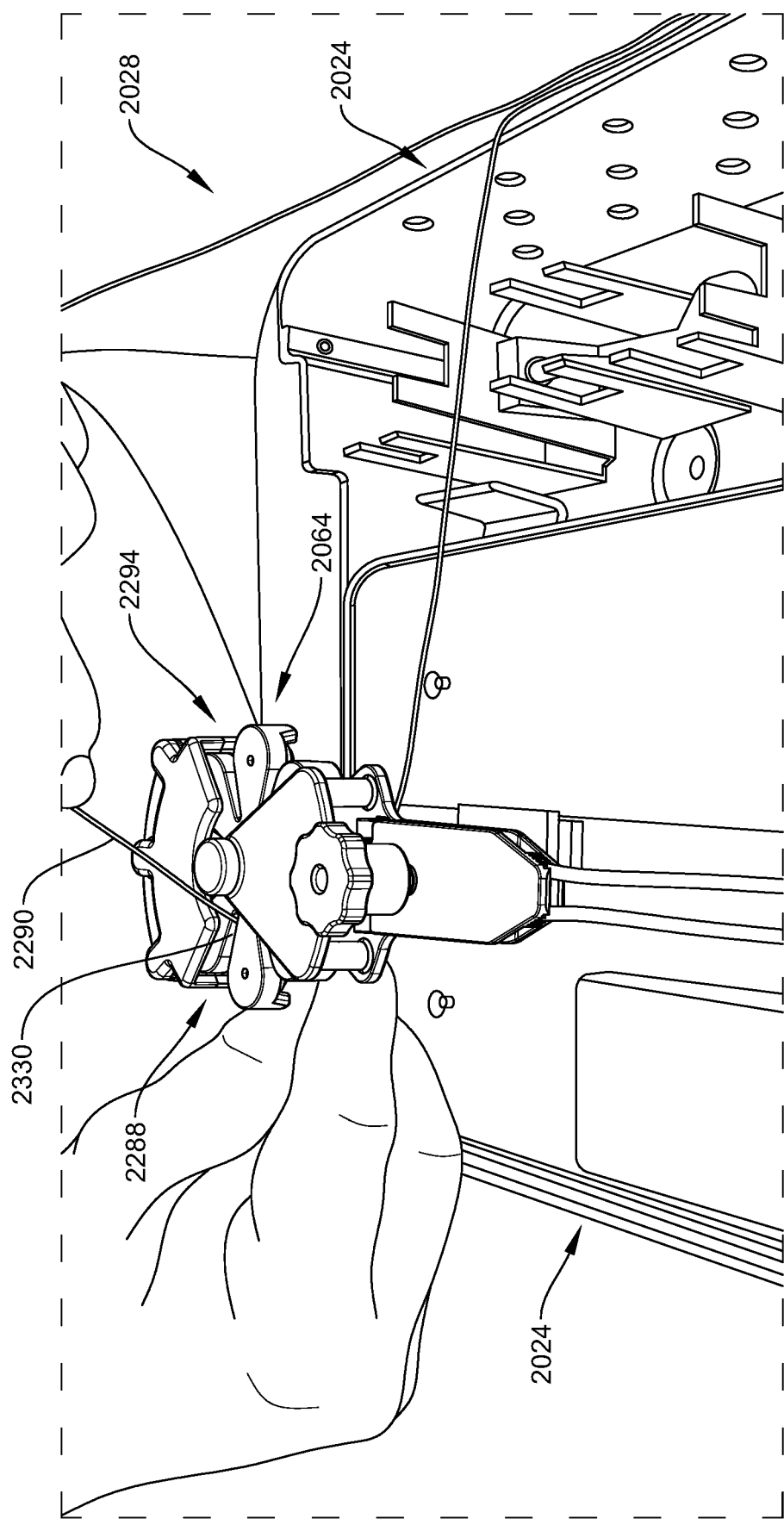
FIG. 91 is a front isometric view of the medical preparation station of FIG. 40A, illustrating the user moving the loop segment (within one of the cord transport spaces) while the rotor pivots or rotates relative to the retainer.
Figure 92:
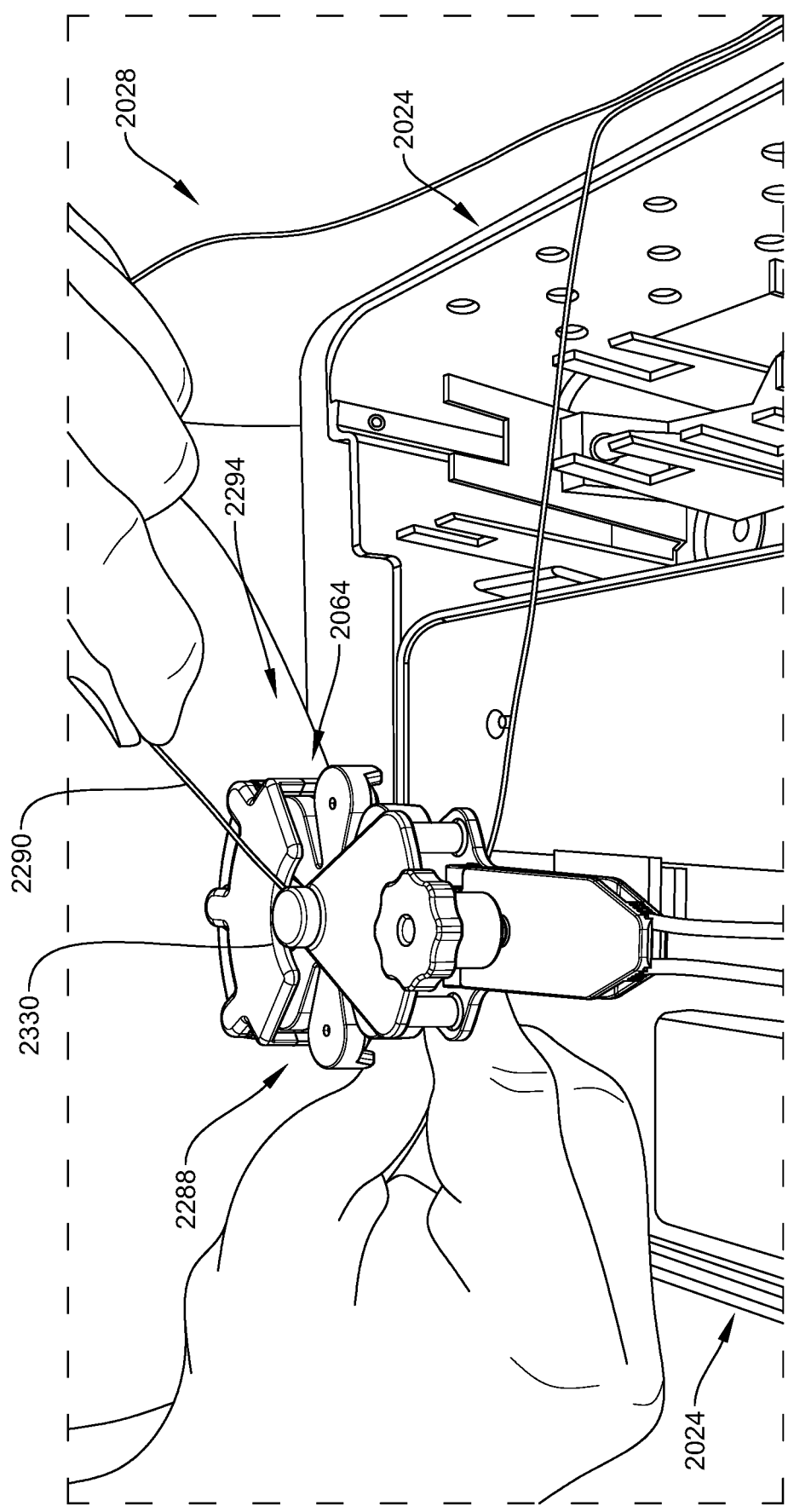
FIG. 92 is a front isometric view of the medical preparation station of FIG. 40A, illustrating the user continuing to move the loop segment (within one of the cord transport spaces) while the rotor continues to pivot or rotate relative to the retainer.
Figure 93:
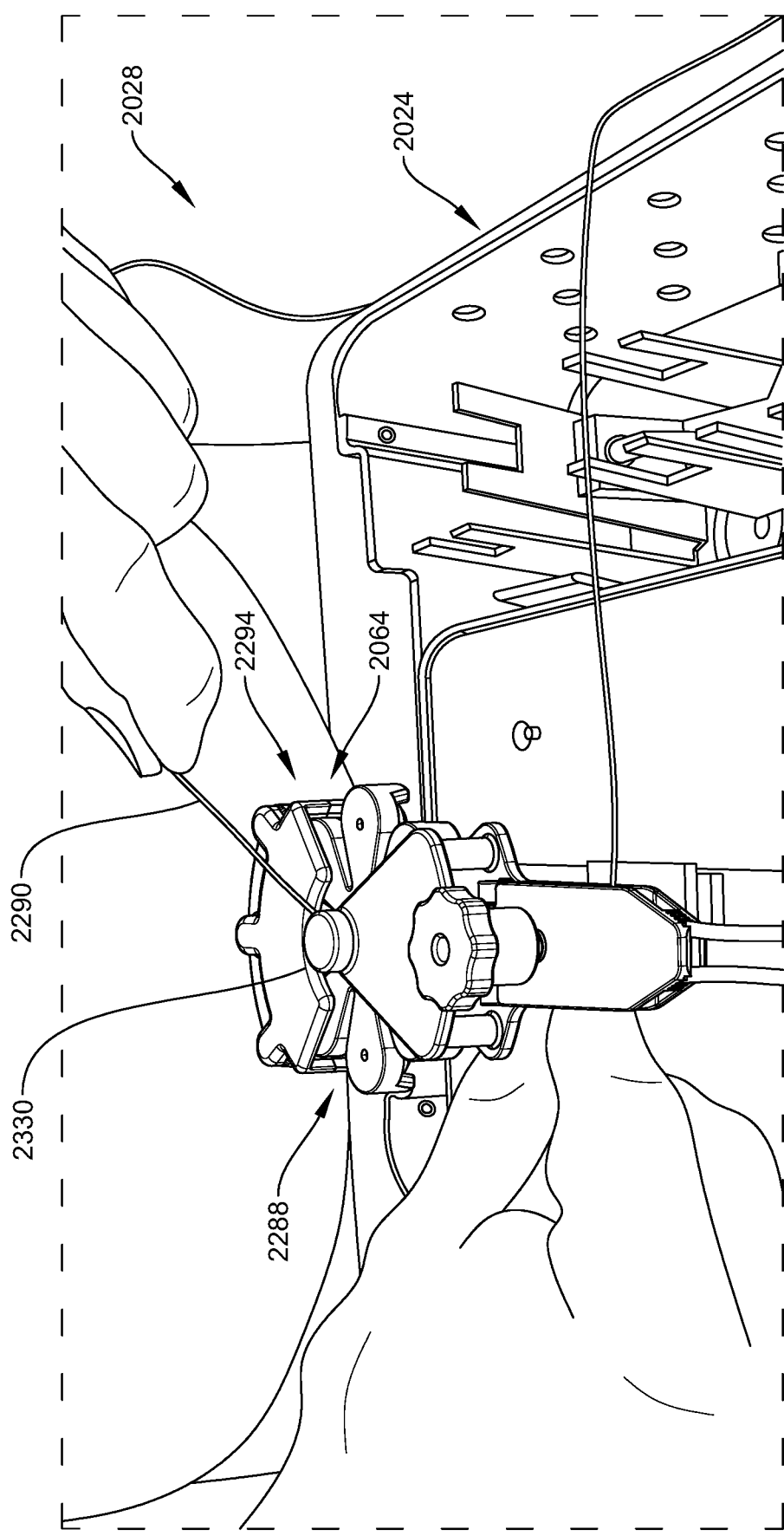
FIG. 93 is a front isometric view of the medical preparation station of FIG. 40A, illustrating the further movement of the loop segment (within one of the cord transport spaces) while the rotor continues to pivot or rotate relative to the retainer.
Figure 94:
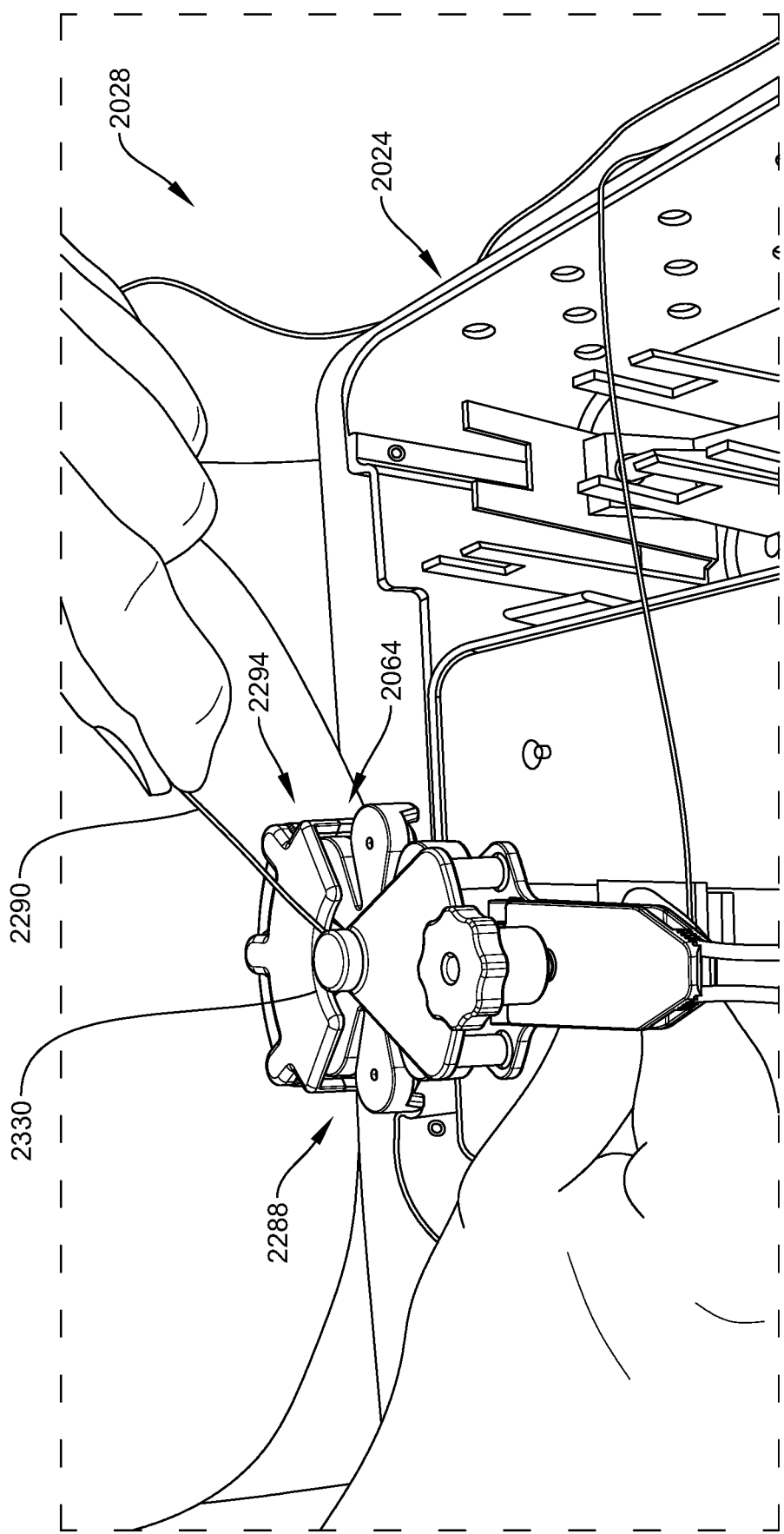
FIG. 94 is a front isometric view of the medical preparation station of FIG. 40A, illustrating the user beginning to move the loop segment from the cord transport space, through the cord outlet space and to the second environmental space.

As illustrated in FIGS. 90-94, the rotor 2064 is configured to continuously rotate as the user moves the loop segment 2290 from the entry space 2288, into the cord transport space 2330 and then pulls the loop segment 2290 through the outlet space 2294, in this example, from the user's right to left. For example, FIG. 90 shows the arm 2289 at the 10 PM position 2291. As the user performs multiple pass-through steps for suturing, the arm 2289 will rotate and eventually return to the 10 PM position 2291.

Figure 95:
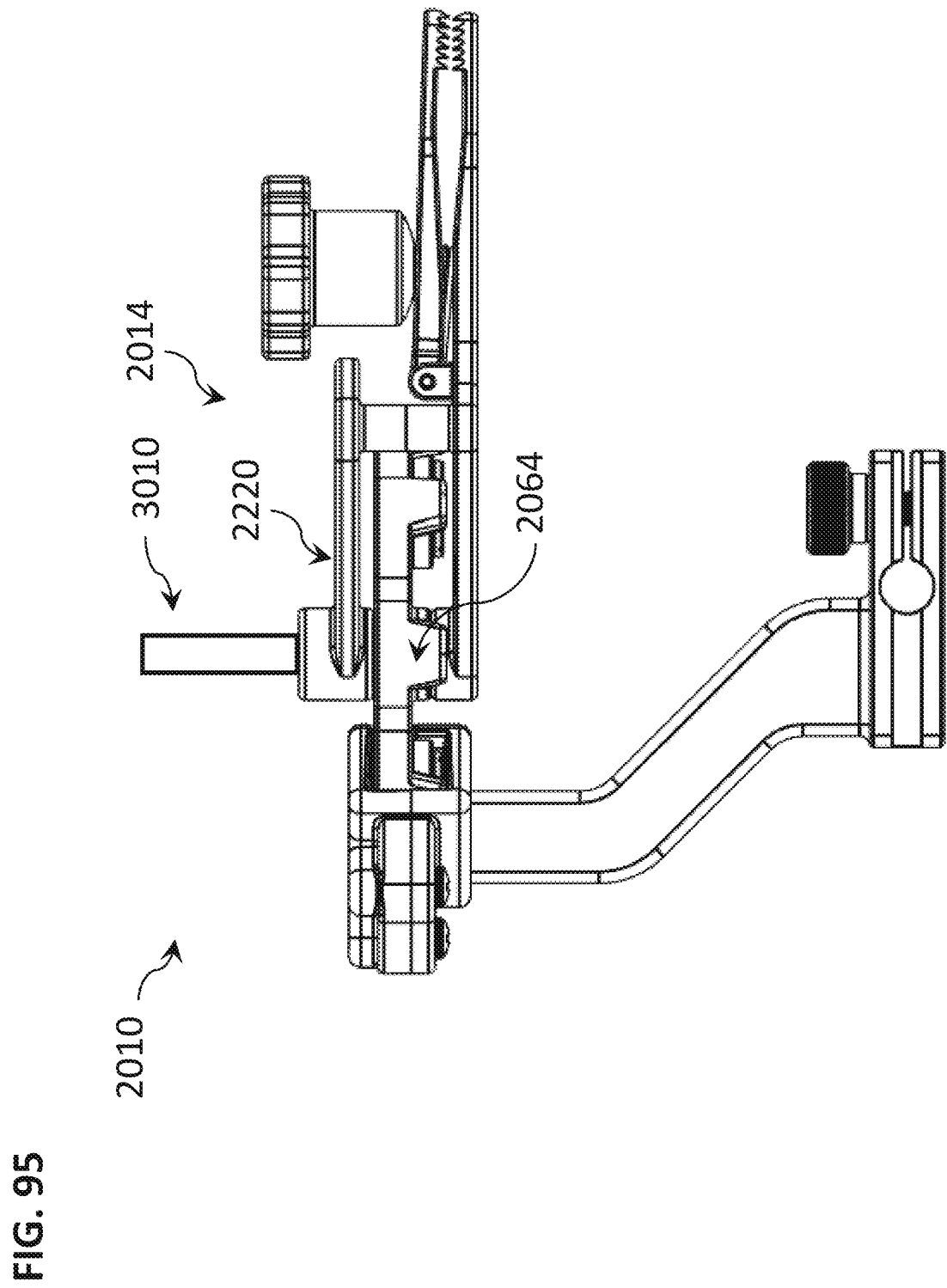
FIG. 95 is a side elevation view of an embodiment of the medical holding system that has an embodiment of a cord management device.
Figure 96:
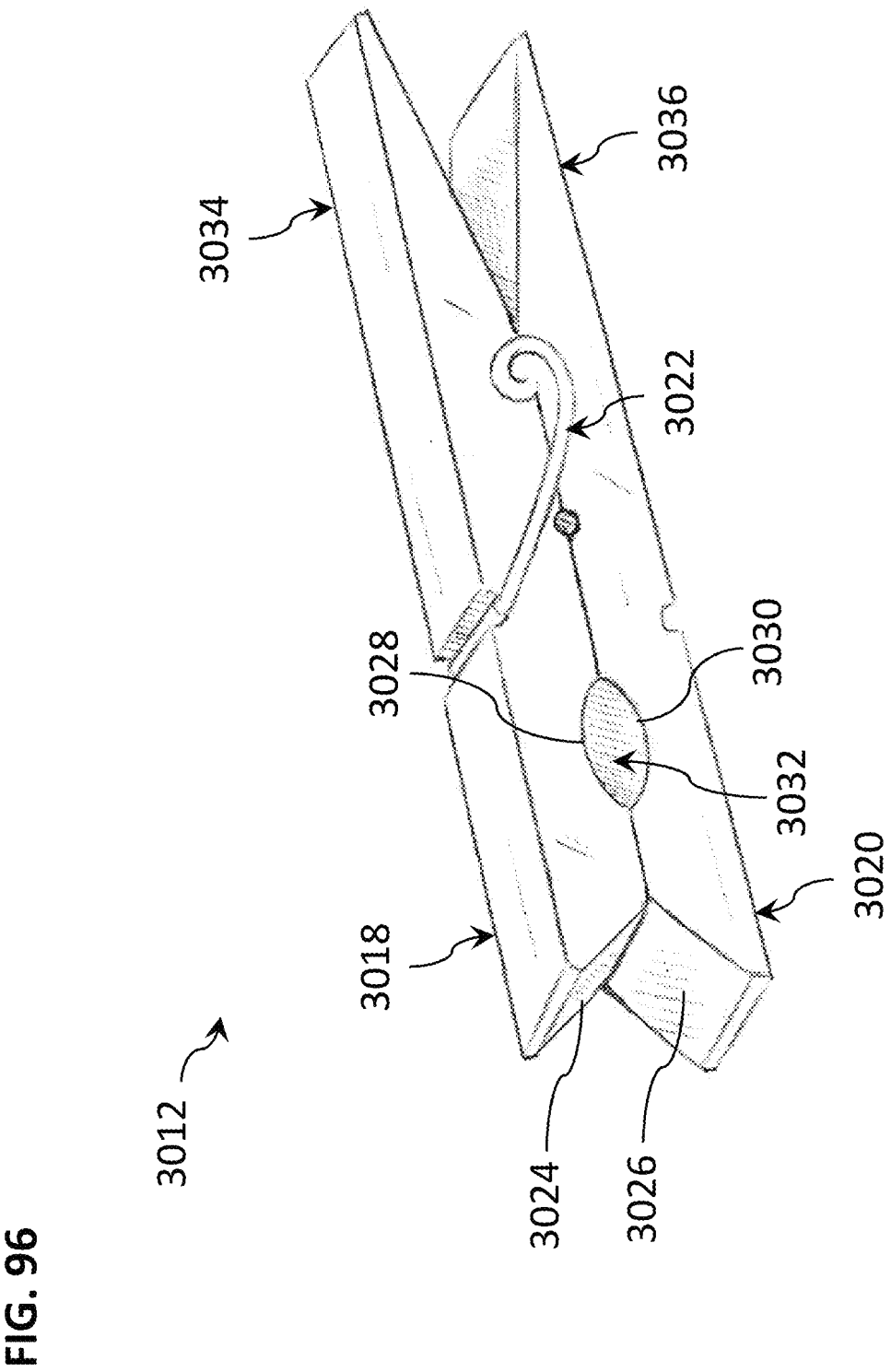
FIG. 96 is a top, side isometric view of an embodiment of the cord management device of FIG. 95, illustrating an embodiment of a clip of such cord management device.

Referring to FIG. 95, in an embodiment, the medical holding system 2010 includes a cord management device 3010 coupled, directly or indirectly, to the holder 2014. In the example shown, the cord management device 3010 is mounted to or a part of the grasper coupler 2220. It should be appreciated, however, that the cord management device 3010 can be attached or integrated into any part of the holder 2014. The cord management device 3010 is structured and configured to reversibly or releasably hold part of the looped cord 2310, shown in FIG. 65, once the user pulls the segment 2290 through the rotor 2064. For example, once the user completes a pass-through step, as described above, the looped cord 2310 can obstruct and interfere with the process of suturing and piercing the implantable element 2030. To overcome or lessen the effects of this disadvantage, the user can fully or partially position the looped cord 2310 within the cord management device 3010 or otherwise removably attach the looped cord 2310 to the cord management device 3010. While the user performs the suturing, the cord management device 3010 keeps the looped cord 2310 out of the way of the suturing space. To the extent the user needs to use a part of the looped cord 2310 held by the cord management device 3010, the cord management device 2290 is operable to release the desired part of the looped cord 2310 for the suturing process.

In an embodiment, referring to FIGS. 96-99, the cord management device 2290 includes or incorporates part or all of the elements and functionality of a clip 3012, a clip 3014, or any suitable combination of such clips. Clip 3012 has a plurality of jaws 3018, 3020 and a spring or biasing member 3022 that couples the jaws 3018, 3020 together. The jaws 3018, 3020 have: (a) angled or slanted cord engagement surfaces 3024, 3026, respectively; and (b) concave-shaped surfaces 3028, 3030 which, when joined together, define a cord holding space 3032. In operation, the user can slide the looped cord 2310 along either of the cord engagement surfaces 3024, 3026 and then push or pull the looped cord 2310 between the jaws 3018, 3020, causing the jaws 3018, 3020 to partially separate, enabling the user to place at least part of the looped cord 2310 into the cord holding space 3032. As an aid, the user can press the handles 3034, 3036 together to facilitate the separation of the jaws 3018, 3020, which are urged together by the biasing member 3022. In an embodiment, the cord holding space 3032 is large enough to enable the user to stuff part or all of the looped cord 2310, in balled-up form, into the cord holding space 3032. While the user performs the suturing, the cord holding space 3032 keeps the looped cord 2310 out of the way of the suturing space. To the extent the user needs to use a part of the looped cord 2310 held in the cord holding space 3032, the jaws 3018, 3020 are separable to release the desired part of the looped cord 2310 for the suturing process.

Figure 99:
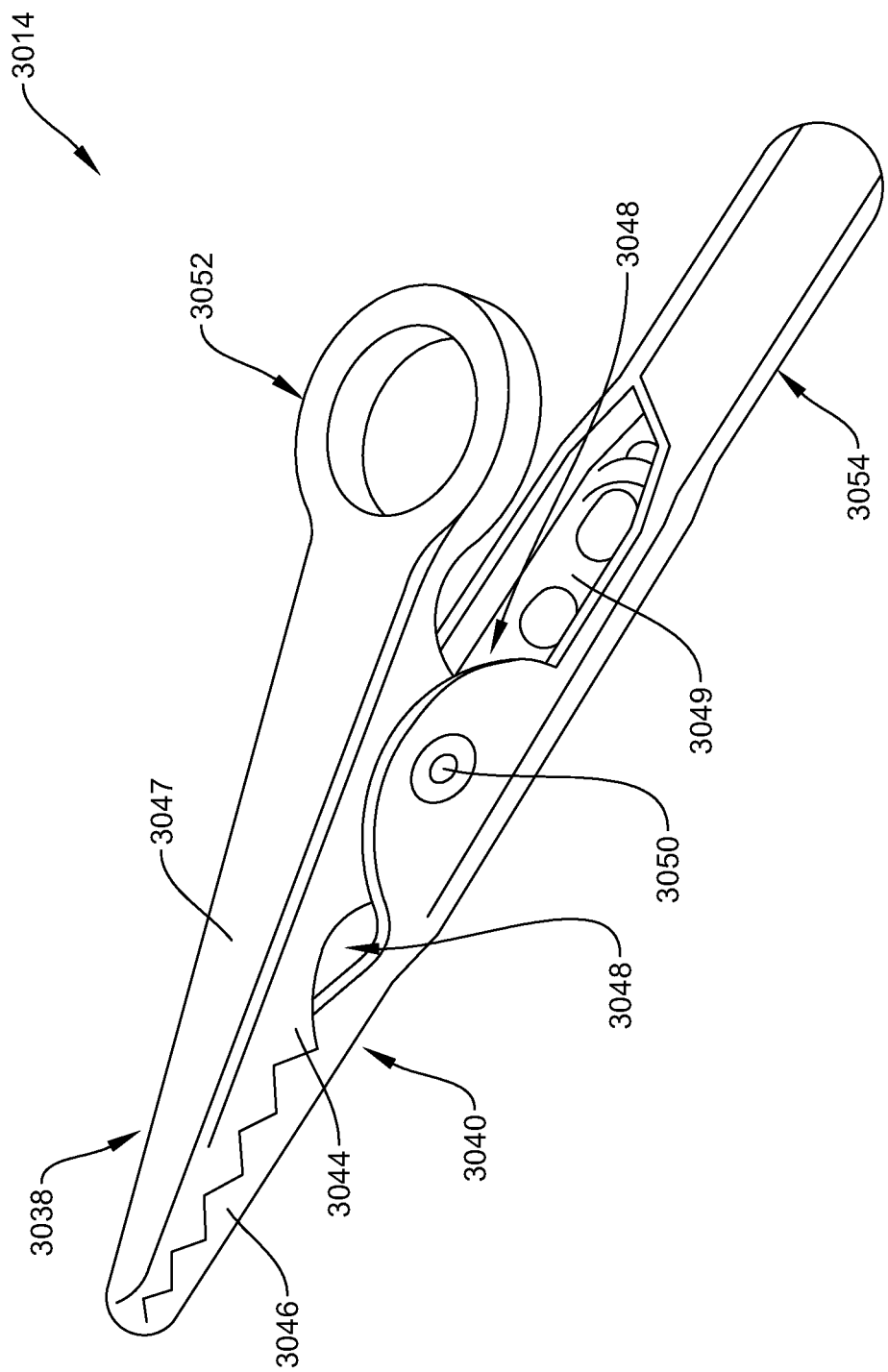
FIG. 99 is a top isometric view of the clip of FIG. 97, illustrating the cord holding space defined by such clip.

Referring to FIGS. 97-99, clip 3014 has a plurality of jaws 3038, 3040 and a spring or biasing member 3042 that couples the jaws 3038, 3040 together. The jaws 3038, 3040 have: (a) a plurality of side retaining walls 3044, 3046, respectively, each of which has grippers or teeth; (b) a plurality of oppositely-positioned side retaining walls (not shown) located opposite of side retaining walls 3044, 3046; (c) a top retaining surface 3047 connected to the side retaining walls 3044, 3046 and to the opposite side retaining walls; (d) a bottom retaining surface 3049 connected to the side retaining walls 3044, 3046 and to the opposite side retaining walls; (e) a cord holding space 3048 defined by, and located between: (i) the side retaining wall 3044 and the corresponding, opposite retaining wall (not shown); and (ii) the side retaining wall 3046 and the corresponding, opposite retaining wall (not shown); (d) a pivot member 3050 that pivotally couples the jaws 3038, 3040 together. In an embodiment, the clip 3014 includes a spring or other biasing member configured to urge the jaws 3038, 3040 together. In operation, the user can push the handles 3052, 3054 together, causing the jaws 3038, 3040 to partially separate, enabling the user to at least partially place the looped cord 2310 into the cord holding space 3048. In an embodiment, the cord holding space 3048 is large enough to enable the user to stuff the looped cord 2310, in balled-up form, into the cord holding space 3032. While the user performs the suturing, the cord holding space 3048 keeps the looped cord 2310 out of the way of the suturing space. To the extent the user needs to use a part of the looped cord 2310 held in the cord holding space 3048, the jaws 3038, 3040 are separable to release the desired part of the looped cord 2310 for the suturing process.

Figure 100:
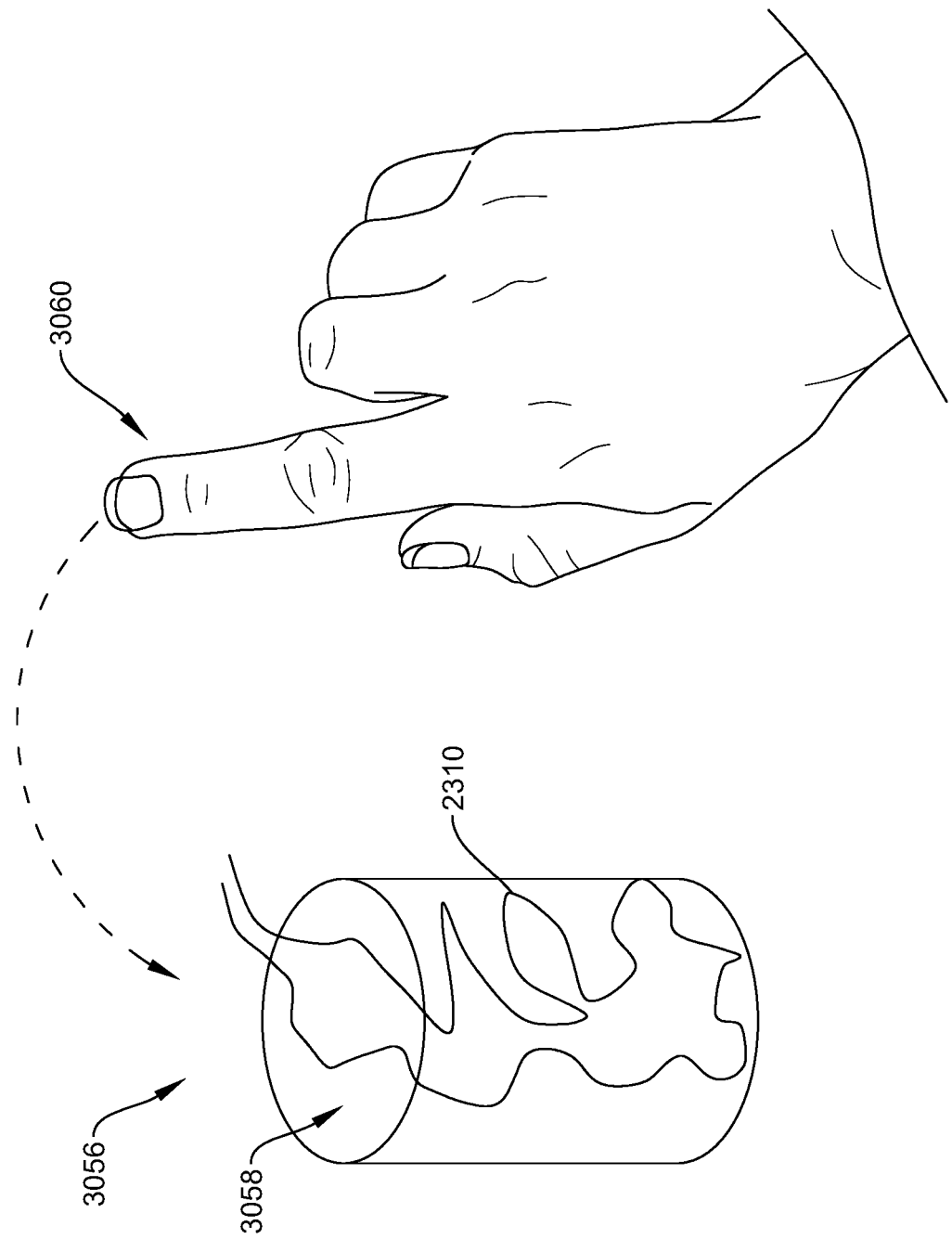
FIG. 100 is an isometric view of an embodiment of the cord management device of FIG. 95, illustrating an embodiment of a cord container of such cord management device.

Referring to FIG. 100, in an embodiment, the cord management device 2290 includes or incorporates part or all of the elements and functionality of a container 3056. Depending on the embodiment, the container 3056 can be flexible, rigid or semi-rigid. For example, the container 3056 can be constructed of a rigid material, a flexible mesh material or a polymeric layer. The container 3056 defines a cord holding space 3058. The cord holding space 3058 is large enough to at least partially receive one or more fingers of the user, such as a finger 3060 of the user. In operation, the user can insert the looped cord 2310 into the cord holding space 3058. In an embodiment, the cord holding space 3058 is large enough to enable the user to stuff the looped cord 2310, in balled-up form, into the cord holding space 3058. While the user performs the suturing, the cord holding space 3058 keeps the looped cord 2310 out of the way of the suturing space. To the extent the user needs to use a part of the looped cord 2310 stored in the cord holding space 3048, the user can pull on the looped cord 2310, causing such part of the looped cord 2310 to gradually move outside of the cord holding space 3058 for use in the suturing process.

Figure 101:
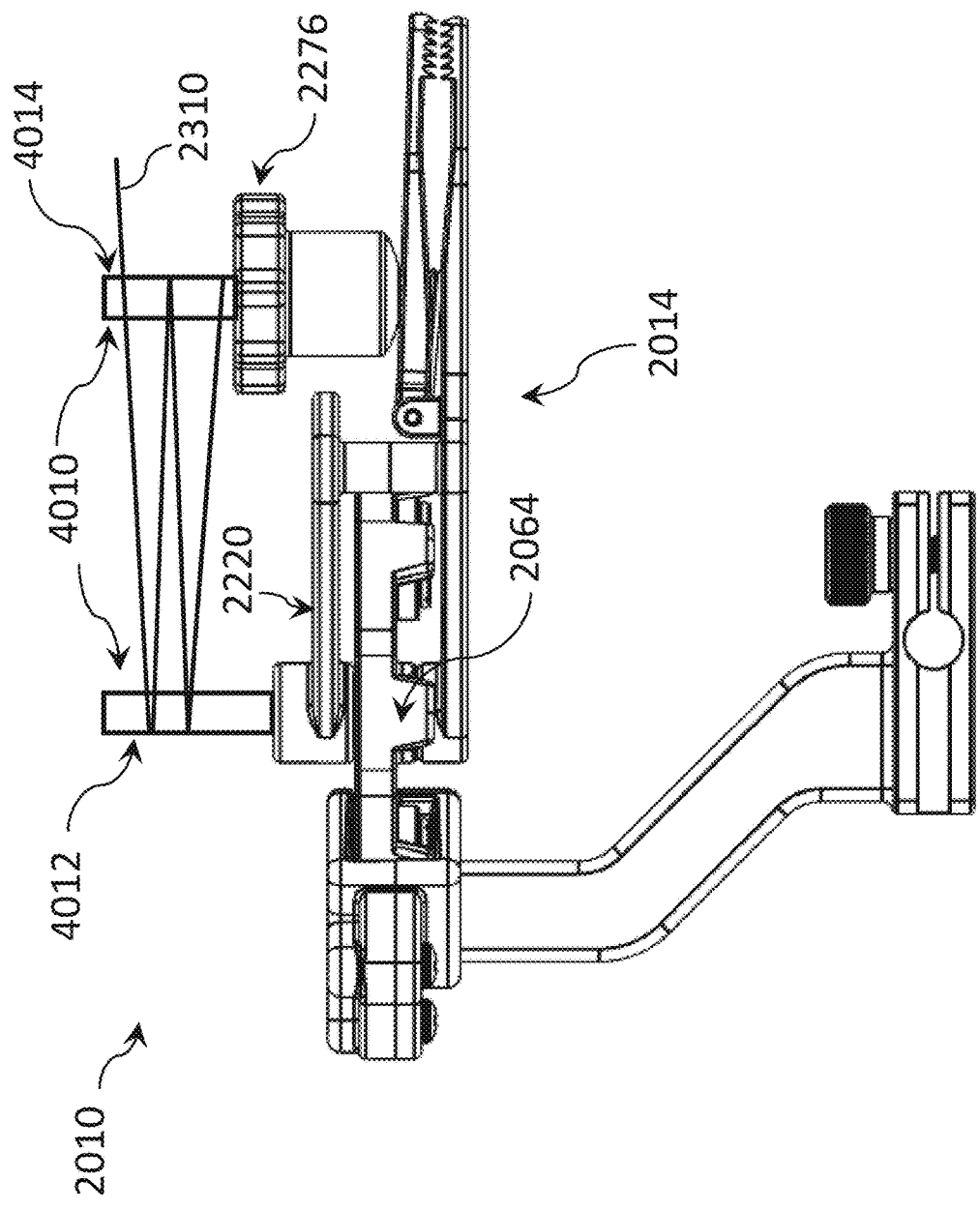
FIG. 101 is a side elevation view of an embodiment of the medical holding system that has another embodiment of a cord management device, illustrating the looped cord wound around a plurality of cord supports.

Referring to FIG. 101, in an embodiment, the medical holding system 2010 includes a cord management device 4010 coupled, directly or indirectly, to the holder 2014. The cord management device 4010 includes a plurality of poles, posts, uprights or cord supports 4012, 4014. Depending on the embodiment, the cord supports 4012, 4014 can be tubular or rod-shaped, having any suitable circumferential geometry, including, but not limited to, cylindrical or square. Also, the exterior surfaces of the cord supports 4012, 4014 can define one or more circumferential grooves configured to receive and interface with the looped cord 2310. As shown, the cord supports 4012, 4014 are spaced apart from each other. In the example shown, the cord support 4012 is mounted to or a part of the grasper coupler 2220, and the cord support 4014 is mounted to or a part of the grasp knob 2276. It should be appreciated, however, that the cord supports 4012, 4014 can be attached or integrated into any part of the holder 2014. In operation, after each pass-through step, as described above, the user can wind or wrap the looped cord 2310 around both of the cord supports 4012, 4014 so that the looped cord 2310 extends, in loop-fashion, from the cord support 4012 to the cord support 4014. Depending on the length of the looped cord 2310, the user can wind the looped cord 2310 multiple times around the cord supports 4012, 4014. Each winding takes-up a length of the looped cord 2310 substantially equal to twice the distance between the cord supports 4012, 4014. While the user performs the suturing, the cord supports 4012, 4014 keep the looped cord 2310 out of the way of the suturing space. To the extent the user needs to use a part of the looped cord 2310 wrapped around the cord supports 4012, 4014, the user can unwind or unwrap such part of the looped cord 2310 from the cord supports 4012, 4014, retrieving such part of the looped cord 2310 for use in the suturing process.

In an embodiment, a method for preparing an implantable element includes the following steps:

Securing the second element portion 2034 of the implantable element 2030 to the hanger 2026 so that the second element portion 2034 is suspended above the support structure 2024;

Sliding the foot 2118 of the medical holding system 2010 within the track 2152 in a forward direction 2332 until the grippers 2238, 2241 are positioned to hold onto the first element portion 2032; Inserting the first element portion 2032 into the mouth 2304 of the grippers 2238, 2241;

Rotating the grasp knob 2276 to cause the grippers 2238, 2241 to compress the first element portion 2032 until the first element portion 2032 is securely suspended above the support structure 2024;

Sliding the foot 2118 of the medical holding system 2010 within the track 2152 in a rearward direction 2306 to generate or increase the tension in the implantable element 2030;

Testing the level of tension in the implantable element 2030 by pushing or pulling the suspended implantable element 2030;

Repeating the rearward sliding and testing steps until the testing results in a suitable level of tension in the implantable element 2030;

Rotating the foot knob 2150, causing the upper and lower foot portions 2120, 2122 to clamp onto the edges 2154, 2156 until the foot 2118 is fixedly secured to the support structure 2024;

Moving the loop segment 2290 of the cord assembly 2308 from the entry space 2288 into any one of the cord transport spaces 2078 that is accessible through the entry space 2288;

Pulling the loop segment 2290, causing the rotor 2064 to rotate relative to the retainer 2016;

Continuing to pull the loop segment 2290 until such cord transport space 2078 is adjacent to or otherwise aligned with the outlet space 2294;

Moving the loop segment 2290 from such cord transport space 2078 to the outlet space 2294 so that the looped cord 2310 encircles the implantable element 2030;

Piercing the implantable element 2020 with the needle 2313 while the looped cord 2310 encircles the implantable element 2030, wherein the piercing is located rearward of the looped cord 2310; and Pulling the looped cord 2310 through the implantable element 2030 so as to establish a relatively tight, first suture line or first stitch 2318.

In an embodiment, each of the medical holding systems 139, 150, 310, 410, 510, 610, 710, 810, 1010, and 2010 is operable to suture, stitch, graft or otherwise prepare items other than implantable elements, including, but not limited to, medical devices, medical materials, biological materials, human tissue and animal tissue. In such case, the foregoing disclosure will apply as if the implantable elements described above are replaced with either such type of item.

Additional embodiments include any one of the embodiments described above, where one or more of its components, functionalities or structures is interchanged with, replaced by or augmented by one or more of the components, functionalities or structures of a different embodiment described above. For example, the foot 2118 can be replaced with the foot 2119 or the foot 2155.

The parts, components, and structural elements of each of the medical holding systems 139, 150, 310, 410, 510, 610, 710, 810, 1010 and 2010 can be combined into an integral or unitary, one-piece object, or such parts, components, and structural elements can be distinct, removable items that are attachable to each other through screws, bolts, pins and other suitable fasteners. For example, the grasper and coupler can be integral or separate components depending on the embodiment. In another example, the support device and release interface can be integral or separate components depending on the embodiment.

In the foregoing description, certain components or elements have been described as being configured to mate with each other. For example, an embodiment may be described as a first element (functioning as a male) configured to be inserted into a second element (functioning as a female). It should be appreciated that an alternate embodiment includes the first element (functioning as a female) configured to receive the second element (functioning as a male). In either such embodiment, the first and second elements are configured to mate with or otherwise interlock with each other.

It should be understood that various changes and modifications to the embodiments described herein will be apparent to those skilled in the art. Such changes and modifications can be made without departing from the spirit and scope of the present disclosure and without diminishing its intended advantages. It is therefore intended that such changes and modifications be covered by the appended claims.

Although several embodiments of the disclosure have been disclosed in the foregoing specification, it is understood by those skilled in the art that many modifications and other embodiments of the disclosure will come to mind to which the disclosure pertains, having the benefit of the teaching presented in the foregoing description and associated drawings. It is thus understood that the disclosure is not limited to the specific embodiments disclosed herein above, and that many modifications and other embodiments are intended to be included within the scope of the appended claims. Moreover, although specific terms are employed herein, as well as in the claims which follow, they are used only in a generic and descriptive sense, and not for the purposes of limiting the present disclosure, nor the claims which follow.

The following is claimed:

1. A medical holding system comprising:
   a retainer defining a retainer interface;
   a pivot device comprising a plurality of arms, wherein:
      each of the arms comprises a first arm portion and a second arm portion; and
      each of the second arm portions comprises an arm interface configured to mate with the retainer interface; and
      the first arm portions are separated by a cord transport space; and
   a grasper coupled to the pivot device, wherein the grasper is configured to grasp an implantable element;
   wherein the pivot device is configured to be pivoted, relative to the retainer, between an entry position and an outlet position,
   wherein, in the entry position, there comprises an entry space between the retainer and one of the second arm portions so that a cord segment of a medical cord is moveable through the entry space to the cord transport space,
   wherein, in the outlet position, there comprises an outlet space between the retainer and one of the second arm portions so that the cord segment is moveable from the cord transport space and through the outlet space,
   wherein the pivoting of the pivot device causes the cord transport space to move along a cord passageway extending from the entry space to the outlet space,
   wherein at least one of the arm interfaces remains mated with the retainer interface during the pivoting of the pivot device between the entry position and the outlet position.

2. The medical holding system of claim 1, wherein:
   the retainer interface comprises a bottom retainer surface and a plurality of side retainer surfaces extending from the bottom retainer surface;
   the bottom retainer surface and the side retainers surfaces collectively define a retainer channel; and
   the retainer channel comprises an arc shape.

3. The medical holding system of claim 2, wherein each of the arm interfaces comprises an arm guide configured to at least partially fit in the retainer channel.

4. The medical holding system of claim 3, wherein each of the arm interfaces comprises a friction reducer configured to at least partially fit in the retainer channel.

5. The medical holding system of claim 4, wherein each of the friction reducers comprises a roller.

6. The medical holding system of claim 5, wherein the grasper comprises:
   a plurality of grippers; and
   a securement device coupled to the grippers,
   wherein the securement device is adjustable to apply a securement force to the grippers.

7. The medical holding system of claim 1, wherein the retainer comprises:
   a bottom retainer portion configured to support the pivot device; and
   a top retainer portion configured to be coupled to the bottom retainer portion, wherein the bottom retainer portion and the top retainer portion are configured to trap the arm interface of at least one of the arms,
   wherein the bottom retainer portion comprises a bottom retainer surface and a plurality of bottom side retainer surfaces extending from the bottom retainer surface,
   wherein the bottom retainer surface and the bottom side retainer surfaces collectively define a bottom retainer channel,
   wherein the bottom retainer channel comprises an arc shape.

8. The medical holding system of claim 7, wherein:
   the top retainer portion comprises a top retainer surface and a top side retainer surface extending from the top retainer surface;
   the top retainer surface and the top side retainer surface collectively define a top retainer channel; and
   the top retainer channel comprises the arc shape.

9. The medical holding system of claim 1, wherein the pivot device is configured to be pivoted through less than three-hundred sixty degrees relative to the retainer.

10. The medical holding system of claim 1, wherein:
    the pivot device comprises a rotor;
    the rotor comprises a central rotor portion and at least three of the arms extending from the central rotor portion;
    there comprises a plurality of cord transport spaces comprising:
       the cord transport space between one pair of the first arm portions; and
       another cord transport space between another pair of the first arm portions;
    the central rotor portion partially defines each of the cord transport spaces;
    the rotor is configured to be rotated through three-hundred sixty degrees relative to the retainer,
    the rotor is configured to be rotated to comprise:
       a plurality of entry positions comprising the entry position; and
       a plurality of outlet positions comprising the outlet position, in each of the entry positions, one of the cord transport spaces is aligned with the entry space; and in each of the outlet positions, one of the cord transport spaces is aligned with the outlet space.

11. The medical holding system of claim 1, wherein:

the grasper comprises:
- a plurality of grippers configured to sandwich a portion of the implantable element;
- a grasper base supporting a first one of the grippers;
- a jaw pivotally coupled to the grasper base, wherein the jaw comprises a second one of the grippers; and
- a biaser coupled to the jaw; and the medical holding system comprises a pivot member that pivotally couples the grasper to the pivot device, wherein the pivot member extends along a pivot axis; and wherein the grasper is configured to pivot about the pivot axis relative to the pivot device.

12. The medical holding system of claim 1, comprising an upright support that supports the retainer, wherein the upright support comprises:
- a foot configured to be coupled to a support structure, wherein the foot is configured to extend along a first vertical axis that intersects with the support structure; and
- a neck coupled to the retainer, wherein the neck is configured to extend along a second vertical axis that intersects with the support structure, wherein the first vertical axis is offset from the second vertical axis.

13. A medical holding system comprising:

a retainer;

a pivot device comprising a plurality of arms, wherein:
- each of the arms comprises a first arm portion and a second arm portion; and
- each of the second arm portions is configured to be engaged with the retainer; and a grasper configured to be coupled to the pivot device, wherein the grasper is configured to grasp a portion of an implantable element, wherein the pivot device is configured to be pivoted relative to the retainer, wherein, when each of the second arm portions is engaged with the retainer, the retainer supports the second arm portion.

14. The medical holding system of claim 13, wherein, when each of the second arm portions is engaged with the retainer, the second arm portion and the retainer comprise a male-female relationship.

15. The medical holding system of claim 14, wherein, based on the male-female relationship:
- each of the second arm portions comprises an arm shape that is one of a male arm shape or a female arm shape; and
- the retainer comprises a retainer shape that is one of: (a) a male retainer shape if the arm shape comprises the female arm shape; or (b) a female retainer shape if the arm shape comprises the male arm shape.

16. A medical holding system comprising:

a retainer;

a pivot device comprising a plurality of arms, wherein:
- each of the arms comprises a first arm portion and a second arm portion; and
- each of the second arm portions is configured to be engaged with the retainer, wherein the second arm portion and the retainer comprise a male-female relationship when engaged with each other; and a grasper configured to be coupled to the pivot device, wherein the grasper is configured to grasp a portion of an implantable element, wherein the pivot device is configured to be pivoted relative to the retainer, wherein the pivoting of the pivot device causes each of the first arm portions to move at least partially along a passageway for a cord segment of a cord, wherein the pivot device defines a cord transport space located between the first arm portions, and wherein the pivot device is configured to be pivoted, relative to the retainer, between an entry position and an outlet position.

17. The medical holding system of claim 16, wherein:

in the entry position:
- there comprises an entry space between the retainer and one of the second arm portions; and
- the entry space extends to the cord transport space; and in the outlet position:
- there comprises an outlet space between the retainer and one of the second arm portions; and
- the outlet space extends to the cord transport space.

18. The medical holding system of claim 16, wherein, based on the male-female relationship:
- each of the second arm portions comprises an arm shape that is one of a male arm shape or a female arm shape; and
- the retainer comprises a retainer shape that is one of: (a) a male retainer shape if the arm shape comprises the female arm shape; or (b) a female retainer shape if the arm shape comprises the male arm shape.

19. A method for manufacturing a medical holding system, the method comprising:

configuring a retainer;

configuring a pivot device to comprise a plurality of arms so that:
- each of the arms comprises a first arm portion and a second arm portion; and
- each of the second arm portions is configured to be engaged with the retainer so that the second arm portion and the retainer comprise a male-female relationship when engaged with each other;

configuring a grasper to be coupled to the pivot device;

configuring the grasper to grasp a portion of an implantable element; and configuring the pivot device to be pivoted relative to the retainer.

20. The method of claim 19, comprising one of:

configuring the retainer to at least partially fit within a space defined by any one of the second arm portions; or configuring the retainer to define a space configured to at least partially receive any one of the second arm portions.

21. The method of claim 19, comprising configuring the pivot device so that:

the pivot device is pivotal, relative to the retainer, between an entry position and an outlet position; and at least one of the second arm portions remains mated with the retainer during the pivoting between the entry position and the outlet position.

22. The method of claim 19, wherein, based on the male-female relationship:

each of the second arm portions comprises an arm shape that is one of a male arm shape or a female arm shape; and the retainer comprises a retainer shape that is one of: (a) a male retainer shape if the arm shape comprises the female arm shape; or (b) a female retainer shape if the arm shape comprises the male arm shape.

23. A method for manufacturing a medical holding system, the method comprising:
configuring a retainer;
configuring a pivot device to comprise a plurality of arms so that:
  each of the arms comprises a first arm portion and a second arm portion; and
  each of the second arm portions is configured to be engaged with the retainer;
configuring a grasper to be coupled to the pivot device;
configuring the grasper to grasp a portion of an implantable element;
configuring the pivot device to be pivoted relative to the retainer;
configuring the pivot device so that the pivoting causes each of the first arm portions to move at least partially along a passageway for a cord segment of a medical cord; and
configuring the pivot device so that the pivot device defines a cord transport space located between the first arm portions;
configuring the pivot device to pivot, relative to the retainer, between an entry position and an outlet position;
configuring the pivot device so that, in the entry position:
  there comprises an entry space between the retainer and one of the second arm portions; and
  the entry space extends to the cord transport space; and
configuring the pivot device so that, in the outlet position:
  there comprises an outlet space between the retainer and one of the second arm portions; and
  the outlet space extends to the cord transport space.

* * * * *